United States Patent
Treutlein et al.

(10) Patent No.: US 11,091,466 B2
(45) Date of Patent: Aug. 17, 2021

(54) HETEROCYCLIC INHIBITORS OF PCSK9

(71) Applicant: CARDIO THERAPEUTICS PTY LTD, New South Wales (AU)

(72) Inventors: Herbert Treutlein, New South Wales (AU); Jun Zeng, New South Wales (AU); Ian Dixon, New South Wales (AU); Ian James, New South Wales (AU); James T. Palmer, New South Wales (AU)

(73) Assignee: CARDIO THERAPEUTICS PTY LTD, New South Wales (AU)

( * ) Notice: Subject to any disclaimer, the term of this patent is extended or adjusted under 35 U.S.C. 154(b) by 0 days.

(21) Appl. No.: 16/494,899

(22) PCT Filed: Mar. 16, 2018

(86) PCT No.: PCT/AU2018/050243
§ 371 (c)(1),
(2) Date: Sep. 17, 2019

(87) PCT Pub. No.: WO2018/165718
PCT Pub. Date: Sep. 20, 2018

(65) Prior Publication Data
US 2020/0207743 A1   Jul. 2, 2020

(30) Foreign Application Priority Data

Mar. 17, 2017 (AU) ................. 2017900935

(51) Int. Cl.
| | |
|---|---|
| *A61K 31/506* | (2006.01) |
| *A61K 31/164* | (2006.01) |
| *A61P 9/10* | (2006.01) |
| *C07D 233/54* | (2006.01) |
| *C07D 403/10* | (2006.01) |
| *C07D 403/12* | (2006.01) |
| *C07D 403/14* | (2006.01) |
| *C07D 401/10* | (2006.01) |
| *C07D 401/14* | (2006.01) |
| *C07D 413/12* | (2006.01) |
| *C07D 413/14* | (2006.01) |
| *C07D 487/04* | (2006.01) |
| *A61K 31/366* | (2006.01) |

(52) U.S. Cl.
CPC .............. *C07D 403/10* (2013.01); *A61P 9/10* (2018.01); *C07D 401/10* (2013.01); *C07D 401/14* (2013.01); *C07D 403/14* (2013.01); *C07D 413/14* (2013.01); *C07D 487/04* (2013.01); *A61K 31/366* (2013.01)

(58) Field of Classification Search
CPC .............. A61K 31/506; A61K 31/4164; A61K 31/4725; A61P 9/10; C07D 233/54; C07D 403/10; C07D 403/12; C07D 403/14; C07D 401/10; C07D 401/14; C07D 413/12; C07D 413/14; C07D 487/04
See application file for complete search history.

(56) References Cited

U.S. PATENT DOCUMENTS

| | | |
|---|---|---|
| 2011/0118181 A1 | 5/2011 | Seidah et al. |
| 2012/0004223 A1 | 1/2012 | Liu et al. |

FOREIGN PATENT DOCUMENTS

| | | |
|---|---|---|
| CN | 101747330 A | 6/2010 |
| WO | 2004/005281 A1 | 1/2004 |
| WO | 2007/018325 A1 | 2/2007 |
| WO | 2010/026262 A1 | 3/2010 |
| WO | 2010/075869 A1 | 7/2010 |
| WO | 2011/090738 A2 | 7/2011 |
| WO | 2013/120852 A1 | 8/2013 |
| WO | 2013/190508 A1 | 12/2013 |
| WO | 2014/054058 A2 | 4/2014 |
| WO | 2016/040305 A1 | 3/2016 |
| WO | 2016/107603 A1 | 7/2016 |

OTHER PUBLICATIONS

Shukla, S. et al, "Pharmacophore Modeling of Nilotinib as an Inhibitor of ATP-Binding Cassette Drug Transporters and BCR-ABL Kinase Using a Three-Dimensional Quantitative Structure—Activity Relationship Approach." Molecular Pharmaceutics, 2014, 11(7), 2313-2322.

Tan, L. et al, "Discovery of Type II Inhibitors of TGFβ-Activated Kinase 1 (TAK1) and Mitogen-Activated Protein Kinase Kinase Kinase 2 (MAP4K2)." Journal of Medicinal Chemistry, 2015, 58(1), 183-196.

Ma, Y. et al, "Combinatorial Synthesis of Substituted Biaryls and Heterocyclic Arylamines." Journal of Combinatorial Chemistry, 2004, 6(3), 426-430.

International-Type Search Report for Australian National Application No. 2017900935, dated Nov. 2, 2017, 16 pages.

(Continued)

*Primary Examiner* — Brenda L Coleman
(74) *Attorney, Agent, or Firm* — Meunier Carlin & Curfman LLC

(57) ABSTRACT

This application relates to chemical compounds which may act as inhibitors of, or which may otherwise modulate the activity of, PCSK9, or a pharmaceutically acceptable salt, solvate, prodrug or polymorph thereof, and to compositions and formulations comprising such compounds, and methods of using and making such compounds. Compounds include comprising of Formula (I): (I) wherein A, D and Q are described herein.

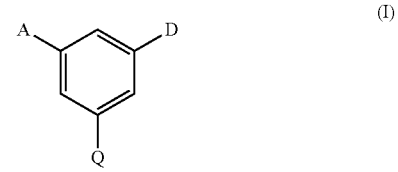

(I)

18 Claims, 5 Drawing Sheets
Specification includes a Sequence Listing.

(56) References Cited

OTHER PUBLICATIONS

International Search Report and Written Opinion of the International Searching Authority for International Application No. PCT/AU2018/050243, dated Apr. 20, 2018, 6 pages.
Poncet-Montagne, G. et al, "Observed bromodomain flexibility reveals histone peptide- and small molecule ligand-compatible forms of ATAD2." Biochemical Journal, 2015, 466, 337-346.
Wang, D. et al, "Hybrid compounds as new Bcr/Abl inhibitors." Bioorganic & Medicinal Chemistry Letters, 2011, 21, 1965-1968.
Duveau, D. et al, "Synthesis and biological evaluation of analogues of the kinase inhibitor nilotinib as Abl and Kit inhibitors." Bioorganic & Medicinal Chemistry Letters, 2013, 23, 682-686.

```
                              160         170         180         190         200         210
                         ....|....| ....|....| ....|....| ....|....| ....|....| ....|....|
Cavia_porcellus          --SVPWNLER ILPVRRQAKE YSAP--SHPV TVYLLDTSIQ SGRREIQGRI TVTDFEN VPQ
Mus_musculus             --SIPWNLER IIPAWRQTEE DRSPD-SSQV EVYLLDTSIQ GARREIEGRV TITDFFN VPE
Rattus_norvegicus        --SIPWNLER IIPAWQQTEE DSSPDOSSQV EVYLLDTSIQ SERREIERRV TITDFFN VPE
Orcinus_orca             --SIPWNLER ILPTRRQADE RRAPTGGGLV EVYLLDTSIQ SGRREIEGRV VVTDFEN VPE
Loxodonta_african        --SIPWNLER MIPAQYKADD YQPPN-SGLV EVYLLDTSIQ SGRREIECRV TVTDFEN VPE
3H42                     --SIPWNLER ITPPRYRADE YQPPDGGSLV EVYLLDTSIQ SDRREIERRV MVTDFEN VPE
4K8R                     --SIPWNLER ITPPRIRADE YQPPDGGSLV EVYLLDTSIQ SDRREIERRV MVTDFEN VPE
Homo_sapiens1            --SIPWNLER ITPPRYRADE YQPPDGGSLV EVYLLDTSIQ SDRREIERRV MVTDFEN VPE
Homo_sapiens2            --SIPWNLER ITPPRYRADE YQPPDGGSLV EVYLLDTSIQ SDRREIERRV MVTDFEN VPE 220         230         240         250         260         270
                         ....|....| ....|....| ....|....| ....|....| ....|....| ....|....|
Cavia_porcellus          EDGTRFRRQA SKEDSHGTRL AGVVSGRDAG VAKGAGLRSL RVLNCQERGT VSGTLR LEF
Mus_musculus             EDGTRFRRQA SKEDSHGTRL AGVVSGRDAG VAKGTSLRSL RVLNCQGKGT VSGTLI LEF
Rattus_norvegicus        EDGTRFRRQA SKEDSHGTRL AGVVSGRDAG VAKGTSLRSL RVLNCQGKGT VSGTLI LEF
Orcinus_orca             EDGTRFRRQA RKEDSHGTRL AGVVSGRDAG VAKGASLRSL RVLNCQEKGT VSSTLT LEF
Loxodonta_african        EDGTRFRRQA NKEESHGTRL AGVVSGRDAG VAKGASLRSL RVLNCQGRGT VSSIVI LEF
3H42                     EDGTRFRRQA SKEDSHGTRL AGVVSGRDAG VAKGASMRSL RVLNCQGKGT VSGTLI LEF
4K8R                     EDGTRFRRQA SKEDSHGTRL AGVVSGRDAG VAKGASMRSL RVLNCQGKGT VSGTLI LEF
Homo_sapiens1            EDGTRFRRQA SKEDSHGTRL AGVVSGRDAG VAKGASMRSL RVLNCQEKGT VSGTLI LEF
Homo_sapiens2            EDGTRFRRQA SKEDSHGTRL AGVVSGRDAG VAKGASMRSL RVLNCQGKGT VSGTLI LEF 280         290         300         310         320         330
                         ....|....| ....|....| ....|....| ....|....| ....|....| ....|....|
Cavia_porcellus          IRKSQLAQPV EPLVVLLPLA GGYSRTLNAA CRLLARAGVV LVAAAGNFRD DACLYSPASA
Mus_musculus             IRKSQLIQPS GPLVVLLPLA GGYSRIINAA CRRLARTEVV LVAAAGNFRD DACLYSPASA
Rattus_norvegicus        IRKSQLIQPS GPLVVLLPLA GGYSRIINTA CQRLARTGVV LVAAAGNFRD DACLYSPASA
Orcinus_orca             IRKSQLAQPA SRLVVLLPLA GGYSPRINAA CQQLAGTGAV LVAAAGNFRD DACLYSPASA
Loxodonta_african        IRKSQLSQPT GPLVLLLPLV GGRSRVINAA CQRLSRAGVV LVAAAGNFRD DACRYSPASA
3H42                     IRKSQLVQPV GPLVVLLPLA GGYSRVINAA CQRLARAGVV LVTAAGNFRD DACLYSPASA
4K8R                     IRKSQLVQPV GPLVVLLPLA GGYSRVINAA CQRLARAGVV LVTAAGNFRD DACLYSPASA
Homo_sapiens1            IRKSQLVQPV GPLVVLLPLA GGYSRVINAA CQRLARAGVV LVTAAGNFRD DACLYSPASA
Homo_sapiens2            IRKSQLVQPV GPLVVLLPLA GGYSRVINAA CQRLARAGVV LVTAAGNFRD DACLYSPASA
```

Figure 4a

```
              160        170        180        190        200        210
         ........|   ....|....|  ....|....|  ....|....|  ....|....|  ....|....|
PCSK3    ------GV   TQRDLNVKAA  WAQGYTGHGI  VVSILDDGIE  KNHPDLAGNY  DPGASFLVND
PCSK1    DTRMTAAL   PKLDLHVIPV  WQKGITGKSV  VITVLDDGLE  WNHTDIYANY  DPEASYLFND
PCSK2    NTGQADGT   PGLDLNVAEA  WELGYTGKGV  TIGIMDDGID  YLHPDLASNY  NAEASYLFSS
PCSK4    ------SE   AQPDLSILQA  WSQGLSGQGI  VVSVLDDGIE  KDHPDLWANY  DPLASYLFED
PCSK5    -CSDNTHP   CQSDMNIEGA  WKRGYTGKNI  VVTILDDGIE  RTHPDLMQNY  DALASCLVNG
PCSK6    -CGDKNSR   CRSEMNVQAA  WKRGYTGKNV  VVTILDDGIE  RNHPDLAPNY  DSYASYLVNG
PCSK9    SIPWNLER   ITPPRYRADE  YQPPDGGSLV  EVYLLDTSIQ  SDHREIEGRV  MVTDFENVPE
PCSK7    ----NRRS   PGRDINVTGV  WERNVTGRGV  TVVVVDDGVE  NTIQDIAPNY  SPEGSYLNS
CONS                              G           D 220        230        240        250        260
         ....|...-.|  ....|....|  ....|....-------.|  ....|....|  ....|-.....|
PCSK3    QDPDPQPRYTQ  MDHRHGTRC   AGEVAAVANNGVCGVG    VAYNARIGGV  RMLDG-EVTDA
PCSK1    NDHDPFPRYDP  TNENKHGTRC  AGEIAMQAENHKCGVG    VAYNSKVGGI  RMLDG-IVTDA
PCSK2    NDPYPYPRYTD  DWFNSHGTRC  AGEVSAAANNNICGVG    VAYNSKVAGI  RMLDQPFMTDI
PCSK4    YDPDPQPRYTP  SKENRHGTRC  AGEVAAMANNGFCGVG    VAFNARIGGV  RMLDG-TITDV
PCSK5    NDLDPMPRYDA  SNENKHGTRC  AGEVAAAANNSHCTVG    IAFNAKIGGV  RMLDG-DVTDM
PCSK6    NDYDPSPRYDA  SNENKHGTRC  AGEVAASANNSYCIVG    IAYNAKIGGI  RMLDG-DVTDV
PCSK9    EDGTRFHR-QA  SKCDSHGTHL  AGVVSGRD-------AG   VAKGASMRSL  RVLNC-QGKGT
PCSK7    NDPDEMPHPDV  ENPNRHGTRC  AGEIAAVPNNSFCAVG    VATGSRIAGI  RVLDG-PLTDS
CONS          D          HGT         AG                G   A         R L 270        280        290        300        310
         ....|....|   ....|....|  ....|....|  ....|....|  ....|...------.|
PCSK3    VEARSISLNP   NNIHIYSASW  GPEDDGKTVD  GPARLAEEAF  FRGVSQGRGGLGSIFV
PCSK1    IEASSIGFNP   GWDIYSASW   GPNDDGKTVE  GPGRLAQKAF  EYGVKQGRQGKGSIFV
PCSK2    IEASSIHMP    QLIDIYSASW  GPTDNGKTVD  GPRELTLQAM  ADGVNKGRGGKGSIFV
PCSK4    IEAQSISLQP   QNIRIYSASW  GPEDDGRTVD  GPGILTREAF  RRGVTKGRGGLGTLFI
PCSK5    VEAKSVGFNP   QNVRIYSASW  GPDDGKTVD   GPAPLTRQAF  ENGVRMGRRGLGSVFV
PCSK6    VEAKSIGIRP   NYIDIYSASW  GPDDDGKTVD  GPGRLAKQAF  EYGIKKGRQGLGSIFV
PCSK9    VSGTLIGLEP   IRKSQLVQPV  GPLVVLLPLA  GGYSRVLNAA  CQRLARAG-------VV
PCSK7    MEAVAENKNY   QINDIYSCSW  GPDDDGKTVD  GPRQLGKAAL  QHGVIAGRQSFGSIFV
CONS                                GP          G   A 320        330        340        350        360        370
         ....|....|  ....|....|  ....|....|  ....|....|  ....|....|  ....|.------.|
PCSK3    WASGNGGREN  DSCNCDGYTN  -SIYTLSISS  ATQFGNVPWY  SEACSSTLAT  TYSSGN--QNEKQIVT
PCSK1    WASGNGGRQG  DNCDCDGYTD  -SIYTISISS  ASQQGLSPWY  AEKCSSTLAT  SYSSGD--YTDQRITS
PCSK2    WASGDGG-SY  DDCNCDGYAS  -SMWTISINS  AINDGRTALF  DESCSSTLAS  TFSNGRKRNPEAGVAT
PCSK4    WASGNGGLHY  DNCNCDGYTN  -SIHTLSVGS  TTQQGRVPWY  SEACASTLTT  TYSSGV--ATDPQIVT
PCSK5    WASGNGGRSK  DRCSCDGYTN  -SIYTISISS  TAESGKKPWY  LEECSSTLAT  TYSSGE--SYDKKIIT
PCSK6    WASGNGGREG  DYCSCDGYTN  -SIYTISVSS  ATENGYKPWY  LEECASTLAT  TYSSGA--FYERKIVT
PCSK9    LVTAAGNFRD  DACLYSPASA  PEVITVGATN  AQDQPVTLGT  LGTNFGRCVD  LFAPGE------DIIG
PCSK7    VASGNGGQRN  DNCNYDGYAN  -SIFTVTIGA  VDEEGRMPFY  AEECASMLAV  TFSGGD--KMLRSIVT
CONS        G        D  C          T                                       G
```

Figure 4b

SEQUENCE LISTING

<160> NUMBER OF SEQ ID NOS: 1

<210> SEQ ID NO 1
<211> LENGTH: 691
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu

```
            100                 105                 110
His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
            130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
            290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Ser Gln Ser Gly Thr
            370                 375                 380

Ser Gln Ala Ala Ala His Val Ala Gly Ile Ala Ala Met Met Leu Ser
385                 390                 395                 400

Ala Glu Pro Glu Leu Thr Leu Ala Glu Leu Arg Gln Arg Leu Ile His
                405                 410                 415

Phe Ser Ala Lys Asp Val Ile Asn Glu Ala Trp Phe Pro Glu Asp Gln
            420                 425                 430

Arg Val Leu Thr Pro Asn Leu Val Ala Ala Leu Pro Pro Ser Thr His
            435                 440                 445

Gly Ala Gly Trp Gln Leu Phe Cys Arg Thr Val Trp Ser Ala His Ser
            450                 455                 460

Gly Pro Thr Arg Met Ala Thr Ala Val Ala Arg Cys Ala Pro Asp Glu
465                 470                 475                 480

Glu Leu Leu Ser Cys Ser Ser Phe Ser Arg Ser Gly Lys Arg Arg Gly
            485                 490                 495
```

```
Glu Arg Met Glu Ala Gln Gly Gly Lys Leu Val Cys Arg Ala His Asn
        500             505                 510
Ala Phe Gly Gly Glu Gly Val Tyr Ala Ile Ala Arg Cys Cys Leu Leu
        515             520                 525
Pro Gln Ala Asn Cys Ser Val His Thr Ala Pro Pro Ala Glu Ala Ser
        530             535                 540
Met Gly Thr Arg Val His Cys His Gln Gln Gly His Val Leu Thr Gly
545             550             555                 560
Cys Ser Ser His Trp Glu Val Glu Asp Leu Gly Thr His Lys Pro Pro
            565             570                 575
Val Leu Arg Pro Arg Gly Gln Pro Asn Gln Cys Val Gly His Arg Glu
        580             585                 590
Ala Ser Ile His Ala Ser Cys Cys His Ala Pro Gly Leu Glu Cys Lys
        595             600                 605
Val Lys Glu His Gly Ile Pro Ala Pro Gln Glu Gln Val Thr Val Ala
        610             615                 620
Cys Glu Glu Gly Trp Thr Leu Thr Gly Cys Ser Ala Leu Pro Gly Thr
625             630             635                 640
Ser His Val Leu Gly Ala Tyr Ala Val Asp Asn Thr Cys Val Val Arg
            645             650                 655
Ser Arg Asp Val Ser Thr Thr Gly Ser Thr Ser Glu Gly Ala Val Thr
            660             665                 670
Ala Val Ala Ile Cys Cys Arg Ser Arg His Leu Ala Gln Ala Ser Gln
        675             680                 685
Glu Leu Gln
    690
```

HETEROCYCLIC INHIBITORS OF PCSK9

FIELD OF THE INVENTION

The present disclosure relates to compounds for the treatment of LDL related disorders, to their compositions and methods for their use, and to PCSK9 inhibition.

BACKGROUND OF THE INVENTION

Cardiovascular diseases are said to cause an estimated 17.5 million (over 30%) of all deaths as of 2012 (E. Corey, The Pharmaceutical Journal, 2015). A particular risk factor, atherosclerosis, results from high levels of circulating low-density lipoprotein (LDL-C, a.k.a. "bad" cholesterol) in the blood. LDL-C accumulation in the inner walls of arteries results in atherosclerosis and can provoke an inflammatory response, which in turn can lead to cardiovascular events such as heart attack and stroke. Thus, LDL-C measurement is an effective surrogate marker for the risk of cardiovascular events.

Proprotein convertase subtilisin kexin type 9 (PCSK9) was discovered in 2003 (Seidah, N. G. et al, PNAS, 2003), is a serine protease, and is highly expressed in the liver. It is a genetically validated target for hypercholesterolemia (Abifadel, M. et al, Nature Genetics, 2003). Loss-of-function mutations of the PCSK9 gene have been linked to lower levels of LDL-C and a reduction of cardiovascular risk (Cohen, J. C. et al, NEJM, 2006). Its regulatory mechanisms have been reviewed (Lagace, T. A, Curr. Opin. Lipidol. (2014), 387-393). PCSK9 is synthesized as an enzyme precursor. Following synthesis, PCSK9 undergoes autocatalytic cleavage, which is required for secretion from the cell. The cleaved prodomain remains with PCSK9, blocking access to the active site of the enzyme. While LDL-C normally binds to the LDL receptor (LDL-R), which are together internalized and degraded intracellularly, PCSK9 attaches to the LDL-R/LDL complex for internalization/degradation. As a result, recirculation of LDL-R is reduced, resulting in increased circulatory LDL. Inhibition of PCSK9 or prevention of LDL-R attachment thereto results in increased cell surface expression of LDL-R, lowering circulatory LDL.

Because PCSK9's only substrate is itself, targeting circulating PCSK9 by small molecule inhibitors is unlikely to represent an option for LDL reduction because the mechanism of action of PCSK9 in reducing cellular LDLR does not involve proteolytic activity. However, small cell-permeable molecules targeting the catalytic site of PCSK9 pro-enzyme could theoretically inhibit the auto-processing of PCSK9, thereby promoting its degradation in the ER. However, cross-reactivity associated with such inhibitors raises concern that PCSK9 pro-enzyme inhibition could co-inhibit other proprotein convertases. (Mousavi, S. A. et al., J. Int. Med. (2009) 266, 517-519).

Despite the discovery of PCSK9 and its role in LDL regulation, statins have served as the primary therapy used to prevent cardiovascular events. By inhibiting the rate-limiting enzyme HMG-CoA reductase, which has a vital role in internal (hepatic) cholesterol production through the reduction of 3-hydroxy-3-methylglutaryl coenzyme A to mevalonic acid, various statins can reduce LDL-C levels from 10-60% and have been shown to reduce the risk of heart attack and stroke.

Familial hypercholesterolemia (FH) is a hereditary disorder of LDL cholesterol metabolism, affects 1 in 250 persons and is characterized by greatly increased levels of LDL-C (Besseling, J. et al., J. Am. Coll. Cardiol. (2016) 68, 252-268). Patients with heterozygous FH are at 3- to 4-fold higher risk for coronary artery disease (CAD) and tend to develop CAD on average 10 years earlier in life than unaffected persons. Statins lower LDL cholesterol in patients with heterozygous FH, approximately to the same extent as in the general population while the average relative risk reduction of statins for CAD is estimated to be 22% per mmol/l among the general population it was unknown whether there is a comparable risk reduction in the setting of heterozygous FH because it would be unethical to withhold treatment from these patients. In the Besseling study to estimate the relative risk reduction for CAD and mortality by statins in heterozygous FH patients, the authors concluded that moderate- to high-intensity statin therapy lowered the risk for CAD and mortality by 44%. However, reduction in LDL-C is not considered sufficient in many cases. One mechanism by which statins display a countervailing mechanism is in the upregulation of sterol regulatory element binding protein 2 (SREBP-2, see Wong, J. et al., Biochem. J. (2006), 400, 485-491.). This increased activity results in the activation of both LDL receptors (LDLR) and PCSK9. Increased expression and secretion binds LDLR, resulting in higher LDLC. Thus, while statins reduce LDL via HMGCoA inhibition, their effect on SREPB acts as a counterbalance. Adding PCSK9 inhibitors to therapy can help override this mechanism.

While statins have been on the market for almost 30 years, some patients find statins to be ineffective or are burdened by intolerable side effects such as muscle pain (Abd, T. T., Jacobson, T. A., Expert Opinion on Drug Safety, p 373-387, 2011). Observationally, up to 10-15% of statin users develop muscle side effects ranging from mild myalgia to more severe symptoms. Furthermore, it has been reported that statin therapy is associated with a slightly higher risk of diabetes (2-17%, Sattar, N. et al., Lancet, (2010) 375, 735-742.) Given that familial hypercholesterolemia patients may not sufficiently benefit from statin therapy even in the absence of adverse side effects, there exists a need for alternative therapy avenues such as PCSK9 inhibition.

To date, there are no marketed small molecule inhibitors of PCSK9. Monoclonal antibody based drugs alirocumab and evolocumab have shown evidence of large improvements in lipid levels. These drugs are administered by injection, for instance biweekly. Alirocumab, when delivered every 2 weeks, showed greatest effect in heterozygous FH patients at cardiovascular risk who had not achieved LCL-C goals with statin therapy alone. Alirocumab also showed a moderate increase in "good" cholesterol (HDL-C) of 6-12% over this period. However, legal disputes over the intellectual property surrounding alirocumab have resulted in an injunction from its marketing in some jurisdictions. These issues, together with the substantially higher costs typically associated with monoclonal antibody production over small molecule inhibitors, clearly illustrates the very high need for competitive small molecule inhibitors of PCSK9.

Small molecule approaches have been described in the following: See WO2014170786, (Pfizer), WO2014150395, WO2014150326 (Shifa), WO2011051961, WO2014002106 (Cadila Healthcare) and US20120004223 (CVI), none of which have progressed beyond the discovery stage. Additional reported approaches include RNAi and gene-silencing oligonucleotides.

The present invention seeks to provide small molecule inhibitors of PCSK9.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

As discussed above, the present invention seeks to provide small molecule inhibitors of PCSK9. In one aspect, therefore, the invention provides a compound according to Formula (I):

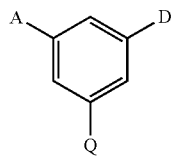
(I)

or a pharmaceutically acceptable salt, solvate, prodrug or polymorph thereof, wherein A is H or an optionally substituted 5-membered heteroaryl ring, wherein the substituent is a methyl group;

Q is selected from the group consisting of optionally substituted: $C_1$-$C_6$ alkyl, $C_2$-$C_6$ alkenyl, $C_1$-$C_6$ haloalkyl, $C_2$-$C_6$ haloalkenyl, $C_1$-$C_6$ alkyloxy, $C_2$-$C_6$ alkenyloxy, $C_1$-$C_6$ alkylamino, $C_2$-$C_6$ alkenylamino, $C_1$-$C_6$ alkylcarboxy, $C_2$-$C_6$ alkenylcarboxy, $C_1$-$C_6$ haloalkoxy, $C_2$-$C_6$ haloalkenyloxy, $C_1$-$C_6$ hydroxyalkyl, $C_2$-$C_6$ hydroxyalkenyl, $C_1$-$C_6$ alkylcarboxyamide, $C_2$-$C_6$ alkenylcarboxyamide, $C_1$-$C_6$ alkylsulfanyl, $C_2$-$C_6$ alkenylsulfanyl, $C_1$-$C_6$ alkylsulfenyl, $C_2$-$C_6$ alkenylsulfenyl, $C_1$-$C_6$ alkylsulfonyl, $C_2$-$C_6$ alkenylsulfonyl, $C_1$-$C_6$ alkylsulfonylamino, $C_2$-$C_6$ alkenylsulfonylamino, $C_4$-$C_7$ heterocyclyl, ($C_1$-$C_3$ alkyl)$C_3$-$C_7$ heterocyclyl, ($C_1$-$C_3$ alkyl)$C_3$-$C_7$ cycloalkyl and $C_3$-$C_7$ cycloalkyl;

wherein D is

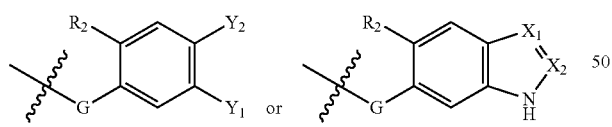

wherein G is selected from the group consisting of —$NR_1C(O)$—, —$C(O)NR_1$—, —$S(O)_2NR_1$—, and —$NR_1S(O)_2$—;

wherein $R_1$ is H or methyl and $R_2$ is H, or wherein G is —$NR_1C(O)$— and $R_1$ and $R_2$, together with the atoms between them, form an optionally substituted $C_3$-$C_6$ heterocyclic ring, thereby creating a bicyclic or tricyclic ring; and wherein $X_1$ is $CR_3$ and $X_2$ is N, or $X_1$ is N and $X_2$ is $CR_3$, or both $X_1$ and $X_2$ are $CR_3$;

wherein $R_3$ is H, $C_1$-$C_2$ alkyl, $C_1$-$C_2$ hydroxyalkyl, $C_1$-$C_2$ alkoxy or $C_1$-$C_2$ alkylamino; and wherein $Y_1$ is H or methyl and $Y_2$ is

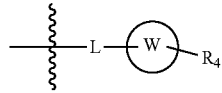

or $Y_2$ is H or methyl and $Y_1$ is

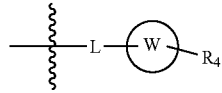

or both $Y_1$ and $Y_2$ are independently selected from H or methyl;

wherein L is selected from the group consisting of —O—, —NH—, —C(O)—, —$NH(CH_2)_m$—, $C_1$-$C_3$ alkoxy, $C_1$-$C_3$ alkylamino;

where m is 1 or 2; and wherein

is aryl or heteroaryl; and wherein $R_4$ is H, $NHC(O)CH_3$, substituted or unsubstituted aryl, substituted or unsubstituted heteroaryl.

Typically, when A is methyl-substituted imidazole, Q is —$CF_3$, and D is

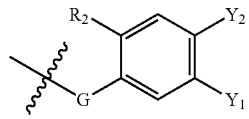

wherein G is —$NR_1C(O)$— where $R_1$ is H and $Y_2$ is methyl, $Y_1$ is not

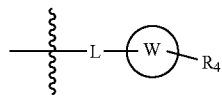

wherein L is —NH— and

is substituted pyrimidinyl where the substituent is 3-pyridinyl.

Typically,

is named relative to the position of attachment to L.

Typically,

is not pyrazolopyridinyl, ortho-substituted pyridine, 4-pyrimidinyl or imidazole. Accordingly, when

is not ortho-substituted pyridine, 4-pyrimidinyl, $Y_1$ or $Y_2$ is not

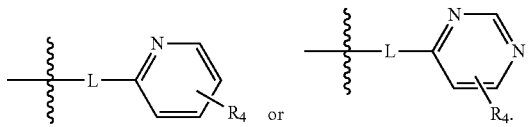

In one aspect, therefore, the invention provides a compound according to Formula (I):

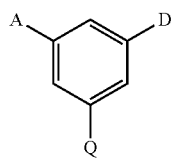

or a pharmaceutically acceptable salt, solvate, prodrug or polymorph thereof,
wherein
A is H or an optionally substituted 5-membered heteroaryl ring, wherein the substituent is a methyl group;
Q is selected from the group consisting of optionally substituted: $C_1$-$C_6$ alkyl, $C_2$-$C_6$ alkenyl, $C_1$-$C_6$ haloalkyl, $C_2$-$C_6$ haloalkenyl, $C_1$-$C_6$ alkyloxy, $C_2$-$C_6$ alkenyloxy, $C_1$-$C_6$ alkylamino, $C_2$-$C_6$ alkenylamino, $C_1$-$C_6$ alkylcarboxy, $C_2$-$C_6$ alkenylcarboxy, $C_1$-$C_6$ haloalkoxy, $C_2$-$C_6$ haloalkenyloxy, $C_1$-$C_6$ hydroxyalkyl, $C_2$-$C_6$ hydroxyalkenyl, $C_1$-$C_6$ alkylcarboxyamide, $C_2$-$C_6$ alkenylcarboxyamide, $C_1$-$C_6$ alkylsulfanyl, $C_2$-$C_6$ alkenylsulfanyl, $C_1$-$C_6$ alkylsulfenyl, $C_2$-$C_6$ alkenylsulfenyl, $C_1$-$C_6$ alkylsulfonyl, $C_2$-$C_6$ alkenylsulfonyl, $C_1$-$C_6$ alkylsulfonylamino, $C_2$-$C_6$ alkenylsulfonylamino, $C_4$-$C_7$ heterocyclyl, ($C_1$-$C_3$ alkyl)$C_3$-$C_7$ heterocyclyl, ($C_1$-$C_3$ alkyl)$C_3$-$C_7$ cycloalkyl and $C_3$-$C_7$ cycloalkyl;
wherein D is

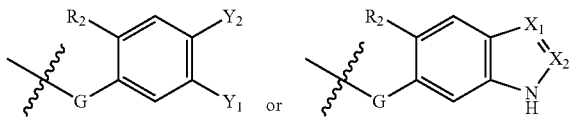

wherein G is selected from the group consisting of —NR$_1$C(O)—, —C(O)NR$_1$—, —S(O)$_2$NR$_1$—, and —NR$_1$S(O)$_2$—;

wherein $R_1$ is H or methyl and $R_2$ is H,
or wherein G is —NR$_1$C(O)— and $R_1$ and $R_2$, together with the atoms between them, form an optionally substituted $C_3$-$C_6$ heterocyclic ring, thereby creating a bicyclic or tricyclic ring; and
wherein $X_1$ is CR$_3$ and $X_2$ is N, or $X_1$ is N and $X_2$ is CR$_3$, or both $X_1$ and $X_2$ are CR$_3$;
wherein $R_3$ is H, $C_1$-$C_2$ alkyl, $C_1$-$C_2$ hydroxyalkyl, $C_1$-$C_2$ alkoxy or $C_1$-$C_2$ alkylamino; and
wherein $Y_1$ is H or methyl and $Y_2$ is

or $Y_2$ is H or methyl and $Y_1$ is

or both $Y_1$ and $Y_2$ are independently selected from H or methyl;
wherein L is selected from the group consisting of —O—, —NH—, —C(O)—, —NH(CH$_2$)$_m$—, $C_1$-$C_3$ alkoxy, $C_1$-$C_3$ alkylamino;
where m is 1 or 2; and
wherein

is aryl or heteroaryl; and
wherein $R_4$ is H, NHC(O)CH$_3$, substituted or unsubstituted aryl, substituted or unsubstituted heteroaryl.
Typically,

is not pyrazolopyridinyl, ortho-substituted pyridine, 4-pyrimidinyl or imidazole. Accordingly, when

is not ortho-substituted pyridine, 4-pyrimidinyl, $Y_1$ or $Y_2$ is not

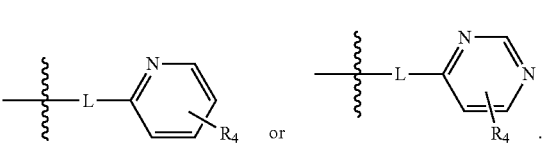

In one aspect, the invention provides a compound of formula II:

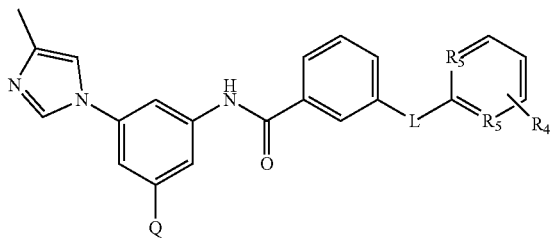

(II)

or a pharmaceutically acceptable salt, solvate, prodrug or polymorph thereof,
wherein
L, $R_4$ and Q are as defined above; and
each $R_5$ is independently CH or N.

In one aspect, the invention provides a compound of formula III:

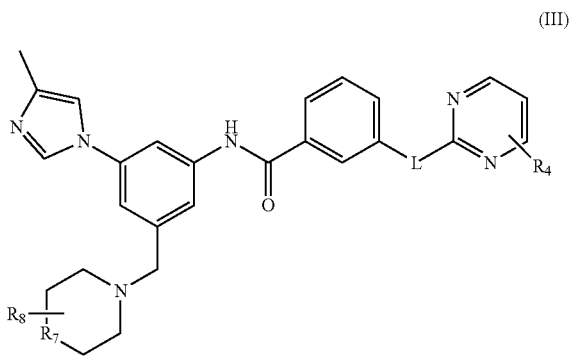

(III)

or a pharmaceutically acceptable salt, solvate, prodrug or polymorph thereof,
wherein
L and $R_4$ are as defined above;
$R_7$ is O, $CHR_6$ or $NR_6$; wherein $R_6$ is independently selected from the group consisting of H, —COOH, —CONH$_2$, —NH$_2$, $C_1$-$C_4$ alkylamino, $C_1$-$C_3$ alkyl, —OH; and
$R_8$ is independently selected from the group consisting of H, —COOH, —CONH$_2$, —NH$_2$, $C_1$-$C_3$ alkyl, $C_1$-$C_4$ alkylamino, $C_1$-$C_3$ alkoxy, —OH.

In one aspect, the invention provides a compound of formula IV:

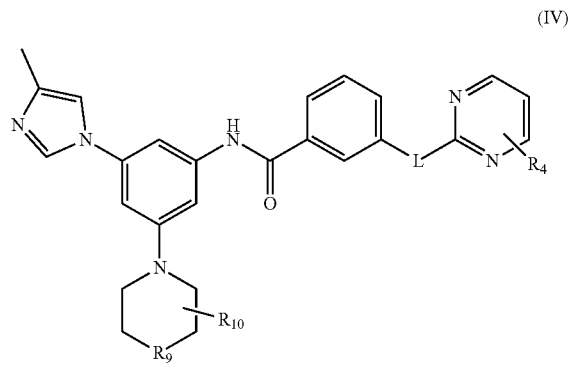

(IV)

or a pharmaceutically acceptable salt, solvate, prodrug or polymorph thereof,
wherein
L and $R_4$ are as defined above;
$R_9$ is O, $CHR_{11}$ or $NR_{11}$; wherein $R_{11}$ is independently selected from the group consisting of H, —COOH, —CONH$_2$, —NH$_2$, $C_1$-$C_3$ alkyl, $C_1$-$C_4$ alkylamino, $C_1$-$C_3$ alkoxy, —OH; and
$R_{10}$ is independently selected from the group consisting of H, —COOH, —CONH$_2$, —NH$_2$, $C_1$-$C_4$ alkylamino, $C_1$-$C_3$ alkoxy, $C_1$-$C_3$ alkyl, —OH;

In one aspect, there is provided a composition comprising a compound according to Formula (I), Formula (II), Formula (III) and/or Formula (IV) or a pharmaceutically acceptable salt, solvate, prodrug or polymorph thereof, and a pharmaceutically acceptable excipient.

In one aspect, there is provided a method for inhibiting PCSK9 in a subject in need thereof, the method comprising administering a therapeutically effective amount of a compound or a pharmaceutically acceptable salt, solvate, prodrug or polymorph thereof of Formula (I), Formula (II), Formula (III) and/or Formula (IV) to a subject.

In one aspect, there is provided a method for inhibiting PCSK9 in a subject in need thereof, the method comprising administering a therapeutically effective amount of a composition comprising a compound or a pharmaceutically acceptable salt, solvate, prodrug or polymorph thereof of Formula (I), Formula (II), Formula (III) and/or Formula (IV) to a subject.

In one aspect, there is provided a method for reducing LDL in a subject in need thereof, the method comprising administering a therapeutically effective amount of a compound or a pharmaceutically acceptable salt, solvate, prodrug or polymorph thereof of Formula (I), Formula (II), Formula (III) and/or Formula (IV) to a subject.

In one aspect, there is provided a method for reducing LDL in a subject in need thereof, the method comprising administering a therapeutically effective amount of a composition comprising a compound or a pharmaceutically acceptable salt, solvate, prodrug or polymorph thereof of Formula (I), Formula (II), Formula (III) and/or Formula (IV) to a subject.

In one aspect, there is provided a method for treating a disease or condition in a subject in need thereof, wherein the disease or condition is any one of the following: cardiovascular disease, cerebrovascular disease, atherosclerosis and/or their associated diseases or their symptoms, the method comprising administering a therapeutically effective amount of a compound according to formula (I), formula (II), formula (III) and/or formula (IV), or a pharmaceutically acceptable salt, solvate, prodrug or polymorph thereof to a subject.

In one aspect, there is provided a method for treating a disease or condition in a subject in need thereof, wherein the disease or condition is any one of the following: cardiovascular disease, cerebrovascular disease, atherosclerosis and/or their associated diseases or their symptoms, the method comprising administering a therapeutically effective amount of a composition comprising a compound according to formula (I), formula (II), formula (III) and/or formula (IV), or a pharmaceutically acceptable salt, solvate, prodrug or polymorph thereof to a subject.

In another aspect, there is provided use of a compound of Formula (I), Formula (II), Formula (III) and/or Formula (IV) or a pharmaceutically acceptable salt, solvate, prodrug or polymorph thereof, in the preparation of a medicament for the inhibition of PCSK9 in a subject.

In another aspect, there is provided use of a composition comprising a compound of Formula (I), Formula (II), Formula (III) and/or Formula (IV) or a pharmaceutically acceptable salt, solvate, prodrug or polymorph thereof, in the preparation of a medicament for the inhibition of PCSK9 in a subject.

In another aspect, there is provided use of a compound of Formula (I), Formula (II), Formula (III) and/or Formula (IV) or a pharmaceutically acceptable salt, solvate, prodrug or polymorph thereof, in the preparation of a medicament for the reduction of LDL in a subject.

In another aspect, there is provided use of a composition comprising a compound of Formula (I), Formula (II), Formula (III) and/or Formula (IV) or a pharmaceutically acceptable salt, solvate, prodrug or polymorph thereof, in the preparation of a medicament for the reduction of LDL in a subject.

In another aspect, there is provided use of a compound of Formula (I), Formula (II), Formula (III) and/or Formula (IV) or a pharmaceutically acceptable salt, solvate, prodrug or polymorph thereof in the preparation of a medicament for the treatment of a disease or condition in a subject, wherein the disease or condition is any one of the following: cardiovascular disease, cerebrovascular disease, atherosclerosis and/or their associated diseases or their symptoms.

In another aspect, there is provided use of a composition comprising a compound of Formula (I), Formula (II), Formula (III) and/or Formula (IV) or a pharmaceutically acceptable salt, solvate, prodrug or polymorph thereof in the preparation of a medicament for the treatment of a disease or condition in a subject, wherein the disease or condition is any one of the following: cardiovascular disease, cerebrovascular disease, atherosclerosis and/or their associated diseases or their symptoms.

In another aspect, there is provided use of a compound according to Formula (I), Formula (II), Formula (III) and/or Formula (IV) or a pharmaceutically acceptable salt, solvate, prodrug or polymorph thereof, for the inhibition of PCSK9.

In another aspect, there is provided use of a composition comprising a compound according to Formula (I), Formula (II), Formula (III) and/or Formula (IV) or a pharmaceutically acceptable salt, solvate, prodrug or polymorph thereof, for inhibiting PCSK9.

In another aspect, there is provided use of a compound according to Formula (I), Formula (II), Formula (III) and/or Formula (IV) or a pharmaceutically acceptable salt, solvate, prodrug or polymorph thereof, for the reduction of LDL.

In another aspect, there is provided use of a composition comprising a compound according to Formula (I), Formula (II), Formula (III) and/or Formula (IV) or a pharmaceutically acceptable salt, solvate, prodrug or polymorph thereof, for the reduction of LDL.

In another aspect, there is provided use of a compound Formula (I), Formula (II), Formula (III) and/or Formula (IV) or a pharmaceutically acceptable salt, solvate, prodrug or polymorph thereof, for the treatment of a disease or condition in a subject, wherein the disease or condition is any one of the following: cardiovascular disease, cerebrovascular disease, atherosclerosis and/or their associated diseases or their symptoms.

In another aspect, there is provided use of a composition comprising a compound Formula (I), Formula (II), Formula (III) and/or Formula (IV) or a pharmaceutically acceptable salt, solvate, prodrug or polymorph thereof, for the treatment of a disease or condition in a subject, wherein the disease or condition is any one of the following: cardiovascular disease, cerebrovascular disease, atherosclerosis and/or their associated diseases or their symptoms.

In yet another aspect, there is provided a compound according to Formula (I), Formula (II), Formula (III) and/or Formula (IV) or a pharmaceutically acceptable salt, solvate, prodrug or polymorph thereof, for use in inhibiting PCSK9.

In another aspect, there is provided a composition comprising a compound according to Formula (I), Formula (II), Formula (III) and/or Formula (IV) or a pharmaceutically acceptable salt, solvate, prodrug or polymorph thereof, for use in inhibiting PCSK9.

In another aspect, there is provided a compound according to Formula (I), Formula (II), Formula (III) and/or Formula (IV) or a pharmaceutically acceptable salt, solvate, prodrug or polymorph thereof, for use in reducing LDL.

In another aspect, there is provided a composition comprising a compound according to Formula (I), Formula (II), Formula (III) and/or Formula (IV) or a pharmaceutically acceptable salt, solvate, prodrug or polymorph thereof, for use in reducing LDL.

In another aspect, there is provided a compound according to Formula (I), Formula (II), Formula (III) and/or Formula (IV) or a pharmaceutically acceptable salt, solvate, prodrug or polymorph thereof, for use in the treatment of a disease or condition in a subject, wherein the disease or condition is any one of the following: cardiovascular disease, cerebrovascular disease, atherosclerosis and/or their associated diseases or their symptoms.

In another aspect, there is provided a composition comprising a compound according to Formula (I), Formula (II), Formula (III) and/or Formula (IV) or a pharmaceutically acceptable salt, solvate, prodrug or polymorph thereof, for use in the treatment of a disease or condition in a subject, wherein the disease or condition is any one of the following: cardiovascular disease, cerebrovascular disease, atherosclerosis and/or their associated diseases or their symptoms.

In yet another aspect, there is provided a compound according to Formula (I), Formula (II), Formula (III) and/or Formula (IV) or a pharmaceutically acceptable salt, solvate, prodrug or polymorph thereof, when used for inhibiting PCSK9.

In yet another aspect, there is provided a composition comprising a compound according to Formula (I), Formula (II), Formula (III) and/or Formula (IV) or a pharmaceutically acceptable salt, solvate, prodrug or polymorph thereof, when used for inhibiting PCSK9.

In yet another aspect, there is provided a compound according to Formula (I), Formula (II), Formula (III) and/or Formula (IV) or a pharmaceutically acceptable salt, solvate, prodrug or polymorph thereof, when used for reducing LDL.

In yet another aspect, there is provided a composition comprising a compound according to Formula (I), Formula (II), Formula (III) and/or Formula (IV) or a pharmaceutically acceptable salt, solvate, prodrug or polymorph thereof, when used for reducing LDL.

In yet another aspect, there is provided a compound of Formula (I), Formula (II), Formula (III) and/or Formula (IV) or a pharmaceutically acceptable salt, solvate, prodrug or polymorph thereof, when used for the treatment of a disease or condition in a subject, wherein the disease or condition is any one of the following: cardiovascular disease, cerebrovascular disease, atherosclerosis and/or their associated diseases or their symptoms.

In yet another aspect, there is provided a composition comprising a compound of Formula (I), Formula (II), Formula (III) and/or Formula (IV) or a pharmaceutically acceptable salt, solvate, prodrug or polymorph thereof, when used for the treatment of a disease or condition in a subject, wherein the disease or condition is any one of the following: cardiovascular disease, cerebrovascular disease, atherosclerosis and/or their associated diseases or their symptoms.

Any embodiment herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
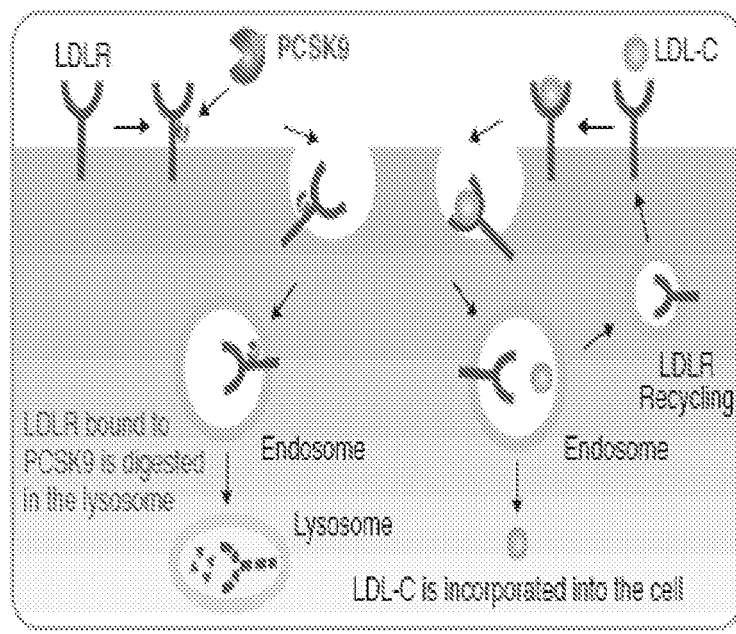
FIG. 1: Mechanism of LDL uptake following PCSK9-LDLR binding.

The inventors have designed the compounds described herein as being applicable to LDL related conditions, potentially as small molecule inhibitors of PCSK9. Without wishing to be bound to any theory and on the basis of these molecular modelling studies, these compounds may target extracellular PCSK9, thereby preventing the PCSK9 from interacting with the LDLR.

In one aspect, therefore, the invention provides a compound according to Formula (I):

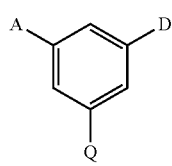

(I)

or a pharmaceutically acceptable salt, solvate, prodrug or polymorph thereof,
wherein
A is H or an optionally substituted 5-membered heteroaryl ring, wherein the substituent is a methyl group;
Q is selected from the group consisting of optionally substituted: $C_1$-$C_6$ alkyl, $C_2$-$C_6$ alkenyl, $C_1$-$C_6$ haloalkyl, $C_2$-$C_6$ haloalkenyl, $C_1$-$C_6$ alkyloxy, $C_2$-$C_6$ alkenyloxy, $C_1$-$C_6$ alkylamino, $C_2$-$C_6$ alkenylamino, $C_1$-$C_6$ alkylcarboxy, $C_2$-$C_6$ alkenylcarboxy, $C_1$-$C_6$ haloalkoxy, $C_2$-$C_6$ haloalkenyloxy, $C_1$-$C_6$ hydroxyalkyl, $C_2$-$C_6$ hydroxyalkenyl, $C_1$-$C_6$ alkylcarboxyamide, $C_2$-$C_6$ alkenylcarboxyamide, $C_1$-$C_6$ alkylsulfanyl, $C_2$-$C_6$ alkenylsulfanyl, $C_1$-$C_6$ alkylsulfenyl, $C_2$-$C_6$ alkenylsulfenyl, $C_1$-$C_6$ alkylsulfonyl, $C_2$-$C_6$ alkenylsulfonyl, $C_1$-$C_6$ alkylsulfonylamino, $C_2$-$C_6$ alkenylsulfonylamino, $C_4$-$C_7$ heterocyclyl, ($C_1$-$C_3$ alkyl)$C_3$-$C_7$ heterocyclyl, ($C_1$-$C_3$ alkyl)$C_3$-$C_7$ cycloalkyl and $C_3$-$C_7$ cycloalkyl;
wherein D is

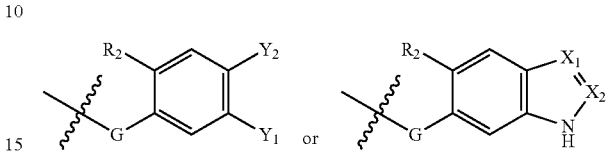

wherein G is selected from the group consisting of —$NR_1C(O)$—, —$C(O)NR_1$—, —$S(O)_2NR_1$—, and —$NR_1S(O)_2$—;
wherein $R_1$ is H or methyl and $R_2$ is H,
or wherein G is —$NR_1C(O)$— and $R_1$ and $R_2$, together with the atoms between them, form an optionally substituted $C_3$-$C_6$ heterocyclic ring, thereby creating a bicyclic or tricyclic ring; and
wherein $X_1$ is $CR_3$ and $X_2$ is N, or $X_1$ is N and $X_2$ is $CR_3$, or both $X_1$ and $X_2$ are $CR_3$;
wherein $R_3$ is H, $C_1$-$C_2$ alkyl, $C_1$-$C_2$ hydroxyalkyl, $C_1$-$C_2$ alkoxy or $C_1$-$C_2$ alkylamino; and
wherein $Y_1$ is H or methyl and $Y_2$ is

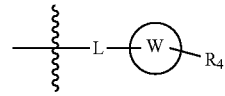

or $Y_2$ is H or methyl and $Y_1$ is

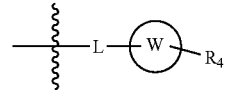

or both $Y_1$ and $Y_2$ are independently selected from H or methyl;
wherein L is selected from the group consisting of —O—, —NH—, —C(O)—, —$NH(CH_2)_m$—, $C_1$-$C_3$ alkoxy, $C_1$-$C_3$ alkylamino;
where m is 1 or 2; and
wherein

is aryl or heteroaryl; and
wherein $R_4$ is H, $NHC(O)CH_3$, substituted or unsubstituted aryl, substituted or unsubstituted heteroaryl.

In one embodiment, when A is methyl-substituted imidazole, Q is —$CF_3$, and D is

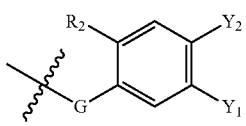

wherein G is —NR$_1$C(O)— where R$_1$ is H and Y$_2$ is methyl, Y$_1$ is not

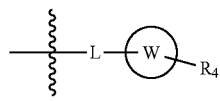

wherein L is —NH— and

is substituted pyrimidinyl where the substituent is 3-pyridinyl.

Typically,

is named relative to the position of attachment to L.

In another embodiment,

is not pyrazolopyridinyl, ortho-substituted pyridine, 4-pyrimidinyl or imidazole.

In one embodiment therefore, the invention provides a compound according to Formula (I):

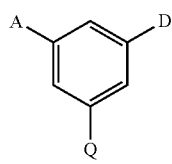

(I)

or a pharmaceutically acceptable salt, solvate, prodrug or polymorph thereof, wherein A is H or an optionally substituted 5-membered heteroaryl ring, wherein the substituent is a methyl group;

Q is selected from the group consisting of optionally substituted: C$_1$-C$_6$ alkyl, C$_2$-C$_6$ alkenyl, C$_1$-C$_6$ haloalkyl, C$_2$-C$_6$ haloalkenyl, C$_1$-C$_6$ alkyloxy, C$_2$-C$_6$ alkenyloxy, C$_1$-C$_6$ alkylamino, C$_2$-C$_6$ alkenylamino, C$_1$-C$_6$ alkylcarboxy, C$_2$-C$_6$ alkenylcarboxy, C$_1$-C$_6$ haloalkoxy, C$_2$-C$_6$ haloalkenyloxy, C$_1$-C$_6$ hydroxyalkyl, C$_2$-C$_6$ hydroxyalkenyl, C$_1$-C$_6$ alkylcarboxyamide, C$_2$-C$_6$ alkenylcarboxyamide, C$_1$-C$_6$ alkylsulfanyl, C$_2$-C$_6$ alkenylsulfanyl, C$_1$-C$_6$ alkylsulfenyl, C$_2$-C$_6$ alkenylsulfenyl, C$_1$-C$_6$ alkylsulfonyl, C$_2$-C$_6$ alkenylsulfonyl, C$_1$-C$_6$ alkylsulfonylamino, C$_2$-C$_6$ alkenylsulfonylamino, C$_4$-C$_7$ heterocyclyl, (C$_1$-C$_3$ alkyl)C$_3$-C$_7$ heterocyclyl, (C$_1$-C$_3$ alkyl)C$_3$-C$_7$ cycloalkyl and C$_3$-C$_7$ cycloalkyl;

wherein D is

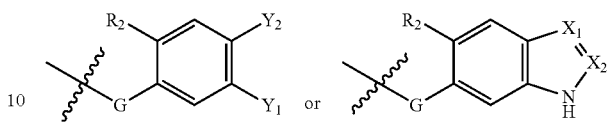

wherein G is selected from the group consisting of —NR$_1$C(O)—, —C(O)NR$_1$—, —S(O)$_2$NR$_1$—, and —NR$_1$S(O)$_2$—;

wherein R$_1$ is H or methyl and R$_2$ is H, or wherein G is —NR$_1$C(O)— and R$_1$ and R$_2$, together with the atoms between them, form an optionally substituted C$_3$-C$_6$ heterocyclic ring, thereby creating a bicyclic or tricyclic ring; and wherein X$_1$ is CR$_3$ and X$_2$ is N, or X$_1$ is N and X$_2$ is CR$_3$, or both X$_1$ and X$_2$ are CR$_3$;

wherein R$_3$ is H, C$_1$-C$_2$ alkyl, C$_1$-C$_2$ hydroxyalkyl, C$_1$-C$_2$ alkoxy or C$_1$-C$_2$ alkylamino; and wherein Y$_1$ is H or methyl and Y$_2$ is

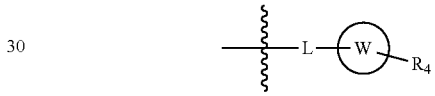

or Y$_2$ is H or methyl and Y$_1$ is

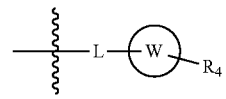

or both Y$_1$ and Y$_2$ are independently selected from H or methyl;

wherein L is selected from the group consisting of —O—, —NH—, —C(O)—, —NH(CH$_2$)$_m$—, C$_1$-C$_3$ alkoxy, C$_1$-C$_3$ alkylamino;

where m is 1 or 2; and wherein

is aryl or heteroaryl and wherein R$_4$ is H, NHC(O)CH$_3$, substituted or unsubstituted aryl, substituted or unsubstituted heteroaryl.

In another embodiment typically,

is not pyrazolopyridinyl, ortho-substituted pyridine, 4-pyrimidinyl or imidazole. Accordingly, when

is not ortho-substituted pyridine, 4-pyrimidinyl, $Y_1$ or $Y_2$ is not

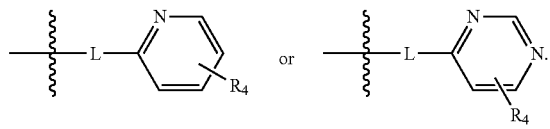

In one embodiment A is an optionally substituted 5-membered heteroaryl ring, wherein the substituent is a methyl group.

In one embodiment, A is hydrogen,

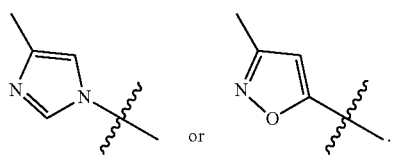

Preferably, A is

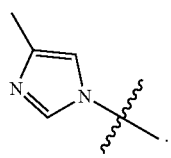

In one embodiment, Q is selected from the group consisting of optionally substituted: $C_1$-$C_6$ alkyl, $C_2$-$C_6$ alkenyl, $C_2$-$C_6$ haloalkenyl, $C_1$-$C_6$ alkyloxy, $C_2$-$C_6$ alkenyloxy, $C_1$-$C_6$ alkylamino, $C_2$-$C_6$ alkenylamino, $C_1$-$C_6$ alkylcarboxy, $C_2$-$C_6$ alkenylcarboxy, $C_1$-$C_6$ haloalkoxy, $C_2$-$C_6$ haloalkenyloxy, $C_1$-$C_6$ hydroxyalkyl, $C_2$-$C_6$ hydroxyalkenyl, $C_1$-$C_6$ alkylcarboxyamide, $C_2$-$C_6$ alkenylcarboxyamide, $C_1$-$C_6$ alkylsulfanyl, $C_2$-$C_6$ alkenylsulfanyl, $C_1$-$C_6$ alkylsulfenyl, $C_2$-$C_6$ alkenylsulfenyl, $C_1$-$C_6$ alkylsulfonyl, $C_2$-$C_6$ alkenylsulfonyl, $C_1$-$C_6$ alkylsulfonylamino, $C_2$-$C_6$ alkenylsulfonylamino, $C_4$-$C_7$ heterocyclyl, ($C_1$-$C_3$ alkyl)$C_3$-$C_7$ heterocyclyl, ($C_1$-$C_3$ alkyl)$C_3$-$C_7$ cycloalkyl and $C_3$-$C_7$ cycloalkyl.

In preferred embodiments, Q is optionally substituted $C_4$-$C_7$ heterocyclyl or ($C_1$-$C_3$ alkyl)$C_3$-$C_7$ heterocyclyl and more preferably, the $C_4$-$C_7$ heterocyclyl is a $C_6$ heterocyclyl group. Even more preferably, the $C_6$ heterocyclyl group of $C_4$-$C_7$ heterocyclyl or ($C_1$-$C_3$ alkyl)$C_3$-$C_7$ heterocyclyl is a substituted or unsubstituted morpholino, piperidinyl or piperazinyl group. More preferably, the $C_6$ heterocyclyl group of $C_4$-$C_7$ heterocyclyl or ($C_1$-$C_3$ alkyl)$C_3$-$C_7$ heterocyclyl is selected from the groups consisting of piperazinyl, morpholino, 4-methyl piperazinyl, 4-($C_3$ alkoxy)piperazinyl, ($C_1$-$C_3$ alkyl)(amino-substituted piperidinyl), ($C_1$-$C_3$ alkyl)(hydroxy-substituted piperidinyl) and optionally substituted ($C_1$-$C_3$ alkyl)piperidinyl preferably where the piperidinyl group is mono or bis-substituted with substituents independently selected from the group consisting of methyl, amino and hydroxyl.

In one particularly preferred embodiment, Q is:

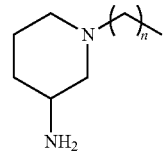

where n is 1-2. Preferably n is 1.

Where substituents on any of the heterocyclic rings are chiral, the compound may be racemic, predominantly one enantiomer, or completely one enantiomer.

In a preferred embodiment, G is —$NR_1C(O)$—. More preferably G is —$NR_1C(O)$— and $R_1$ is H.

In another preferred embodiment, $Y_2$ is H or methyl and $Y_1$ is

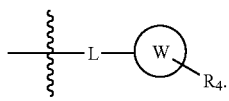

In one embodiment,

is aryl and $R_4$ is H or optionally substituted aryl, preferably halo-substituted aryl.

In another embodiment,

is heteroaryl wherein the heteroaryl group is 2-pyrimidinyl, wherein 2-pyrimidinyl refers to the position of attachment to L.

In yet another embodiment,

is heteroaryl wherein the heteroaryl group is a bicyclic heteroaryl group and $R_4$ is H, preferably isoquinolinyl, In one aspect, the invention provides a compound of formula II:

(II)

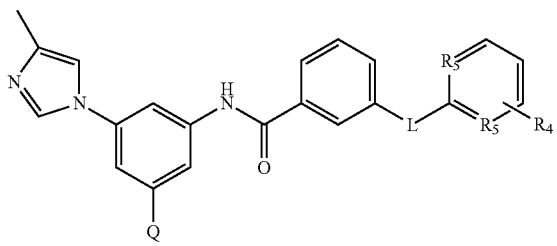

or a pharmaceutically acceptable salt, solvate, prodrug or polymorph thereof,
wherein
L, $R_4$ and Q are as defined above; and
each $R_5$ is independently CH or N.

In one aspect, the invention provides a compound of formula III:

(III)

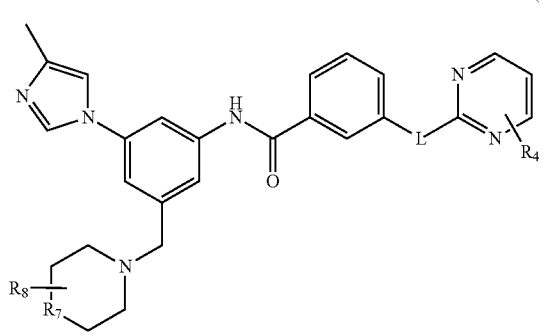

or a pharmaceutically acceptable salt, solvate, prodrug or polymorph thereof,
wherein
L and $R_4$ are as defined above;
$R_7$ is O, $CHR_6$ or $NR_6$; wherein $R_6$ is independently selected from the group consisting of H, —COOH, —CONH$_2$, —NH$_2$, $C_1$-$C_4$ alkyl, $C_1$-$C_4$ alkylamino, $C_1$-$C_4$ alkoxy and —OH; and
$R_8$ is independently selected from the group consisting of H, —COOH, —CONH$_2$, —NH$_2$, $C_1$-$C_4$ alkyl, $C_1$-$C_4$ alkylamino, $C_1$-$C_4$ alkoxy and —OH.
In a preferred embodiment, $R_7$ is $CHR_6$ or $NR_6$.
Preferably $R_8$ is positioned as shown:

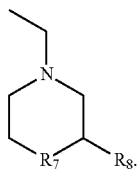

In one embodiment, $R_7$ is $NR_6$ wherein $R_6$ is H or methyl, preferably methyl.
In another embodiment, $R_7$ is $CHR_6$ and $R_6$ is —OH or —NH$_2$.
Preferably, $R_8$ is H, —NH$_2$ or methyl.
In one preferred embodiment, $R_7$ is $CHR_6$ and $R_6$ is H, and $R_8$ is —NH$_2$.

In one aspect, the invention provides a compound of formula IV:

(IV)

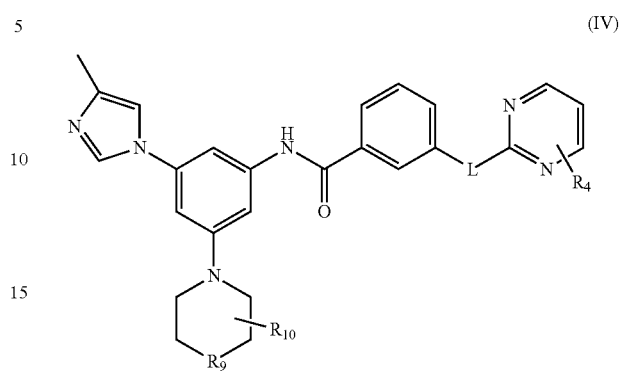

or a pharmaceutically acceptable salt, solvate, prodrug or polymorph thereof,
wherein
L and $R_4$ are as defined above;
$R_9$ is O, $CHR_{11}$ or $NR_{11}$; wherein $R_{11}$ is independently selected from the group consisting of H, —COOH, —CONH$_2$, —NH$_2$, $C_1$-$C_4$ alkyl, $C_1$-$C_4$ alkylamino, $C_1$-$C_4$ alkoxy and —OH; and
$R_{10}$ is independently selected from the group consisting of H, —COOH, —CONH$_2$, —NH$_2$, $C_1$-$C_4$ alkyl, $C_1$-$C_4$ alkylamino, $C_1$-$C_4$ alkoxy and —OH.
Preferably $R_{10}$ is positioned as shown:

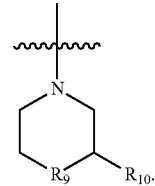

In one preferred embodiment, $R_9$ is $CHR_{11}$ or $NR_{11}$; In another preferred embodiment, $R_9$ is $NR_{11}$ wherein $R_{11}$ is H or methyl.
Preferably $R_{10}$ is H, —NH$_2$ or methyl.
In one particularly preferred embodiment, $R_9$ is $CHR_{11}$ and $R_{11}$ is H, and $R_{10}$ is —NH$_2$.
In particular embodiments of the invention, the compound of formula I has a structure selected from any one of the following:

Example 1

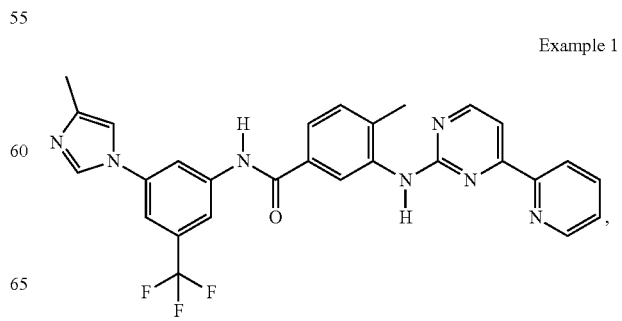

-continued
Example 2
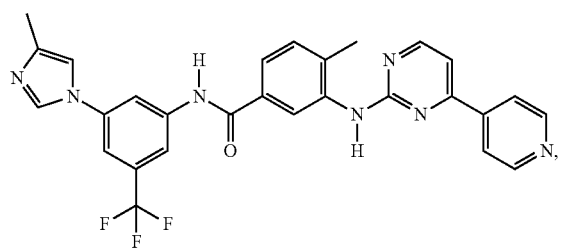
Example 3
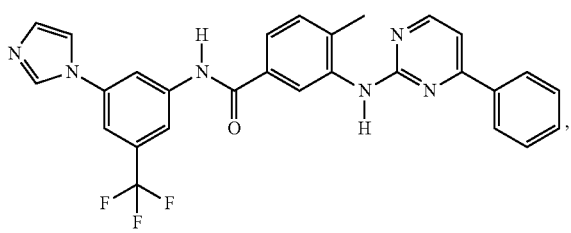
Example 4
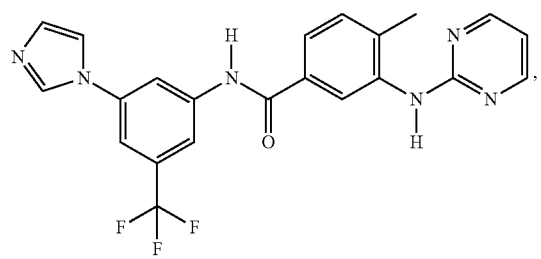
Example 5
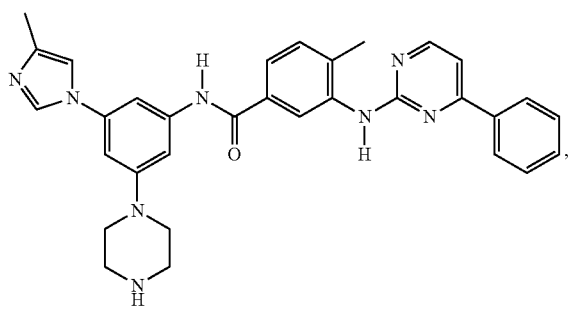
Example 6
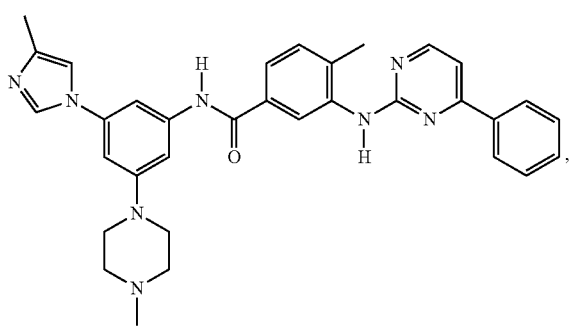
-continued
Example 7
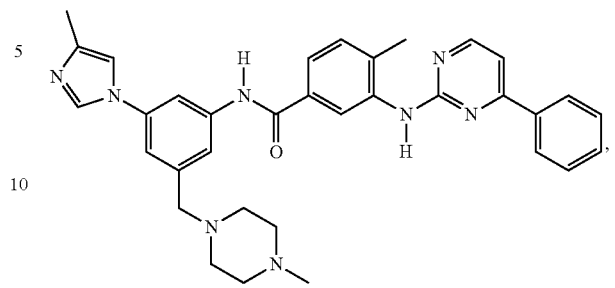
Example 8
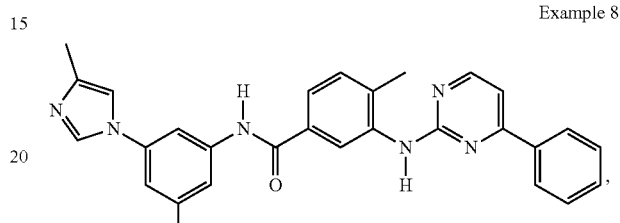
Example 9
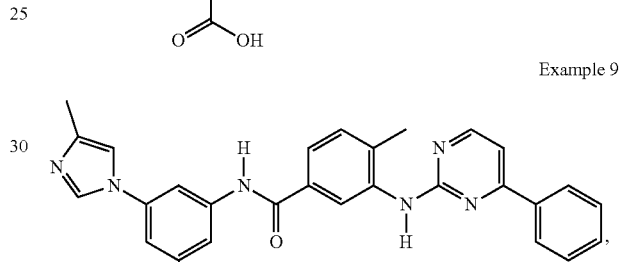
Example 10
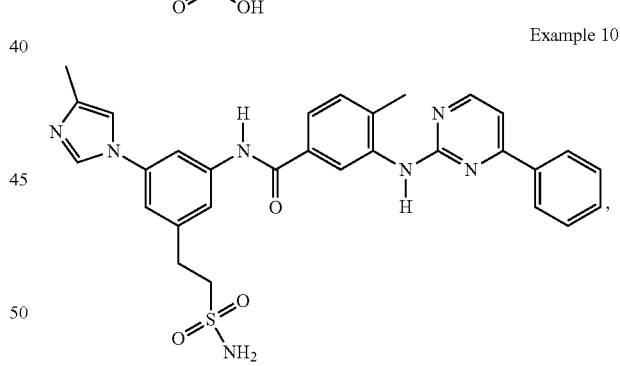
Example 11
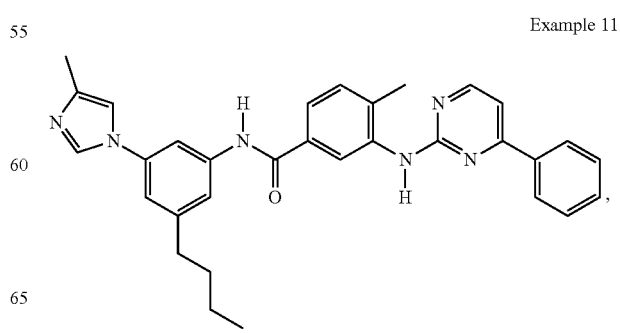

Example 12
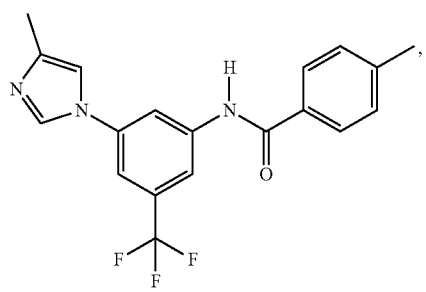
Example 13
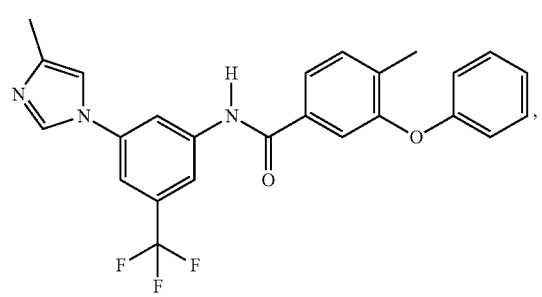
Example 14
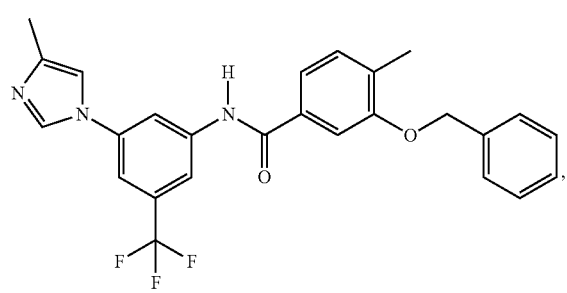
Example 15
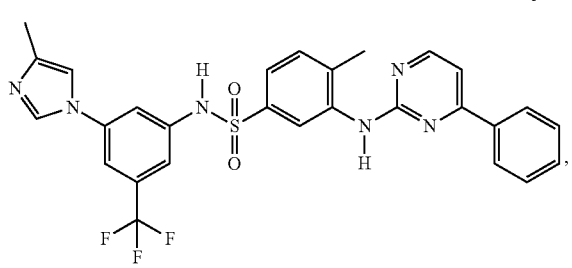
Example 16
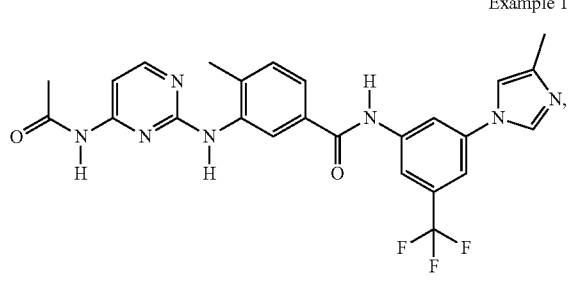
Example 17
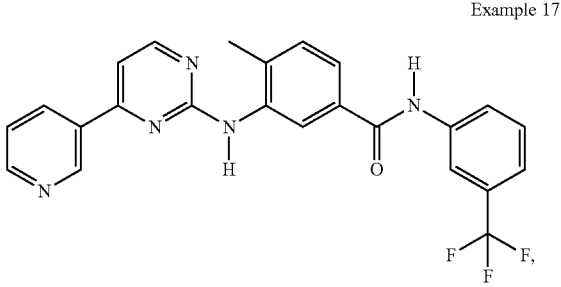 [SMILES: Cc1ccc(C(=O)Nc2cccc(C(F)(F)F)c2)cc1Nc1nccc(-c2cccnc2)n1]
Example 18
Example 19
Example 20
Example 21
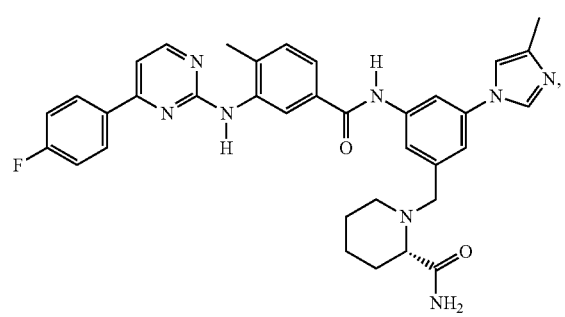

Example 22
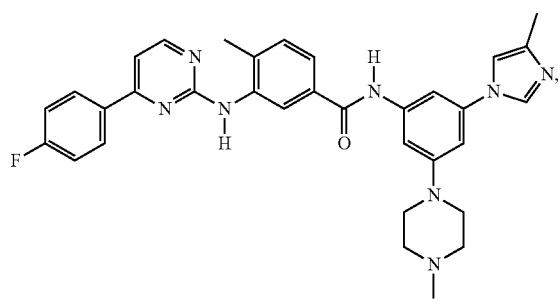
Example 23
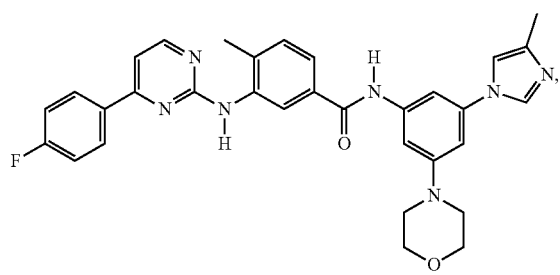
Example 24
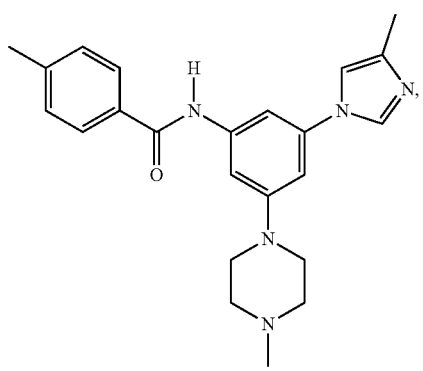
Example 25
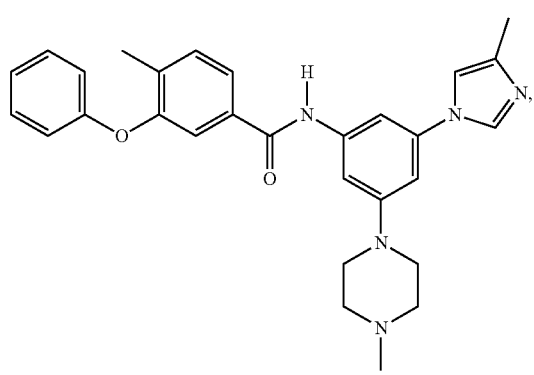
Example 26
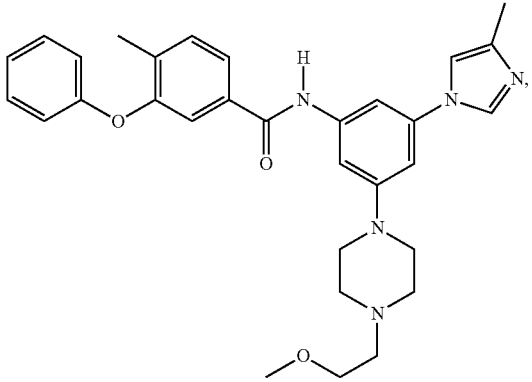
Example 27
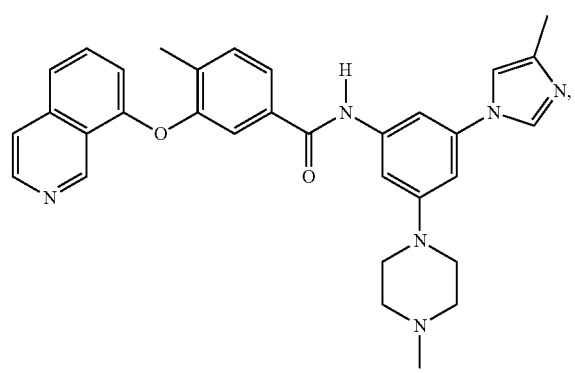
Example 28
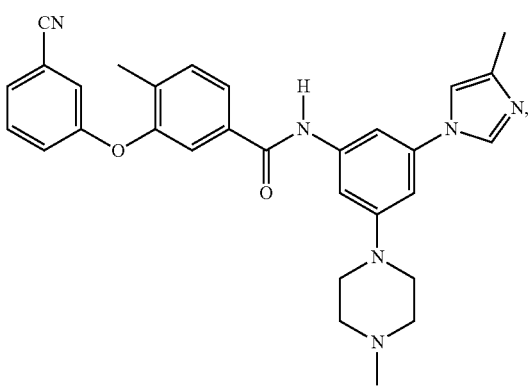
Example 29
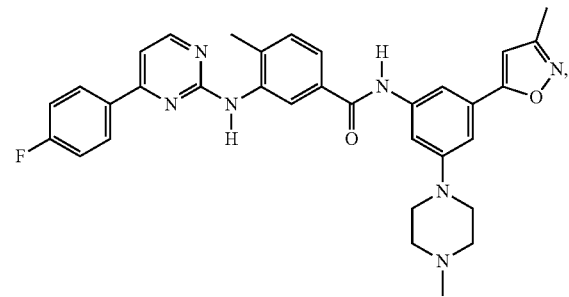

Example 30
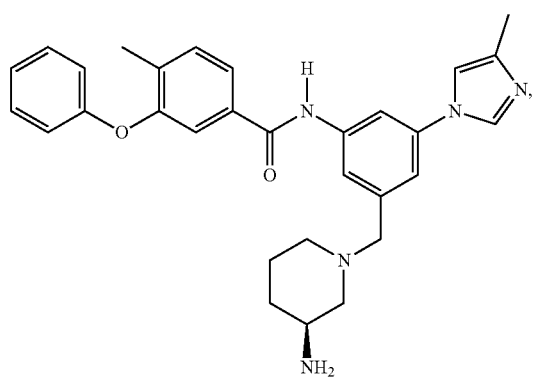
Example 31
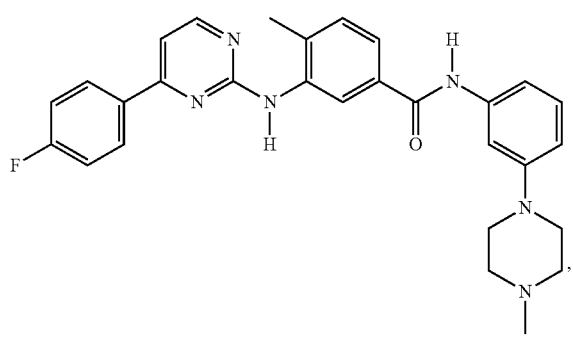
Example 32
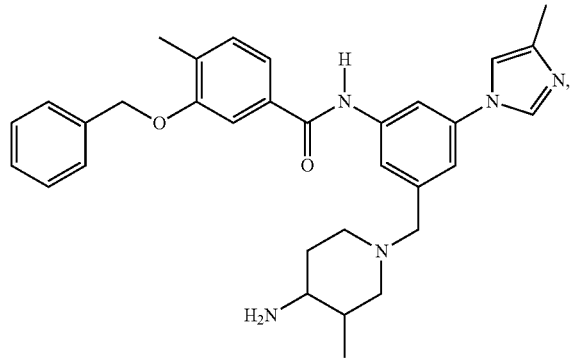
Example 33
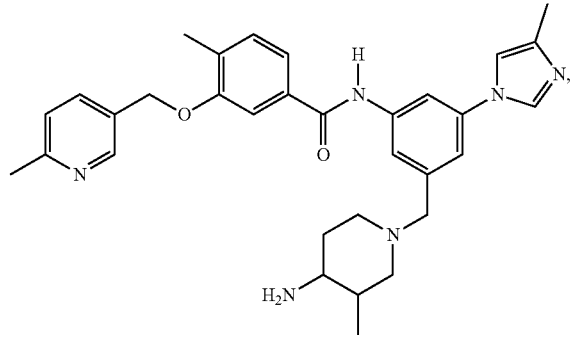
Example 34
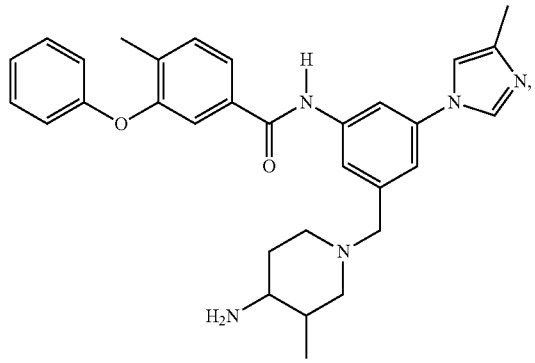
Example 35
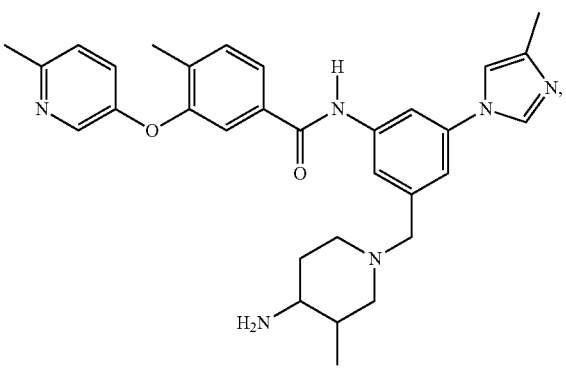
Example 36
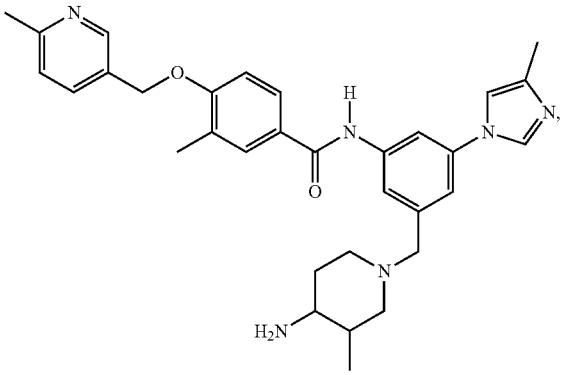
Example 37
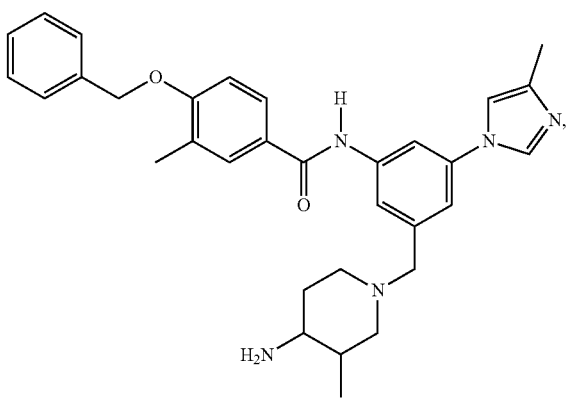

-continued
Example 38
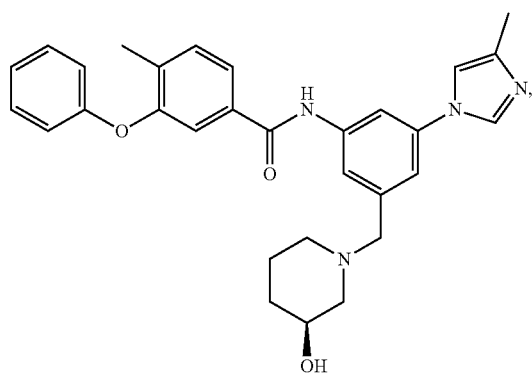
Example 39
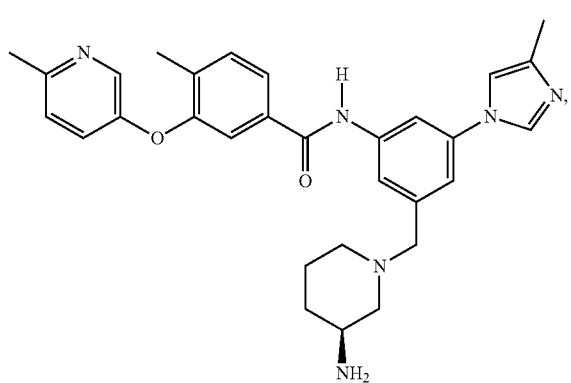
Example 40
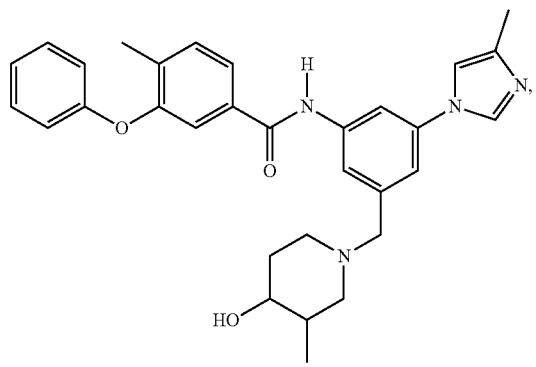
Example 41
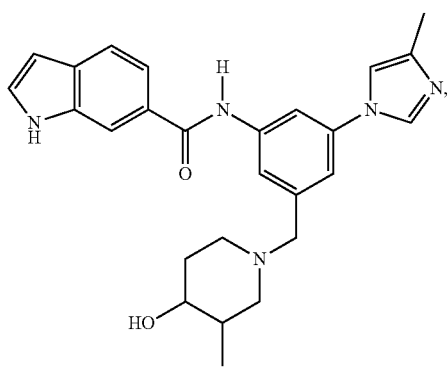
-continued
Example 42
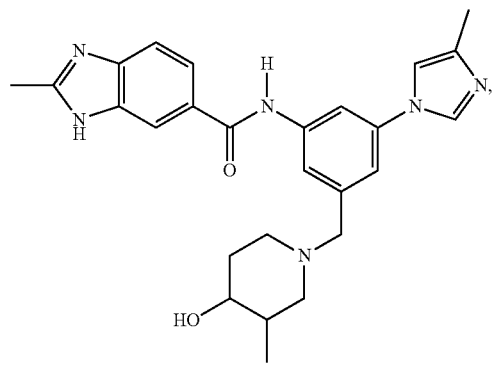
Example 43
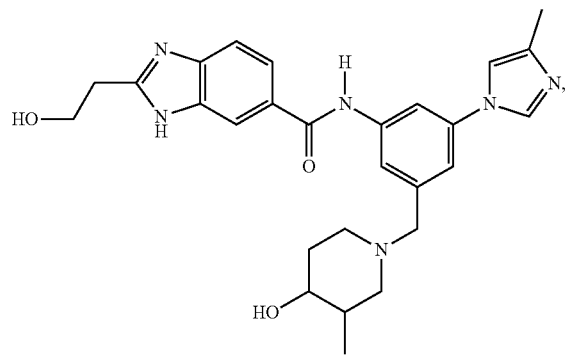
Example 44
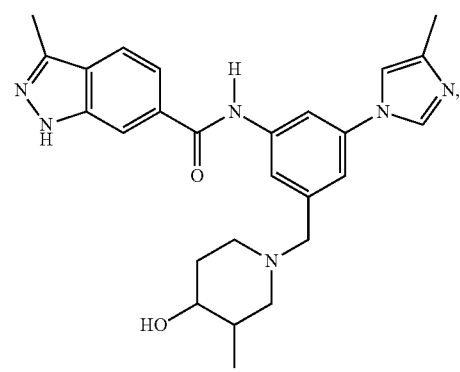
Example 45
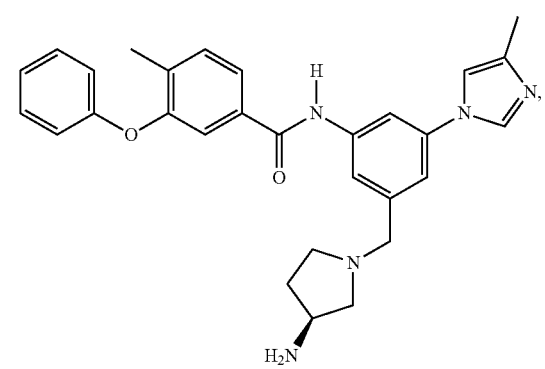

Example 46
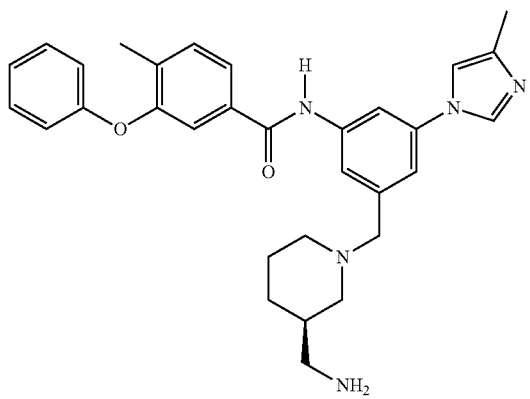
Example 47
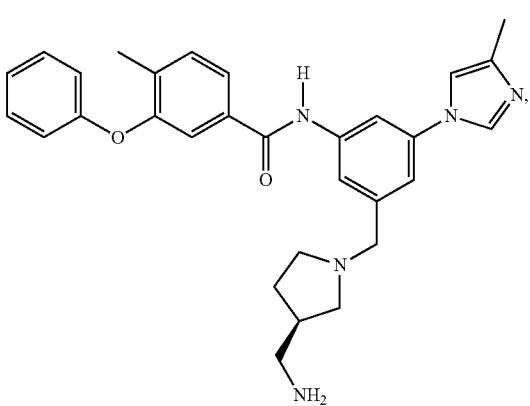
Example 48
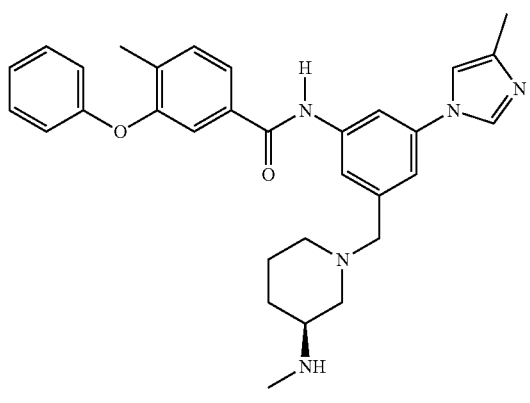
Example 49
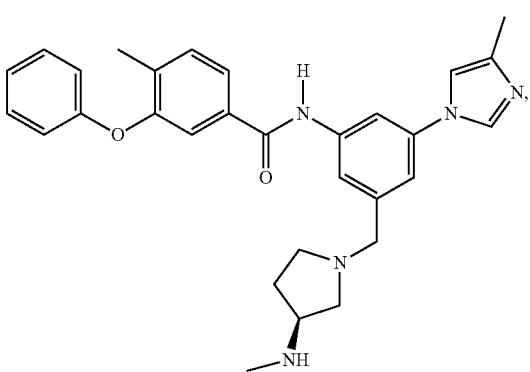
Example 50
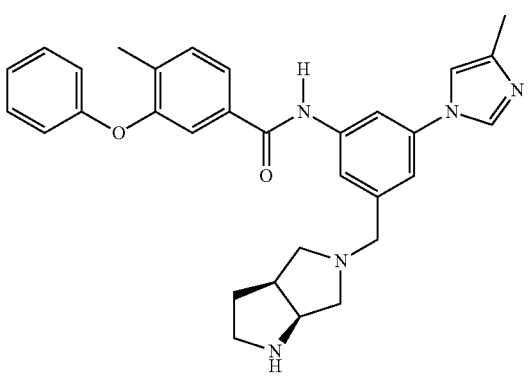
Example 51
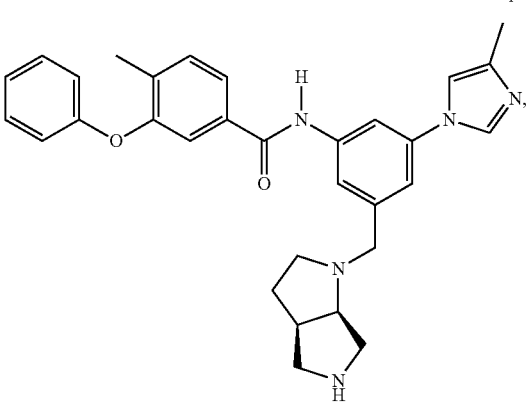
Example 52
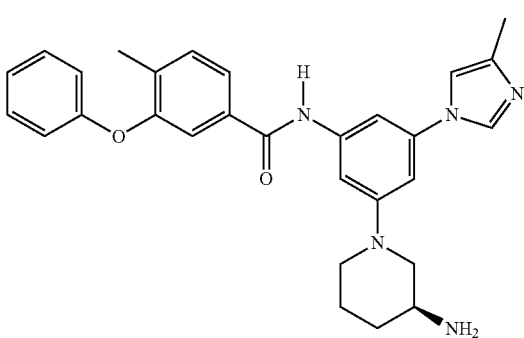
Example 53
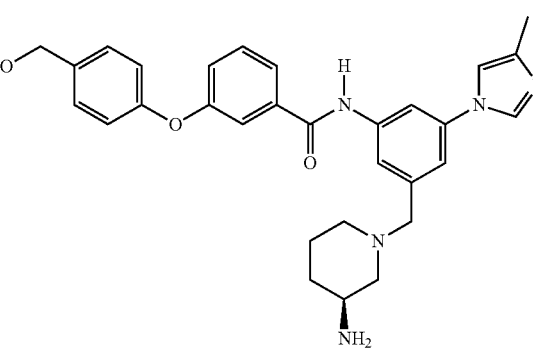

-continued
Example 54
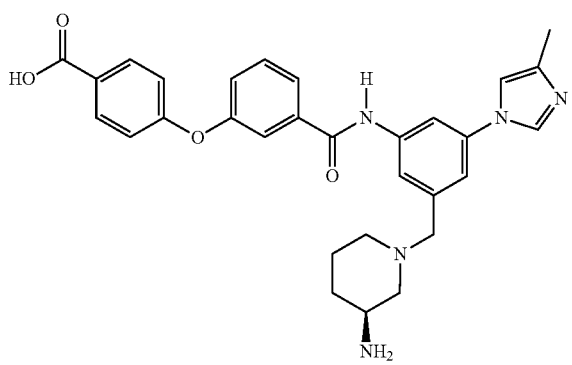
Example 55
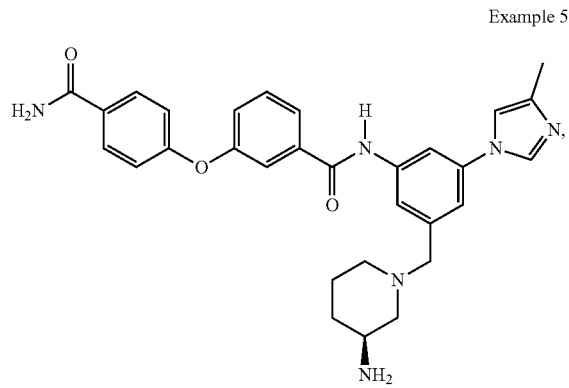
Example 56
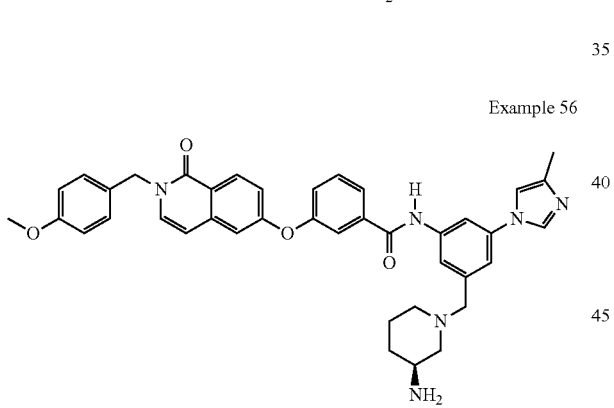
Example 57
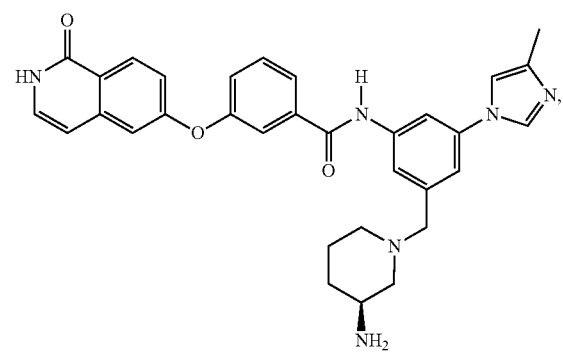
-continued
Example 58
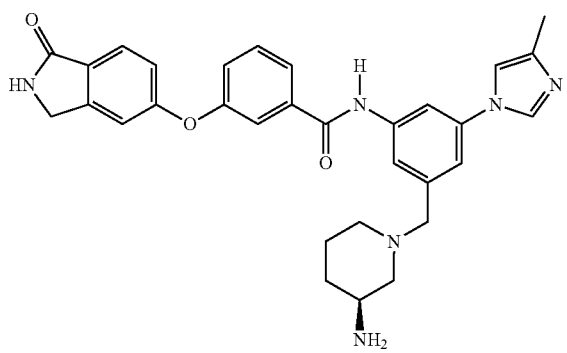
Example 59
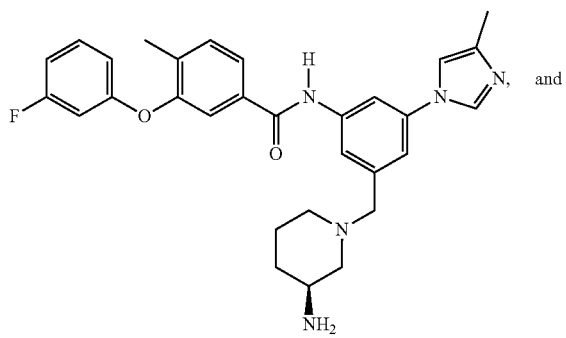
, and
Example 60
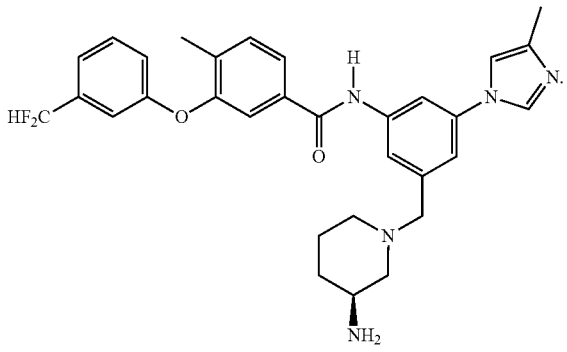
or a salt, solvate, prodrug or polymorph thereof.
In particular embodiments of the invention, the compound of formula I has a structure selected from any one of the following:
Example 5
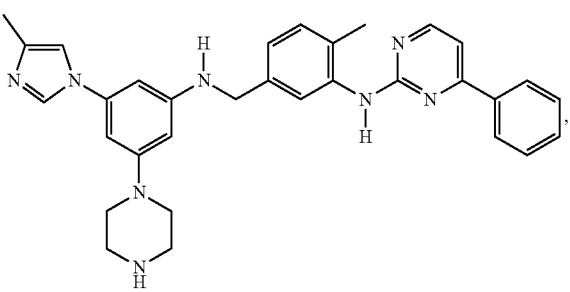
, Example 6
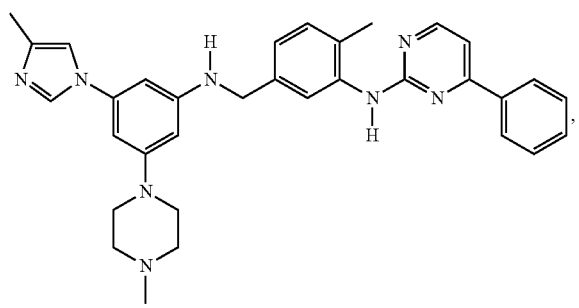
Example 7
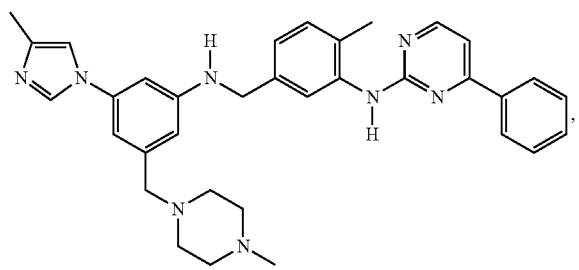
Example 8
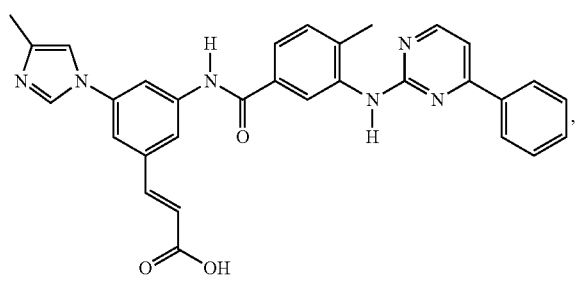
Example 9
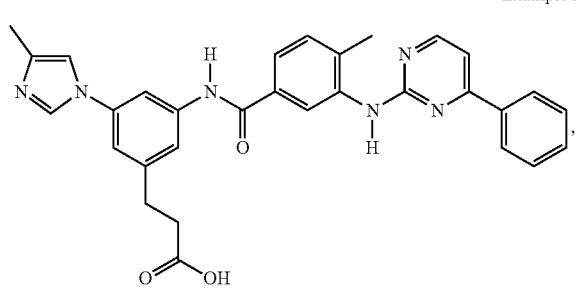
Example 10
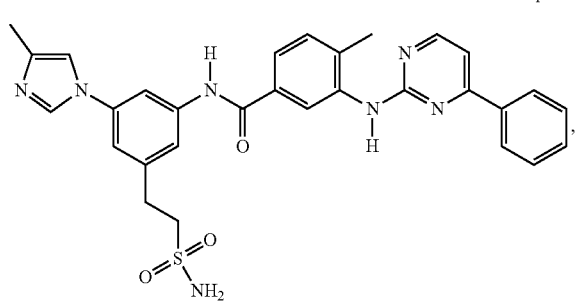
Example 11
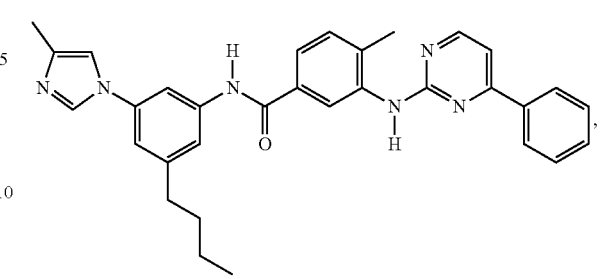
Example 19
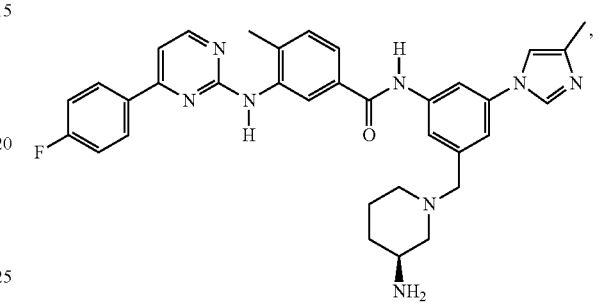
Example 20
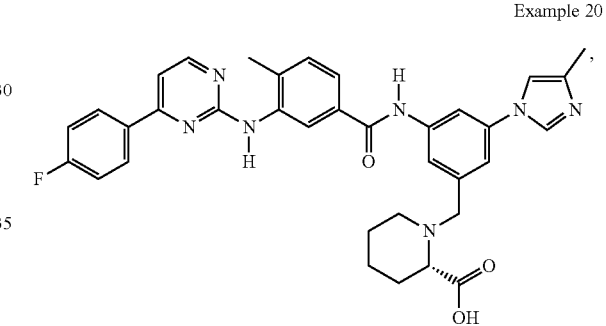
Example 21
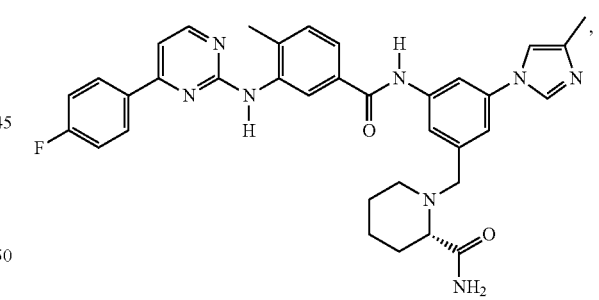
Example 22
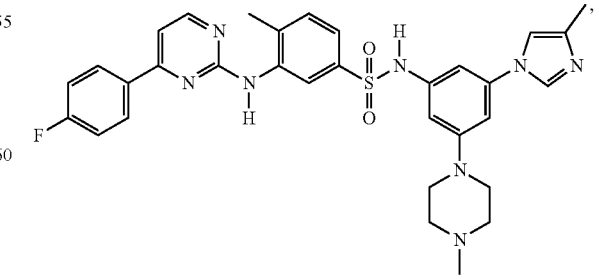

Example 23
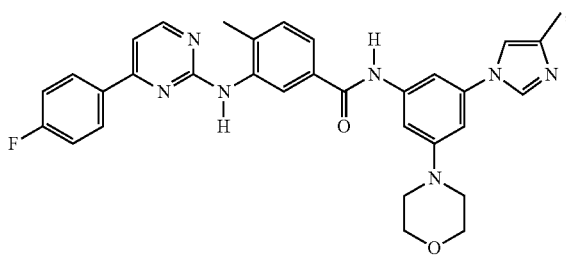
Example 27
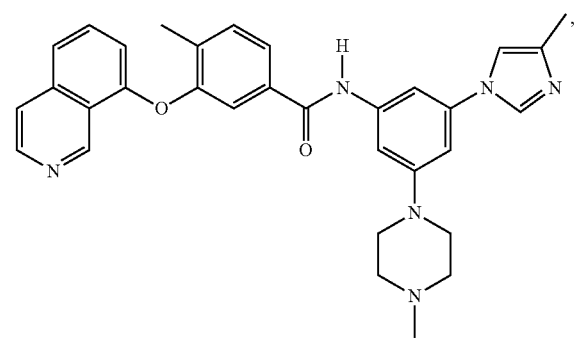
Example 24
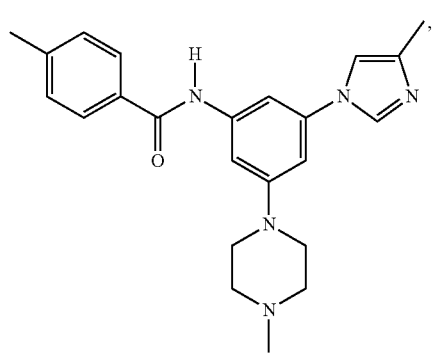
Example 28
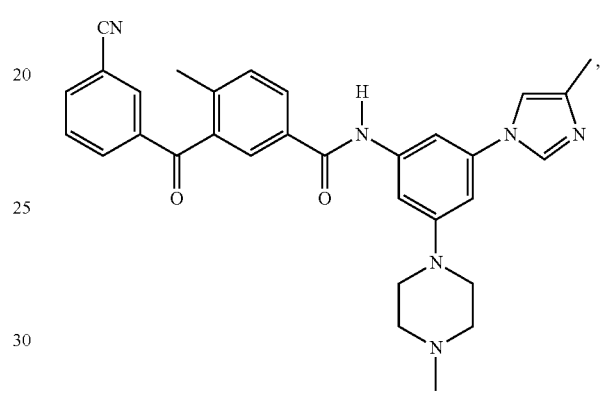
Example 25
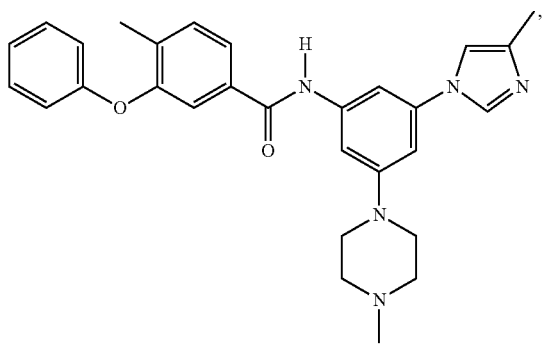
Example 29
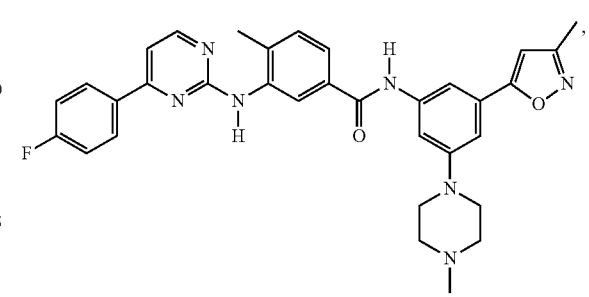
Example 26
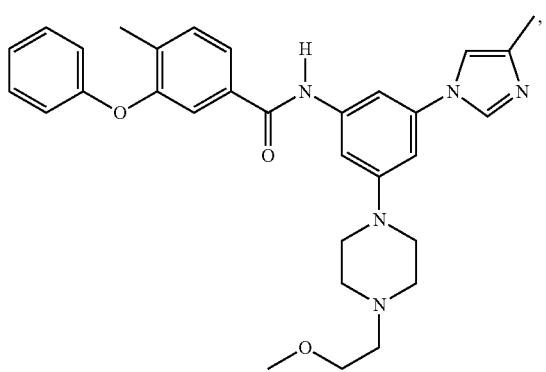
Example 30
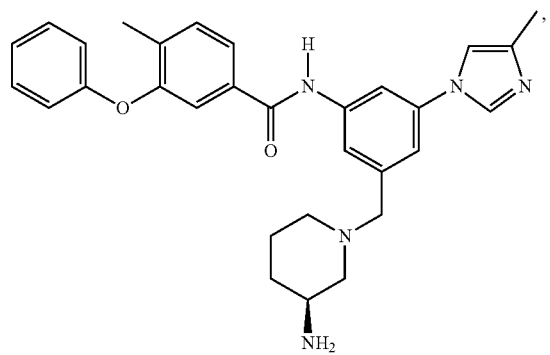

Example 32
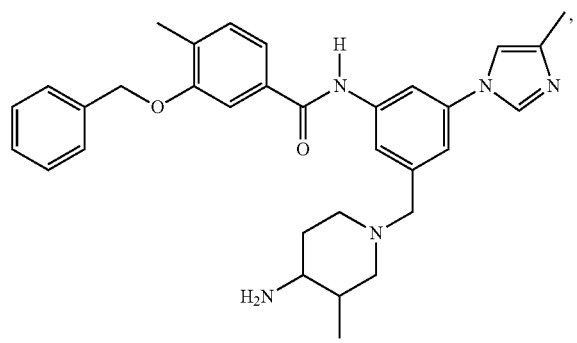
Example 33
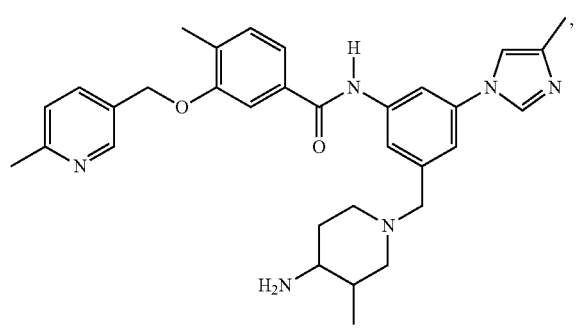
Example 34
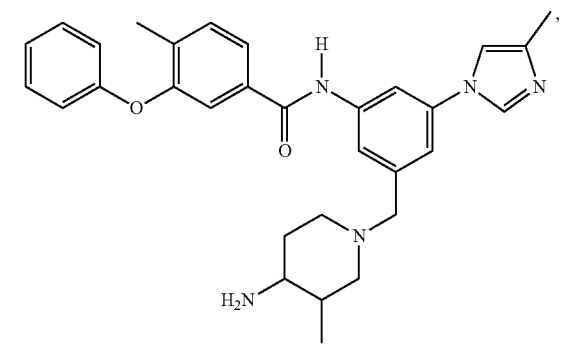
Example 35
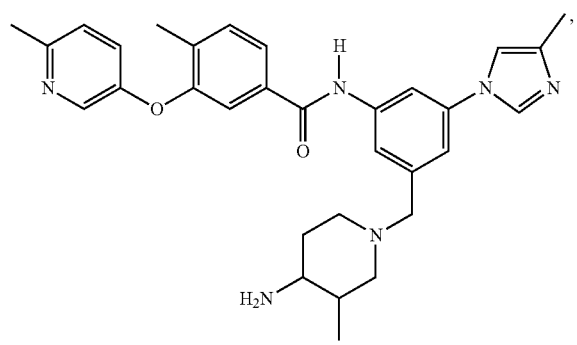
Example 36
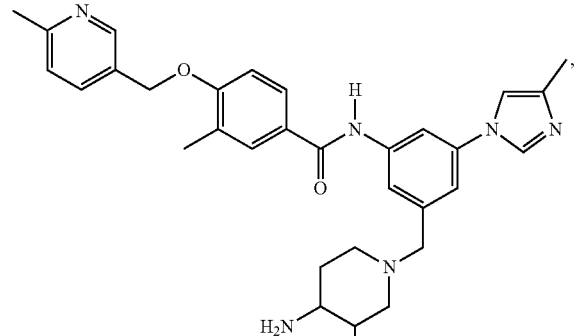
Example 37
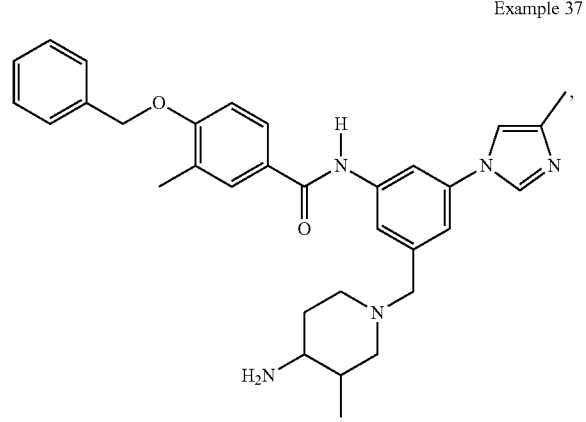
Example 38
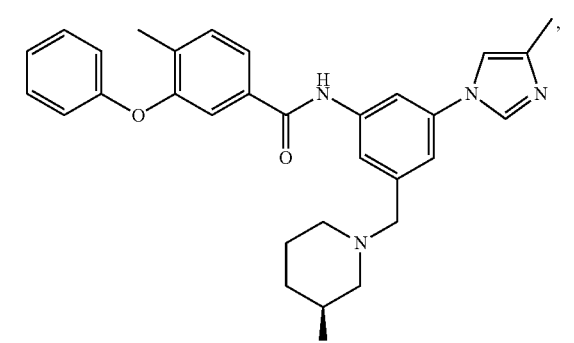
Example 39
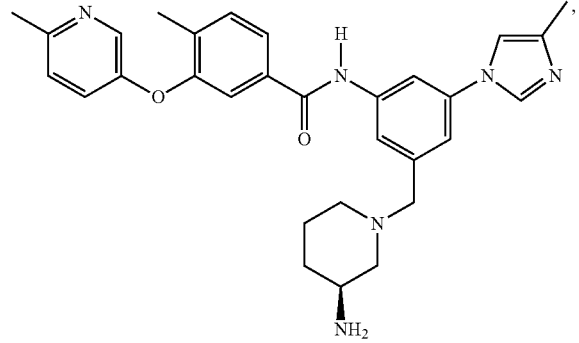

Example 40
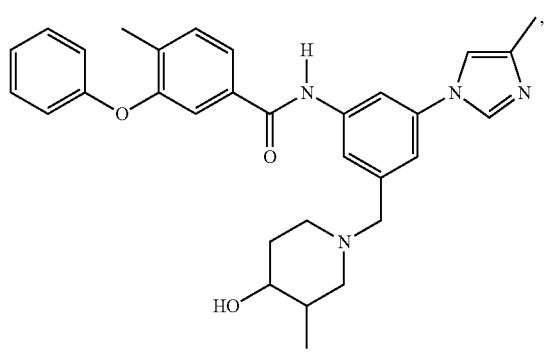
Example 41
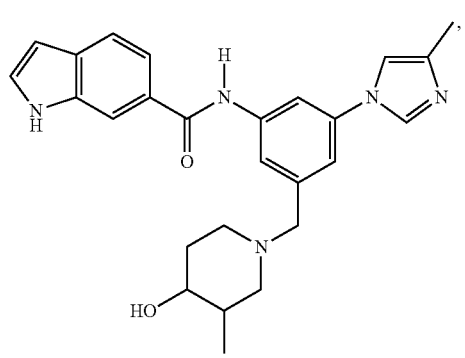
Example 42
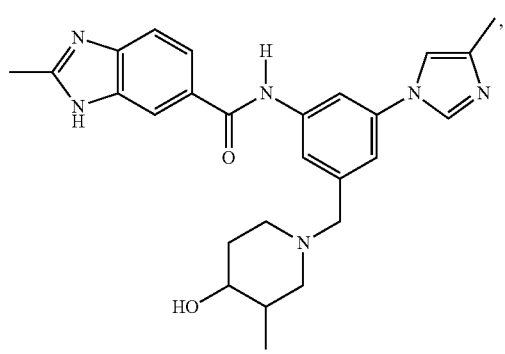
Example 43
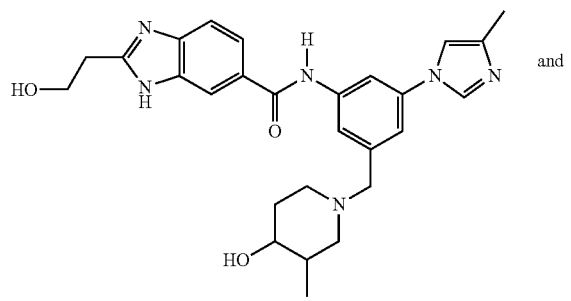
and
Example 44
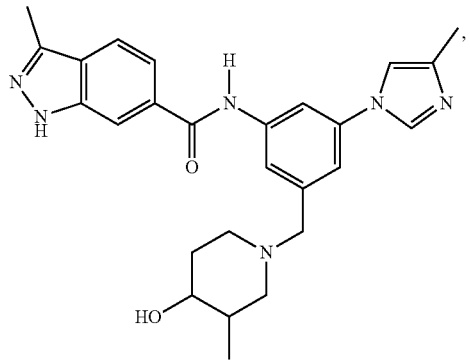
Example 45
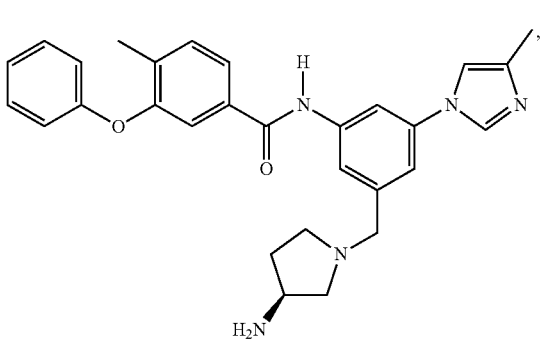
Example 46
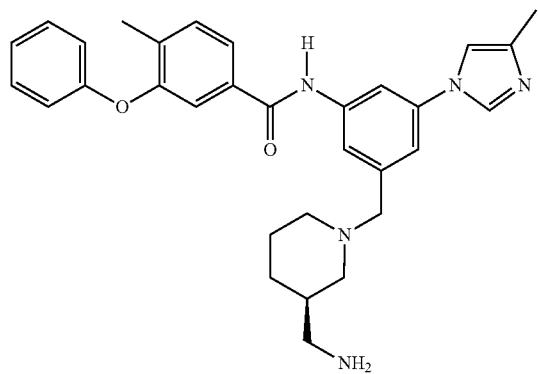
Example 47
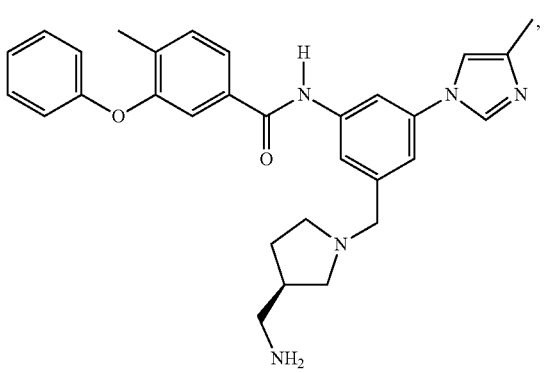

-continued
Example 48
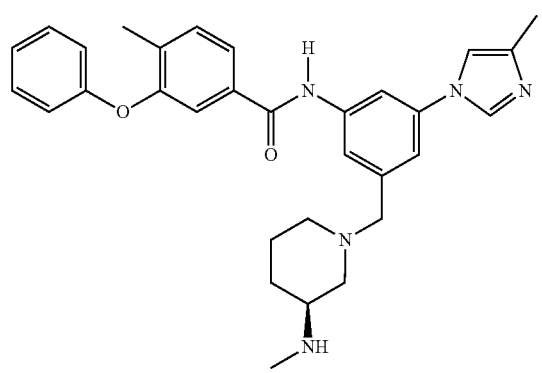
Example 49
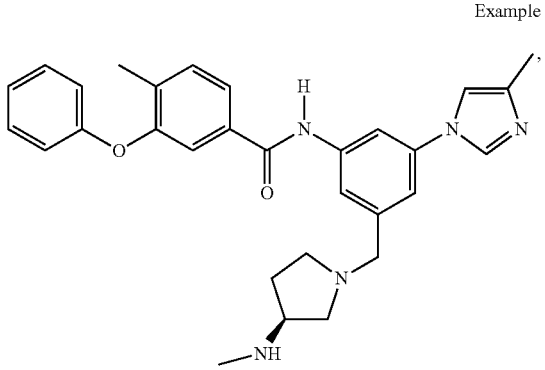
Example 50
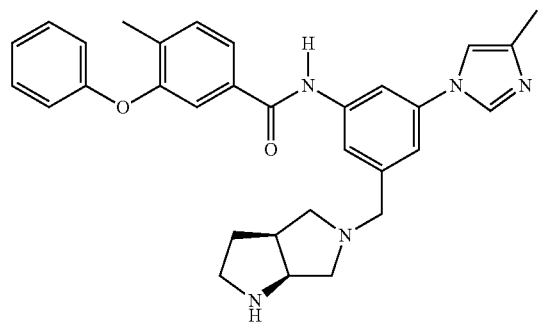
Example 51
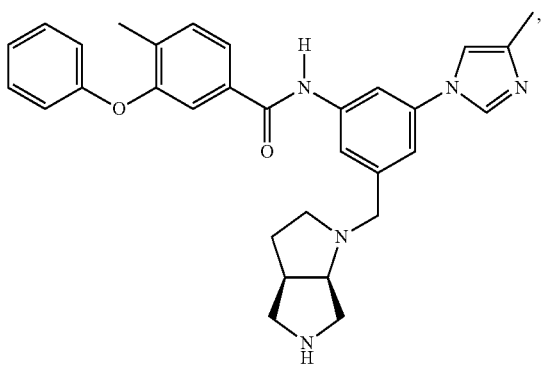
Example 52
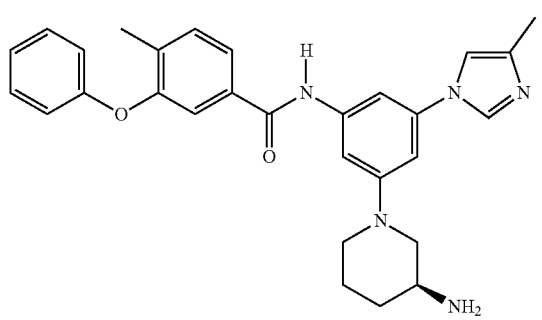
Example 53
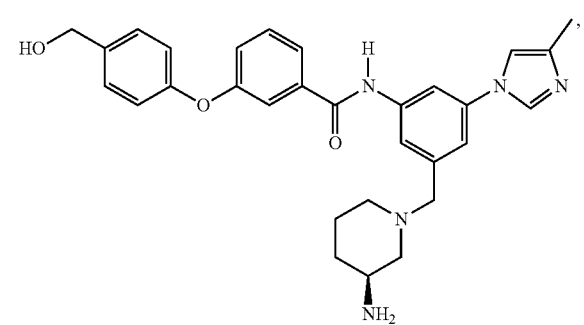
Example 54
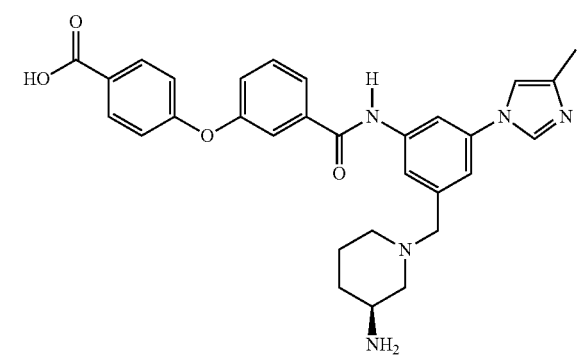
Example 55
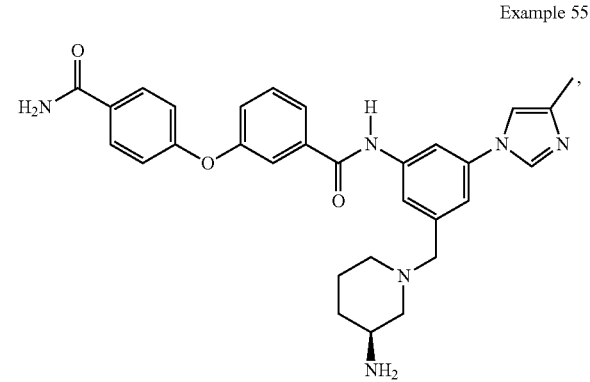

Example 56
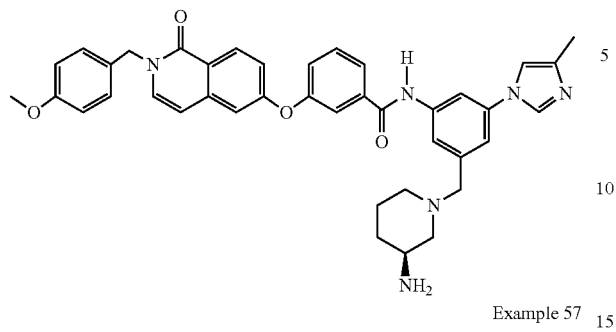
Example 59
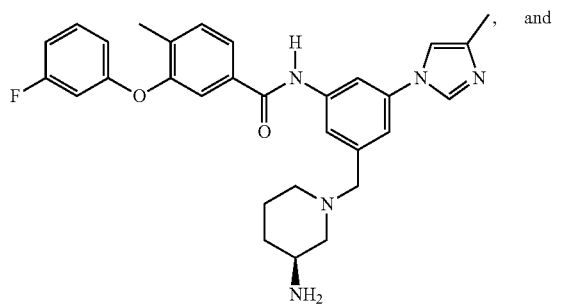
Example 57
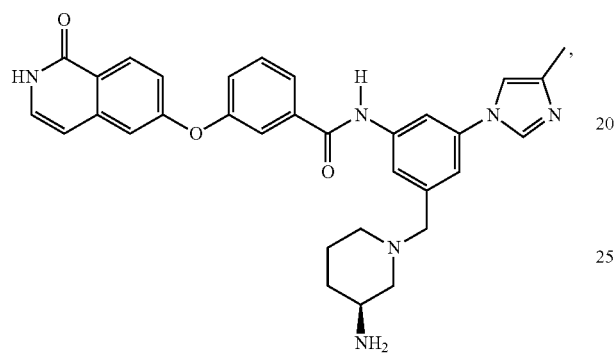
Example 60
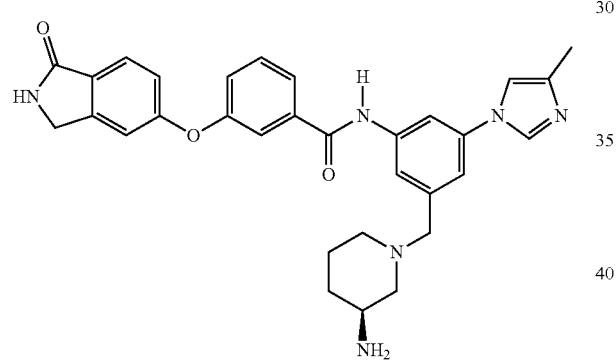
Example 58
or a salt, solvate, prodrug or polymorph thereof.
Preferably, the compound has a structure selected from any one of the following:
Example 5
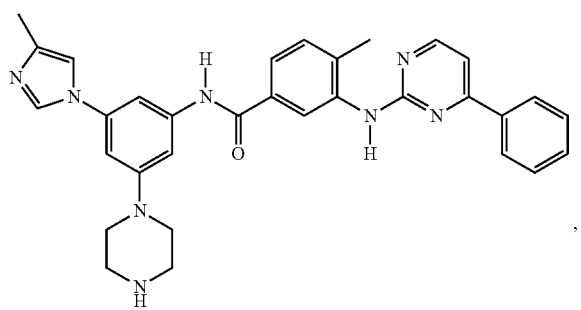
Example 6
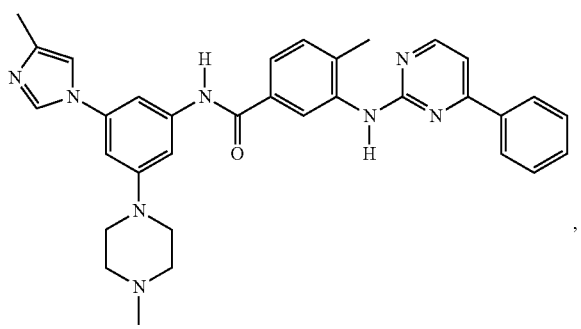

-continued
Example 7
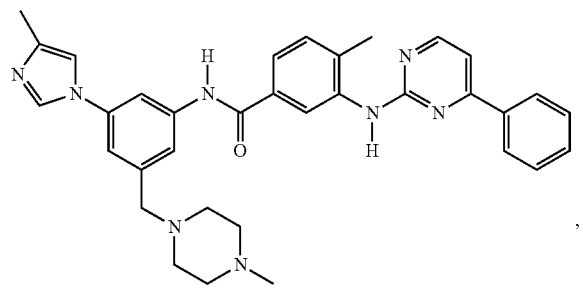
Example 19
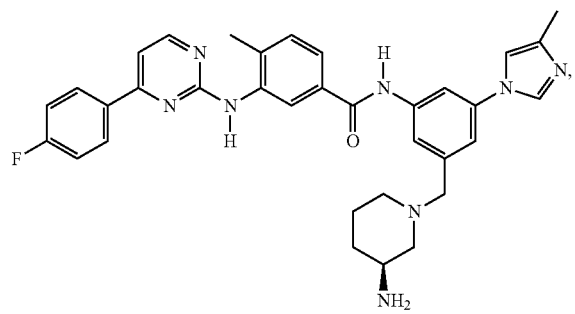
Example 27
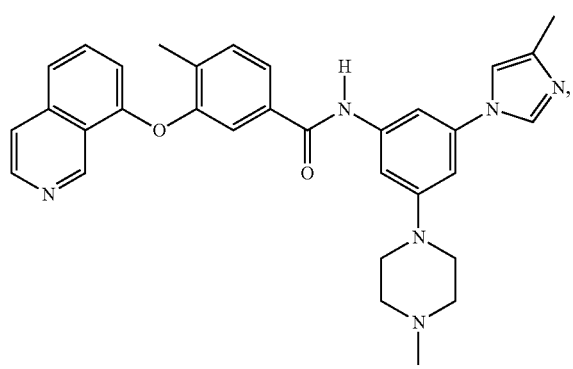
Example 30
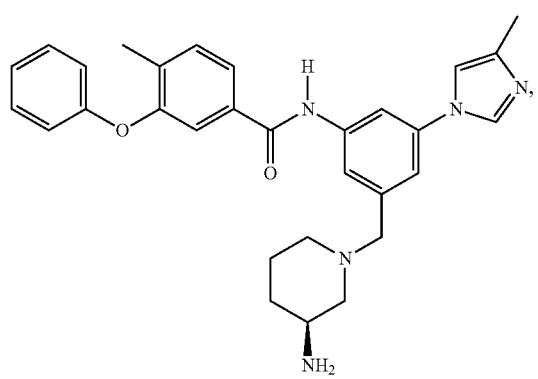
Example 45
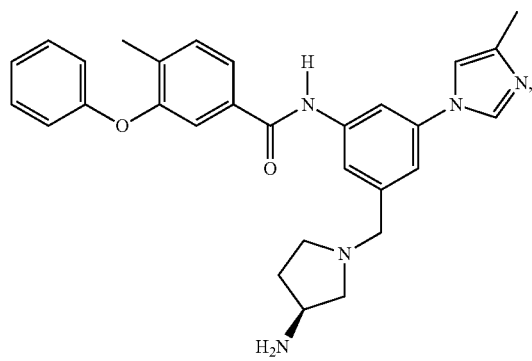
Example 46
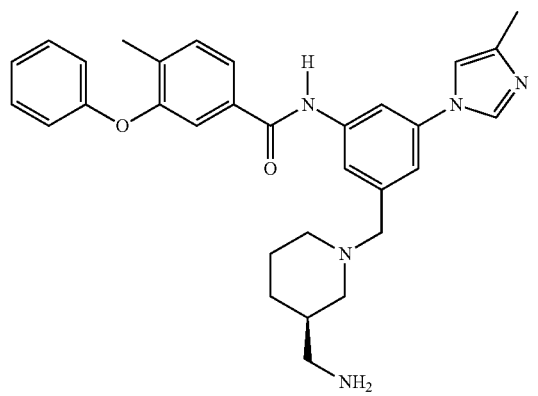
Example 47
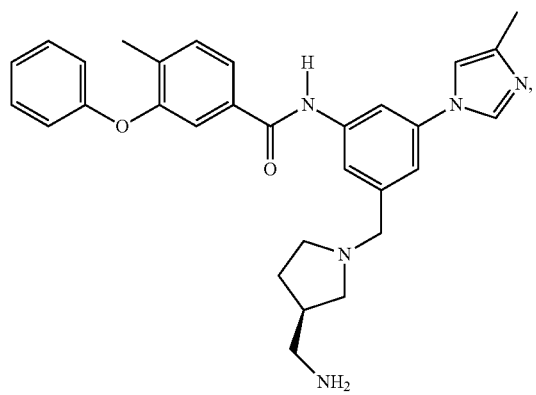
Example 48
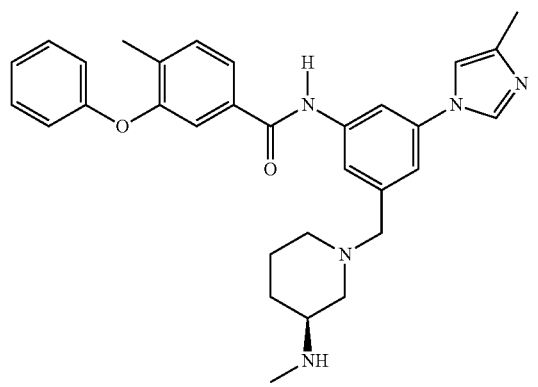

-continued
Example 49
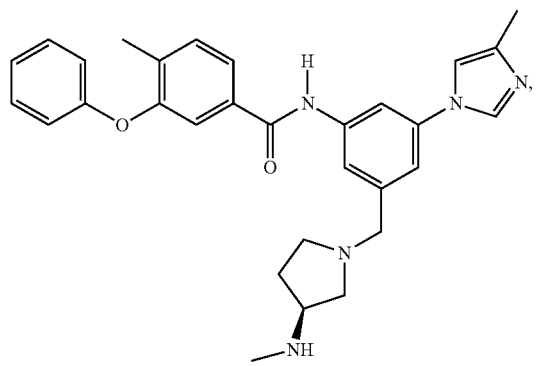
Example 50
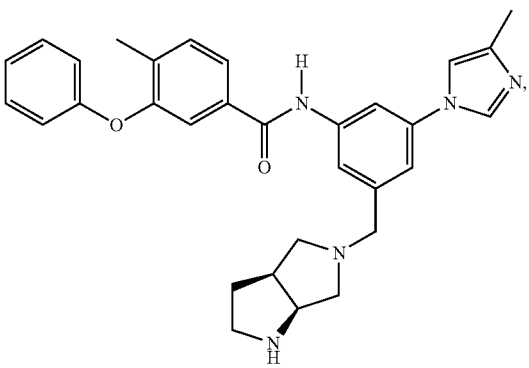
Example 51
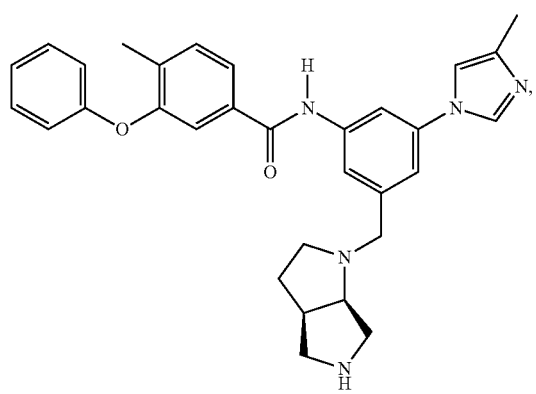
Example 52
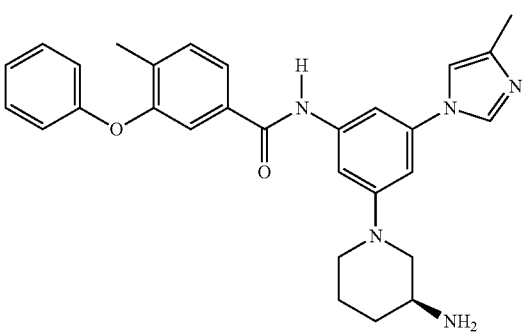
Example 53
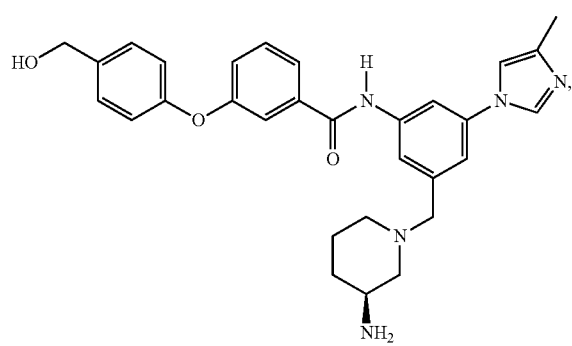
Example 54
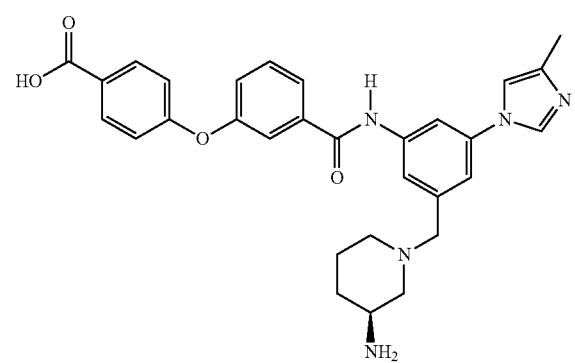
Example 55
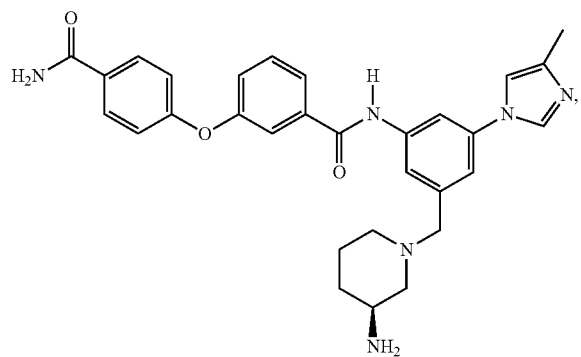

Example 56
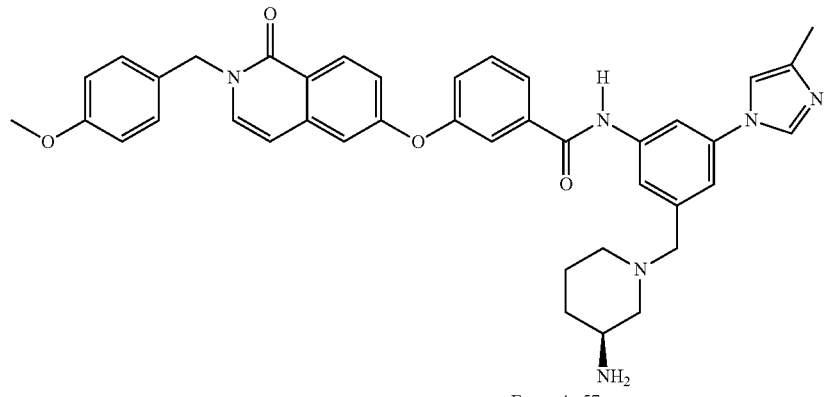
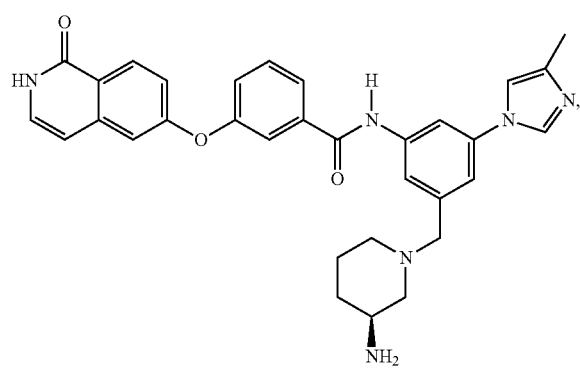
Example 57
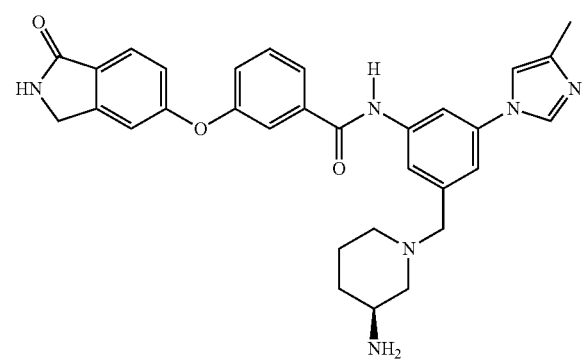
Example 57
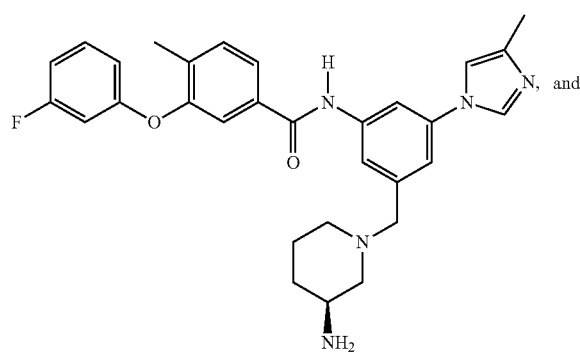
Example 59
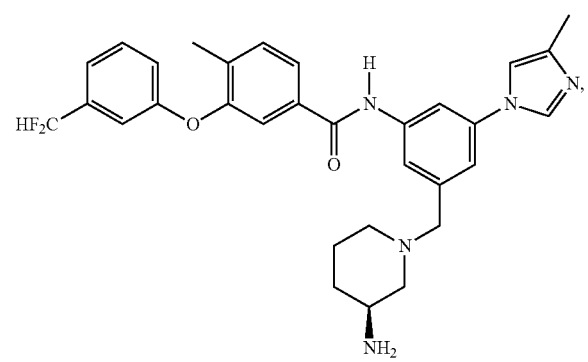
Example 60
or a salt, solvate, prodrug or polymorph thereof.
Preferably, the compound has a structure selected from any one of the following:
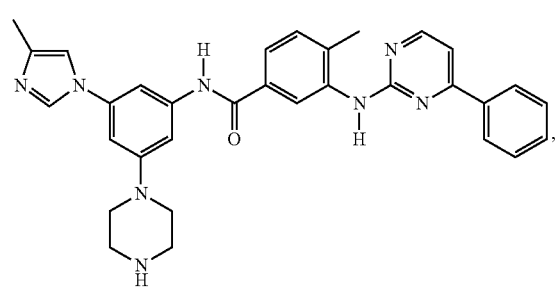
Example 5
-continued
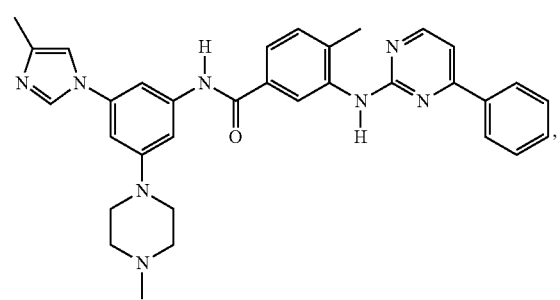
Example 6

Example 7
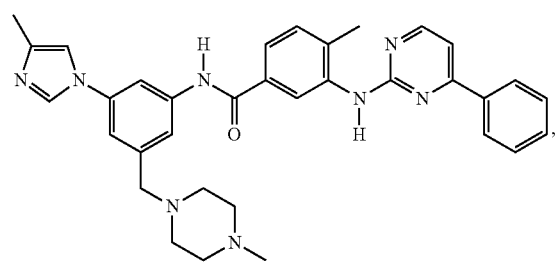
Example 19
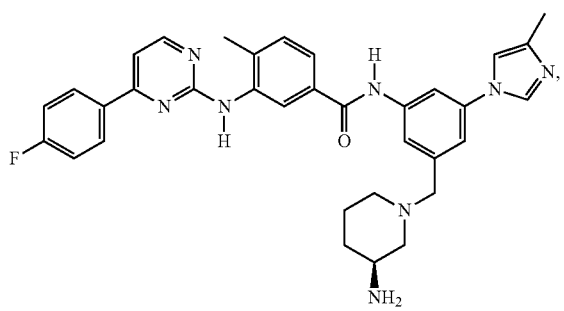
Example 27
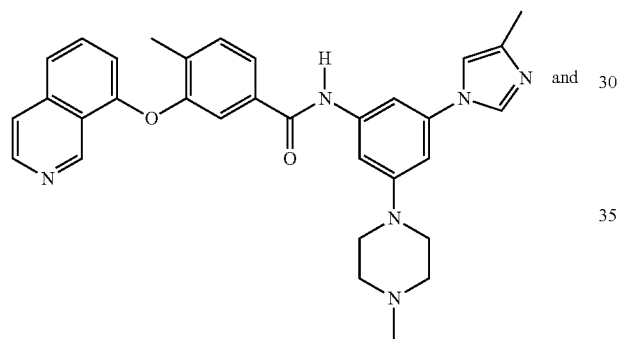
Example 30
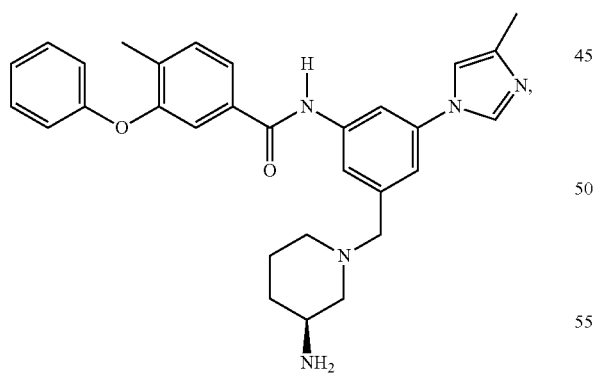
or a salt, solvate, prodrug or polymorph thereof.
Preferably, the compound has a structure selected from any one of the following:
Example 30
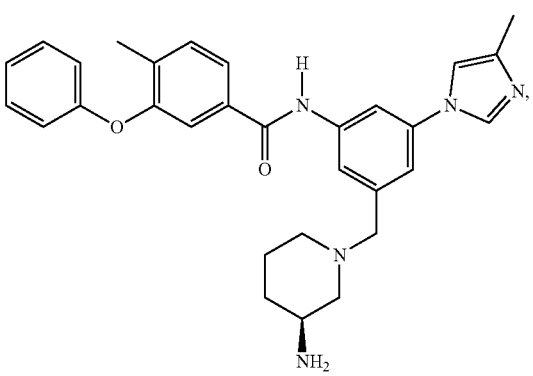
Example 45
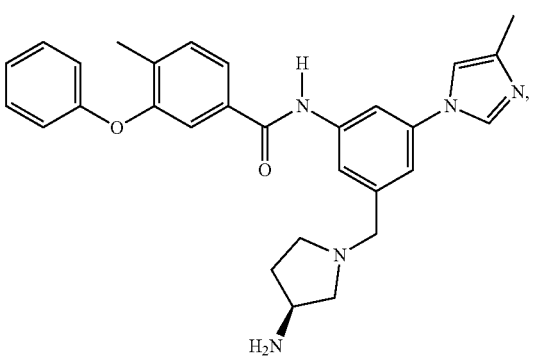
Example 46
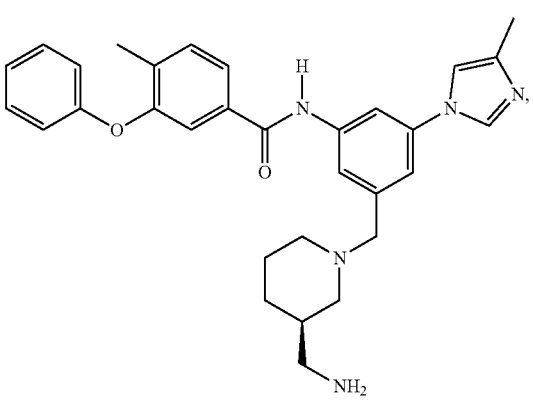
Example 47
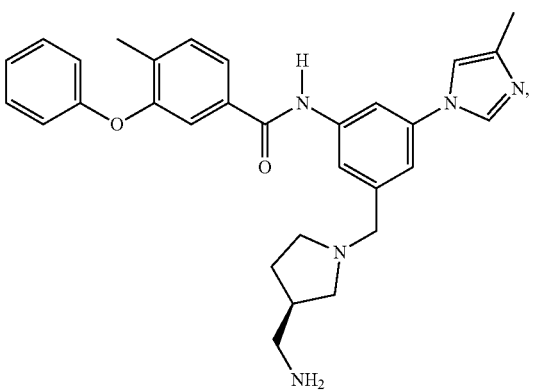

Example 48
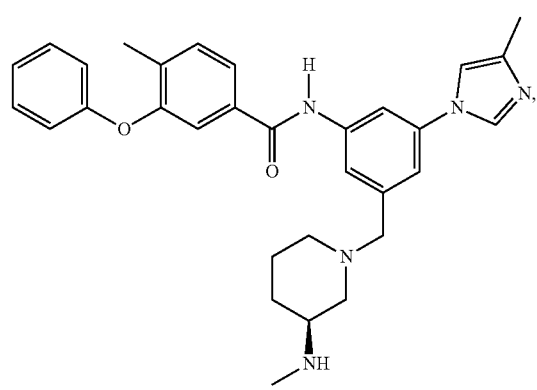
Example 49
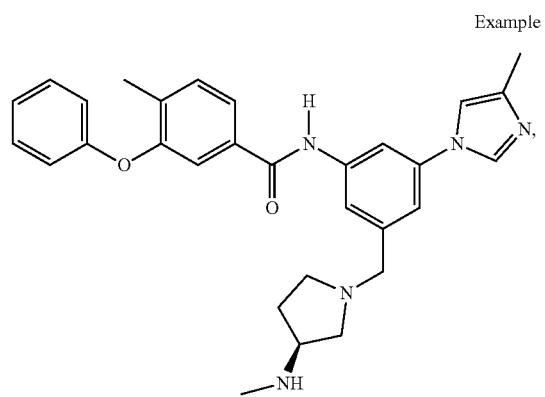
Example 50
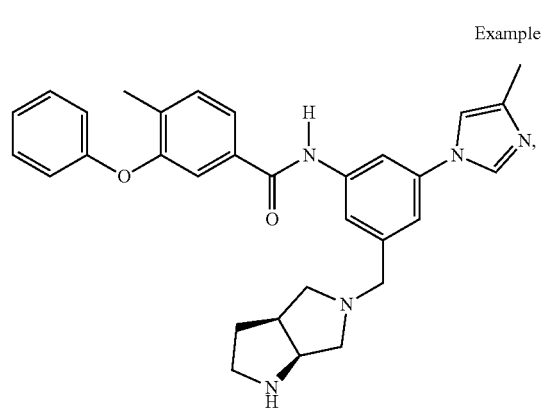
Example 51
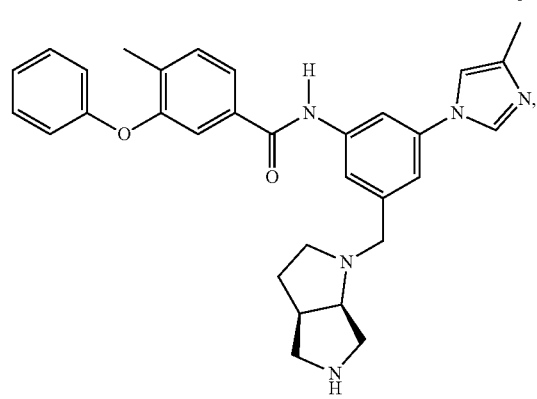
Example 52
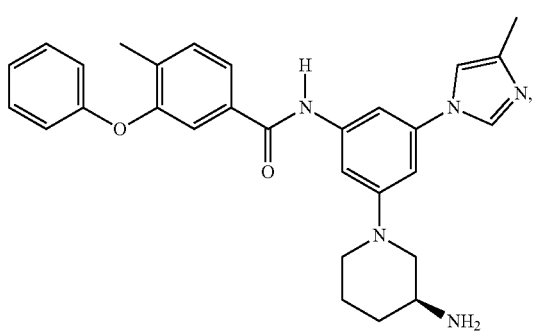
Example 53
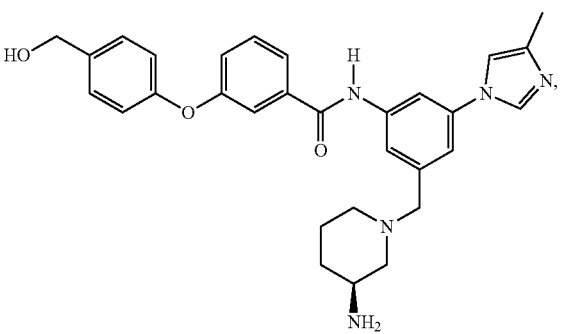
Example 54
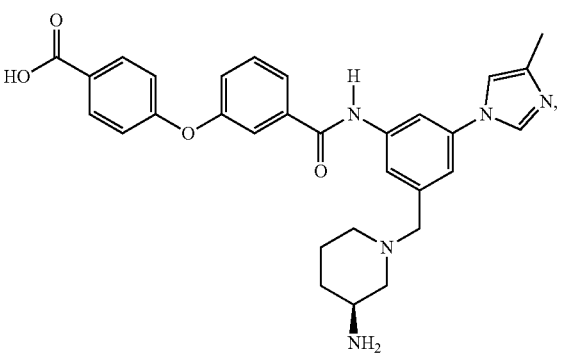
Example 55
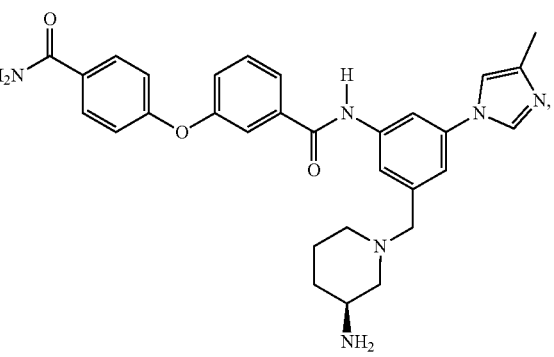

Example 56

Example 57

Example 58

Example 59

Example 60 or a salt, solvate, prodrug or polymorph thereof.

Most preferably, the compound has the structure:

Example 27

, or

Example 30 or a salt, solvate, prodrug or polymorph thereof.

In a particularly preferred embodiment, the compound has the structure

Example 27

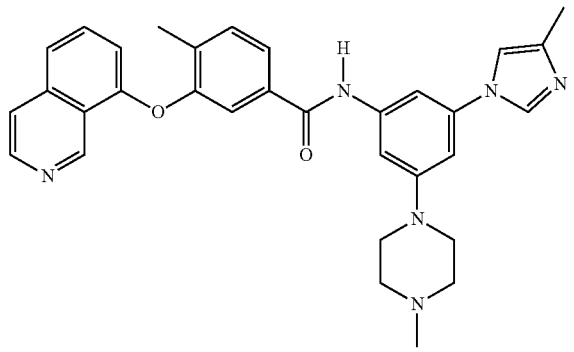

or a salt, solvate, prodrug or polymorph thereof.

In another particularly preferred embodiment, the compound has the structure

Example 30

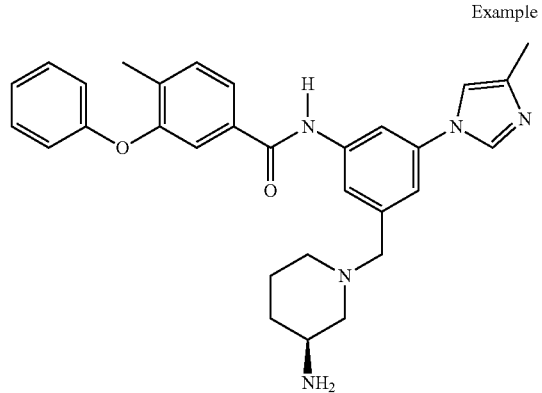

or a salt, solvate, prodrug or polymorph thereof.

In some embodiments, the compounds may not inhibit kinase activity at physiologically relevant concentrations, particularly c-KIT, SRC, ABL and PDGFR kinases.

In one aspect, therefore, there is provided a composition comprising a compound according to Formula (I), Formula (II), Formula (III) and/or Formula (IV) or a pharmaceutically acceptable salt, solvate, prodrug or polymorph thereof, and a pharmaceutically acceptable excipient.

As used herein, except where the context requires otherwise, the term "comprise" and variations of the term, such as "comprising", "comprises" and "comprised", are not intended to exclude further additives, components, integers or steps.

As used herein the term "alkyl" refers to a straight or branched chain hydrocarbon radical having from one to twelve carbon atoms, or any range between, i.e. it contains 1, 2, 3, 4, 5, 6, 7, 8, 9, 10, 11 or 12 carbon atoms. The alkyl group is optionally substituted with substituents, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the terms "$C_1$-$C_2$ alkyl", "$C_1$-$C_4$ alkyl" and "$C_1$-$C_6$ alkyl" refer to an alkyl group, as defined above, containing at least 1, and at most 2, 4 or 6 carbon atoms respectively, or any range in between (e.g. alkyl groups containing 2-5 carbon atoms are also within the range of $C_1$-$C_6$).

As used herein the term "alkenyl" refers to an alkyl group containing a double bond. It may also be optionally substituted with substituents, multiple degrees of substitution being allowed.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I). Preferably, 'halo' is fluoro or chloro.

As used herein, the term "cycloalkyl" refers to a non-aromatic cyclic hydrocarbon ring. In a like manner the term "$C_3$-$C_7$ cycloalkyl" refers to a non-aromatic cyclic hydrocarbon ring having from five to eight carbon atoms, or any range in between. For example, the $C_3$-$C_7$ cycloalkyl group would also include cycloalkyl groups containing 6 to 7 carbon atoms. The alkyl group is as defined above, and may be substituted. The cycloalkyl group refers to a nonaromatic cyclic ring, being saturated or having one or more degrees of unsaturation. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the terms "heterocyclic" or "heterocyclyl" refer to a nonaromatic heterocyclic ring, being saturated or having one or more degrees of unsaturation, containing one or more heteroatom substitutions selected from S, S(O), $S(O)_2$, O, N, $Si(R_aR_b)$, P, $P(O)R_aR_b$, or $B(OR_c)$, wherein $R_a$ and $R_b$ are $C_1$-$C_6$ alkyl or aryl, or together with the atom between them form a 5- or 6-membered heterocyclyl ring, and $R_c$ is hydrogen or $C_1$-$C_6$ alkyl. The term "$C_3$-$C_7$ heterocyclyl" refers to a non-aromatic cyclic hydrocarbon ring having from three to seven carbon atoms containing one or more heteroatom substitutions as referred to herein. The heterocyclic moiety may be substituted, multiple degrees of substitution being allowed. The term "$C_3$-$C_7$ heterocyclyl" also includes heterocyclyl groups containing $C_4$-$C_5$, $C_5$-$C_7$, $C_6$-$C_7$, $C_4$-$C_7$, $C_4$-$C_6$ and $C_5$-$C_6$ carbon atoms. Preferably, the heterocyclic ring contains four to six carbon atoms and one or two heteroatoms. More preferably, the heterocyclic ring contains five carbon atoms and one heteroatom, or four carbon atoms and two heteroatom substitutions, or five carbon atoms and one heteroatom. Such a ring may be optionally fused to one or more other "heterocyclic" ring(s) or cycloalkyl ring(s). Examples of "heterocyclic" moieties include, but are not limited to, tetrahydrofuran, pyran, oxetane, 1,4-dioxane, 1,3-dioxane, piperidine, piperazine, N-methylpiperazinyl, 2,4-piperazinedione, pyrrolidine, imidazolidine, pyrazolidine, morpholine, thiomorpholine, tetrahydrothiopyran, tetrahydrothiophene, and the like.

As an example of substituted heterocyclic groups, the term "($C_1$-$C_3$ alkyl)$C_3$-$C_7$ heterocyclyl" includes heterocyclyl groups containing an alkyl group of one to three carbons in length as a linker between the compound and the heterocycle, (e.g. —$CH_2$-heterocycle or —$CH_2CH_2$-heterocycle). These heterocycles may be further substituted.

Substituted cycloalkyl and heterocyclyl groups may be substituted with any suitable substituent as described below.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Examples of "aryl" groups include, but are not limited to, phenyl, 2-naphthyl, 1-naphthyl, biphenyl, as well as substituted derivatives thereof. Preferred aryl groups include arylamino, aralkyl and aralkoxy groups.

As used herein, the term "heteroaryl" refers to a monocyclic five, six or seven membered aromatic ring, or to a fused bicyclic or tricyclic aromatic ring system comprising at least one monocyclic five, six or seven membered aromatic ring. These heteroaryl rings contain one or more nitrogen, sulfur, and/or oxygen heteroatoms, where N-oxides and sulfur oxides and dioxides are permissible heteroatom substitutions and may be optionally substituted with up to three members. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, cinnolyl, phthalazyl, naphthyridinyl, benzofuranyl, benzothiophenyl, indolyl, indazolyl, benzimidazolyl, and substituted versions thereof. Preferred heteroaryl groups include isoquinolinyl, imidazolyl and oxazolyl groups.

A "substituent" as used herein, refers to a molecular moiety that is covalently bonded to an atom within a molecule of interest. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterized and tested for biological activity.

The terms "optionally substituted" or "may be substituted" and the like, as used throughout the specification, denotes that the group may or may not be further substituted or fused (so as to form a polycyclic system), with one or more non-hydrogen substituent groups. Suitable chemically viable substituents for a particular functional group will be apparent to those skilled in the art.

Examples of substituents include but are not limited to: $C_1$-$C_6$ alkyl, $C_1$-$C_6$ haloalkyl, $C_1$-$C_6$ haloalkoxy, $C_1$-$C_6$ hydroxyalkyl, $C_3$-$C_7$ heterocyclyl, $C_3$-$C_7$ cycloalkyl, $C_1$-$C_6$ alkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino, acyl, carboxy, carbamoyl, aryl, aryloxy, heteroaryl, aminosulfonyl, aroyl, aroylamino, heteroaroyl, acyloxy, aroyloxy, heteroaroyloxy, alkoxycarbonyl, nitro, cyano, halogen, ureido, $C_1$-$C_6$ perfluoroalkyl or phosphorus containing groups such as phosphine oxides, $P(O)R_a$, $P(O)OR_aOR_b$, $P(O)R_aR_b$, $C_1$-$C_6$ alkyl-$P(O)R_aR_b$ or the like, wherein $R_a$ and $R_b$ are $C_1$-$C_6$ alkyl or aryl, or together with the atom between them form a 5- or 6-membered heterocyclyl ring.

Any of these groups may be further substituted by any of the above-mentioned groups, where appropriate. For example, alkylamino, or dialkylamino, $C_1$-$C_6$ alkoxy, etc.

Unless specified otherwise, the compounds disclosed herein refer to compounds of formula (I), formula (II), formula (III) and/or formula (IV) or pharmaceutically acceptable salts, solvates, prodrugs or polymorphs thereof, as well as all stereoisomers (including diastereoisomers and enantiomers), tautomers, and isotopically labelled compounds (including deuterium substitutions), as well as inherently formed moieties (e.g., polymorphs and/or solvates).

Where the compounds are chiral, the compound may exist as a racemic mixture, predominantly one enantiomer, or only one enantiomer.

In one embodiment of the invention, in a compound of formula I described herein, A may be selected to interact with Ser221 of a PCSK9 protein having an amino acid sequence shown in SEQ ID No 1.

In one embodiment of the invention, in a compound of formula I and/or formula II described herein, Q may be selected to interact with Asp212 of a PCSK9 protein having an amino acid sequence shown in SEQ ID No 1.

In one embodiment of the invention, in a compound of formula I and/or formula II described herein, Q may be selected to interact with Lys223 of a PCSK9 protein having an amino acid sequence shown in SEQ ID No 1.

In one embodiment, the invention provides compounds of the present invention as described herein, wherein D is selected to interact with the Lys258 of a PCSK9 protein having an amino acid sequence shown in SEQ ID No 1.

In one embodiment, the invention provides compounds of the present invention as described herein, wherein A may be selected to interact with Ser221, Q may be selected to interact with the Asp212 and D may be selected to interact with the Lys258 of a PCSK9 protein having an amino acid sequence shown in SEQ ID No 1.

Figure 4C:
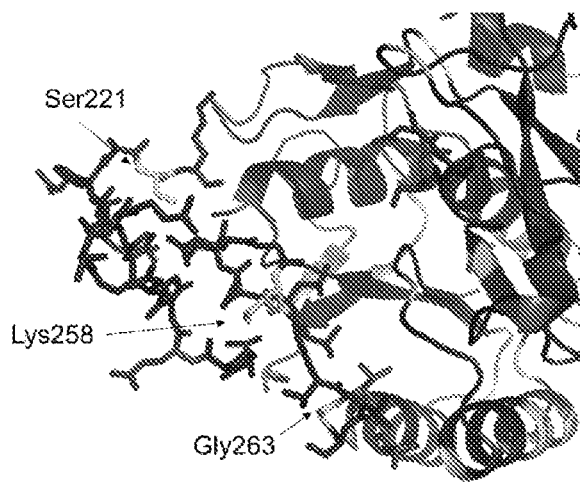
FIG. 4: a) Sequence alignment of sequences for existing PCSK9 structures and key species from NCBI database; b) lack of sequence conservation across the PCSK family (PCSK1 to PCSK7 and PCSK9); and c) PCSK9 conservation mapped to structure, illustrating several relevant amino acids for compound binding. The sequences and alignments in the Figures and provided in SEQ ID 1 are based on a particular UNIPROT sequence database.

See FIG. 4c for the PCSK9 conservation mapped to structure, illustrating several relevant amino acids for compound binding.

The activity of the compounds of the invention was measured first in a binding assay wherein the compounds interfered with the above-mentioned protein-protein interaction between the LDLR and PCSK9. Selected compounds were then subjected to a functional, cell-based assay wherein positive activity was recorded as a measure of increase of LDL uptake in cells. This assay therefore demonstrated the link between the targeted molecular interaction and the intended consequence, namely, to reduce circulatory, or plasma LDL by increasing its cellular uptake through inhibition of PCSK9.

The compounds have demonstrated efficacy and the levels of LDL have been decreased with their use. Accordingly, the present invention also provides for the use of these compounds in inhibiting PCSK9, preventing the protein-protein interaction between PCSK9 and LDLR, and in reducing LDL levels.

The targeted site is specific to the PCSK9 protein and the homology of this region is conserved across species. For example, it is conserved between humans, mice, rats, guinea pigs, pigs, elephants and killer whales (see FIG. 4a).

The PCSK family show very low levels of sequence identity. Cross-reactivity of the compounds with other PCSK molecules is therefore unlikely (See FIG. 4b).

In one aspect, therefore, there is provided a method for inhibiting PCSK9 in a subject in need thereof, the method comprising administering a therapeutically effective amount of a compound or a pharmaceutically acceptable salt, solvate, prodrug or polymorph thereof of Formula (I), Formula (II), Formula (III) and/or Formula (IV) to a subject.

In one aspect, there is provided a method for inhibiting PCSK9 in a subject in need thereof, the method comprising administering a therapeutically effective amount of a composition comprising a compound or a pharmaceutically acceptable salt, solvate, prodrug or polymorph thereof of Formula (I), Formula (II), Formula (III) and/or Formula (IV) to a subject.

In one aspect, there is provided a method for reducing LDL in a subject in need thereof, the method comprising administering a therapeutically effective amount of a compound or a pharmaceutically acceptable salt, solvate, prodrug or polymorph thereof of Formula (I), Formula (II), Formula (III) and/or Formula (IV) to a subject.

In one aspect, there is provided a method for reducing LDL in a subject in need thereof, the method comprising administering a therapeutically effective amount of a composition comprising a compound or a pharmaceutically acceptable salt, solvate, prodrug or polymorph thereof of Formula (I), Formula (II), Formula (III) and/or Formula (IV) to a subject.

In one aspect, there is provided a method for treating a disease or condition in a subject in need thereof, wherein the disease or condition is any one of the following: cardiovascular disease, cerebrovascular disease, atherosclerosis and/or their associated diseases or their symptoms, the method comprising administering a therapeutically effective amount of a compound according to formula (I), formula (II), formula (III) and/or formula (IV), or a pharmaceutically acceptable salt, solvate, prodrug or polymorph thereof to a subject.

In one aspect, there is provided a method for treating a disease or condition in a subject in need thereof, wherein the disease or condition is any one of the following: cardiovascular disease, cerebrovascular disease, atherosclerosis and/or their associated diseases or their symptoms, the method comprising administering a therapeutically effective amount of a composition comprising a compound according to formula (I), formula (II), formula (III) and/or formula (IV), or a pharmaceutically acceptable salt, solvate, prodrug or polymorph thereof to a subject.

In another aspect, there is provided use of a compound of Formula (I), Formula (II), Formula (III) and/or Formula (IV) or a pharmaceutically acceptable salt, solvate, prodrug or polymorph thereof, in the preparation of a medicament for the inhibition of PCSK9 in a subject.

In another aspect, there is provided use of a composition comprising a compound of Formula (I), Formula (II), Formula (III) and/or Formula (IV) or a pharmaceutically acceptable salt, solvate, prodrug or polymorph thereof, in the preparation of a medicament for the inhibition of PCSK9 in a subject.

In another aspect, there is provided use of a compound of Formula (I), Formula (II), Formula (III) and/or Formula (IV) or a pharmaceutically acceptable salt, solvate, prodrug or polymorph thereof, in the preparation of a medicament for the reduction of LDL in a subject.

In another aspect, there is provided use of a composition comprising a compound of Formula (I), Formula (II), Formula (III) and/or Formula (IV) or a pharmaceutically acceptable salt, solvate, prodrug or polymorph thereof, in the preparation of a medicament for the reduction of LDL in a subject.

In another aspect, there is provided use of a compound of Formula (I), Formula (II), Formula (III) and/or Formula (IV) or a pharmaceutically acceptable salt, solvate, prodrug or polymorph thereof in the preparation of a medicament for the treatment of a disease or condition in a subject, wherein the disease or condition is any one of the following: cardiovascular disease, cerebrovascular disease, atherosclerosis and/or their associated diseases or their symptoms.

In another aspect, there is provided use of a composition comprising a compound of Formula (I), Formula (II), Formula (III) and/or Formula (IV) or a pharmaceutically acceptable salt, solvate, prodrug or polymorph thereof in the preparation of a medicament for the treatment of a disease or condition in a subject, wherein the disease or condition is any one of the following: cardiovascular disease, cerebrovascular disease, atherosclerosis and/or their associated diseases or their symptoms.

In another aspect, there is provided use of a compound according to Formula (I), Formula (II), Formula (III) and/or Formula (IV) or a pharmaceutically acceptable salt, solvate, prodrug or polymorph thereof, for the inhibition of PCSK9.

In another aspect, there is provided use of a composition comprising a compound according to Formula (I), Formula (II), Formula (III) and/or Formula (IV) or a pharmaceutically acceptable salt, solvate, prodrug or polymorph thereof, for inhibiting PCSK9.

In another aspect, there is provided use of a compound according to Formula (I), Formula (II), Formula (III) and/or Formula (IV) or a pharmaceutically acceptable salt, solvate, prodrug or polymorph thereof, for the reduction of LDL.

In another aspect, there is provided use of a composition comprising a compound according to Formula (I), Formula (II), Formula (III) and/or Formula (IV) or a pharmaceutically acceptable salt, solvate, prodrug or polymorph thereof, for the reduction of LDL.

In another aspect, there is provided use of a compound Formula (I), Formula (II), Formula (III) and/or Formula (IV) or a pharmaceutically acceptable salt, solvate, prodrug or polymorph thereof, for the treatment of a disease or condition in a subject, wherein the disease or condition is any one of the following: cardiovascular disease, cerebrovascular disease, atherosclerosis and/or their associated diseases or their symptoms.

In another aspect, there is provided use of a composition comprising a compound Formula (I), Formula (II), Formula (III) and/or Formula (IV) or a pharmaceutically acceptable salt, solvate, prodrug or polymorph thereof, for the treatment of a disease or condition in a subject, wherein the disease or condition is any one of the following: cardiovascular disease, cerebrovascular disease, atherosclerosis and/or their associated diseases or their symptoms.

In yet another aspect, there is provided a compound according to Formula (I), Formula (II), Formula (III) and/or Formula (IV) or a pharmaceutically acceptable salt, solvate, prodrug or polymorph thereof, for use in inhibiting PCSK9.

In another aspect, there is provided a composition comprising a compound according to Formula (I), Formula (II), Formula (III) and/or Formula (IV) or a pharmaceutically acceptable salt, solvate, prodrug or polymorph thereof, for use in inhibiting PCSK9.

In another aspect, there is provided a compound according to Formula (I), Formula (II), Formula (III) and/or Formula (IV) or a pharmaceutically acceptable salt, solvate, prodrug or polymorph thereof, for use in reducing LDL.

In another aspect, there is provided a composition comprising a compound according to Formula (I), Formula (II), Formula (III) and/or Formula (IV) or a pharmaceutically acceptable salt, solvate, prodrug or polymorph thereof, for use in reducing LDL.

In another aspect, there is provided a compound according to Formula (I), Formula (II), Formula (III) and/or Formula (IV) or a pharmaceutically acceptable salt, solvate, prodrug or polymorph thereof, for use in the treatment of a disease or condition in a subject, wherein the disease or condition is any one of the following: cardiovascular disease, cerebrovascular disease, atherosclerosis and/or their associated diseases or their symptoms.

In another aspect, there is provided a composition comprising a compound according to Formula (I), Formula (II), Formula (III) and/or Formula (IV) or a pharmaceutically acceptable salt, solvate, prodrug or polymorph thereof, for use in the treatment of a disease or condition in a subject, wherein the disease or condition is any one of the following: cardiovascular disease, cerebrovascular disease, atherosclerosis and/or their associated diseases or their symptoms.

In yet another aspect, there is provided a compound according to Formula (I), Formula (II), Formula (III) and/or Formula (IV) or a pharmaceutically acceptable salt, solvate, prodrug or polymorph thereof, when used for inhibiting PCSK9.

In yet another aspect, there is provided a composition comprising a compound according to Formula (I), Formula (II), Formula (III) and/or Formula (IV) or a pharmaceutically acceptable salt, solvate, prodrug or polymorph thereof, when used for inhibiting PCSK9.

In yet another aspect, there is provided a compound according to Formula (I), Formula (II), Formula (III) and/or Formula (IV) or a pharmaceutically acceptable salt, solvate, prodrug or polymorph thereof, when used for reducing LDL.

In yet another aspect, there is provided a composition comprising a compound according to Formula (I), Formula (II), Formula (III) and/or Formula (IV) or a pharmaceutically acceptable salt, solvate, prodrug or polymorph thereof, when used for reducing LDL.

In yet another aspect, there is provided a compound of Formula (I), Formula (II), Formula (III) and/or Formula (IV) or a pharmaceutically acceptable salt, solvate, prodrug or polymorph thereof, when used for the treatment of a disease or condition in a subject, wherein the disease or condition is any one of the following: cardiovascular disease, cerebrovascular disease, atherosclerosis and/or their associated diseases or their symptoms.

In yet another aspect, there is provided a composition comprising a compound of Formula (I), Formula (II), Formula (III) and/or Formula (IV) or a pharmaceutically acceptable salt, solvate, prodrug or polymorph thereof, when used for the treatment of a disease or condition in a subject, wherein the disease or condition is any one of the following: cardiovascular disease, cerebrovascular disease, atherosclerosis and/or their associated diseases or their symptoms.

The term "pharmaceutically acceptable" may be used to describe any pharmaceutically acceptable salt, hydrate or prodrug, or any other compound which upon administration to a subject, is capable of providing (directly or indirectly) a compound of Formula (I), Formula (II), Formula (III) and/or Formula (IV) or an active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1st edition, 2002, Wiley-VCH.

In the case of compounds that are solids, it will be understood by those skilled in the art that the inventive compounds, agents and salts may exist in different crystalline or polymorphic forms, all of which are intended to be within the scope of the present invention and specified formulae.

The term "polymorph" includes any crystalline form of compounds of Formula (I), Formula (II), Formula (III) and/or Formula (IV), such as anhydrous forms, hydrous forms, solvate forms and mixed solvate forms.

Formula (I), Formula (II), Formula (III) and Formula (IV) are intended to cover, where applicable, solvated as well as unsolvated forms of the compounds. Thus, Formula (I), Formula (II), Formula (III) and/or Formula (IV) include compounds having the indicated structures, including the hydrated or solvated forms, as well as the non-hydrated and non-solvated forms.

As used herein, the term "solvate" refers to a complex of variable stoichiometry formed by a solute (in this invention, a compound of formula (I), Formula (II), Formula (III) and/or Formula (IV) or a salt, prodrug or polymorph thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four) amino acid residues which are covalently joined to free amino, and amido groups of compounds of Formula (I). The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of Formula (I), Formula (II), Formula (III) and/or Formula (IV) through the carbonyl carbon prodrug sidechain.

The compounds of Formula (I), Formula (II), Formula (III) and/or Formula (IV) and prodrugs thereof may be covalent irreversible or covalent reversible inhibitors of the active site of a protein.

Pharmaceutical compositions may be formulated from compounds according to Formula (I), Formula (II), Formula (III) and/or Formula (IV) for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of components are described in Martindale—The Extra Pharmacopoeia (Pharmaceutical Press, London 1993) and Martin (ed.), Remington's Pharmaceutical Sciences.

In the context of this specification the term "administering" and variations of that term including "administer" and "administration", includes contacting, applying, delivering or providing a compound or composition of the invention to an organism, or a surface by any appropriate means.

For the inhibition of PCSK9, the dose of the biologically active compound according to the invention may vary within wide limits and may be adjusted to individual requirements. Active compounds according to the present invention are generally administered in a therapeutically effective amount. Preferred doses range 5 from about 0.1 mg to about 140 mg per kilogram of body weight per day (e.g. about 0.5 mg to about 7 g per patient per day). The daily dose may be administered as a single dose or in a plurality of doses. The amount of active ingredient that may be combined with the carrier materials to produce a single dosage form will vary depending upon the subject treated and the particular mode of administration. Dosage unit forms will generally contain between about 1 mg to about 500 mg of an active ingredient.

It will be understood, however, that the specific dose level for any particular subject and will depend upon a variety of factors including the activity of the specific compound employed, the age, body weight, general health, sex, diet, time of administration, route of administration, and rate of excretion, drug combination (i.e. other drugs being used to treat the subject), and the severity of the particular disorder undergoing therapy. The dosage will generally be lower if the compounds are administered locally rather than systemically, and for prevention rather than for treatment. Such treatments may be administered as often as necessary and for the period of time judged necessary by the treating physician. A person skilled in the art will appreciate that the dosage regime or therapeutically effective amount of the compound of formula (I) to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

It will also be appreciated that different dosages may be required for treating different disorders. An effective amount of an agent is that amount which causes a statistically significant decrease in LDL levels.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treating", "treatment" and "therapy" are used herein to refer to curative therapy, prophylactic therapy and preventative therapy. Thus, in the context of the present disclosure the term "treating" encompasses reducing the severity of elevated LDL levels, thereby resulting in the treatment or a reduced risk of cardiovascular diseases such as stroke, heart attack, coronary artery disease, hypercholesterolemia, and/or cerebrovascular diseases, atherosclerosis and/or associated diseases or their symptoms.

"Preventing" or "prevention" means preventing the occurrence of, or tempering the severity of, the above-mentioned diseases or conditions.

"Subject" includes any human or non-human animal. Thus, in addition to being useful for human treatment, the compounds of the present invention may also be useful for veterinary treatment of mammals, including companion animals and farm animals, such as, but not limited to dogs, cats, horses, cows, sheep, and pigs.

The term "inhibit" is used to describe any form of inhibition of PCSK9 that results in prevention, reduction or otherwise amelioration of the above-mentioned diseases or conditions, including complete and partial inhibition of PCSK9.

The compounds of the present invention may be administered along with a pharmaceutical carrier, diluent or excipient as described above.

The methods of the present disclosure can be used to prevent or treat elevated LDL levels, which may or not have been diagnosed as one of the diseases or conditions referred to above.

Generally, the optimal level of LDL in a human adult is less than 100 mg/dL. LDL levels in the range of 100-129 mg/dL are considered as slightly elevated, 130-159 mg/dL are considered as borderline high, 160-189 mg/dL is considered as high and over 190 mg/dL as very high.

Accordingly, in one aspect of the invention, the patients receiving treatment have an LDL level greater than 100 mg/dL. In another embodiment, the patients receiving treatment will have an LDL level above 130 mg/dL. In another embodiment, the patients receiving treatment will have an LDL level above 160 mg/dL. In yet embodiment, the patients receiving treatment will have an LDL level above 190 mg/dL.

In another aspect, the compounds of the present invention may be used to treat patients with a high diastolic blood pressure. In one embodiment of the invention, the patient receiving the treatment may have a diastolic blood pressure greater than 80. In another embodiment, the patient receiving the treatment may have a diastolic blood pressure greater than 90.

Diabetes can be associated with hypercholesterolemia, both in terms of a potential risk due to hypercholesterolemia or as a result of previous treatments, such as statin treatment. Accordingly, a high blood glucose level may represent a cohort of patients for which treatment using the compounds of the invention may be appropriate. For example, it may be beneficial to treat patients with high blood glucose levels who may or may not be considered to be diabetic with compounds of the present invention rather than with medication that can further increase the risk of diabetes and/or an even higher blood glucose level. Alternatively, such patients may benefit from a lower dose of the other treatment in combination with the compounds of the present invention, as discussed below.

Accordingly, in one aspect, the compounds of the present invention may be used to treat patients with a high blood glucose level. For the majority of healthy individuals, normal blood sugar levels are below 6.1 mmol/L (108 mg/dL) when fasting, and up to 7.8 mmol/L (140 mg/dL) two hours after eating. For patients with pre-diabetes, blood sugar levels are increased from between 6.1-6.9 mmol/L (108-125 mg/dL) or more when fasting, and between 7.8-11.0 mmol/L (140-199 mg/dL) or more two hours after eating. For patients with diabetes, blood sugar levels are increased to 7 mmol/L (126 mg/dL) or more when fasting, and 11.1 mmol/L (200 mg/dL) or more two hours after eating. In one aspect, therefore, the compounds of the present invention are particularly suited for patients with pre-diabetes or diabetes.

Combination Therapy

As discussed above, the compounds of the present invention are useful in reducing LDL. The compounds provide this result by inhibiting PCSK9, which is a different mechanism of action to that of the statins. Consequently, these compounds may provide treatment for the diseases or conditions listed above for patients who do not want or who are unable to take statins. This may be due, for example, to the side effects of the statins, or simply that the statins will be (or have been) ineffective at (sufficiently) treating the disease or condition, such as some forms of hypercholesterolemia.

Statins inhibit the synthesis of cholesterol being produced by the liver, thereby decreasing the amount of LDL. They increase activity of sterol regulatory element-binding protein 2 (SREBP-2), resulting in activation of both LDL receptor (LDLR) and PCSK9. Increased expression and secretion of PCSK9 binds LDLR, resulting in higher LDL-C. Thus, while statins reduce LDL, as HMGcoA inhibitors, their effect on SREBP-2 acts as a counterbalance.

The addition of PCKS9 inhibitors to statin therapies may therefore help override this mechanism. Accordingly, the compounds of the present invention may therefore also be used together with statins to provide a more effective reduction in LDL than the statins alone, or to enable a lower dose of the statins to be used to reach a similar efficacy. This could then result in more effective treatments and/or fewer side effects for the patient than treatment or prophylaxis with statins alone.

Accordingly, in one aspect, the invention also provides a composition comprising:
 a compound of the present invention, or a pharmaceutically acceptable salt, solvate, prodrug or polymorph thereof; and
 a statin.

In another aspect, the present invention provides a method for reducing LDL in a subject in need thereof, the method comprising administering a therapeutically effective amount of a composition comprising:
 compound of formula (I), formula (II), formula (III) or formula (IV), or a pharmaceutically acceptable salt, solvate, prodrug or polymorph thereof; and
 a statin.

In one aspect, there is provided a method for treating a disease or condition in a subject in need thereof, wherein the disease or condition is any one of the following: cardiovascular disease, cerebrovascular disease, atherosclerosis and/or their associated diseases or their symptoms, the method comprising administering a therapeutically effective amount of a composition comprising:
 a compound according to formula (I), formula (II), formula (III) and/or formula (IV), or a pharmaceutically acceptable salt, solvate, prodrug or polymorph thereof; and
 a statin.

In another aspect, the present invention provides use of a composition comprising:
 compound of formula (I), formula (II), formula (III) or formula (IV), or a pharmaceutically acceptable salt, solvate, prodrug or polymorph thereof; and
 a statin
 in the preparation of a medicament for reducing LDL in a subject.

In another aspect, there is provided use of a composition comprising:
 a compound of Formula (I), Formula (II), Formula (III) and/or Formula (IV) or a pharmaceutically acceptable salt, solvate, prodrug or polymorph thereof; and
 a statin
 in the preparation of a medicament for the treatment of a disease or condition in a subject, wherein the disease or condition is any one of the following: cardiovascular disease, cerebrovascular disease, atherosclerosis and/or their associated diseases or their symptoms.

In another aspect, the present invention provides use of a composition comprising:
 compound of formula (I), formula (II), formula (III) or formula (IV), or a pharmaceutically acceptable salt, solvate, prodrug or polymorph thereof; and
 a statin
 for reducing LDL.

In another aspect, there is provided use of a composition comprising:
 a compound Formula (I), Formula (II), Formula (III) and/or Formula (IV) or a pharmaceutically acceptable salt, solvate, prodrug or polymorph thereof, and
 a statin
 for the treatment of a disease or condition in a subject, wherein the disease or condition is any one of the following: cardiovascular disease, cerebrovascular disease, atherosclerosis and/or their associated diseases or their symptoms.

In another aspect, the present invention provides use of a composition comprising:

compound of formula (I), formula (II), formula (III) or formula (IV), or a pharmaceutically acceptable salt, solvate, prodrug or polymorph thereof; and
a statin
for use in reducing LDL.

In another aspect, there is provided a composition comprising:
a compound according to Formula (I), Formula (II), Formula (III) and/or Formula (IV) or a pharmaceutically acceptable salt, solvate, prodrug or polymorph thereof, and
a statin
for use in the treatment of a disease or condition in a subject, wherein the disease or condition is any one of the following: cardiovascular disease, cerebrovascular disease, atherosclerosis and/or their associated diseases or their symptoms.

In another aspect, the present invention provides use of a composition comprising:
compound of formula (I), formula (II), formula (III) or formula (IV), or a pharmaceutically acceptable salt, solvate, prodrug or polymorph thereof; and
a statin
when used for reducing LDL.

In yet another aspect, there is provided a composition comprising:
a compound of Formula (I), Formula (II), Formula (III) and/or Formula (IV) or a pharmaceutically acceptable salt, solvate, prodrug or polymorph thereof, and
a statin
when used for the treatment of a disease or condition in a subject, wherein the disease or condition is any one of the following: cardiovascular disease, cerebrovascular disease, atherosclerosis and/or their associated diseases or their symptoms.

The statins referred to in these aspects of the invention can include any statin that is approved for medical use. For example, the following statins may be used: atorvastatin (Lipitor), fluvastatin (Lescol, Lescol XL), lovastatin (Mevacor, Altoprev), pravastatin (Pravachol), rosuvastatin (Crestor), simvastatin (Zocor), and pitavastatin (Livalo).

It will be understood that the invention disclosed and defined in this specification extends to all alternative combinations of two or more of the individual features mentioned or evident from the text or drawings. All of these different combinations constitute various alternative aspects of the invention.

The methods and compounds described herein are described by the following illustrative and non-limiting examples.

EXAMPLES

Definitions

TLC Thin layer chromatography
Prep-TLC Preparative thin layer chromatography
DIPEA Diisopropyl ethyl amine
TPP Triphenylphosphine
DIAD Diisopropyl azodicarboxylate
NBS N-bromosuccinimide
HATU O-(7-Azabenzotriazol-1-yl)-N,N,N',N'-tetramethyl-uronium hexafluorophosphate
TFA Trifluoroacetic acid
DMF Dimethylformamide
mL milliliter(s)
mmol millimole(s)
h hour or hours
min minute or minutes
g gram(s)
mg milligram(s)
μL microlitres
eq equivalent(s
rt or RT room temperature, ambient, about 25° C.
MS mass spectrometry
Experimental Procedure:

Yields reported herein refer to purified products (unless specified) and are not optimized. Analytical TLC was performed on Merck silica gel 60 $F_{254}$ aluminium-backed plates. Compounds were visualised by UV light and/or stained with either $I_2$ or potassium permanganate solution followed by heating. Flash column chromatography was performed on silica gel. $^1$H-NMR spectra were recorded on a 400 MHz spectrometer with a BBO (Broad Band Observe) and BBFO (Broad Band Fluorine Observe) probe. Chemical shifts (δ) are expressed in parts per million (ppm) downfield by reference to tetramethylsilane as the internal standard. Splitting patterns are designated as s (singlet), d (doublet), triplet (t) m (multiplet). The abbreviation br (broad) may be included with any of these. A partially obscured or merged signal is represented by an asterisk (e.g. d* (merged doublet). Coupling constants (J) are given in Hertz (Hz). LCMS analysis was performed using the Electrospray Ionisation (ESI) technique. The following solvents, reagents or scientific terminology may be referred to by their abbreviations as defined above:

Example 1. Synthesis of 4-methyl-N-(3-(4-methyl-1H-imidazol-1-yl)-5-(trifluoromethyl)phenyl)-3-((4-(pyridin-2-yl)pyrimidin-2-yl)amino)benzamide

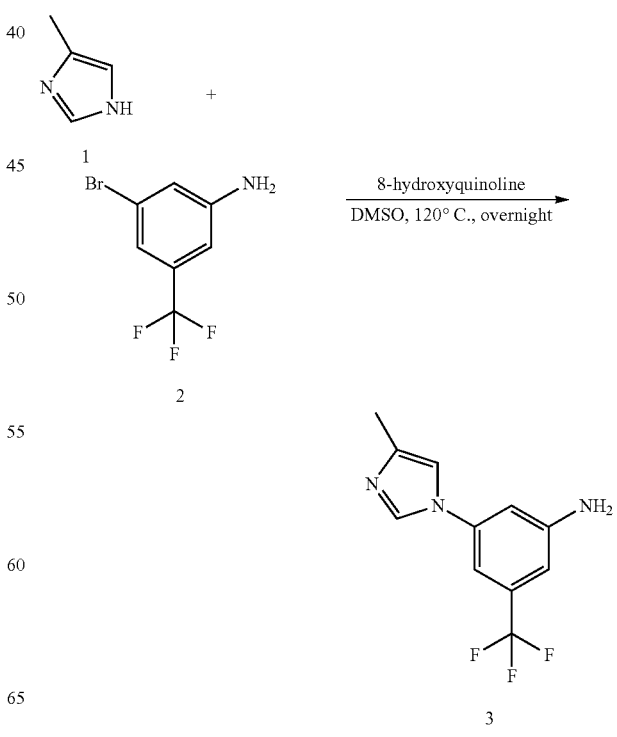

-continued

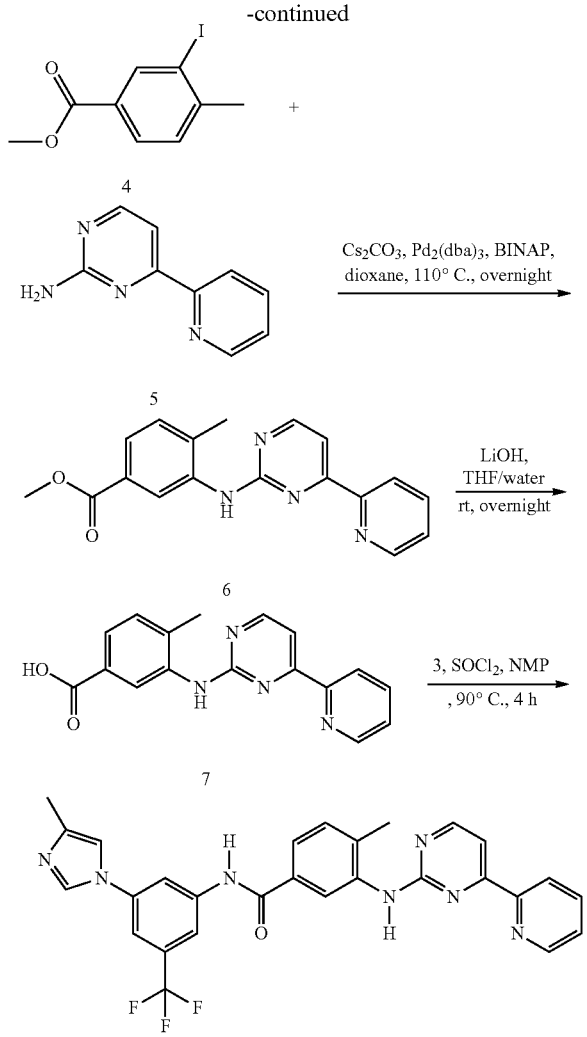

Example 1

A suspension of 1 (3.0 g, 36 mmol), 2 (4.8 g, 20 mmol), K$_2$CO$_3$ (4.5 g, 33 mmol), CuI (1.14 g, 6 mmol) and 8-hydroxyquinoline (0.56 g, 4 mmol) in DMSO (20 mL) was heated at 120° C. overnight under nitrogen. After cooling, water was added and the mixture was extracted with EtOAc twice. The combined organic layers were washed with brine, dried over Na$_2$SO$_4$ and concentrated. The residue was purified by silica gel column chromatography to give 3 (2.8 g, 58%) as a yellow solid. LCMS (m/z: m+1): 242.2.

A mixture of 4 (321 mg, 1.16 mmol), 5 (100 mg, 0.58 mmol), Cs$_2$CO$_3$ (378 mg, 1.16 mmol), Pd$_2$(dba)$_3$ (45 mg) and BINAP (63 mg) in 2 ml of dioxane was stirred at 110° C. under N$_2$ overnight. The mixture was filtered, concentrated and purified by column chromatography to give 6 (82 mg, 44%) as a slightly yellow solid. LCMS (m/z: m+1): 321.1.

To a solution of 6 (200 mg, 0.624 mmol) in THF/H$_2$O (10/5 mL) was added LiOH (45 mg, 1.87 mmol). The reaction was stirred at room temperature overnight, concentrated. To the residue water (10 ml) was added and then acidified to pH 4 with aqueous KHSO$_4$. The precipitate was filtered and washed with water. The cake was collected and dried to give 7 (160 mg, 84%) as a white solid. LCMS (m/z: m+1): 308.3.

To a solution of 7 (100 mg, 0.33 mmol) in NMP (2 mL) was added SOCl$_2$ (58 mg, 0.49 mmol). The reaction was heated at 90° C. for 1 hour before 3 (80 mg, 0.33 mmol) was added. The resulting mixture was stirred at 90° C. for 3 hours. The reaction was quenched with water and basified with aqueous NaOH. The mixture was extracted with EtOAc twice. The combined organic layers were washed with brine, dried over Na$_2$SO$_4$ and concentrated. The residue was purified by silica gel column chromatography to give 4-methyl-N-(3-(4-methyl-1H-imidazol-1-yl)-5-(trifluoromethyl)phenyl)-3-((4-(pyridin-2-yl)pyrimidin-2-yl)amino)benzamide (23 mg, 13%) as a gray solid.

Example 2. Synthesis of 4-methyl-N-(3-(4-methyl-1H-imidazol-1-yl)-5-(trifluoromethyl)phenyl)-3-((4-(pyridin-4-yl)pyrimidin-2-yl)amino)benzamide

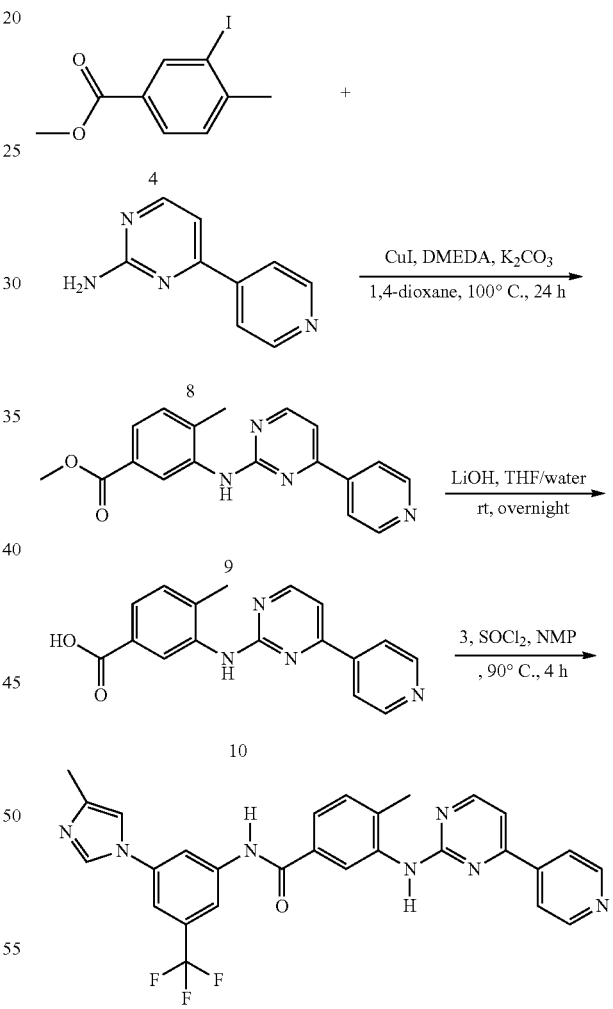

Example 2

A mixture of 4 (1443 mg, 5.23 mmol), 8 (600 mg, 3.48 mmol), K$_2$CO$_3$ (963 mg, 6.97 mmol), DMEDA (77 mg, 0.871 mmol) and CuI (166 mg, 0.871 mmol) in 18 ml of dioxane was stirred at 100° C. under N$_2$ for 24 h. The mixture was filtered, concentrated and purified by column chromatography to give 9 (918 mg, 82%) as a slightly yellow solid. LCMS (m/z: m+1): 321.1.

To a solution of 9 (500 mg, 1.56 mmol) in THF/H₂O (20/10 mL) was added LiOH (112 mg, 4.68 mmol). The reaction was stirred at room temperature overnight, concentrated. To the residue water (30 ml) was added and then acidified to pH 4 with aqueous KHSO₄. The precipitate was filtered and washed with water and EtOAc. The cake was collected and dried to give 10 (320 mg, 67%) as a white solid.

To a solution of 10 (150 mg, 0.49 mmol) in NMP (3 mL) was added SOCl₂ (87 mg, 0.73 mmol). The reaction was heated at 90° C. for 1 hour before 3 (118 mg, 0.49 mmol) was added. The resulting mixture was stirred at 90° C. for 3 hours. The reaction was quenched with water and basified with aqueous NaOH. The mixture was extracted with EtOAc twice. The combined organic layers were washed with brine, dried over Na₂SO₄ and concentrated. The residue was purified by silica gel column chromatography to give 4-methyl-N-(3-(4-methyl-1H-imidazol-1-yl)-5-(trifluoromethyl)phenyl)-3-((4-(pyridin-4-yl)pyrimidin-2-yl)amino)benzamide (30 mg, 12%) as a yellow solid.

Example 3. Synthesis of 4-methyl-N-(3-(4-methyl-1H-imidazol-1-yl)-5-(trifluoromethyl)phenyl)-3-((4-phenylpyrimidin-2-yl)amino)benzamide A mixture of 4 (7.26 g, 26.3 mmol), 11 (3.0 g, 17.5 mmol), K₂CO₃ (4.84 g, 35.0 mmol), DMEDA (386 mg, 4.38 mmol) and CuI (834 mg, 0.871 mmol) in 90 ml of dioxane was stirred at 100° C. under N₂ for 18 h. The mixture was filtered, concentrated and purified by column chromatography to give 12 (2.2 g, 39%) as a slightly yellow solid. LCMS (m/z: m+1): 320.2.

To a solution of 12 (2.2 g, 6.89 mmol) in THF/water (60/30 mL) was added LiOH (496 mg, 20.7 mmol). The reaction was stirred at room temperature overnight, concentrated. To the residue water (30 ml) was added and then acidified to pH 4 with aqueous KHSO₄. The precipitate was filtered and washed with water and EtOAc. The cake was collected and dried to give 13 (1.4 g, 67%) as a white solid. LCMS (m/z: M+1): 306.2

To a solution of 13 (100 mg, 0.33 mmol) in NMP (2 mL) was added SOCl₂ (58 mg, 0.49 mmol). The reaction was heated at 90° C. for 1 hour before 3 (80 mg, 0.33 mmol) was added. The resulting mixture was stirred at 90° C. for 3 hours. The reaction was quenched with water and basified with aqueous NaOH. The mixture was extracted with EtOAc twice. The combined organic layers were washed with brine, dried over Na₂SO₄ and concentrated. The residue was purified by reverse prep-HPLC and then silica gel prep-TLC to give 4-methyl-N-(3-(4-methyl-1H-imidazol-1-yl)-5-(trifluoromethyl)phenyl)-3-((4-phenylpyrimidin-2-yl)amino)benzamide (22 mg, 13%) as a white solid.

Example 4. Synthesis of 4-methyl-N-(3-(4-methyl-1H-imidazol-1-yl)-5-(trifluoromethyl)phenyl)-3-(pyrimidin-2-ylamino)benzamide

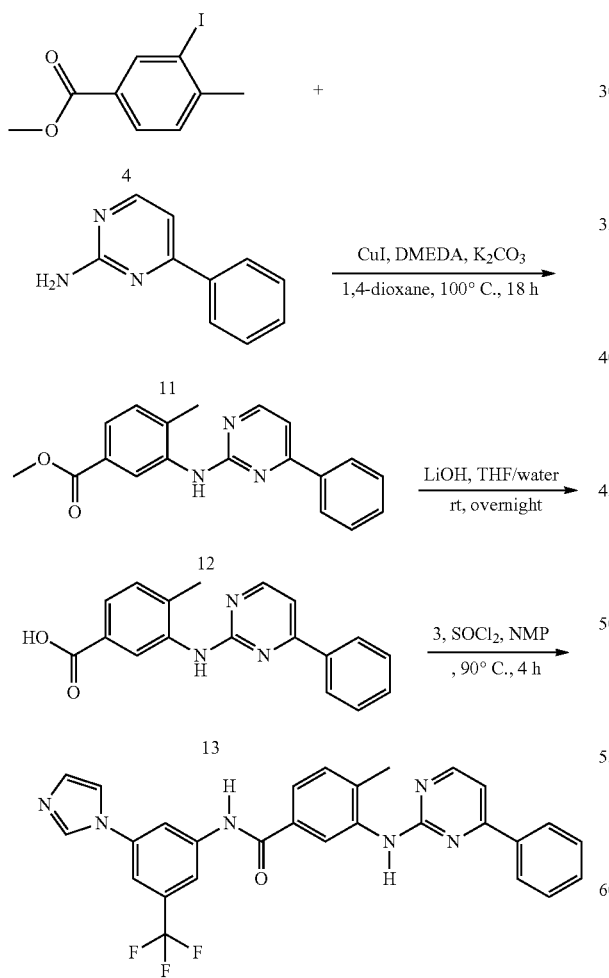

Example 3

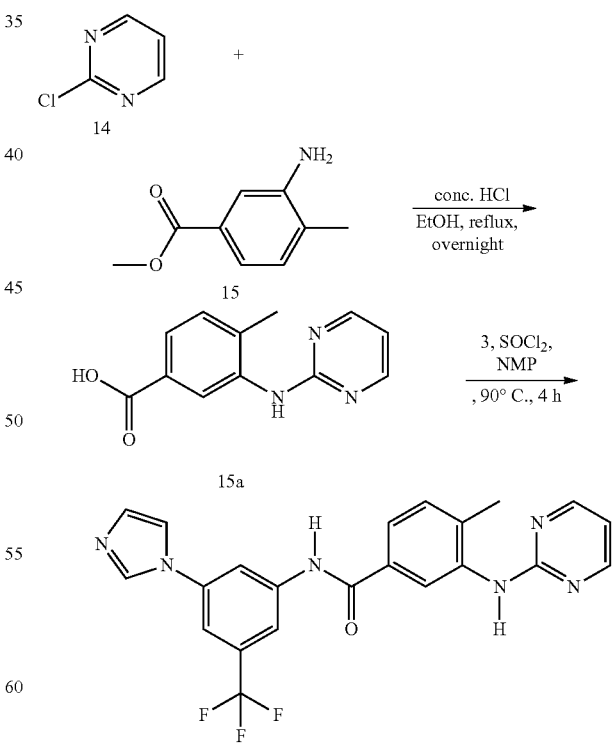

Example 4

To a solution of 14 (347 mg, 3.03 mmol) and 15 (500 mg, 3.03 mmol) in EtOH (10 mL) was added conc. HCl (1 mL).

The reaction was heated to reflux overnight before being concentrated. The residue was purified by silica gel column chromatography and then reverse prep-HPLC to give 15a (80 mg, 12%) as a white solid. LCMS (m/z: m+1): 230.2.

To a solution of 15a (80 mg, 0.35 mmol) in NMP (2 mL) was added SOCl$_2$ (62 mg, 0.52 mmol). The reaction was heated at 90° C. for 1 hour before 3 (84 mg, 0.35 mmol) was added. The resulting mixture was stirred at 90° C. for 3 hours. The reaction was quenched with water and basified with aqueous NaOH. The mixture was extracted with EtOAc twice. The combined organic layers were washed with brine, dried over Na$_2$SO$_4$ and concentrated. The residue was purified by reverse prep-HPLC and then silica gel prep-TLC to give 4-methyl-N-(3-(4-methyl-1H-imidazol-1-yl)-5-(trifluoromethyl)phenyl)-3-(pyrimidin-2-ylamino)benzamide (12 mg, 7.6%) as a slightly yellow solid.

Example 5. Synthesis of 4-methyl-N-(3-(4-methyl-1H-imidazol-1-yl)-5-(piperazin-1-yl)phenyl)-3-((4-phenylpyrimidin-2-yl)amino)benzamide

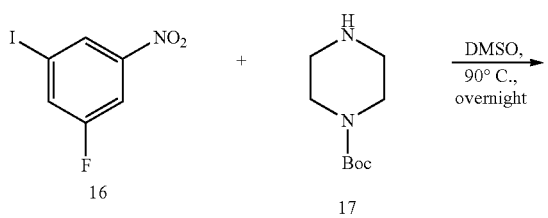

16   17

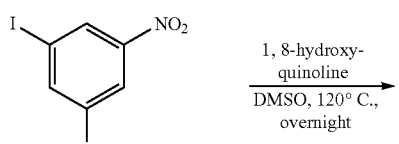

18

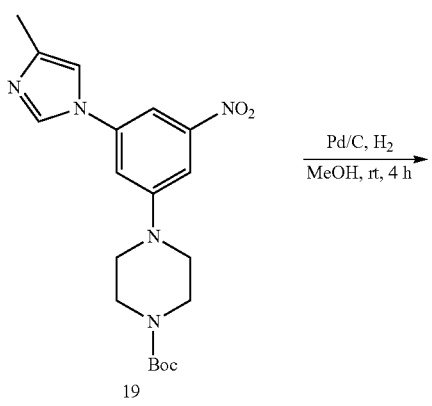

19

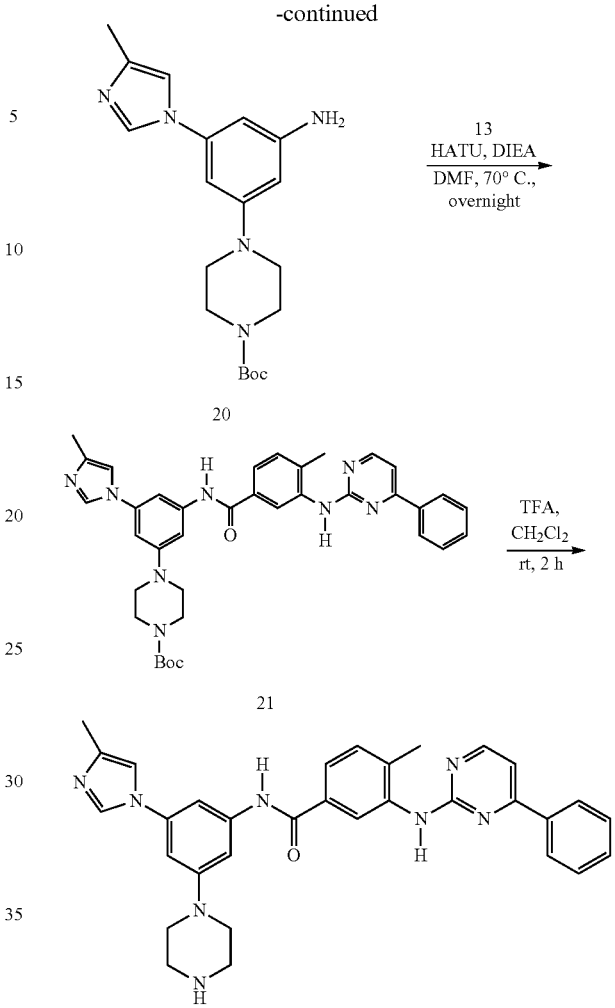

Example 5

A mixture of 16 (0.24 g, 0.9 mmol) and 17 (0.5 g, 2.7 mmol) in DMSO (1.5 mL) was heated at 90° C. overnight. After cooling, water was added and the resulting yellow precipitate was collected by filtration. The cake was dried to give 18 (0.35 g, 90%) as a yellow solid.

A suspension of 18 (0.86 g, 2 mmol), 1, (0.32 g, 4 mmol), K$_2$CO$_3$ (0.55 g, 4 mmol), CuI (0.12 g, 0.6 mmol), and 8-hydroxyquinoline (0.05 g, 0.4 mmol) in DMSO (4 mL) was heated at 120° C. overnight under nitrogen. After cooling, water was added and the mixture was extracted with EtOAc twice. The combined organic layers were washed with brine, dried over Na$_2$SO$_4$ and concentrated. The residue was purified by silica gel column chromatography to give 19 (0.5 g, 65%) as a yellow solid. LCMS (m/z: m+1): 388.3.

A mixture of 19 (0.5 g, 1.3 mmol) and Pd/C (100 mg) in MeOH (10 mL) was stirred at room temperature under hydrogen atmosphere for 4 hours. The reaction mixture was filtered and concentrated. The crude product was purified by silica gel column chromatography to give 20 (0.4 g, 79%) as a slightly yellow oil. LCMS (m/z: M+1): 358.3.

A mixture of 13 (60 mg, 0.20 mmol), 20 (80 mg, 0.22 mmol), HATU (152 mg, 0.40 mmol) and DIEA (103 mg, 0.80 mmol) in DMF (1.5 mL) was heated at 70° C. overnight. After cooling, the reaction was directly purified by reverse prep-HPLC and then silica gel prep-TLC to give 21 (43 mg, 34%) as a slightly yellow solid. LCMS (m/z: m+Na): 667.3.

To a solution of 21 (43 mg, 0.067 mmol) in CH$_2$Cl$_2$ (2 mL) was added TFA (0.5 mL). The reaction was stirred at room temperature for 2 hours before evaporated under reduced pressure. The residue was treated with water and basified with aqueous NaOH. The precipitate was filtered and washed with water. The cake was collected and dried to give Example 5 (35 mg, 96%) as a yellow solid.

Example 6. Synthesis of 4-methyl-N-(3-(4-methyl-1H-imidazol-1-yl)-5-(4-methylpiperazin-1-yl)phenyl)-3-((4-phenylpyrimidin-2-yl)amino)benzamide

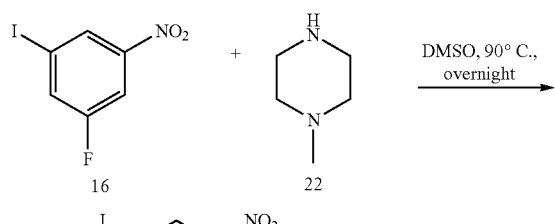

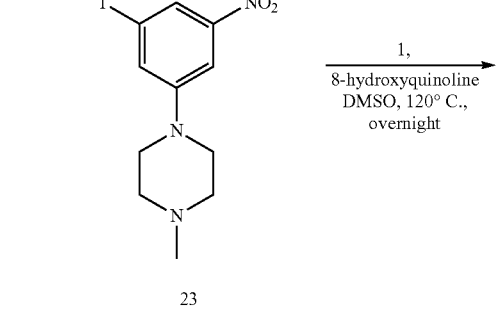

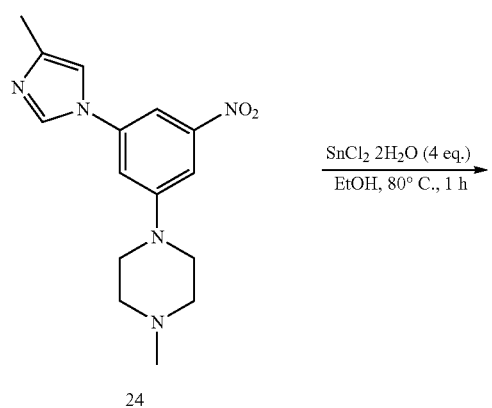

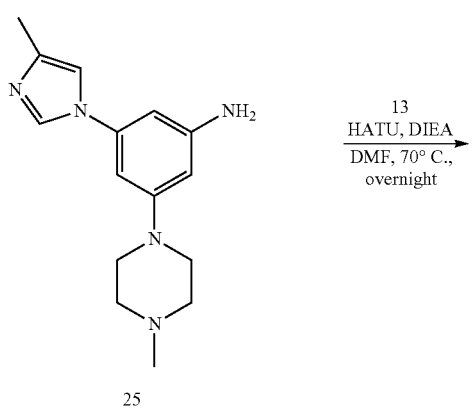

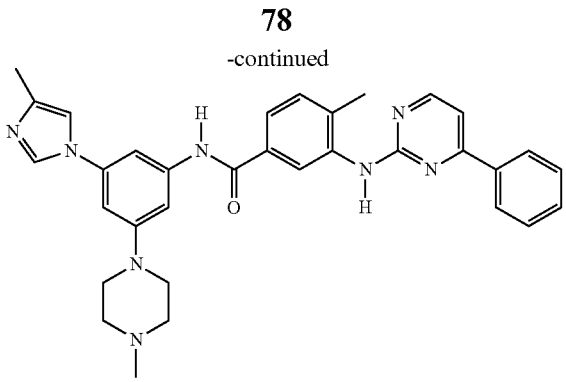

Example 6

A solution of 16 (0.97 g, 3.6 mmol) and 22 (4.02 ml, 36 mmol) in DMSO (3 mL) was heated at 90° C. for 4 h. overnight. After cooling, water was added and the resulting yellow precipitate was collected by filtration. The cake was collected and dried to give 23 (1.1 g, 88%) as a yellow solid. LCMS (m/z: m+1): 348.1.

A suspension of 23 (0.7 g, 2 mmol), 1 (0.32 g, 4 mmol), K$_2$CO$_3$ (0.55 g, 4 mmol), CuI (0.12 g, 0.6 mmol) and 8-hydroxyquinoline (0.05 g, 0.4 mmol) in DMSO (4 mL) was heated at 120° C. overnight under nitrogen. After cooling, water was added and the mixture was extracted with EtOAc twice. The combined organic layers were washed with brine, dried over Na$_2$SO$_4$ and concentrated. The residue was purified by silica gel column chromatography to give 24 (0.4 g, 66%) as a yellow solid. LCMS (m/z: m+1): 302.1.

A mixture of 24 (100 mg, 0.33 mmol) and SnCl$_2$2H$_2$O (250 mg, 1.33 mmol) in EtOH (3 ml) was heated at 80° C. for 1 hour. After cooling, silica gel was added to the reaction and the mixture was concentrated to dryness. The residue was purified by silica gel column chromatography to give 25 (80 mg, 89%) as a yellow solid.

A mixture of 13 (90 mg, 0.29 mmol), 25 (80 mg, 0.29 mmol), HATU (220 mg, 0.58 mmol) and DIEA (150 mg, 1.16 mmol) in DMF (2 mL) was heated at 70° C. overnight. After cooling, the reaction was directly purified by reverse prep-HPLC and then silica gel prep-TLC to give 4-methyl-N-(3-(4-methyl-1H-imidazol-1-yl)-5-(4-methylpiperazin-1-yl)phenyl)-3-((4-phenylpyrimidin-2-yl)amino)benzamide (64 mg, 40%) as a slight yellow solid.

Example 7. Synthesis of 4-methyl-N-(3-(4-methyl-1H-imidazol-1-yl)-5-((4-methylpiperazin-1-yl)methyl)phenyl)-3-((4-phenylpyrimidin-2-yl)amino)benzamide

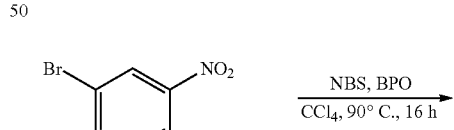

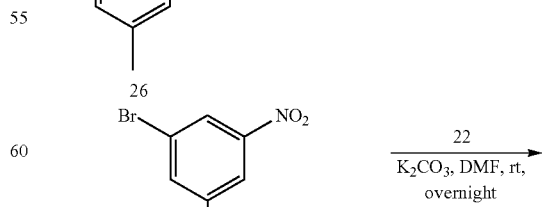

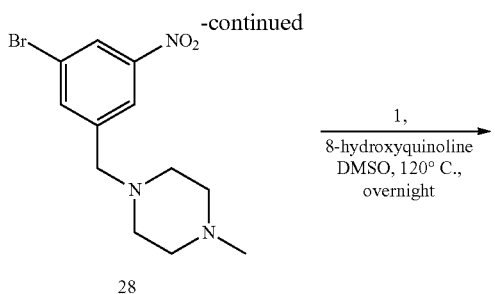

28

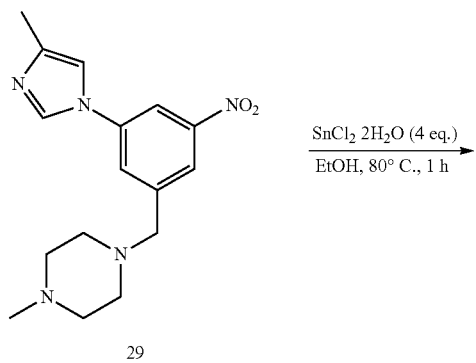

29

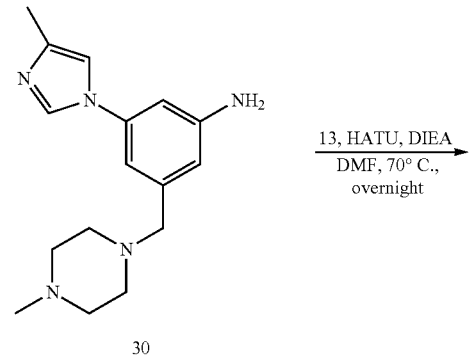

30

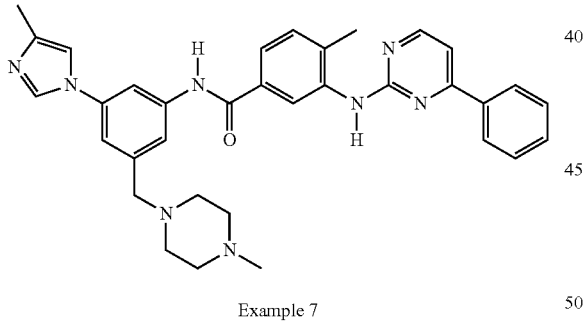

Example 7

A mixture of 26 (2.16 g, 10 mmol), N-bromosuccinimide (1.78 g, 10 mmol) and benzoyl peroxide (0.24 g, 1 mmol) in $CCl_4$ (30 mL) was heated at 90° C. for 16 h. After cooling, the precipitate was removed by filtration and the filtrate was evaporated under reduced pressure to give 27 (3.3 g, 100%) as yellow solid which was used for the next step without purification.

A mixture of 27 (1.0 g, 3.4 mmol), N-methylpiperazine (22; 0.7 g, 7 mmol) and $K_2CO_3$ (0.9 g, 7 mmol) in DMF (10 mL) was stirred at room temperature overnight. Water was added and the mixture was extracted with EtOAc twice. The combined organic layers were washed with brine, dried over $Na_2SO_4$ and concentrated. The residue was purified by silica gel column chromatography to give 28 (0.64 g, 60%) as a yellow solid. LCMS (m/z: m+1): 314.1, 316.1.

A suspension of 28 (0.63 g, 2 mmol), 1, (0.49 g, 6 mmol), $K_2CO_3$ (0.55 g, 4 mmol), CuI (0.12 g, 0.6 mmol) and 8-hydroxyquinoline (0.05 g, 0.4 mmol) in DMSO (4 mL) was heated at 120° C. overnight under nitrogen. After cooling, water was added and the mixture was extracted with EtOAc twice. The combined organic layers were washed with brine, dried over $Na_2SO_4$ and concentrated. The residue was purified by silica gel column chromatography to give 29 (0.30 g, 48%) as a yellow solid. LCMS (m/z: m+1): 316.3.

A mixture of 29 (250 mg, 0.79 mmol) and $SnCl_2 \cdot 2H_2O$ (720 mg, 3.2 mmol) in EtOH (5 ml) was heated at 80° C. for 1 hour. After cooling, silica gel was added to the reaction and concentrated to dryness. The residue was purified by silica gel column chromatography to give 30 (205 mg, 82%) as a yellow solid. LCMS (m/z: m+1): 286.4.

A mixture of 13 (107 mg, 0.35 mmol), 30 (100 mg, 0.35 mmol), HATU (266 mg, 0.70 mmol) and DIEA (181 mg, 1.4 mmol) in DMF (2 mL) was heated at 70° C. overnight. After cooling, the reaction was directly purified by reverse prep-HPLC and then silica gel prep-TLC to give 4-methyl-N-(3-(4-methyl-1H-imidazol-1-yl)-5-((4-methylpiperazin-1-yl)methyl)phenyl)-3-((4-phenylpyrimidin-2-yl)amino)benzamide (25 mg, 12%) as a slightly yellow solid.

Example 8. Synthesis of (E)-3-(3-(4-methyl-1H-imidazol-1-yl)-5-(4-methyl-3-((4-phenylpyrimidin-2-yl)amino)benzamido)phenyl)acrylic acid

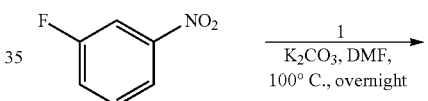

31

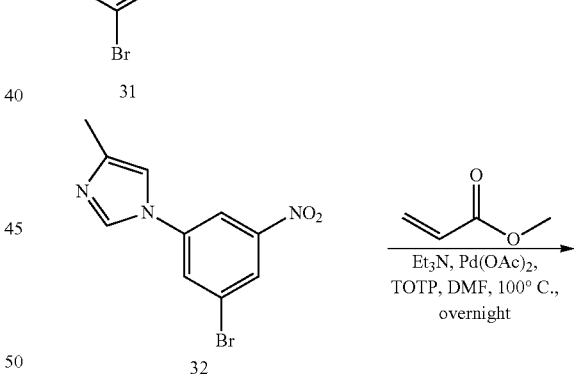

32

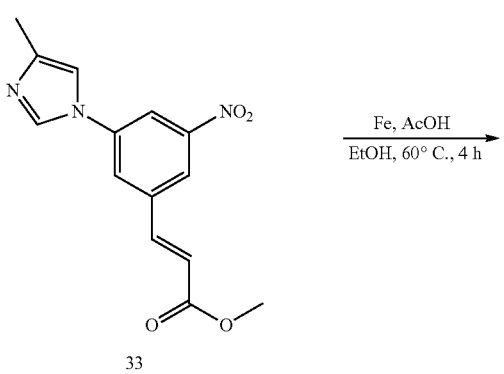

33

-continued

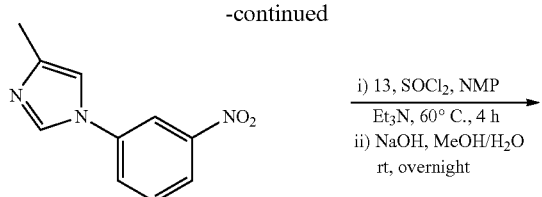

i) 13, SOCl$_2$, NMP
Et$_3$N, 60° C., 4 h
ii) NaOH, MeOH/H$_2$O
rt, overnight

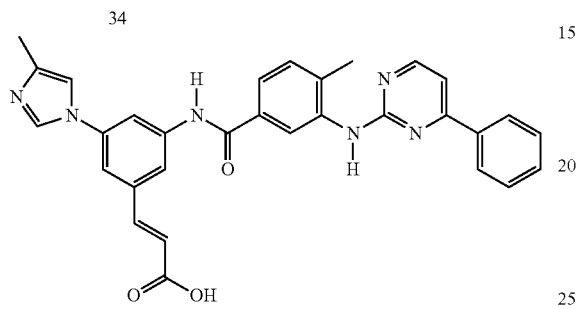

Example 8

A mixture of 31 (0.66 g, 3 mmol), 1 (0.8 g, 10 mmol) and K$_2$CO$_3$ (0.8 g, 6 mmol) in DMF (5 mL) was heated at 100° C. overnight. After cooling, water was added and the mixture was extracted with EtOAc twice. The combined organic layers were washed with brine, dried over Na$_2$SO$_4$ and concentrated. The residue was purified by silica gel column chromatography to give 32 (0.76 g, 90%) as a yellow solid. LCMS (m/z: m+1): 282.0, 284.0.

A mixture of 32 (1 g, 3.5 mmol), methyl acrylate (0.45 g, 5.25 mmol), Et$_3$N (0.7 g, 7 mmol), Pd(OAc)$_2$ (0.07 g, 0.35 mmol) and TOTP (0.2 g, 0.7 mmol) in DMF (5 mL) was heated at 100° C. overnight under nitrogen. After cooling, water was added and the mixture was extracted with EtOAc twice. The combined organic layers were washed with brine, dried over Na$_2$SO$_4$ and concentrated. The residue was purified by silica gel column chromatography to give 33 (0.8 g, 80%) as a yellow solid. LCMS (m/z: m+1): 288.2.

A mixture of 33 (200 mg, 0.70 mmol) and Fe (195 mg, 3.5 mmol) in EtOH (3 mL) and AcOH (1 mL) was heated at 60° C. for 4 h. After cooling, water was added, basified with aqueous NaHCO$_3$ and the mixture was extracted with EtOAc twice. The combined organic layers were washed with brine, dried over Na$_2$SO$_4$ and concentrated. The residue was purified by silica gel column chromatography to give 34 (150 mg, 84%) as a yellow oil. LCMS (m/z: m+1): 258.2.

To a solution of 13 (119 mg, 0.39 mmol) in NMP (2 mL) was added SOCl$_2$ (70 mg, 0.59 mmol). The reaction was heated at 60° C. for 1 hour before 34 (100 mg, 0.39 mmol) and Et$_3$N (158 mg, 1.6 mmol) was added. The resulting mixture was stirred at 60° C. for 3 hours. The reaction was directly purified by reverse prep-HPLC and then silica gel prep-TLC to give the methyl ester of Example 8 (80 mg, 38%) as a slight yellow solid. LCMS (m/z, m+1): 545.3. This material (80 mg, 0.15 mmol) was dissolved in MeOH/H$_2$O (3/1 mL) and was treated with NaOH (18 mg, 0.45 mmol). The mixture was stirred at room temperature overnight. The reaction was diluted with water and acidified with aqueous KHSO$_4$. The precipitate was filtered and washed with water. The cake was collected and dried to give (E)-3-(3-(4-methyl-1H-imidazol-1-yl)-5-(4-methyl-3-((4-phenylpyrimidin-2-yl)amino)benzamido)phenyl)acrylic acid (62 mg, 80%) as a slightly yellow solid.

Example 9. Synthesis of 3-(3-(4-methyl-1H-imidazol-1-yl)-5-(4-methyl-3-((4-phenylpyrimidin-2-yl)amino)benzamido)phenyl)propanoic acid

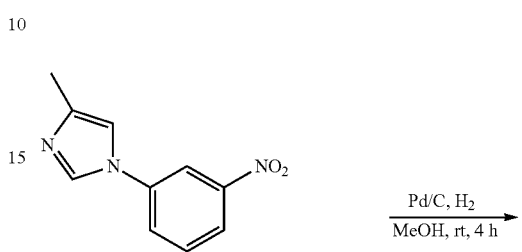

Pd/C, H$_2$
MeOH, rt, 4 h

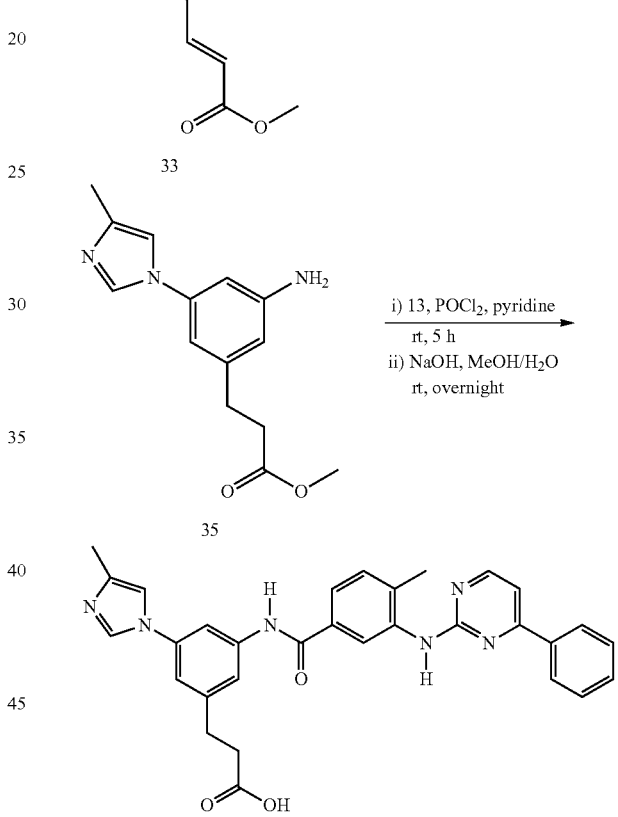

Example 9

A mixture of 33 (300 mg, 1.05 mmol) and Pd/C (100 mg) in MeOH (10 mL) was stirred at room temperature under hydrogen atmosphere for 4 hours. The reaction mixture was filtered and the filtrate was evaporated under reduced pressure to give 35 (300 mg, 100%) as a yellow oil that was used in next step without purification. LCMS (m/z: m+1): 260.2.

To a solution of 13 (122 mg, 0.40 mmol) and 35 (130 mg, 0.50 mmol) in pyridine (1.5 mL) was added POCl$_3$ (123 mg, 0.80 mmol) dropwise. The reaction was stirred at room temperature for 5 hours. The reaction was poured in ice-water and the precipitate was collected by filtration. The solid was further purified by silica gel prep-TLC to give the methyl ester of Example 9 (60 mg, 27%) as a slightly yellow solid. LCMS (m/z: m+1): 547.3. To a solution of this material (60 mg, 0.11 mmol) in MeOH/H$_2$O (3/1 mL) was added NaOH (13 mg, 0.33 mmol). The mixture was stirred at room temperature overnight. The reaction was diluted with water and acidified with aqueous KHSO₄. The precipitate was filtered and washed with water. The cake was collected, dried and washed with CH₂Cl₂ to give Synthesis of 3-(3-(4-methyl-1H-imidazol-1-yl)-5-(4-methyl-3-((4-phenylpyrimidin-2-yl)amino)benzamido)phenyl)propanoic acid (25 mg, 43%) as a slightly yellow solid.

Example 10. Synthesis of 4-methyl-N-(3-(4-methyl-1H-imidazol-1-yl)-5-(2-sulfamoylethyl)phenyl)-3-((4-phenylpyrimidin-2-yl)amino)benzamide

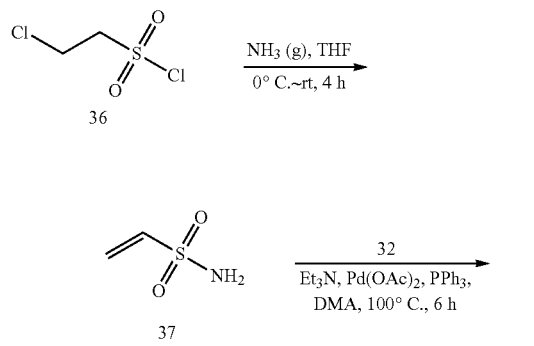

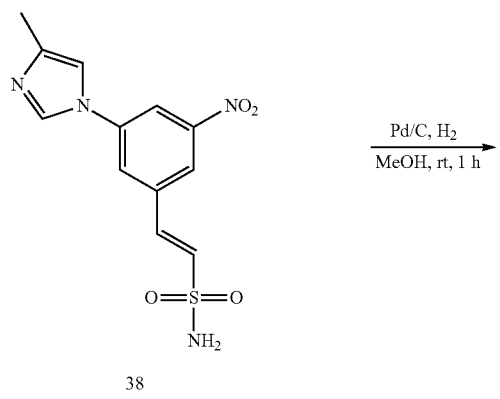

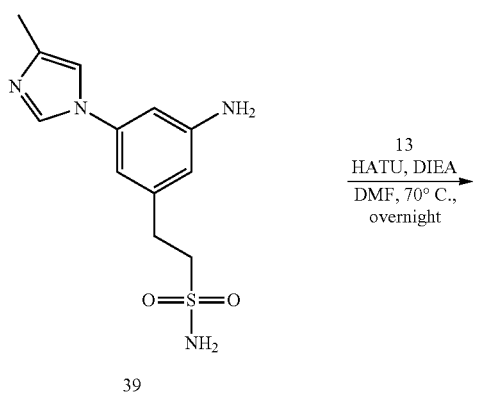

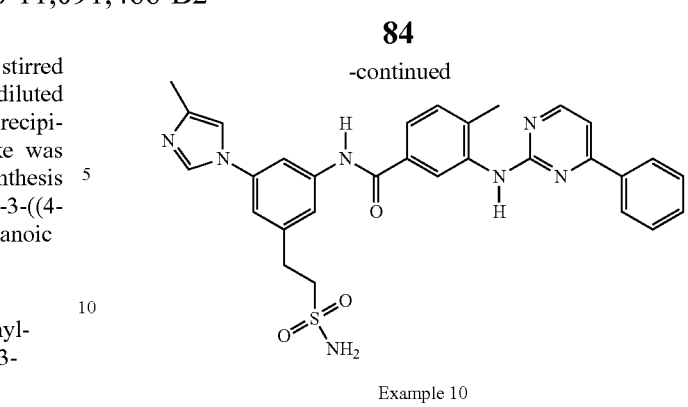

Example 10

To a solution of 36 (1.0 g, 6.13 mmol) in THF (10 mL) was bubbled NH₃ (gas) slowly at 0° C. for 2 hours. The reaction was then stirred at room temperature for 2 hours. The reaction mixture was filtered and the filtrate was evaporated under reduced pressure. The residue was purified by silica gel column chromatography to give 37 (300 mg, 45%) as a colorless oil. ¹H NMR (400 MHz, DMSO-d6): δ 7.05 (br s, 2H); 6.78 (dd, J=16.4, 10 Hz, 1H); 6.00 (d, J=16.4 Hz, 1H); 5.82 (d, J=10 Hz, 1H).

A mixture of 32 (350 mg, 1.25 mmol), 37 (200 mg, 1.87 mmol), Et₃N (253 mg, 2.5 mmol), Pd(OAc)₂ (28 mg, 0.125 mmol) and PPh₃ (63 mg, 0.25 mmol) in DMF (3 mL) was heated at 100° C. for 6 hours under nitrogen. After cooling, water was added and the mixture was extracted with EtOAc twice. The combined organic layers were washed with brine, dried over Na₂SO₄ and concentrated. The residue was purified by silica gel column chromatography to give 38 (220 mg, 57%) as a yellow solid. LCMS (m/z: m+1): 309.1.

A mixture of 38 (80 mg, 0.26 mmol) and Pd/C (80 mg) in MeOH (5 mL) was stirred at room temperature under hydrogen atmosphere for 1 hour. The reaction mixture was filtered and the filtrate was evaporated under reduced pressure to give 39 (72 mg, 99%) as a yellow solid which was used in next step without purification. LCMS (m/z: m+1): 281.2.

A mixture of 13 (78 mg, 0.26 mmol), 39 (72 mg, 0.26 mmol), HATU (198 mg, 0.52 mmol) and DIEA (134 mg, 1.04 mmol) in DMF (1.5 mL) was heated at 70° C. overnight. After cooling, the reaction was directly purified by reverse prep-HPLC and then silica gel prep-TLC to give 4-methyl-N-(3-(4-methyl-1H-imidazol-1-yl)-5-(2-sulfamoylethyl)phenyl)-3-((4-phenylpyrimidin-2-yl)amino)benzamide (13 mg, 8.9%) as an off-white solid.

Example 11. Synthesis of N-(3-butyl-5-(4-methyl-1H-imidazol-1-yl)phenyl)-4-methyl-3-((4-phenylpyrimidin-2-yl)amino)benzamide

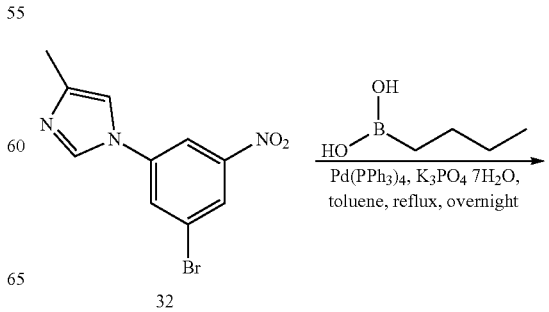

85

-continued

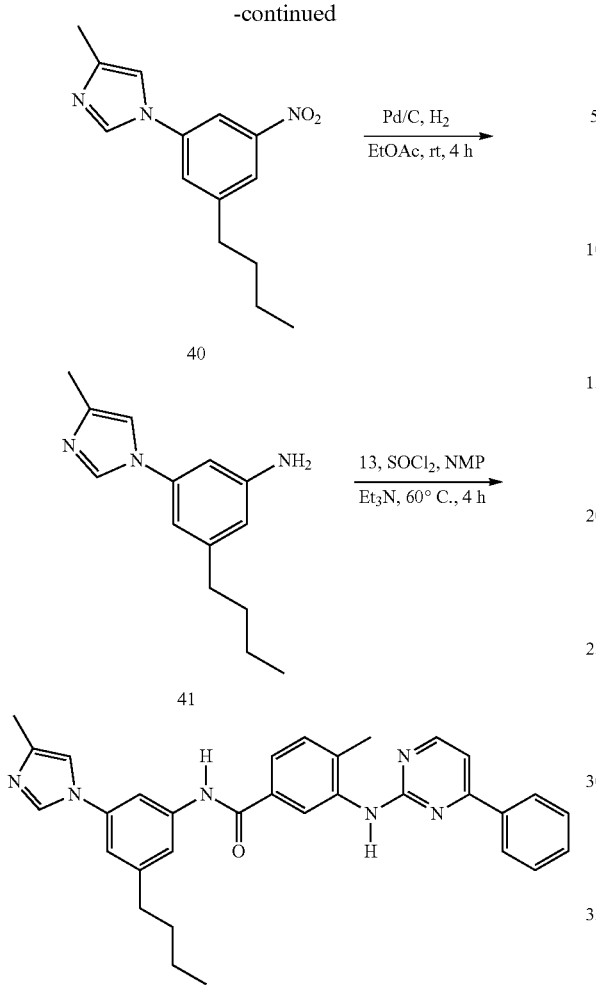

Example 11

Example 12. Synthesis of 4-methyl-N-(3-(4-methyl-1H-imidazol-1-yl)-5-(trifluoromethyl)phenyl)benzamide

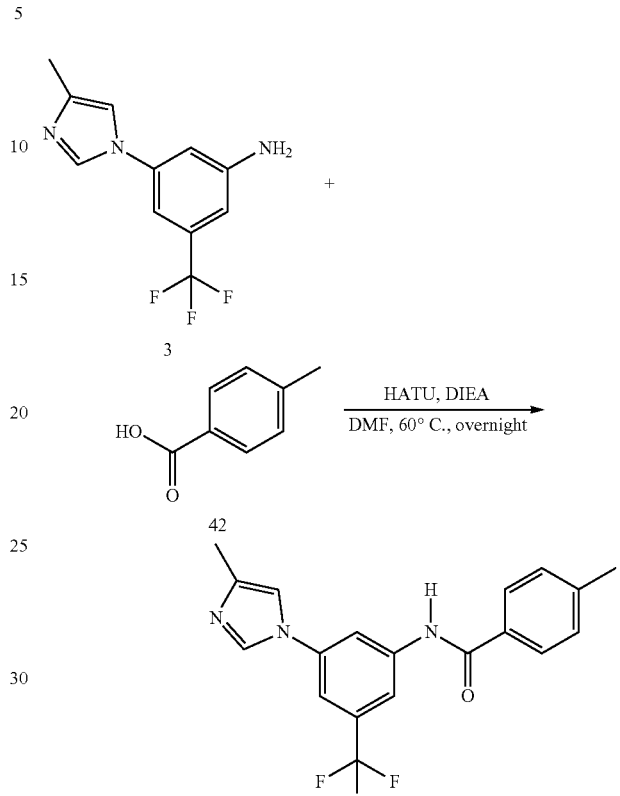

Example 12

A mixture of 32 (200 mg, 0.7 mmol), butylboronic acid (289 mg, 2.8 mmol), K₃PO₄ 7H₂O (720 mg, 2.1 mmol) and Pd(PPh₃)₄ (243 mg, 0.21 mmol) in toluene (5 mL) was refluxed overnight under nitrogen. After cooling, water was added and the mixture was extracted with EtOAc twice. The combined organic layers were washed with brine, dried over Na₂SO₄ and concentrated. The residue was purified by silica gel column chromatography to give 40 (53 mg, 29%) as a slightly yellow solid. LCMS (m/z: m+1): 260.2.

A mixture of 40 (53 mg, 0.2 mmol) and Pd/C (50 mg) in EtOAc (5 mL) was stirred at room temperature under hydrogen atmosphere for 4 hours. The reaction mixture was filtered and the filtrate was evaporated under reduced pressure to give 41 (50 mg, 100%) as a slightly yellow solid that was used in next step without further purification. LCMS (m/z: m+1): 230.3.

To a solution of 13 (67 mg, 0.22 mmol) in NMP (1 mL) was added SOCl₂ (39 mg, 0.33 mmol). The reaction was heated at 60° C. for 1 hour before 41 (50 mg, 0.22 mmol) and Et₃N (89 mg, 0.88 mmol) was added. The resulting mixture was stirred at 60° C. for 3 hours. The reaction was directly purified by reverse prep-HPLC and then silica gel prep-TLC to give N-(3-butyl-5-(4-methyl-1H-imidazol-1-yl)phenyl)-4-methyl-3-((4-phenylpyrimidin-2-yl)amino)benzamide (23 mg, 20%) as a slightly yellow solid.

A mixture of 3 (100 mg, 0.41 mmol), p-toluic acid (42) (56 mg, 0.41 mmol), HATU (312 mg, 0.82 mmol) and DIEA (207 mg, 1.6 mmol) in DMF (2 mL) was heated at 60° C. overnight. After cooling, the reaction was directly purified by reverse prep-HPLC and then silica gel prep-TLC to give 4-methyl-N-(3-(4-methyl-1H-imidazol-1-yl)-5-(trifluoromethyl)phenyl)benzamide (21 mg, 14%) as an off-white solid.

Example 13. Synthesis of 4-methyl-N-(3-(4-methyl-1H-imidazol-1-yl)-5-(trifluoromethyl)phenyl)-3-phenoxybenzamide

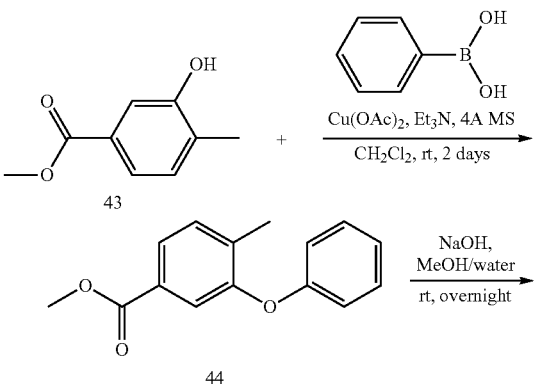

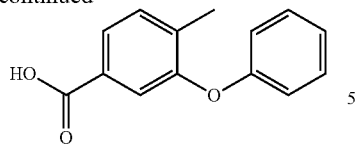

45

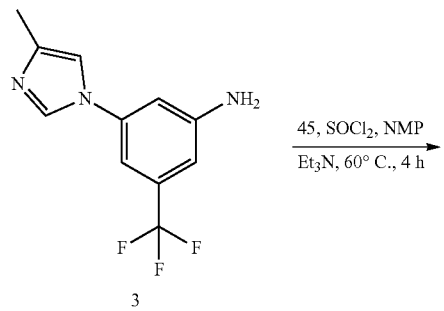

3

Example 14. Synthesis of 3-(benzyloxy)-4-methyl-N-(3-(4-methyl-1H-imidazol-1-yl)-5-(trifluoromethyl)phenyl)benzamide

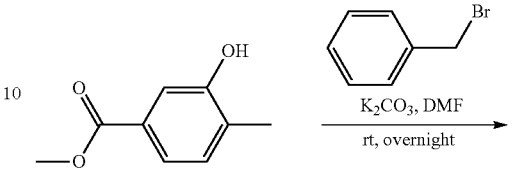

43

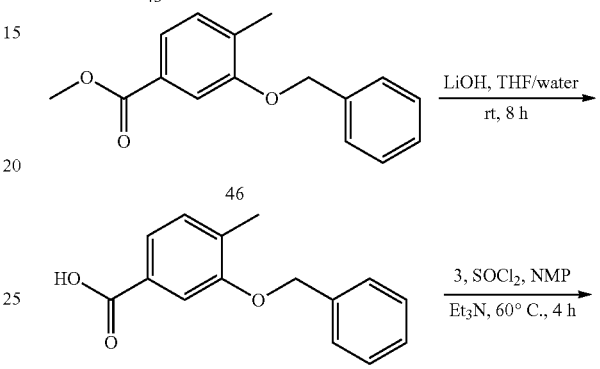

46

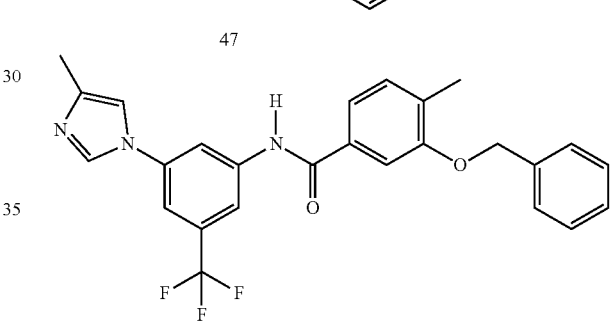

47

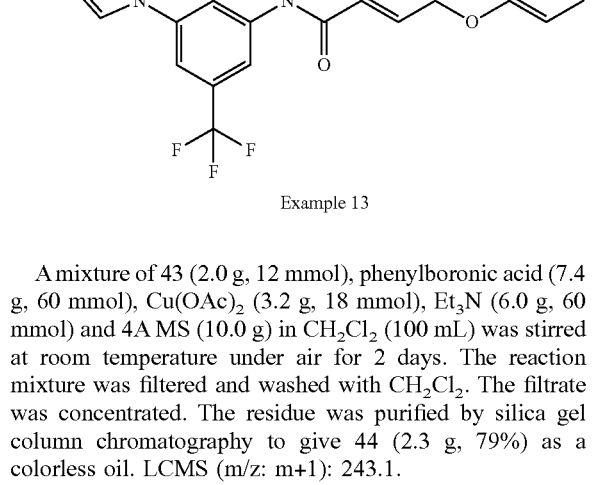

Example 13

Example 14

A mixture of 43 (2.0 g, 12 mmol), phenylboronic acid (7.4 g, 60 mmol), Cu(OAc)$_2$ (3.2 g, 18 mmol), Et$_3$N (6.0 g, 60 mmol) and 4A MS (10.0 g) in CH$_2$Cl$_2$ (100 mL) was stirred at room temperature under air for 2 days. The reaction mixture was filtered and washed with CH$_2$Cl$_2$. The filtrate was concentrated. The residue was purified by silica gel column chromatography to give 44 (2.3 g, 79%) as a colorless oil. LCMS (m/z: m+1): 243.1.

A mixture of 44 (2.3 g, 9.5 mmol) and NaOH (759 mg, 19 mmol) in MeOH/H$_2$O (20/5 mL) was stirred at room temperature overnight. The reaction mixture was concentrated. The residue dissolved in water, acidified to pH 3 with aqueous HCl and extracted with EtOAc twice. The combined organic layers were washed with brine, dried over Na$_2$SO$_4$ and evaporated under reduced pressure to give 45 (1.9 g, 88%) as a white solid. To a solution of this material (48 mg, 0.21 mmol) in NMP (1 mL) was added SOCl$_2$ (38 mg, 0.32 mmol). The reaction was heated at 60° C. for 1 hour before 3 (50 mg, 0.21 mmol) and Et$_3$N (85 mg, 0.84 mmol) was added. The resulting mixture was stirred at 60° C. for 3 hours. The reaction was directly purified by reverse prep-HPLC and then silica gel prep-TLC to give 4-methyl-N-(3-(4-methyl-1H-imidazol-1-yl)-5-(trifluoromethyl)phenyl)-3-phenoxybenzamide (27 mg, 29%) as a slightly yellow solid.

A mixture of 43 (100 mg, 0.6 mmol), benzyl bromide (103 mg, 0.6 mmol), and K$_2$CO$_3$ (166 mg, 1.2 mmol) in DMF (1 mL) was stirred at room temperature overnight. The reaction mixture was diluted with water and extracted with EtOAc twice. The combined organic layers were washed with water, brine, dried over Na$_2$SO$_4$ and evaporated under reduced pressure. The residue was purified by silica gel prep-TLC to give 46 (100 mg, 65%) as a white solid. LCMS (m/z: m+1): 257.2.

A mixture of 46 (100 mg, 0.39 mmol) and LiOH (28 mg, 1.17 mmol) in THF/H$_2$O (2/1 mL) was stirred at room temperature for 8 hours. TLC indicated the reaction was complete. The reaction mixture was diluted with water and acidified to pH 3 with aqueous HCl. The resulting precipitate was filtered washed with water and dried to give 47 (90 mg, 95%) as a white solid. To a solution of 47 (100 mg, 0.41 mmol) in NMP (1.5 mL) was added SOCl$_2$ (74 mg, 0.62 mmol). The reaction was heated at 60° C. for 1 hour before 3 (100 mg, 0.41 mmol) and Et$_3$N (166 mg, 1.64 mmol) were added. The resulting mixture was stirred at 60° C. for 3 hours. The reaction was directly purified by reverse prep-HPLC and then silica gel prep-TLC to give 3-(benzyloxy)-4-methyl-N-(3-(4-methyl-1H-imidazol-1-yl)-5-(trifluoromethyl)phenyl)benzamide (25 mg, 13%) as a white solid.

Example 15. Synthesis of 4-methyl-N-(3-(4-methyl-1H-imidazol-1-yl)-5-(trifluoromethyl)phenyl)-3-((4-phenylpyrimidin-2-yl)amino)benzenesulfonamide

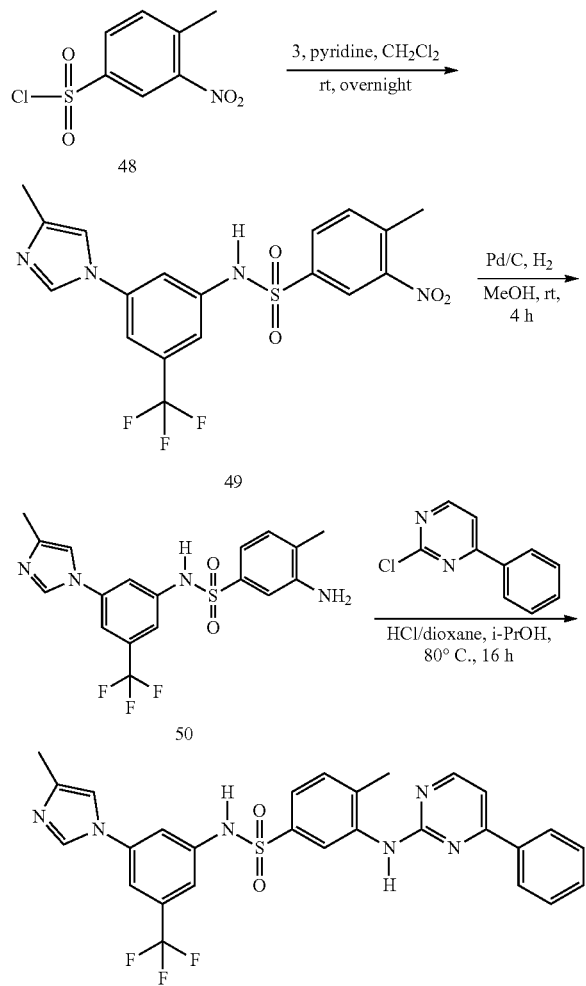

Example 15

To a solution of 3 (500 mg, 2.1 mmol) and 48 (489 mg, 2.1 mmol) in $CH_2Cl_2$ (10 mL) was added pyridine (242 mg, 3.1 mmol), dropwise. The reaction was stirred at room temperature overnight. Water was added and the mixture was extracted with $CH_2Cl_2$ twice. The combined organic layers were dried over $Na_2SO_4$ and concentrated. The residue was purified by silica gel column chromatography to give 49 (180 mg, 20%) as a slightly yellow solid. LCMS (m/z: m+1): 441.1.

A mixture of 49 (180 mg, 0.41 mmol) and Pd/C (60 mg) in MeOH (10 mL) was stirred at room temperature under hydrogen atmosphere for 4 hours. The reaction mixture was filtered and the filtrate was evaporated under reduced pressure to give 50 (170 mg, 100%) as a yellow solid, which was used in next step without further purification. This material (170 mg, 0.41 mmol) and 2-chloro-4-phenylpyrimidine (158 mg, 0.83 mmol) in i-PrOH (3 mL) was added a saturated solution of HCl in dioxane (0.5 mL). The reaction was heated at 80° C. for 16 hours before being concentrated under reduced pressure. The residue was dissolved in $CH_3CN$ and basified with $Et_3N$. The resulting solution was concentrated, then purified by reverse prep-HPLC and then silica gel prep-TLC to give 4-methyl-N-(3-(4-methyl-1H-imidazol-1-yl)-5-(trifluoromethyl)phenyl)-3-((4-phenylpyrimidin-2-yl)amino)benzenesulfonamide (20 mg, 8.5%) as a white solid.

Example 16. 3-((4-acetamidopyrimidin-2-yl)amino)-4-methyl-N-(3-(4-methyl-1H-imidazol-1-yl)-5-(trifluoromethyl)phenyl)benzamide

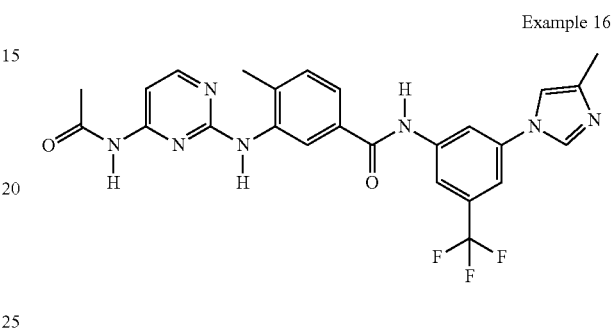

Example 16

This compound was prepared by treating methyl 3-((4-acetamidopyrimidin-2-yl)amino)-4-methylbenzoate with 3 in the presence of trimethylaluminum (2.0M in THF) followed by purification by HPLC to give 3-((4-acetamidopyrimidin-2-yl)amino)-4-methyl-N-(3-(4-methyl-1H-imidazol-1-yl)-5-(trifluoromethyl)phenyl)benzamide in 3% isolated yield as an off white solid. Analytical data are summarized in Table 1.

Example 17. 4-methyl-3-((4-(pyridin-3-yl)pyrimidin-2-yl)amino)-N-(3-(trifluoromethyl)phenyl)benzamide

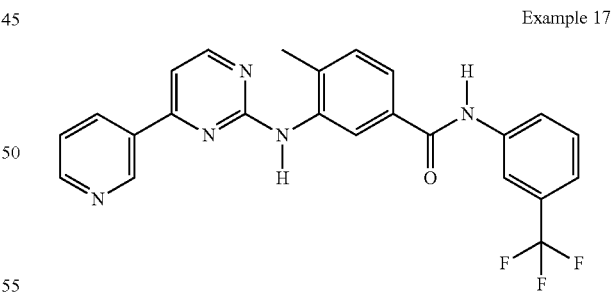

Example 17

This compound was prepared similarly to Example 16 using methyl 4-methyl-3-((4-(pyridin-3-yl)-pyrimidin-2-yl)amino)benzoate, 3-trifluoromethylaniline, and trimethylaluminum (2.0 M in THF) followed by column chromatography to yield 4-methyl-3-((4-(pyridin-3-yl)pyrimidin-2-yl)amino)-N-(3-(trifluoromethyl)phenyl)benzamide in 48% yield as an off-white solid. Analytical data are summarized in Table 1.

Example 18. 5-methyl-2-(3-(4-methyl-1H-imidazol-1-yl)-5-(trifluoromethyl)phenyl)-6-((4-(pyridin-3-yl)pyrimidin-2-yl)amino)isoindoline-1,3-dione

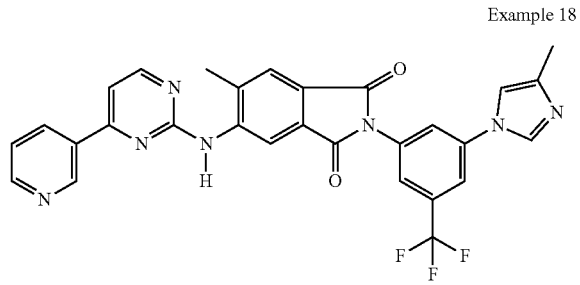 [SMILES: Cc1cn(-c2cc(N3C(=O)c4cc(C)c(Nc5nccc(-c6cccnc6)n5)cc4C3=O)cc(C(F)(F)F)c2)cn1]

Example 18

3 was combined with protected 5-amino-6-methylisobenzofuran-1,3-dione to form 5-amino-6-methyl-2-(3-(4-methyl-1H-imidazol-1-yl)-5-(trifluoromethyl)phenyl)-isoindoline-1,3-dione, which was then coupled with 2-chloro-4-(pyridin-3-yl)pyrimidine in the presence of BINAP (0.1 eq.), palladium diacetate (0.02 eq.) sodium carbonate (4 eq.) in dioxane followed by HPLC purification to yield. 5-methyl-2-(3-(4-methyl-1H-imidazol-1-yl)-5-(trifluoromethyl)phenyl)-6-((4-(pyridin-3-yl)pyrimidin-2-yl)amino)isoindoline-1,3-dione (38 mg, 43%) as a yellow solid. Analytical data are summarized in Table 1.

Example 19. Synthesis of (S)—N-(3-((3-aminopiperidin-1-yl)methyl)-5-(4-methyl-1H-imidazol-1-yl)phenyl)-3-((4-(4-fluorophenyl)pyrimidin-2-yl)amino)-4-methylbenzamide

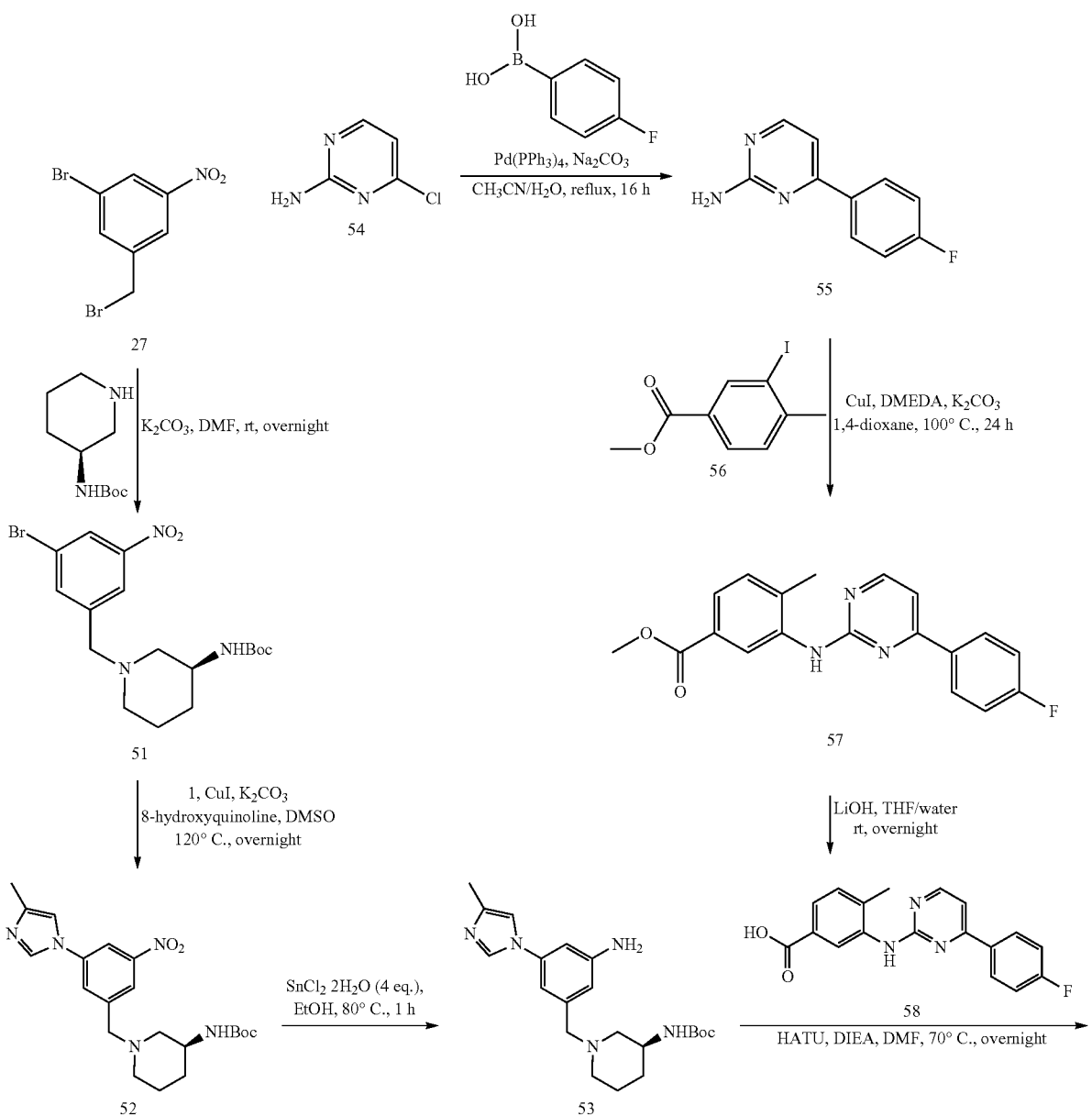

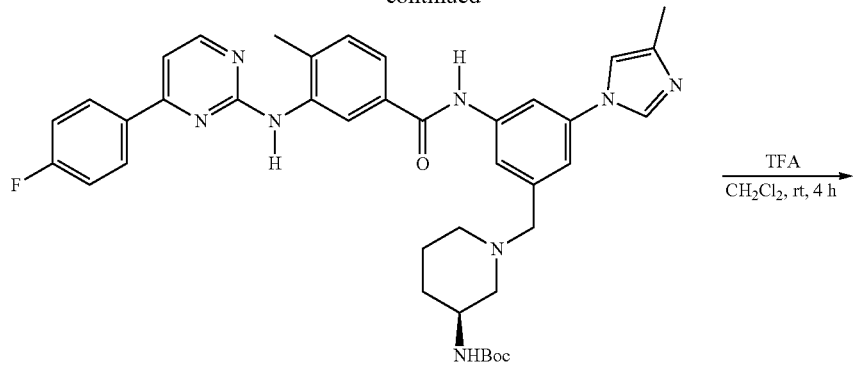

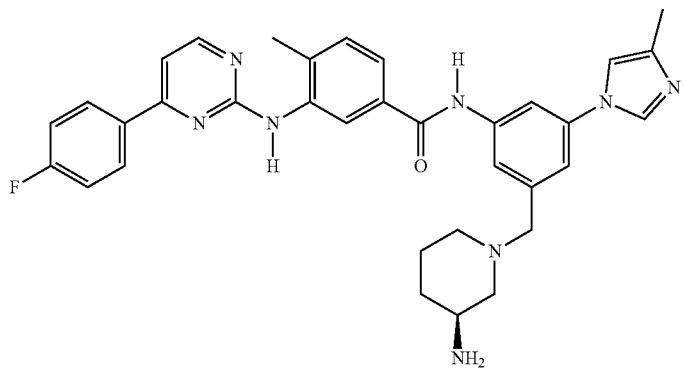

Example 19

A mixture of 27 (1366 mg, 4.63 mmol), (S)-tert-butyl piperidin-3-ylcarbamate (1020 mg, 4.63 mmol) and $K_2CO_3$ (768 mg, 5.56 mmol) in DMF (8 mL) was stirred at room temperature overnight. Water was added and the mixture was extracted with EtOAc twice. The combined organic layers were washed with brine, dried over $Na_2SO_4$ and concentrated. The residue was purified by silica gel column chromatography to give 51 (870 mg, 45%) as a slightly yellow solid. LCMS (m/z: m+1): 414.0, 116.1.

A suspension of 51 (870 mg, 2.1 mmol), 1 (517 mg, 6.3 mmol), $K_2CO_3$ (580 mg, 4.2 mmol), CuI (120 mg, 0.63 mmol) and 8-hydroxyquinoline (61 mg, 0.42 mmol) in DMSO (8 mL) was heated at 120° C. overnight under nitrogen. After cooling, water was added and the mixture was extracted with EtOAc twice. The combined organic layers were washed with brine, dried over $Na_2SO_4$ and concentrated. The residue was purified by silica gel column chromatography to give 52 (630 mg, 72%) as a slightly yellow solid. LCMS (m/z: m+1): 416.3.

A mixture of 52 (630 mg, 1.52 mmol) and $SnCl_2 \cdot 2H_2O$ (1369 mg, 6.06 mmol) in EtOH (13 ml) was heated at 80° C. for 1 hour. After cooling, silica gel was added to the reaction and concentrated to dryness. The residue was purified by silica gel column chromatography to give 53 (430 mg, 74%) as a slightly yellow solid. LCMS (m/z: m+1): 386.4.

A mixture of 54 (9.5 g, 73.3 mmol), 4-fluorophenylboronic acid (10.3 g, 73.3 mmol), $Na_2CO_3$ (15.5 g, 147 mmol), and $Pd(PPh_3)_4$ (1.5 g) in $CH_3CN/H_2O$ (2/1, 200 mL) was refluxed under $N_2$ for 16 hours. After cooling, the mixture was diluted with water and extracted with EtOAc twice. The combined organic layers were washed with brine, fried over $Na_2SO_4$, filtered, concentrated and purified by silica gel column chromatography to give 55 (5.1 g, 37%) as a slightly yellow solid. LCMS (m/z: m+1): 190.2.

A mixture of 56 (11.2 g, 40.4 mmol), 55 (5.1 g, 27.0 mmol), $K_2CO_3$ (7.5 g, 54.0 mmol), DMEDA (476 mg, 5.4 mmol) and CuI (1.28 g, 6.7 mmol) in 100 ml of dioxane was stirred at 100° C. under $N_2$ for 24 hours. The mixture was filtered, concentrated and purified by column chromatography to give 57 (1.6 g, 18%) as a slightly yellow solid. LCMS (m/z: m+1): 338.3.

To a solution of 57 (1.6 g, 4.74 mmol) in $THF/H_2O$ (32/16 mL) was added LiOH (341 mg, 14.2 mmol). The reaction was stirred at room temperature overnight, concentrated. To the residue water was added and then acidified to pH 4 with aqueous $KHSO_4$. The precipitate was filtered and washed with water and EtOAc. The cake was collected and dried to give 58 (1.3 g, 85%) as an off-white solid. LCMS (m/z: m+1): 324.1.

A mixture of 53 (130 mg, 0.34 mmol), 58 (109 mg, 0.34 mmol), HATU (257 mg, 0.68 mmol) and DIEA (218 mg, 1.69 mmol) in DMF (2 mL) was heated at 70° C. overnight. After cooling, the reaction was directly purified by reverse prep-HPLC and then silica gel prep-TLC to give 59 (33 mg, 14%) as a slightly yellow solid. LCMS (m/z: m+1): 691.3

To a solution of 59 (33 mg, 0.048 mmol) in $CH_2Cl_2$ (2 mL) was added TFA (1 mL) and the reaction was stirred at room temperature for 4 hours before concentrated under reduced pressure. The residue was treated with water, basified with 0.5 N NaOH and extracted with $CH_2Cl_2$/MeOH (15/1) 3 times. The combined organic layers were dried over $Na_2SO_4$, filtered, concentrated and purified by reverse prep-HPLC to give (S)—N-(3-((3-aminopiperidin-1-yl)methyl)-5-(4-methyl-1H-imidazol-1-yl)phenyl)-3-((4-(4-fluorophenyl)pyrimidin-2-yl)amino)-4-methylbenzamide (14 mg, 50%) as an off-white solid.

Example 20. Synthesis of (S)-1-(3-(3-((4-(4-fluoro-phenyl)pyrimidin-2-yl)amino)-4-methylbenzamido)-5-(4-methyl-1H-imidazol-1-yl)benzyl)piperidine-2-carboxylic acid
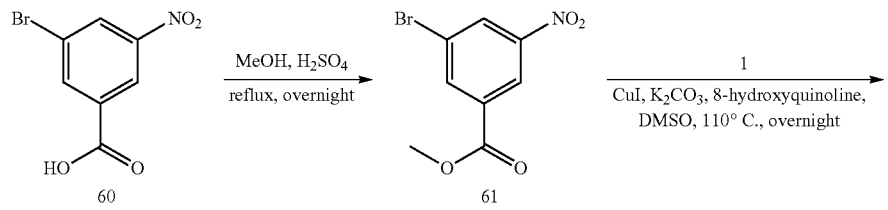
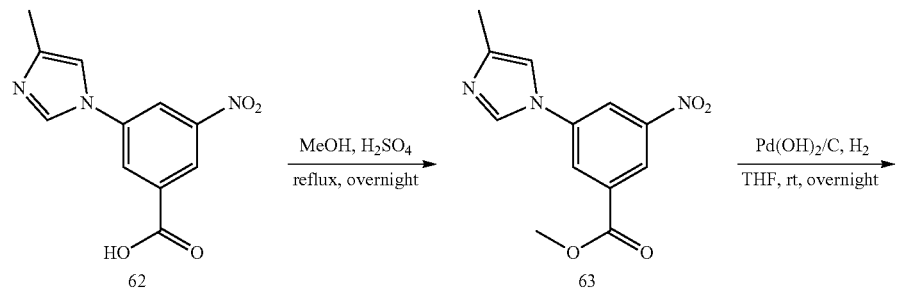
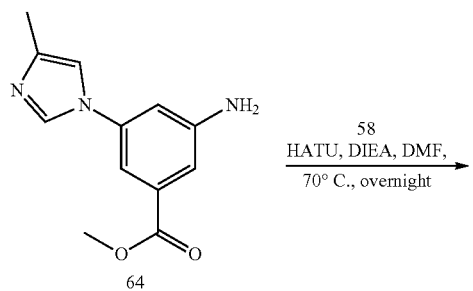
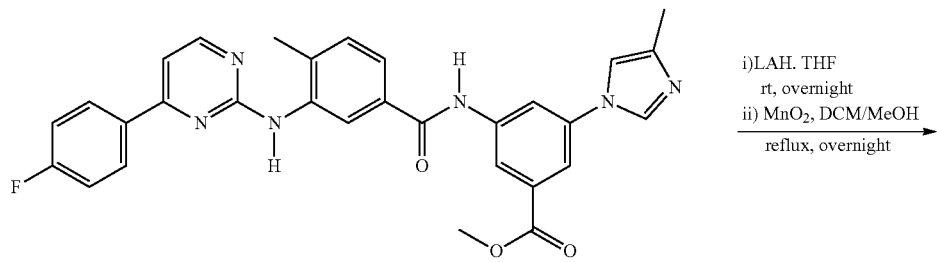

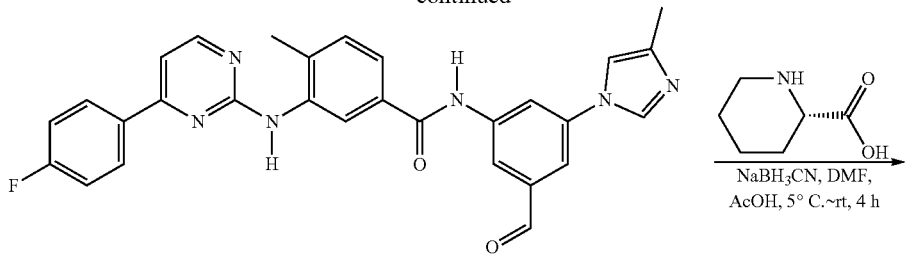

66

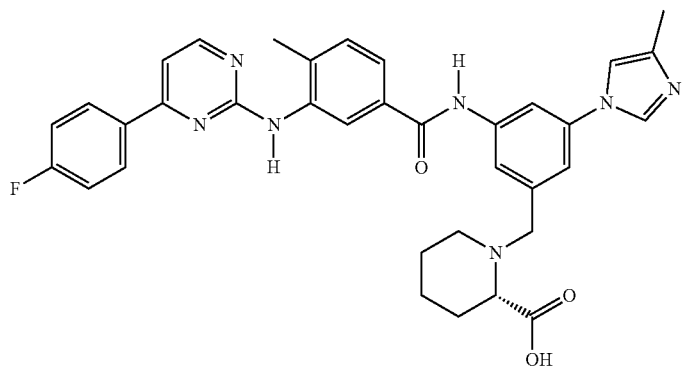

Example 20

To a solution of 60 (1.0 g, 4.1 mmol) in MeOH (30 mL) was added dropwise $H_2SO_4$ (5 mL). The reaction was refluxed overnight before concentrated. The residue was treated with water and extracted with EtOAc twice. The combined organic layers were washed with brine, dried over $Na_2SO_4$ and evaporated under reduced pressure to give 61 (1.1 g, 100%) as an off-white solid. A suspension of 61 (900 mg, 3.46 mmol), 1 (853 mg, 10.4 mmol), $K_2CO_3$ (955 mg, 6.92 mmol), CuI (198 mg, 1.04 mmol) and 8-hydroxyquinoline (100 mg, 0.69 mmol) in DMSO (9 mL) was heated at 110° C. overnight under nitrogen. After cooling, water was added and the mixture was acidified by aqueous $KHSO_4$, and extracted with EtOAc 3 times. The product was in the water phase. The water layer was directly purified by reverse prep-HPLC to give 62 (310 mg, 36%) as a white solid. LCMS (m/z: m+1): 248.1.

To a mixture of 62 (310 mg, 1.26 mmol) in MeOH (30 mL) was added dropwise $H_2SO_4$ (2 mL). The reaction was refluxed overnight before concentrated. The residue treated with water, basified by 2N NaOH under ice-water bath and extracted with $CH_2Cl_2$ 3 times. The combined organic layers were washed with brine, dried over $Na_2SO_4$ and evaporated under reduced pressure to give 63 (260 mg, 79%) as a slightly yellow solid. LCMS (m/z: m+1): 262.1.

A mixture of 63 (260 mg, 1.0 mmol) and Pd/C (80 mg) in THF (10 mL) was stirred at room temperature under hydrogen atmosphere overnight. The reaction mixture was filtered and the filtrate was concentrated under reduced pressure to give 64 (231 mg, 100%) as a slightly yellow oil. LCMS (m/z: m+1): 232.3.

A mixture of 64 (231 mg, 1.0 mmol), 58 (323 mg, 1.0 mmol), HATU (760 mg, 2.0 mmol) and DIEA (646 mg, 5.0 mmol) in DMF (3 mL) was heated at 70° C. overnight. After cooling, the reaction was directly purified by reverse prep-HPLC and then silica gel prep-TLC to give 65 (148 mg, 28%) as a slightly yellow solid. LCMS (m/z: m+1): 537.3.

To a solution of 65 (148 mg, 0.28 mmol) in THF (5 mL) was added LAH (42 mg, 1.10 mmol). The mixture was stirred at room temperature overnight before quenched with water (100 mg). The resulting mixture was filtered through Celite and washed with $CH_2Cl_2$/MeOH (10/1). The filtrate was evaporated under reduced pressure to give the fully reduced benzylic alcohol (145 mg, 100%) as a slightly yellow solid which was used in next step without purification. A mixture of this material (125 mg, 0.25 mmol) and $MnO_2$ (427 mg, 4.9 mmol) in $CH_2Cl_2$/MeOH (20/1, 30 mL) was refluxed overnight. The reaction mixture was filtered and washed with $CH_2Cl_2$/MeOH (20/1, 60 mL). The filtrate was evaporated under reduced pressure to give aldehyde 66 (123 mg, 99%) as a slightly yellow solid. This material was also used in the next step without intermediate purification. To a solution of 66 (103 mg, 0.20 mmol) and (S)-piperidine-2-carboxylic acid (129 mg, 1.0 mmol) in DMF (2 mL) was added AcOH (2 drops) and then $NaBH_3CN$ (63 mg, 1.0 mmol) at 5° C. The mixture was stirred at room temperature for 4 hours. The reaction mixture was directly purified by reverse prep-HPLC to give crude product (48 mg, ~60% purity). 23 mg of the crude product was further purified by silica gel prep-TLC to give pure (S)-1-(3-(3-((4-(4-fluorophenyl)pyrimidin-2-yl)amino)-4-methylbenzamido)-5-(4-methyl-1H-imidazol-1-yl)benzyl)piperidine-2-carboxylic acid (12 mg, 20%) as a white solid.

Example 21. Synthesis of (S)-1-(3-(3-((4-(4-fluoro-phenyl)pyrimidin-2-yl)amino)-4-methylbenzamido)-5-(4-methyl-1H-imidazol-1-yl)benzyl)piperidine-2-carboxamide

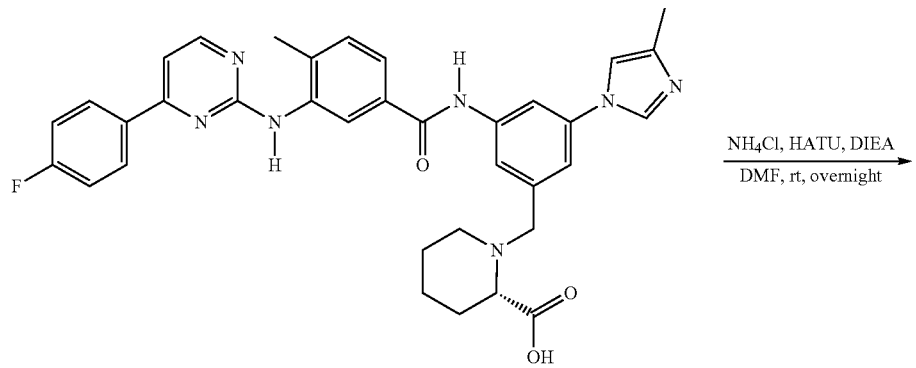
Example 20

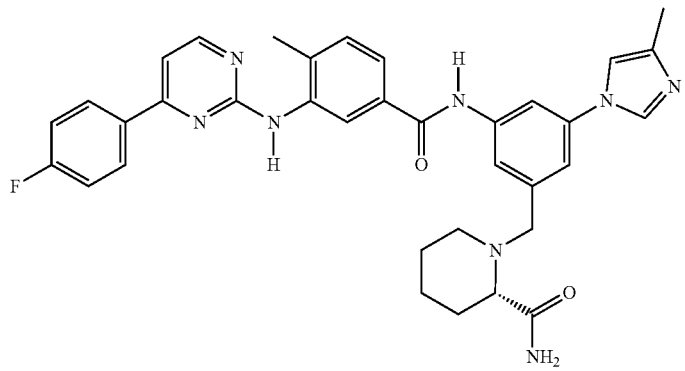
Example 21

A mixture of crude (S)-1-(3-(3-((4-(4-fluorophenyl)pyrimidin-2-yl)amino)-4-methylbenzamido)-5-(4-methyl-1H-imidazol-1-yl)benzyl)piperidine-2-carboxylic acid (25 mg, 0.040 mmol), NH₄Cl (10.8 mg, 0.20 mmol), HATU (46 mg, 0.12 mmol) and DIEA (41 mg, 0.32 mmol) in DMF (1 mL) was stirred at room temperature overnight. The reaction was directly purified by reverse prep-HPLC and then silica gel prep-TLC to give (S)-1-(3-(3-((4-(4-fluorophenyl)pyrimidin-2-yl)amino)-4-methylbenzamido)-5-(4-methyl-1H-imidazol-1-yl)benzyl)piperidine-2-carboxamide (13.5 mg, 54%) as a white solid.

Example 22. Synthesis of 3-((4-(4-fluorophenyl)pyrimidin-2-yl)amino)-4-methyl-N-(3-(4-methyl-1H-imidazol-1-yl)-5-(4-methylpiperazin-1-yl)phenyl)benzenesulfonamide

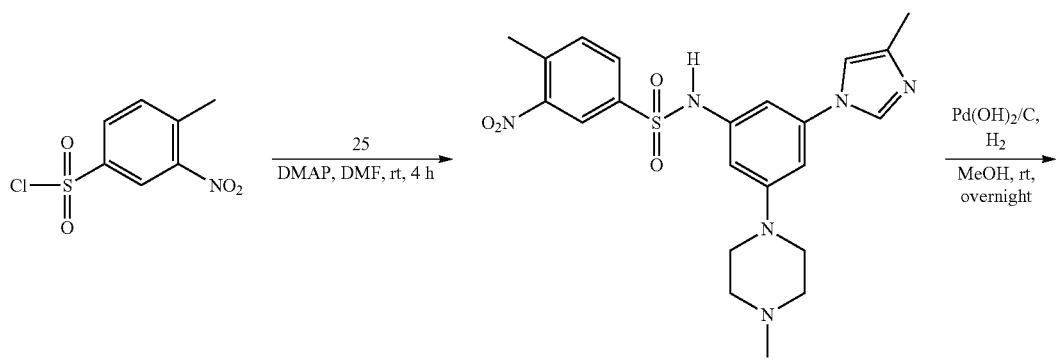

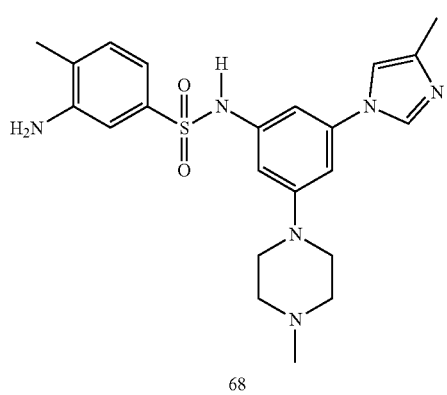

68

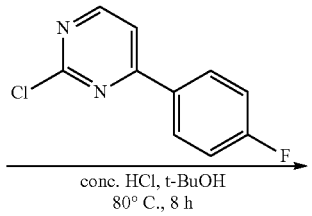

conc. HCl, t-BuOH
80° C., 8 h

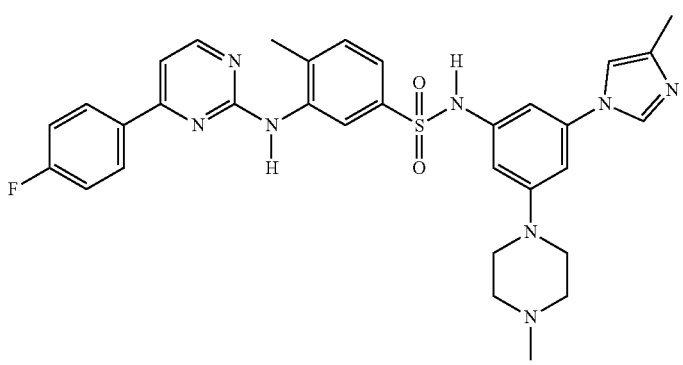

Example 22

To a solution of 25 (500 mg, 1.84 mmol) and 4-methyl-3-nitrobenzenesulfonyl chloride (651 mg, 2.76 mmol) in DMF (5 ml) was added DMAP (449 mg, 3.68 mmol) in portions. The reaction was stirred at room temperature overnight and directly purified by reverse prep-HPLC to give 67 (310 mg, 36%) as a slightly yellow solid. LCMS (m/z: m+1): 471.3.

A mixture of 67 (310 mg, 0.66 mmol) and Pd(OH)$_2$/C (60 mg) in MeOH (15 mL) was stirred at room temperature under hydrogen atmosphere overnight. The reaction mixture was filtered and the filtrate was concentrated under reduced pressure to give 68 (291 mg, 100%) as a slightly yellow solid. LCMS (m/z: m+1): 441.3.

To a solution of 68 (109 mg, 0.25 mmol) and 2-chloro-4-phenylpyrimidine (77 mg, 0.37 mmol) in t-BuOH (3 mL) was added conc. HCl (0.25 mL). The reaction was heated at 80° C. for 8 hours before concentrated under reduced pressure. The residue was dissolved in CH$_3$CN and basified with Et$_3$N. The resulting solution was purified by reverse prep-HPLC and then silica gel prep-TLC to give 3-((4-(4-fluorophenyl)pyrimidin-2-yl)amino)-4-methyl-N-(3-(4-methyl-1H-imidazol-1-yl)-5-(4-methylpiperazin-1-yl)phenyl)benzenesulfonamide (21 mg, 14%) as an off-white solid.

Example 23. Synthesis of 3-((4-(4-fluorophenyl)pyrimidin-2-yl)amino)-4-methyl-N-(3-(4-methyl-1H-imidazol-1-yl)-5-morpholinophenyl)benzamide

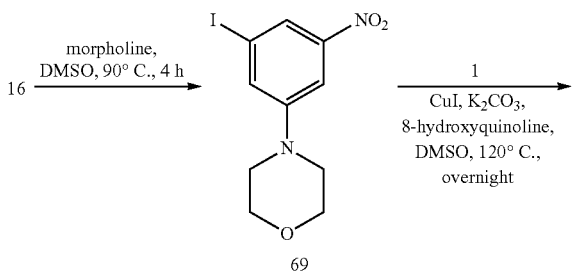

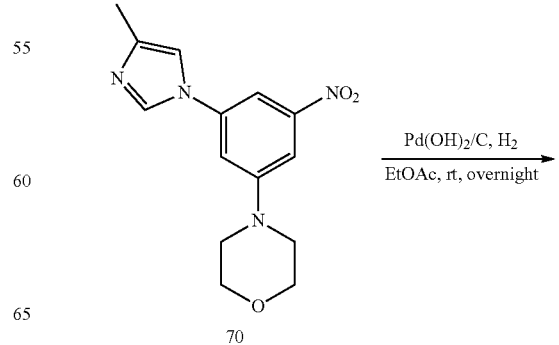

103

-continued

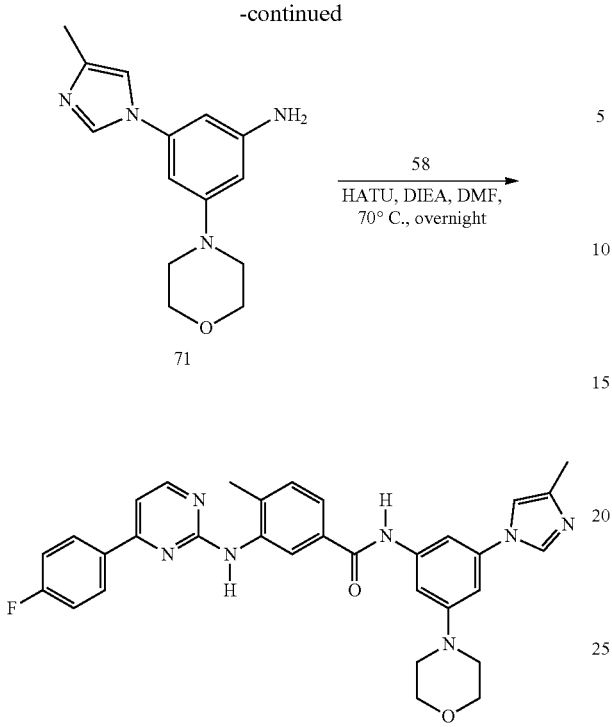

Example 23

A solution of 16 (200 mg, 0.75 mmol) and morpholine (326 mg, 3.75 mmol) in DMSO (2 mL) was heated at 90° C. for 4 hours before poured into water with stirring. The precipitate was filtered and washed with water. The cake was collected and dried to give 69 (220 mg, 88%) as a yellow solid. This material (220 mg, 0.658 mmol), 1 (162 mg, 1.98 mmol), $K_2CO_3$ (182 mg, 1.32 mmol), CuI (38 mg, 0.198 mmol) and 8-hydroxyquinoline (19 mg, 0.132 mmol) in DMSO (2.5 mL) were combined and heated at 120° C. overnight under nitrogen. After cooling, water was added and the mixture was extracted with EtOAc 3 times. The combined organic layers were washed with brine, dried over $Na_2SO_4$ and concentrated. The residue was purified by silica gel column chromatography to give 70 (152 mg, 80%) as a yellow solid. LCMS (m/z: m+1): 289.2.

A mixture of 70 (150 mg, 0.52 mmol) and $Pd(OH)_2/C$ (200 mg) in EtOAc (75 mL) was stirred at room temperature under hydrogen atmosphere overnight. The reaction mixture was filtered and the filtrate was concentrated under reduced pressure to give 71 (135 mg, 100%) as a colorless oil. LCMS (m/z: m+1): 259.2.

A mixture of 71 (134 mg, 0.519 mmol), 58 (201 mg, 0.622 mmol), HATU (394 mg, 1.04 mmol) and DIEA (335 mg, 2.59 mmol) in DMF (2.5 mL) was heated at 70° C. overnight. After cooling, the reaction was directly purified by reverse prep-HPLC to afford the crude product which was rinsed with MeOH/$H_2O$ (3/1) to give 3-((4-(4-fluorophenyl)pyrimidin-2-yl)amino)-4-methyl-N-(3-(4-methyl-1H-imidazol-1-yl)-5-morpholinophenyl)benzamide (82 mg, 28%) as a slightly yellow solid.

104

Example 24. Synthesis of 4-methyl-N-(3-(4-methyl-1H-imidazol-1-yl)-5-(4-methylpiperazin-1-yl)phenyl)benzamide

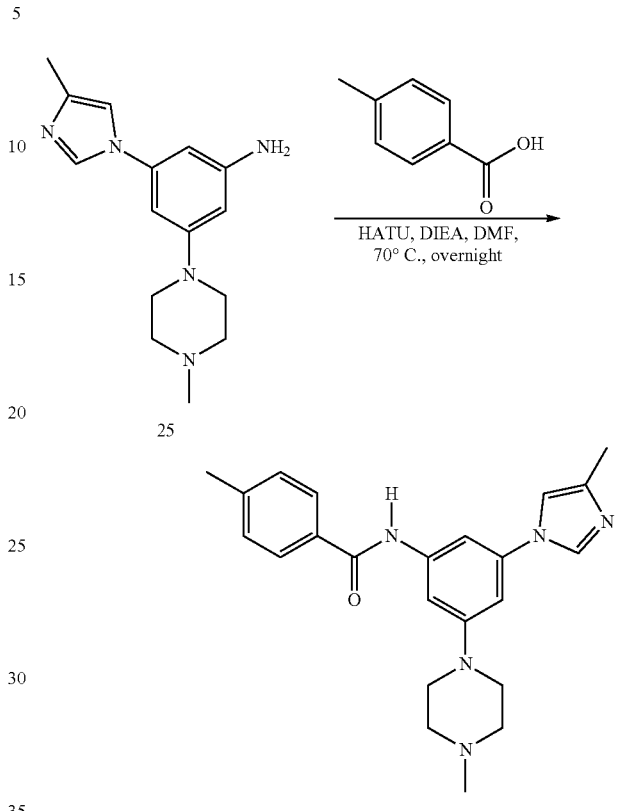

Example 24

A mixture of 25 (200 mg, 0.74 mmol), 4-methylbenzoic acid (151 mg, 1.11 mmol), HATU (562 mg, 1.48 mmol) and DIEA (478 mg, 3.7 mmol) in DMF (4 mL) was heated at 70° C. overnight. After cooling, the reaction was directly purified by reverse prep-HPLC and silica gel prep-TLC to give 4-methyl-N-(3-(4-methyl-1H-imidazol-1-yl)-5-(4-methylpiperazin-1-yl)phenyl)benzamide (64 mg, 22%) as a white solid.

Example 25. Synthesis of 4-methyl-N-(3-(4-methyl-1H-imidazol-1-yl)-5-(4-methylpiperazin-1-yl)phenyl)-3-phenoxybenzamide

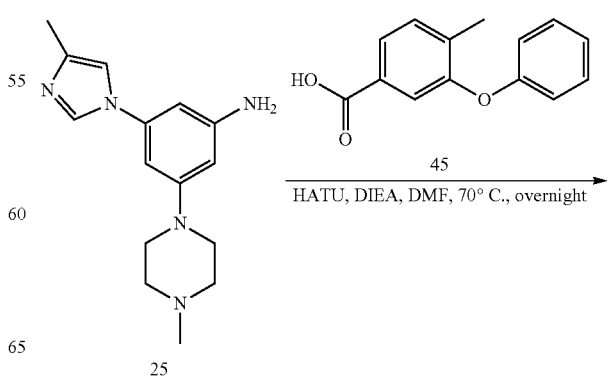

-continued

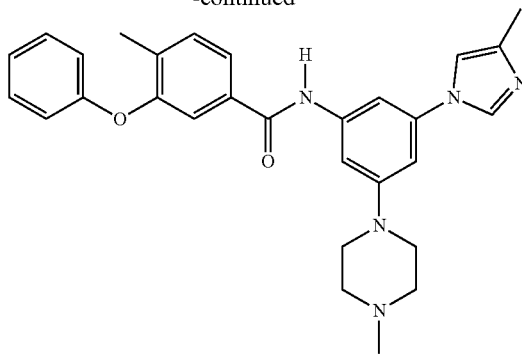

Example 25

A mixture of 25 (119 mg, 0.44 mmol), 45 (100 mg, 0.44 mmol), HATU (333 mg, 0.88 mmol) and DIEA (283 mg, 2.19 mmol) in DMF (2 mL) was heated at 70° C. overnight. After cooling, the reaction was directly purified by reverse prep-HPLC and silica gel prep-TLC to give 4-methyl-N-(3-(4-methyl-1H-imidazol-1-yl)-5-(4-methylpiperazin-1-yl)phenyl)-3-phenoxybenzamide (22 mg, 10%) as a white solid.

Example 26. Synthesis of N-(3-(4-(2-methoxyethyl)piperazin-1-yl)-5-(4-methyl-1H-imidazol-1-yl)phenyl)-4-methyl-3-phenoxybenzamide

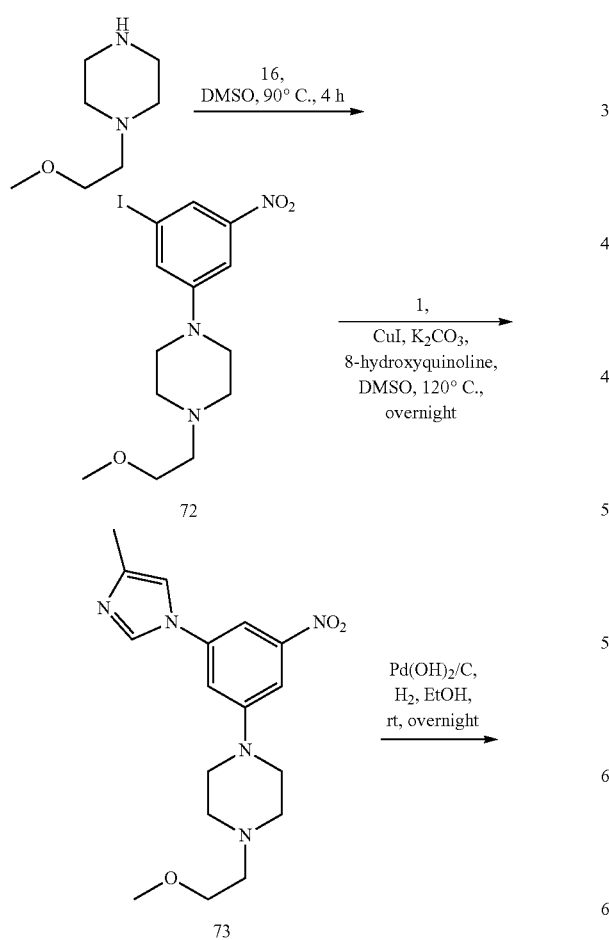

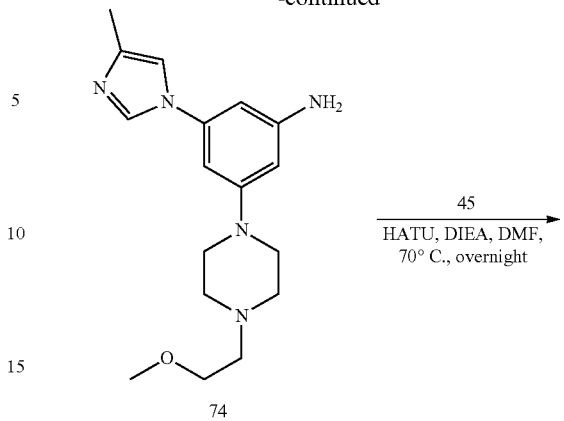

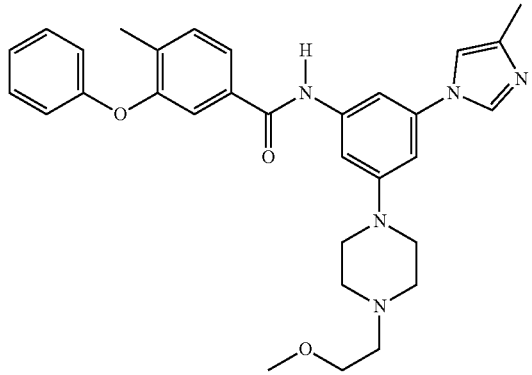

Example 26

A solution of 16 (200 mg, 0.75 mmol) and 1-(2-methoxyethyl)piperazine (324 mg, 2.25 mmol) in DMSO (2 mL) was heated at 90° C. for 4 hours before poured into water with stirring. The mixture was stood at room temperature overnight. The precipitate was filtered and washed with water. The cake was collected and dried to give 72 (278 mg, 95%) as a yellow solid. A suspension of this material (278 mg, 0.711 mmol), 1 (175 mg, 2.13 mmol), $K_2CO_3$ (196 mg, 1.42 mmol), CuI (41 mg, 0.213 mmol) and 8-hydroxyquinoline (21 mg, 0.142 mmol) in DMSO (2.5 mL) was heated at 120° C. overnight under nitrogen. After cooling, water was added and the mixture was extracted with $CH_2Cl_2$/MeOH twice. The combined organic layers were dried over $Na_2SO_4$ and concentrated. The residue was purified by silica gel column chromatography to give 73 (208 mg, 85%) as a yellow solid. LCMS (m/z: m+1): 346.2.

A mixture of 73 (200 mg, 0.56 mmol) and $Pd(OH)_2$/C (100 mg) in EtOH (10 mL) was stirred at room temperature under hydrogen atmosphere overnight. The reaction mixture was filtered and the filtrate was evaporated under reduced pressure to give 74 (183 mg, 100%) as a slightly yellow solid which was used in next step without purification. LCMS (m/z: m+1): 316.3.

A mixture of 74 (90 mg, 0.286 mmol), 45 (85 mg, 0.371 mmol), HATU (217 mg, 0.571 mmol) and DIEA (184 mg, 1.43 mmol) in DMF (1.5 mL) was heated at 70° C. overnight. After cooling, the reaction was directly purified by reverse prep-HPLC and silica gel prep-TLC to give Example 26 (15 mg, 10%) as a slightly yellow solid.

Example 27. Synthesis of 3-(isoquinolin-8-yloxy)-4-methyl-N-(3-(4-methyl-1H-imidazol-1-yl)-5-(4-methylpiperazin-1-yl)phenyl)benzamide

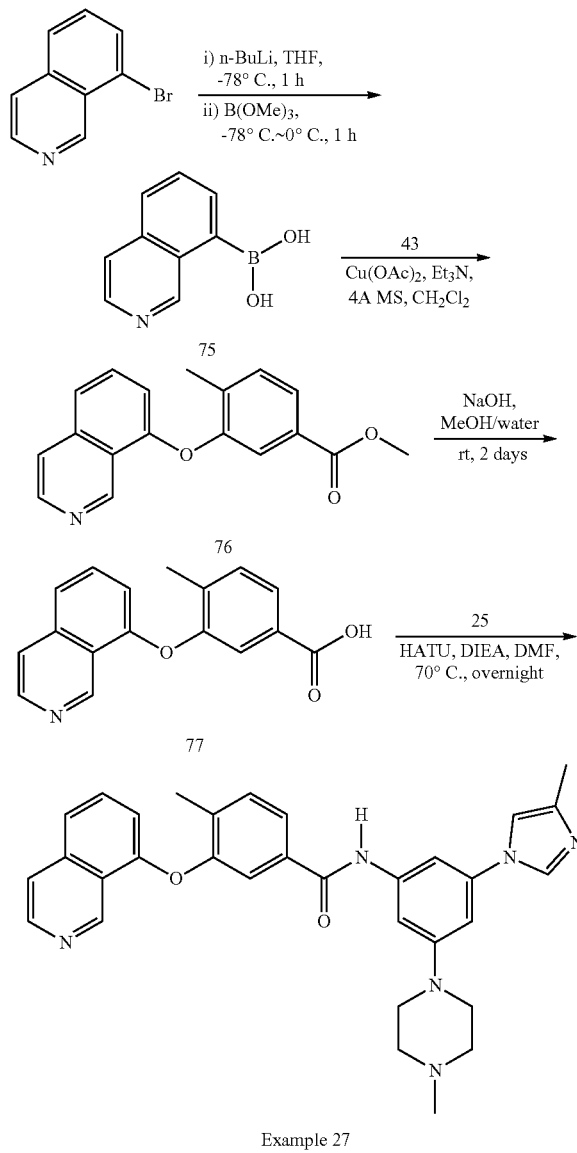

Example 27

To a solution of 8-bromoisoquinoline (2.0 g, 9.6 mmol) in THF (40 mL) was added dropwise n-BuLi (2.5 M, 4.2 mL, 10.6 mmol) at −78° C. under nitrogen. After 1 hour, B(OMe)₃ (2.0 g, 19.2 mmol) was added to the reaction and the mixture was warmed to 0° C. for 1 hour. The reaction was quenched by aqueous NaHCO₃ and extracted with EtOAc 3 times. The combined organic layers were washed with brine, dried over Na₂SO₄ and concentrated. The residue was purified by silica gel column chromatography to give 75 (680 mg, 41%) as a slightly yellow solid. LCMS (m/z: m+1): 174.1.

A mixture of 75 (680 mg, 3.93 mmol), 43 (1306 mg, 7.86 mmol), Cu(OAc)₂ (2142 mg, 11.8 mmol), Et₃N (2387 mg, 23.6 mmol) and 4A MS (5.0 g) in CH₂Cl₂ (50 mL) was stirred at room temperature under air for 3 days. The reaction was filtered and washed with CH₂Cl₂. The filtrate was concentrated and purified by silica gel column chromatography (CH₂Cl₂/MeOH) and then silica gel prep-TLC (petroleum ether/EtOAc) to give 76 (230 mg, 20%) as a slightly yellow solid. LCMS (m/z: m+1): 294.2.

To a solution of this material (230 mg, 0.784 mmol) in MeOH/H₂O (3/0.5 mL) was added NaOH (63 mg, 1.57 mmol). The reaction was stirred at room temperature for 2 days. Water (3 mL) was added to the reaction and then acidified by 1M HCl. The resulting solution was concentrated under reduced pressure to give 77 as a slightly yellow solid that was used in next step without further purification. LCMS (m/z: m+1): 280.1. A mixture of this material (218 mg, 0.784 mmol theoretical amount from previous step), 32 (255 mg, 0.941 mmol), HATU (596 mg, 1.57 mmol) and DIEA (607 mg, 4.70 mmol) in DMF (3 mL) was heated at 70° C. overnight. After cooling, the reaction was directly purified by reverse prep-HPLC and silica gel prep-TLC to give 3-(isoquinolin-8-yloxy)-4-methyl-N-(3-(4-methyl-1H-imidazol-1-yl)-5-(4-methylpiperazin-1-yl)phenyl)benzamide (113 mg, 27% over two steps) as a yellow solid.

Example 28. Synthesis of 3-(3-cyanobenzoyl)-4-methyl-N-(3-(4-methyl-1H-imidazol-1-yl)-5-(4-methylpiperazin-1-yl)phenyl)benzamide

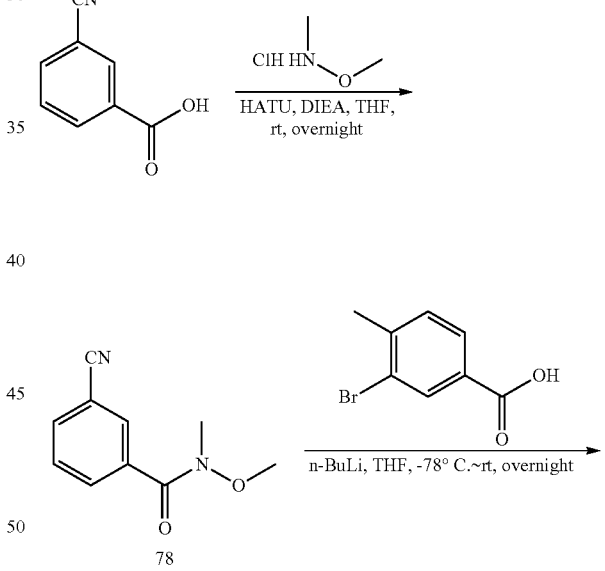

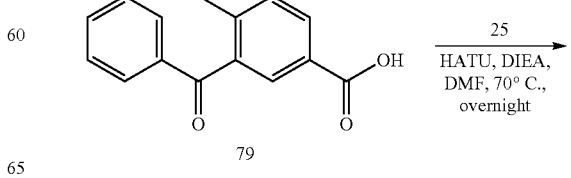

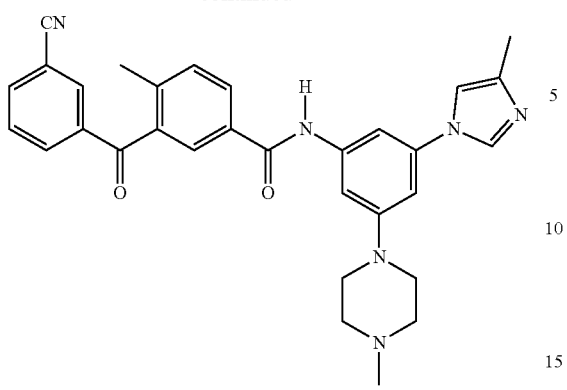

Example 28

A mixture of 3-cyanobenzoic acid (5.0 g, 34 mmol), N,O-dimethylhydroxylamine hydrochloride (5.0 g, 51 mmol), HATU (19.4 g, 51 mmol) and DIEA (17.5 g, 136 mmol) in THF (80 mL) was stirred at room temperature overnight. Water was added and the mixture was extracted with EtOAc twice. The combined organic layers were washed with brine, dried over Na₂SO₄ and concentrated. The residue was purified by silica gel column chromatography to give 86 (6.9 g, 100%) as a colorless oil. LCMS (m/z: m+1): 191.2.

To a solution of 3-bromo-4-methylbenzoic acid (565 mg, 2.63 mmol) in THF (20 mL) was added dropwise n-BuLi (2.5 M, 2.31 mL, 5.78 mmol) at −78° C. under nitrogen. After 1 hour, a THF solution of 78 (500 mg, 2.63 mmol) was added one portion. The mixture was warmed to room temperature and stirred overnight. The reaction was quenched by water and acidified with 1M HCl. The mixture was extracted with EtOAc twice. The combined organic layers were washed with brine, dried over Na₂SO₄ and concentrated. The residue was purified by silica gel column chromatography to give 79 (500 mg, 72%) as an off-white solid. LCMS (m/z: m+1): 266.1.

A mixture of 79 (100 mg, 0.377 mmol), 25 (123 mg, 0.452 mmol), HATU (287 mg, 0.754 mmol) and DIEA (243 mg, 1.88 mmol) in DMF (1.5 mL) was heated at 70° C. overnight. After cooling, the reaction was directly purified by reverse prep-HPLC and silica gel prep-TLC to give 3-(3-cyanobenzoyl)-4-methyl-N-(3-(4-methyl-1H-imidazol-1-yl)-5-(4-methylpiperazin-1-yl)phenyl)benzamide (35 mg, 18%) as a slightly yellow solid.

Example 29. Synthesis of 3-((4-(4-fluorophenyl)pyrimidin-2-yl)amino)-4-methyl-N-(3-(3-methyl-isoxazol-5-yl)-5-(4-methylpiperazin-1-yl)phenyl)benzamide

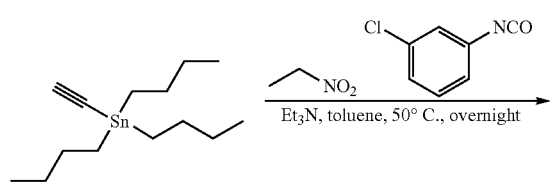

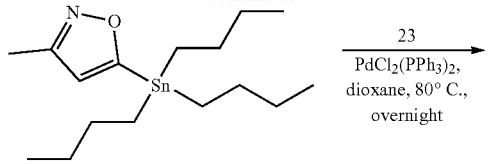

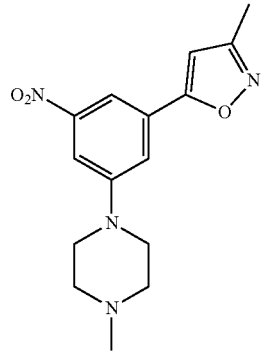

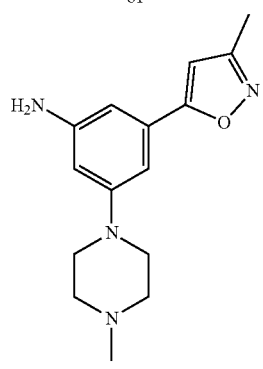

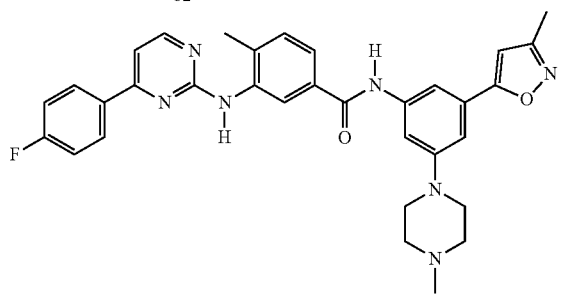

Example 29

To a solution of nitroethane (300 mg, 4.0 mmol) in toluene (12 mL) was added 1-chloro-3-isocyanatobenzene (1226 mg, 8.0 mmol). The mixture was stirred at 50° C. for 10 min before Et₃N (20 mg, 0.2 mmol) and tributylethynylstannane (1195 mg, 3.8 mmol) were added. The mixture was stirred at 50° C. overnight. Water was added to the reaction mixture and the suspension was filtered. The filtrate was extracted with toluene twice. The combined organic layers were washed with brine, dried over Na₂SO₄ and concentrated. The residue was purified by silica gel column chromatography to give 80 (960 mg, 68%) as a slightly yellow oil. LCMS (m/z: m+1): 371.2, 372.2, 374.1.

A mixture of 80 (960 mg, 2.58 mmol), 23 (896 mg, 2.58 mmol) and PdCl₂(PPh₃)₂ (130 mg) in dioxane (10 mL) was heated at 80° C. overnight under nitrogen. The reaction mixture was concentrated and the residue was purified by silica gel column chromatography to give 81 (310 mg, 40%) as a yellow solid. LCMS (m/z: m+1): 303.1. $^1$H NMR (400 MHz, CDCl$_3$): □ 7.94 (t, J=1 Hz, 1H); 7.74 (m, 1H); 7.65 (d, J=1 Hz); 6.49 (s, 1H); 3.38 (m, 4H); 2.61 (m, 4H); 2.39 (s, 3H); 2.38 (s, 3H).

A mixture of 81 (100 mg, 0.33 mmol) and Pd(OH)$_2$/C (50 mg) in EtOAc (10 mL) was stirred at room temperature under hydrogen atmosphere overnight. The reaction mixture was filtered and the filtrate was evaporated under reduced pressure to give 82 (90 mg, 100%) as a slightly yellow oil that was used in next step without purification. LCMS (m/z: m+1): 273.2. A mixture of this material (90 mg, 0.330 mmol), 58 (128 mg, 0.397 mmol), HATU (251 mg, 0.661 mmol) and DIEA (213 mg, 1.65 mmol) in DMF (2 mL) was heated at 70° C. overnight. After cooling, the reaction was directly purified by reverse prep-HPLC and silica gel prep-TLC and reverse prep-HPLC once more to give 3-((4-(4-fluorophenyl)pyrimidin-2-yl)amino)-4-methyl-N-(3-(3-methylisoxazol-5-yl)-5-(4-methylpiperazin-1-yl)phenyl)benzamide (23 mg, 12%) as an off-white solid and at the same time a by-product, 3-((4-(4-fluorophenyl)pyrimidin-2-yl)amino)-4-methyl-N-(3-(4-methylpiperazin-1-yl)phenyl)benzamide resulting from an incomplete Stille coupling between 80 and 23.

Example 30. Synthesis of (S)—N-(3-((3-aminopiperidin-1-yl)methyl)-5-(4-methyl-1H-imidazol-1-yl)phenyl)-4-methyl-3-phenoxybenzamide

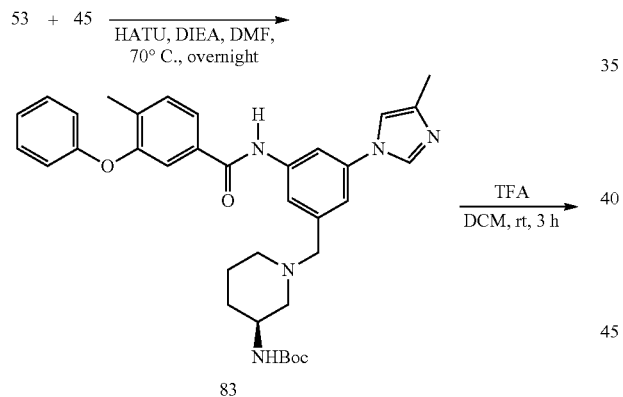

Example 30

A mixture of 53 (150 mg, 0.39 mmol), 45 (107 mg, 0.47 mmol), HATU (296 mg, 0.78 mmol) and DIEA (251 mg, 0.95 mmol) in DMF (2 mL) was heated at 70° C. overnight.

Alternatively, the reaction was performed in the same solvent at room temperature. After cooling, the reaction was directly purified by reverse prep-HPLC and then silica gel prep-TLC to give 83 (65 mg, 28%) as a slightly yellow solid. To a solution of 83 (65 mg, 0.109 mmol) in CH$_2$Cl$_2$ (3 mL) was added TFA (1.5 mL) and the reaction was stirred at room temperature for 3 hours before concentrated under reduced pressure. The residue was treated with water, basified with 0.5 N NaOH and extracted with CH$_2$Cl$_2$/MeOH (15/1) 3 times. The combined organic layers were dried over Na$_2$SO$_4$, filtered, concentrated and purified by silica gel prep-TLC to give (S)—N-(3-((3-aminopiperidin-1-yl)methyl)-5-(4-methyl-1H-imidazol-1-yl)phenyl)-4-methyl-3-phenoxybenzamide (50 mg, 93%) as a white solid.

Example 31. 3-((4-(4-fluorophenyl)pyrimidin-2-yl)amino)-4-methyl-N-(3-(4-methylpiperazin-1-yl)phenyl)benzamide

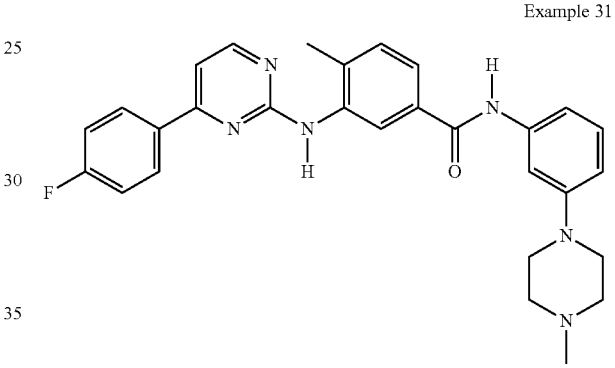

Example 31

This material was isolated as a by-product from the coupling between 80 and 23 and subsequent processing through the reduction and coupling steps described for Example 29.

Example 32. N-(3-((4-amino-3-methylpiperidin-1-yl)methyl)-5-(4-methyl-1H-imidazo-1-yl)phenyl)-3-(benzyloxy)-4-methylbenzamide

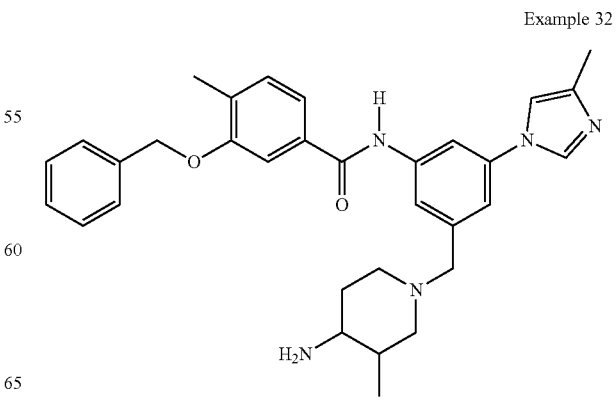

Example 32

Example 33. N-(3-((4-amino-3-methylpiperidin-1-yl)methyl)-5-(4-methyl-1H-imidazol-1-yl)phenyl)-4-methyl-3-((6-methylpyridin-3-yl)methoxy)benzamide

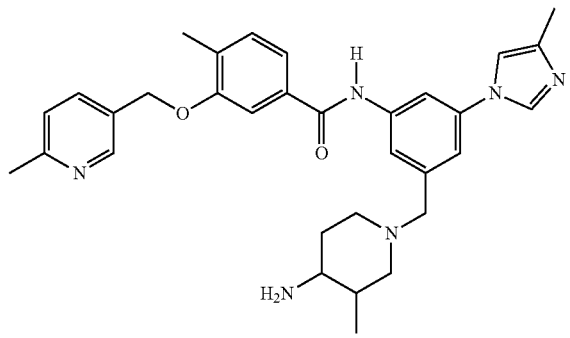

Example 33

Example 34. N-(3-((4-amino-3-methylpiperidin-1-yl)methyl)-5-(4-methyl-1H-imidazol-1-yl)phenyl)-4-methyl-3-phenoxybenzamide

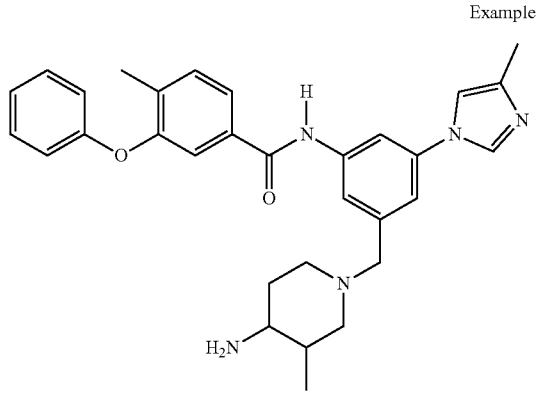

Example 34

Example 35. N-(3-((4-amino-3-methylpiperidin-1-yl)methyl)-5-(4-methyl-1H-imidazol-1-yl)phenyl)-4-methyl-3-((6-methylpyridin-3-yl)oxy)benzamide

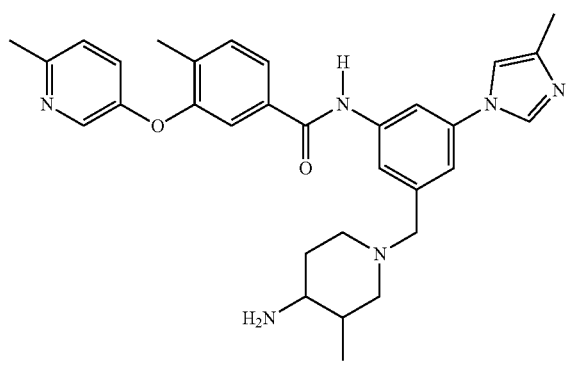

Example 35

Example 36. N-(3-((4-amino-3-methylpiperidin-1-yl)methyl)-5-(4-methyl-1H-imidazol-1-yl)phenyl)-3-methyl-4-((6-methylpyridin-3-yl)methoxy)benzamide Example 36

Example 37. N-(3-((4-amino-3-methylpiperidin-1-yl)methyl)-5-(4-methyl-1H-imidazol-1-yl)phenyl)-4-(benzyloxy)-3-methylbenzamide

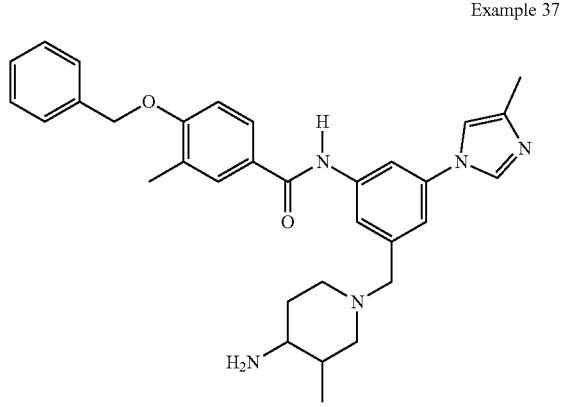 [SMILES: Cc1cn(-c2cc(CN3CCC(N)C(C)C3)cc(NC(=O)c3ccc(OCc4ccccc4)c(C)c3)c2)cn1]

Example 37

Examples 32-37 were prepared using the following general schematic.

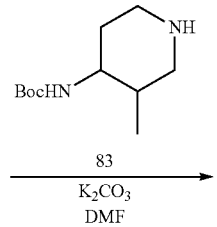

27

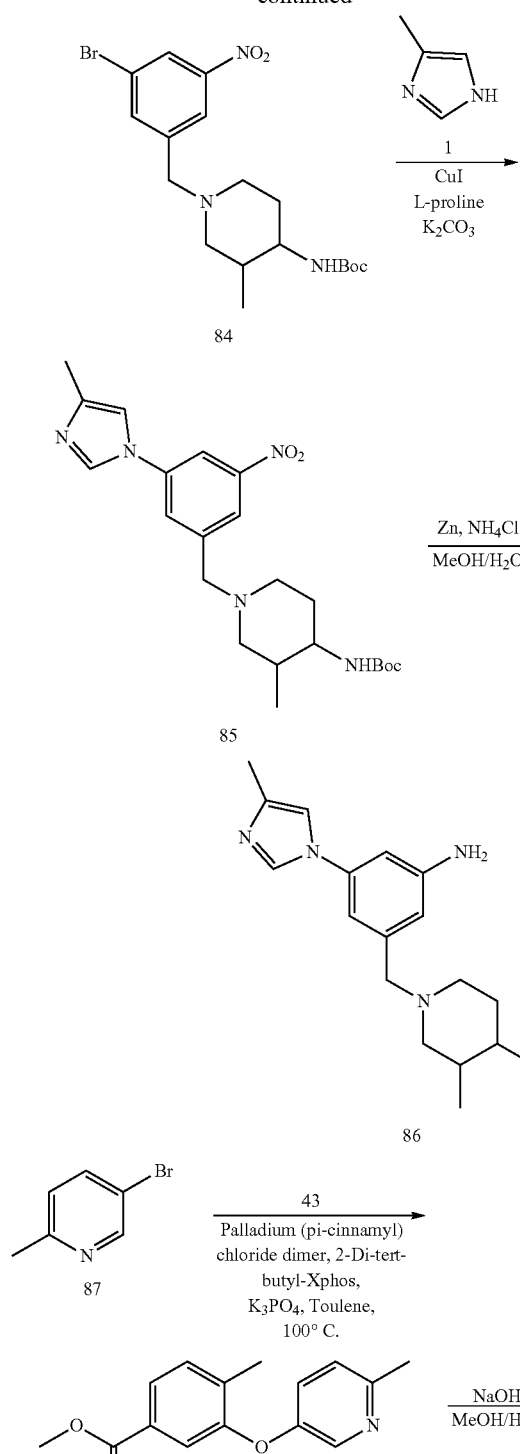
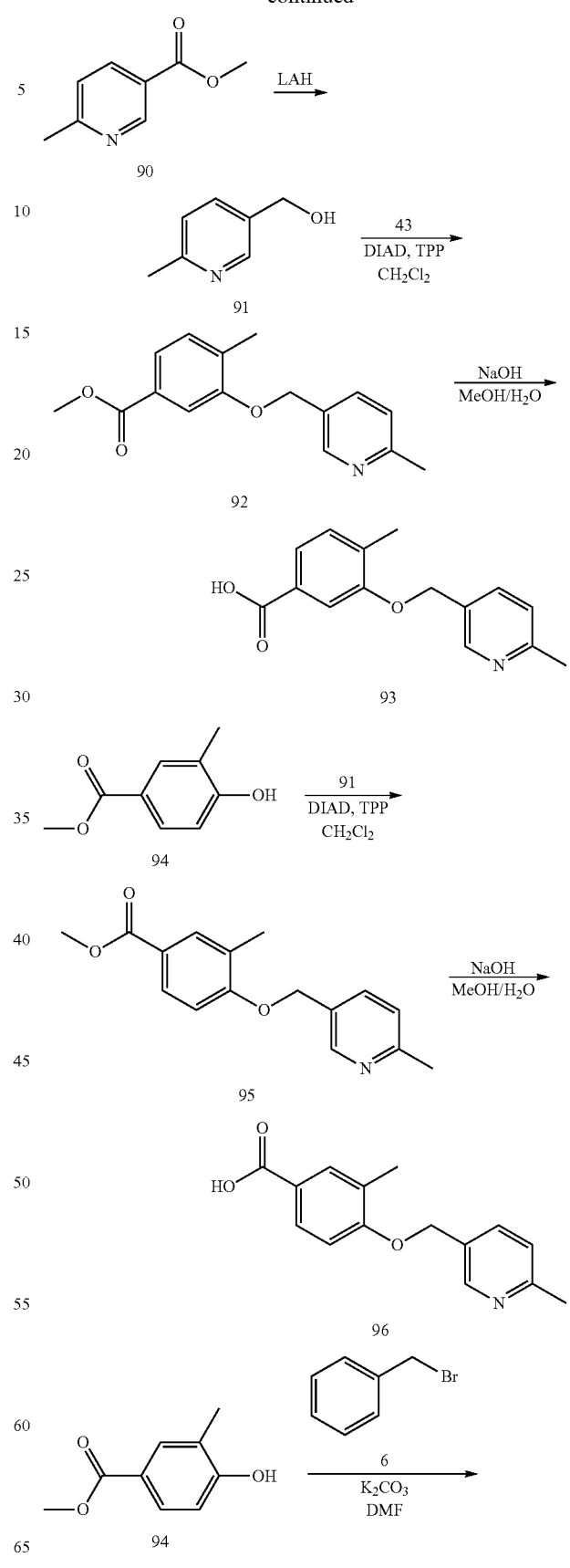

-continued

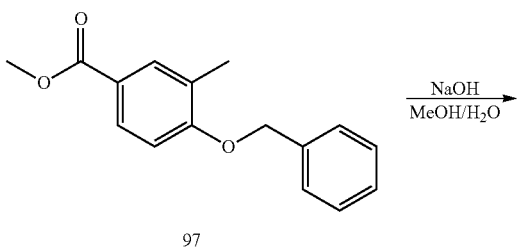

97

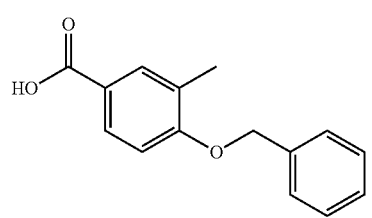

98

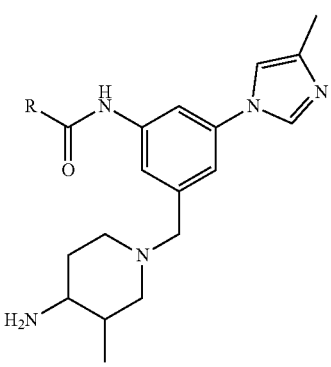

47
93
45
89
96
98 i) 86
HATU, DIPEA
DMF, RT ii) 4M HCl
dioxane

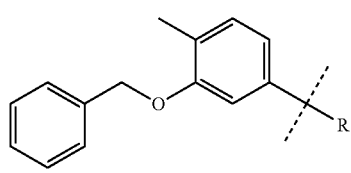

Example 32

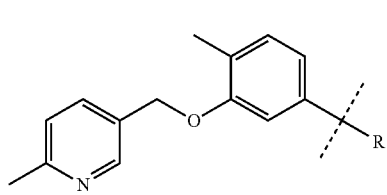

Example 33

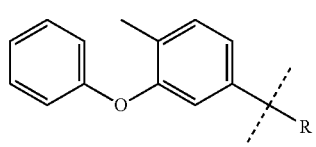

Example 34

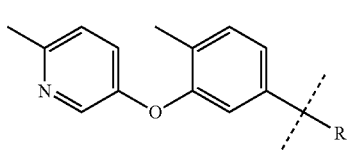

Example 35

-continued

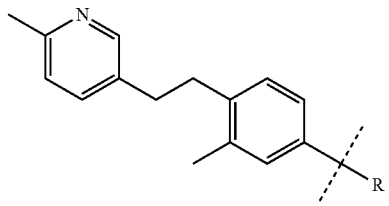

Example 36

Example 37

Intermediate 84 was prepared from 27 and 83 in similar manner as described for Example 19. To a solution of 84 (1.0 eq) in DMSO was added $K_2CO_3$ (2.5 eq), 1 (3.5 eq), CuI (0.8 eq) and L-proline (0.5 eq) under $N_2$. The resulting reaction mass was heated at 120° C. for 16 h. After completion of reaction (TLC monitoring), the reaction mass was diluted with water and extracted with EtOAc (3 times). The combined organics were washed with ice-cold water and brine respectively. The organic layer was dried over anhydrous $Na_2SO_4$, filtered, and concentrated under reduced pressure. The crude product was purified via flash chromatography, eluting with 5% MeOH in DCM to get desired product 85 (1.0 g, 68%) as an off white solid. To a solution of 85 (1.0 eq) in MeOH:$H_2O$ (2:1) was added zinc powder (2.5 eq) and $NH_4Cl$ (3.0 eq). The resulting reaction mass was heated at 90° C. for 3 h. After completion of reaction, the mixture was filtered through Celite, washed with 10% MeOH in DCM (2 times). The combined organics were dried over anhydrous $Na_2SO_4$, filtered, and concentrated under reduced pressure. The crude product was purified via flash chromatography, elution with 8% MeOH in DCM to yield 86 (0.9 g, 96%) as a brown solid.

To a solution of 43 (1.0 g, 6.02 mmol) in toluene (15 mL) was added 87 (1.5 g, 9.03 mmol), $K_3PO_4$ (2.5 g, 12.04 mmol), bis[cinnamyl palladium(II) chloride] (0.25 g, 0.48 mmol) and 2-di-tert-butyl Xphos (0.61 g, 1.44 mmol) under nitrogen degassing. The resulting reaction mass was heated at 100° C. for 16 h. After completion of reaction (TLC monitoring), the mixture was diluted with water (100 mL) and extracted with EtOAc (3 times). The combined organics were washed with brine, dried over anhydrous $Na_2SO_4$, filtered and concentrated under reduced pressure. The crude product was purified via Combiflash® chromatography, eluting with 20% EtOAc in hexanes to yield 88 (0.7 g, 45%) as a light yellow viscous liquid. $^1$H-NMR (400 MHz, $CDCl_3$): δ 8.24 (s, 1H), 7.73 (d, J=8.0 Hz, 1H), 7.48 (s, 1H), 7.31 (d, J=8.0 Hz, 1H), 7.11 (s, 2H), 3.85 (s, 3H), 2.54 (s, 3H) and 2.32 (s, 3H). LC-MS: 258.36 (M+H). To an ice-cold solution of 88 (1.0 eq) in methanol was added aqueous NaOH (3.0 eq). The resulting mixture was stirred at RT for 3-4 h. After completion of reaction the mixture was concentrated under reduced pressure, the crude was diluted with water and washed with EtOAc (2 times) for removal of organic impurities. The aqueous part was acidified with 2M–HCl (adjust pH ~4-5), to yield 89 as a solid white precipitate, which was filtered and dried under vacuum. $^1$H-NMR (400 MHz, DMSO-$d_6$): δ 12.90 (br s, 1H), 8.88 (s, 1H), 8.55 (s, 1H), 7.76-7.77 (m, 1H), 7.54 (s, 1H), 7.46 (d, J=7.6 Hz, 1H), 7.28 (d, J=7.6 Hz, 1H), 5.17 (s, 2H), 2.47 (s, 3H) and 2.22 (s, 3H). LC-MS: 258.14 (M+H).

To a solution of 90 (5.0 g, 3.31 mmol) in THF was cooled to −78° C., followed by addition of LAH solution (2M in THF, 4.13 mL, 8.27 mmol) slowly. The resulting mixture was stirred at −78° C. for 1 h. After completion of reaction (TLC monitoring), water (4.0 mL) and 15% NaOH solution (4 mL) were added slowly. The resulting reaction mixture was filtered through Celite and washed with EtOAc (2 times). The organic layer was dried over anhydrous Na$_2$SO$_4$, filtered, and concentrated under reduce pressure to yield 91 (3.5 g, 87%) as a light yellowish liquid. $^1$H-NMR (400 MHz, DMSO-d6): δ 8.36 (s, 1H), 7.58 (d, J=8.0 Hz, 1H), 7.18 (d, J=8.0 Hz, 1H), 5.21 (t, J=5.6 Hz, 1H), 4.46 (d, J=5.6 Hz, 2H) and 2.45 (s, 3H). LC-MS: 124.06 (M−H). To an ice-cold solution of 43 (1.0 eq) and 91 (1.5 eq) in DCM was added DIAD (3.0 eq) and TPP (3.0 eq). The mixture was stirred at RT for 16 h. After completion of reaction, the mixture was diluted with water and extracted with DCM (3 times). The combined organics was washed with brine, dried over anhydrous Na$_2$SO$_4$, filtered and concentrated under reduced pressure. The product was purified over silica gel column chromatography, eluting with 10% EtOAc in hexanes to yield 92 (1.3 g, 31%) as a light yellow solid. $^1$H-NMR (400 MHz, CDCl$_3$): δ 8.59 (s, 1H), 7.64-7.68 (m, 2H), 7.46-7.47 (m, 1H), 7.14-7.18 (m, 2H), 5.10 (s, 2H), 3.85 (s, 3H), 2.58 (s, 3H) and 2.34 (s, 3H). MS: 272.16 (M+H). This material was then converted to 93 using the same conditions as described for 89. Analtyical data for 93: $^1$H-NMR (400 MHz, DMSO-d$_6$): δ 12.90 (br s, 1H), 8.88 (s, 1H), 8.55 (s, 1H), 7.76-7.77 (m, 1H), 7.54 (s, 1H), 7.46 (d, J=7.6 Hz, 1H), 7.28 (d, J=7.6 Hz, 1H), 5.17 (s, 2H), 2.47 (s, 3H) and 2.22 (s, 3H). LC-MS: 258.14 (M+H).

Likewise, intermediate 96 was prepared from 94 in two steps following similar experimental conditions as described for 92 and 93 (TPP/DIAD followed by NaOH saponification in MeOH/H$_2$O). Analytical data for intermediate 95: $^1$H-NMR (400 MHz, CDCl$_3$): δ 8.58 (s, 1H), 7.85-7.88 (m, 2H), 7.65 (d, J=8.0 Hz, 1H), 7.18 (d, J=8.0 Hz, 1H), 6.89 (d, J=8.4 Hz, 1H), 5.07 (s, 2H), 3.87 (s, 3H), 2.56 (s, 3H) and 2.26 (s, 3H). LC-MS: 272.10 (M+H). Analytical data for 96: $^1$H-NMR (400 MHz, DMSO-d$_6$): δ 12.30 (br s, 1H), 8.55 (s, 1H), 7.75-7.78 (m, 3H), 7.28 (d, J=8.0 Hz, 1H), 7.12 (d, J=8.4 Hz, 1H), 5.28 (s, 2H), 2.47 (s, 3H) and 2.19 (s, 3H). LC-MS: 258.11 (M+H).

Likewise, intermediate 98 was prepared from 94 in two steps following similar experimental conditions as described for the preparation of 47. Analytical data for intermediate 98: $^1$H-NMR (400 MHz, DMSO-d$_6$): δ 12.51 (br s, 1H), 7.75-7.77 (m, 2H), 7.46-7.48 (m, 2H), 7.38-7.42 (m, 2H), 7.33-7.35 (m, 1H), 7.08 (d, J=8.0 Hz, 1H), 5.20 (s, 2H) and 2.22 (s, 3H). LC-MS: 241.05 (M−H).

The synthesis of Examples 32-37 were conducted via the methods described for Example 30 (two steps: HATU/DIPEA/DMF coupling, performed at room temperature or 70° C. overnight) followed by acid-based cleavage (HCl/dioxane or TFA/DCM). For analytical data see Table 1.

Example 38. Synthesis of (S)—N-(3-((3-hydroxypiperidin-1-yl)methyl)-5-(4-methyl-1H-imidazol-1-yl)phenyl)-4-methyl-3-phenoxybenzamide

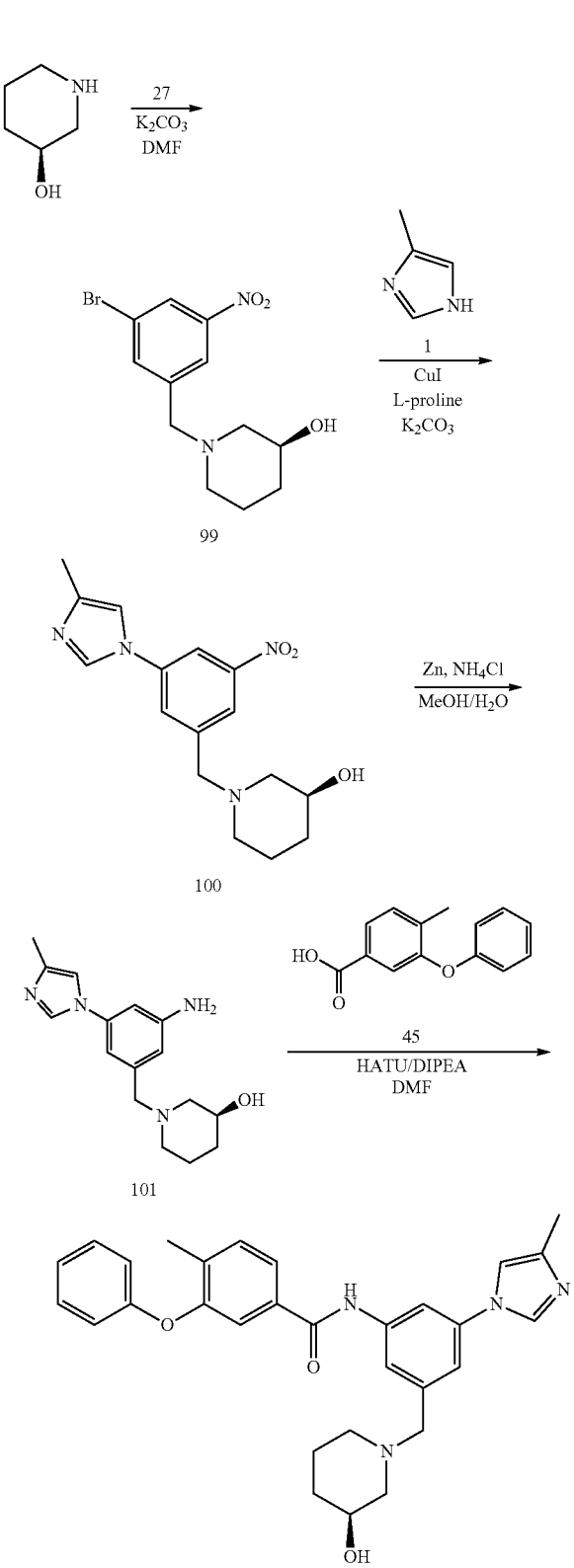

Example 38

99 was prepared from (S)-3-hydroxypiperidine and 27 using the same method as described for Example 19. $^1$H-NMR (400 MHz, DMSO-$d_6$): δ 8.26 (s, 1H), 8.17 (s, 1H), 7.96 (s, 1H), 4.62 (d, J=4.8 Hz, 1H), 3.61-3.64 (m, 2H), 3.48-3.54 (m, 1H), 2.49-2.66 (m, 6H) and 1.90-1.95 (m, 2H). LC-MS: 315.01 (M+H). 99 was then converted to 100 using the same procedure as described for intermediate 85. $^1$H-NMR (400 MHz, DMSO-$d_6$): δ 8.32-8.34 (m, 2H), 8.07 (s, 1H), 8.01 (s, 1H), 7.64 (s, 1H), 4.61 (d, J=4.0 Hz, 1H), 3.65-3.68 (m, 2H), 3.58-3.62 (m, 1H), 2.63-2.66 (m, 2H), 2.17 (s, 3H), 1.90-1.97 (m, 2H), 1.77-1.82 (m, 2H) and 1.43-1.46 (m, 2H). MS: 317.13 (M+H). 100 was then reduced to 101 using the same procedure as described for 86. $^1$H-NMR (400 MHz, DMSO-$d_6$): δ 7.79 (s, 1H), 7.26 (s, 1H), 6.55-6.59 (m, 2H), 6.49 (s, 1H), 5.35 (br s, 2H), 4.57 (d, J=4.0 Hz, 1H), 3.43-3.45 (m, 1H), 2.78-2.80 (m, 1H), 2.63-2.65 (m, 1H), 2.15 (s, 3H), 1.80-1.83 (m, 3H), 1.58-1.64 (m, 3H) and 1.40-1.45 (m, 2H). LC-MS: 288.31 (M+H).

101 and 45 were then coupled in the same manner as described for Example 30. Analytical data for the product, (S)—N-(3-((3-hydroxypiperidin-1-yl)methyl)-5-(4-methyl-1H-imidazol-1-yl)phenyl)-4-methyl-3-phenoxybenzamide, is summarized in Table 1.

Example 39. Synthesis of (S)—N-(3-((3-aminopiperidin-1-yl)methyl)-5-(4-methyl-1H-imidazol-1-yl)phenyl)-4-methyl-3-((6-methylpyridin-3-yl)oxy)benzamide

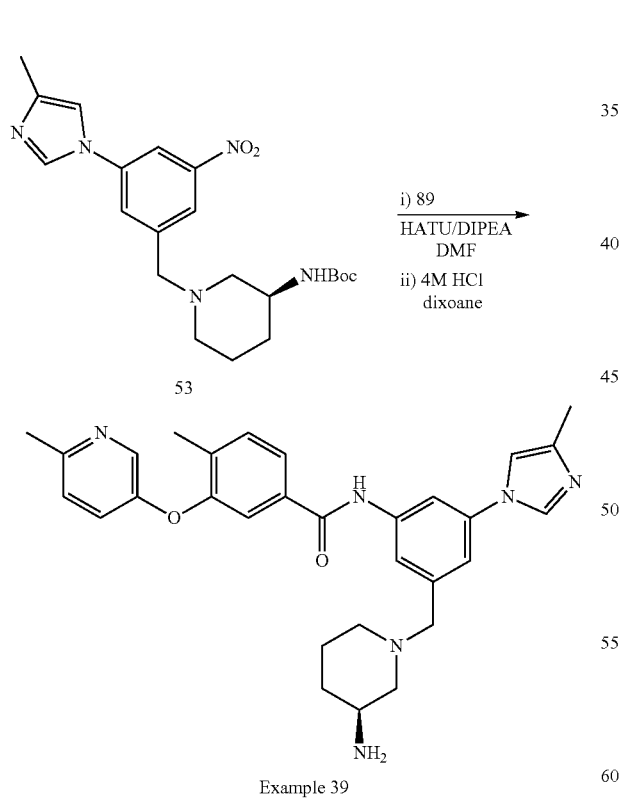

Example 39

53 and 89 were coupled using the same method as described for Examples 32-37. The intermediate was then deprotected using 4M HCL in dioxane according to the same method as described for Examples 32-37, the final product being purified by preparative HPLC. Analytical data for the product, (S)—N-(3-((3-aminopiperidin-1-yl)methyl)-5-(4-methyl-1H-imidazol-1-yl)phenyl)-4-methyl-3-((6-methylpyridin-3-yl)oxy)benzamide, is summarized in Table 1.

Example 40. N-(3-((4-hydroxy-3-methylpiperidin-1-yl)methyl)-5-(4-methyl-1H-imidazol-1-yl)phenyl)-4-methyl-3-phenoxybenzamide

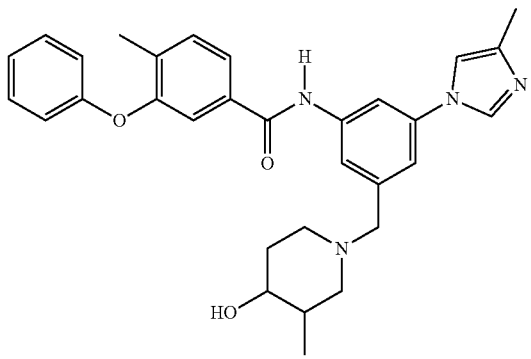

Example 40

Example 41. N-(3-((4-hydroxy-3-methylpiperidin-1-yl)methyl)-5-(4-methyl-1H-imidazol-1-yl)phenyl)-1H-indole-6-carboxamide

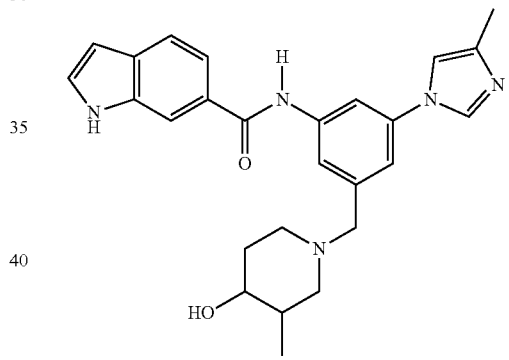

Example 41

Example 42. N-(3-((4-hydroxy-3-methylpiperidin-1-yl)methyl)-5-(4-methyl-1H-imidazol-1-yl)phenyl)-2-methyl-1H-benzo[d]imidazole-6-carboxamide

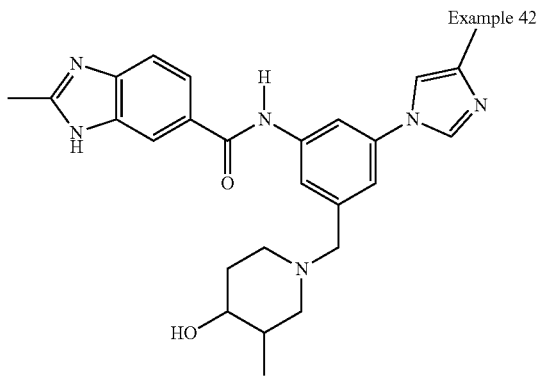 [SMILES: Cc1cn(-c2cc(CN3CCC(O)C(C)C3)cc(NC(=O)c3ccc4nc(C)[nH]c4c3)c2)cn1]

Example 42

Example 43. N-(3-((4-hydroxy-3-methylpiperidin-1-yl)methyl)-5-(4-methyl-1H-imidazol-1-yl)phenyl)-2-(2-hydroxyethyl)-1H-benzo[d]imidazole-6-carboxamide
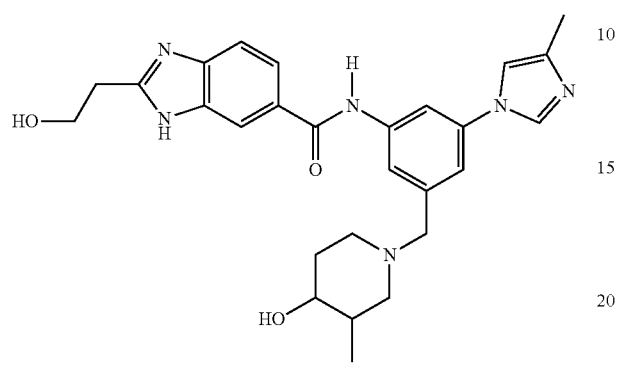
Example 44. N-(3-((4-hydroxy-3-methylpiperidin-1-yl)methyl)-5-(4-methyl-1H-imidazol-1-yl)phenyl)-3-methyl-1H-indazole-6-carboxamide
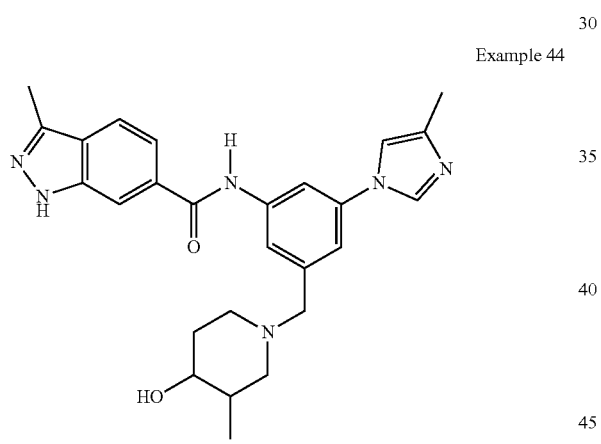
Examples 40-44 were prepared according to the following general schematic:
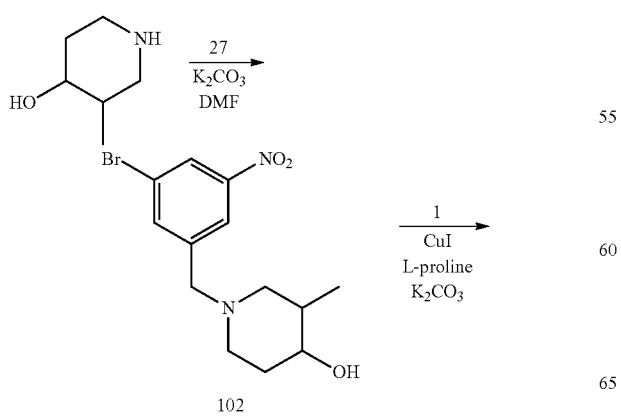
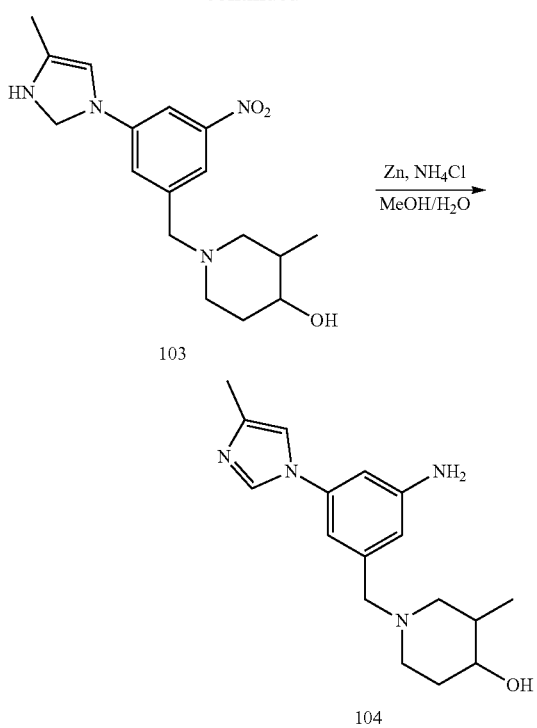
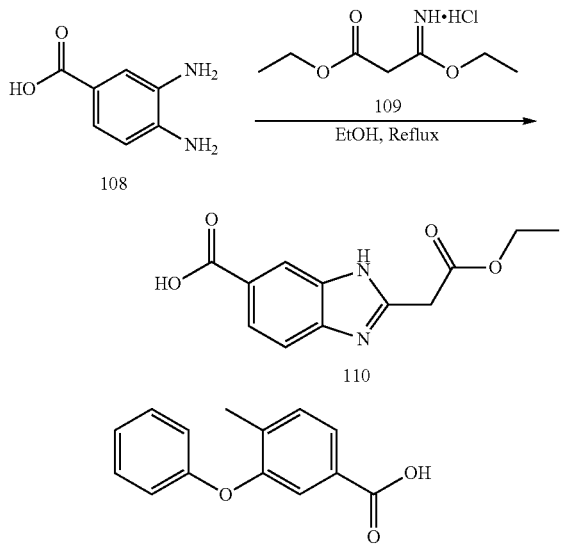
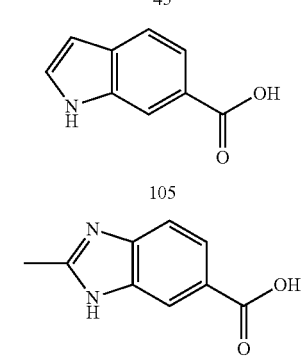

-continued

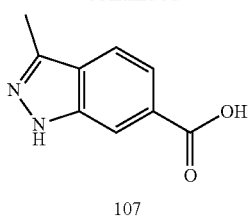

107

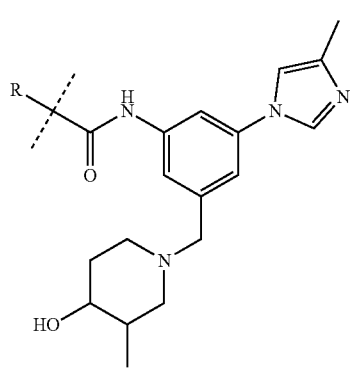

45
105
106   104
107  HATU/DIPEA
110  DMF, RT, 16 hr

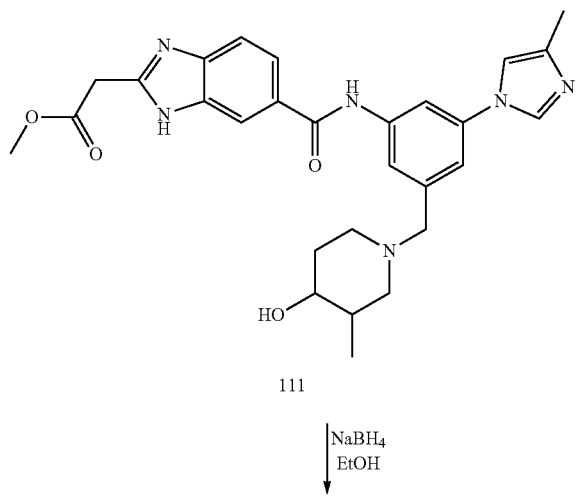

111

NaBH₄
EtOH

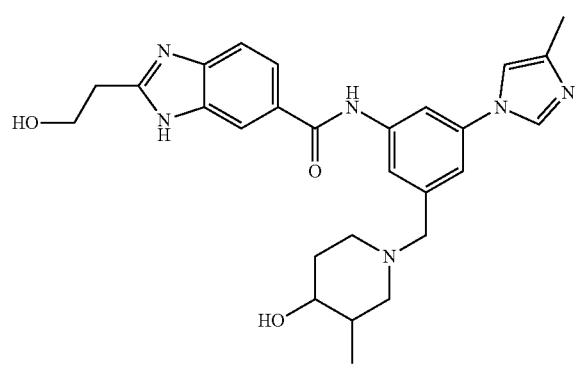

Example 43

-continued

Example 40: R = 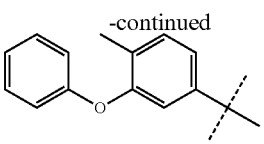

Example 41: R = 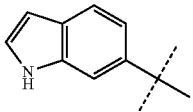

Example 42: R = 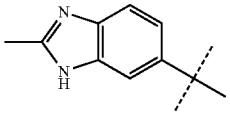

Example 44: R = 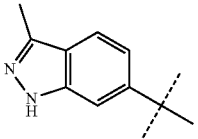

102 was prepared from 27 and 3-methylpiperidin-4-ol according to the method described in Example 19. ¹H-NMR (400 MHz, DMSO-d₆): δ 8.25 (s, 1H), 8.13 (s, 1H), 7.95 (s, 1H), 4.53 (d, J=5.2 Hz, 1H), 3.56 (s, 2H), 2.92 (d, J=4.8 Hz, 1H), 2.66-2.68 (m, 1H), 1.90-1.98 (m, 2H), 1.67-1.73 (m, 2H), 1.38-1.45 (m, 2H) and 0.84 (d, J=6.4 Hz, 3H). MS: 329.02 (M+H). This material was converted to 103 by the same method as described for intermediate 85. ¹H-NMR (400 MHz, DMSO-d₆): δ 8.31-8.33 (m, 2H), 8.07 (s, 1H), 7.98 (s, 1H), 7.63 (s, 1H), 4.55 (d, J=5.2 Hz, 1H), 3.59 (s, 2H), 2.93-2.95 (m, 1H), 2.70-2.78 (m, 3H), 2.16 (s, 3H), 2.00-2.06 (m, 1H), 1.69-1.74 (m, 1H), 1.41-1.46 (m, 2H) and 0.86 (d, J=6.8 Hz, 3H). LC-MS: 331.13 (M+H). Subsequent reduction of 103 to intermediate 104 by zinc/ammonium chloride was facilitated in similar fashion to that described for intermediate 86. ¹H-NMR (400 MHz, DMSO-d₆): δ 7.80 (s, 1H), 7.21 (s, 1H), 6.53 (s, 2H), 6.49 (s, 1H), 5.32 (s, 2H), 4.51 (d, J=5.2 Hz, 1H), 3.28 (s, 2H), 2.87-2.89 (m, 1H), 2.68-2.74 (m, 1H), 2.13 (s, 3H), 1.91-1.98 (m, 1H), 1.88-1.91 (m, 1H), 1.71-1.74 (m, 1H), 1.52-1.59 (m, 1H), 1.38-1.43 (m, 2H) and 0.83 (d, J=6.8 Hz, 3H). LC-MS: 301.22 (M+H).

To a solution of 3,4-diaminobenzoic acid 108 (2.5 g, 12.82 mmol) in EtOH (20 mL) was added ethyl 3-ethoxy-3-iminopropanoate hydrochloride 109 (1.55 g, 10.25 mmol). The resulting mixture was heated at 80° C. for 16 h. After completion of reaction, the mixture was concentrated under reduced pressure. The crude product was dissolved in water and extracted with EtOAc (3 times). The combined organics were dried over anhydrous Na₂SO₄, filtered, and concentrated under reduced pressure to get desired product 110 (0.4 g, 13%) as a light yellowish liquid. The material was used in the next step without further purification. ¹H-NMR (400 MHz, DMSO-d₆): δ 12.69 (br s, 1H), 8.08-8.14 (m, 1H), 7.80-7.81 (m, 1H), 7.53-7.59 (m, 1H), 4.13 (q, J=7.2 Hz, 2H), 4.02 (s, 2H) and 1.19 (t, J=6.8 Hz, 3H). MS: 249.07 (M+H).

Couplings of 104 with 45, 105, 106, and 107 according to the method described for Example 30, using HATU/DIPEA in DMF at room temperature, followed by HPLC purification, to yield N-(3-((4-hydroxy-3-methylpiperidin-1-yl)methyl)-5-(4-methyl-1H-imidazol-1-yl)phenyl)-4-methyl-3-phenoxybenzamide, N-(3-((4-hydroxy-3-methylpiperidin-1-yl)methyl)-5-(4-methyl-1H-imidazol-1-yl)phenyl)-1H-indole-6-carboxamide, N-(3-((4-hydroxy-3- methylpiperidin-1-yl)methyl)-5-(4-methyl-1H-imidazol-1-yl)phenyl)-2-methyl-1H-benzo[d]imidazole-6-carboxamide, and N-(3-((4-hydroxy-3-methylpiperidin-1-yl)methyl)-5-(4-methyl-1H-imidazol-1-yl)phenyl)-3-methyl-1H-indazole-6-carboxamide respectively. Furthermore, the same coupling conditions were used to combine 104 with intermediate 110, to give intermediate 111.

To an ice-cold solution of 111 (160 mg, 0.31 mmol) in ethanol (10 mL) was added NaBH$_4$ (57 mg, 1.51 mmol). The resulting reaction mixture was heated at 80° C. for 6 h. After completion of reaction, the mixture was cooled to RT and water (2-3 mL) was added. The mixture was concentrated was under reduced pressure. The crude residue was purified over prep-HPLC to yield N-(3-((4-hydroxy-3-methylpiperidin-1-yl)methyl)-5-(4-methyl-1H-imidazol-1-yl)phenyl)-2-(2-hydroxyethyl)-1H-benzo[d]imidazole-6-carboxamide (30 mg, 20%) as an off-white solid. Analytical data for Examples 40-44 are summarized in Table 1.

Example 45. (S)—N-(3-((3-aminopyrrolidin-1-yl)methyl)-5-(4-methyl-1H-imidazol-1-yl)phenyl)-4-methyl-3-phenoxybenzamide Example 45

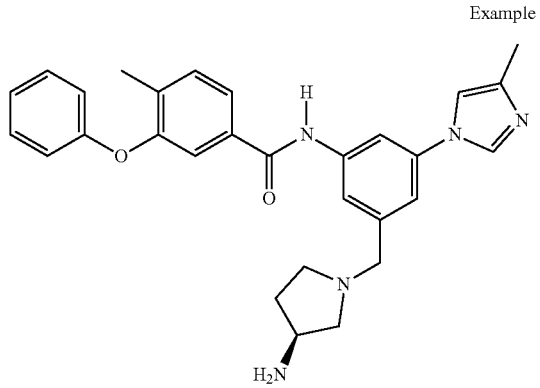

Example 46. (R)—N-(3-((3-(aminomethyl)piperidin-1-yl)methyl)-5-(4-methyl-1H-imidazol-1-yl)phenyl)-4-methyl-3-phenoxybenzamide Example 46

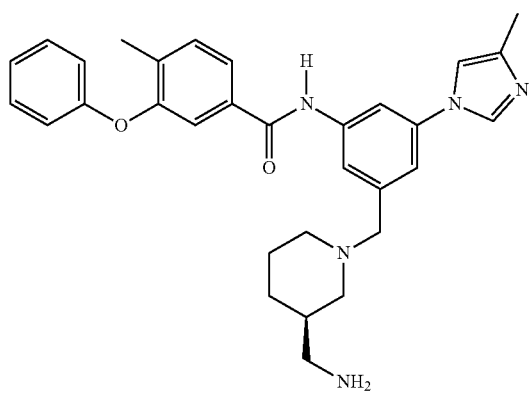

Example 47. (R)—N-(3-((3-(aminomethyl)pyrrolidin-1-yl)methyl)-5-(4-methyl-1H-imidazol-1-yl)phenyl)-4-methyl-3-phenoxybenzamide Example 47

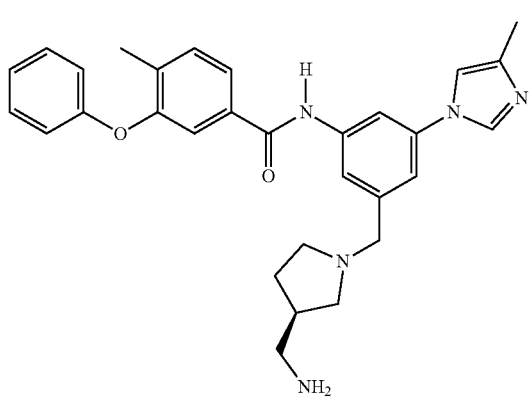

Example 48. (S)-4-methyl-N-(3-(4-methyl-1H-imidazol-1-yl)-5-((3-(methylamino)-piperidin-1-yl)methyl)phenyl)-3-phenoxybenzamide Example 48

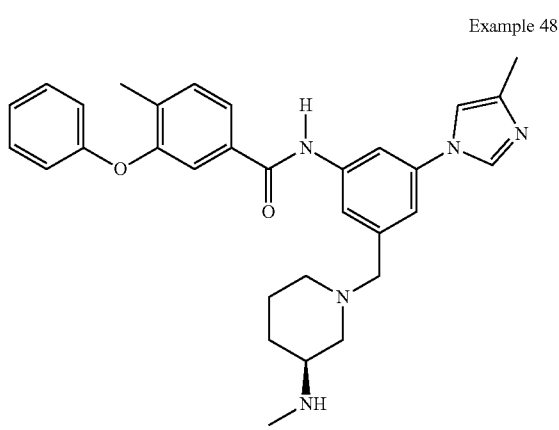 [SMILES: CN[C@H]1CCCN(Cc2cc(NC(=O)c3ccc(C)c(Oc4ccccc4)c3)cc(-n3cnc(C)c3)c2)C1]

Example 49. (S)-4-methyl-N-(3-(4-methyl-1H-imidazol-1-yl)-5-((3-(methylamino)-pyrrolidin-1-yl)methyl)phenyl)-3-phenoxybenzamide Example 49

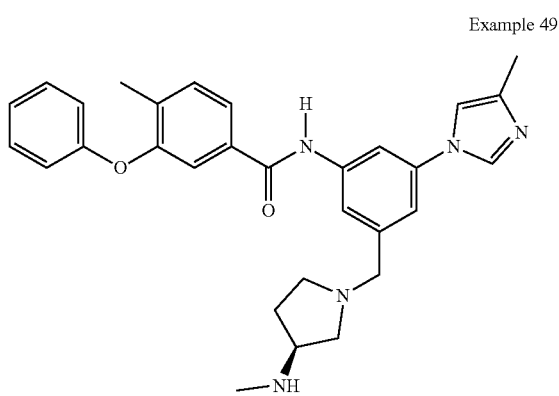 [SMILES: CN[C@H]1CCN(Cc2cc(NC(=O)c3ccc(C)c(Oc4ccccc4)c3)cc(-n3cnc(C)c3)c2)C1]

Example 50. N-(3-(((3aS,6aS)-hexahydropyrrolo[3,4-b]pyrrol-5(1H)-yl)methyl)-5-(4-methyl-1H-imidazol-1-yl)phenyl)-4-methyl-3-phenoxybenzamide Example 50

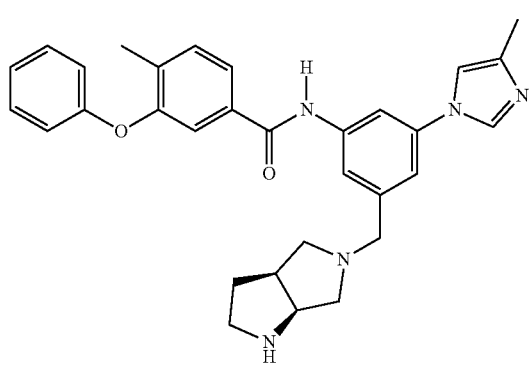

Example 51. N-(3-(((3aR,6aR)-hexahydropyrrolo[3,4-b]pyrrol-1(2H)-yl)methyl)-5-(4-methyl-1H-imidazol-1-yl)phenyl)-4-methyl-3-phenoxybenzamide Example 51

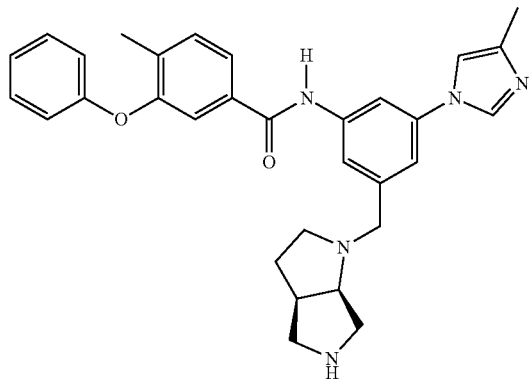

Examples 45-51 were Prepared According to the Following General Schematic:

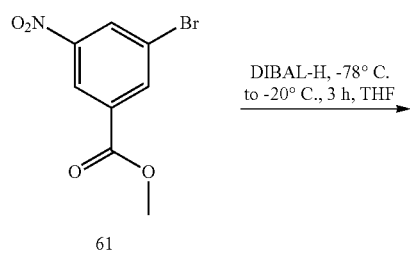

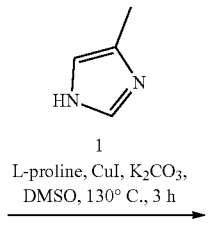

112

L-proline, CuI, K$_2$CO$_3$,
DMSO, 130° C., 3 h

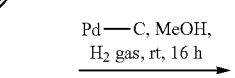

113

Pd—C, MeOH,
H$_2$ gas, rt, 16 h

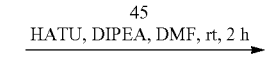

114

45
HATU, DIPEA, DMF, rt, 2 h

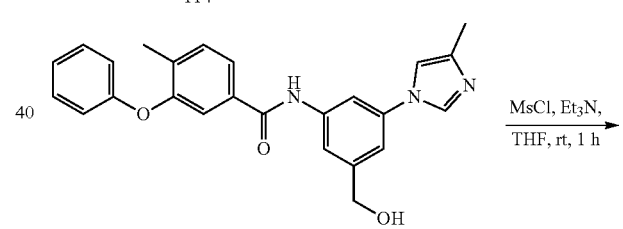

115

MsCl, Et$_3$N,
THF, rt, 1 h

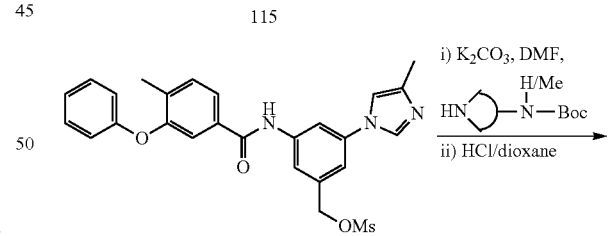

116 i) K$_2$CO$_3$, DMF,
ii) HCl/dioxane

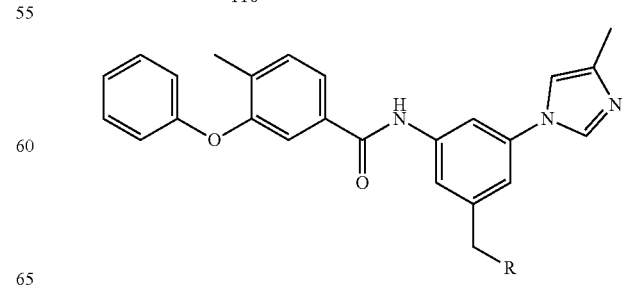

Examples 45-51

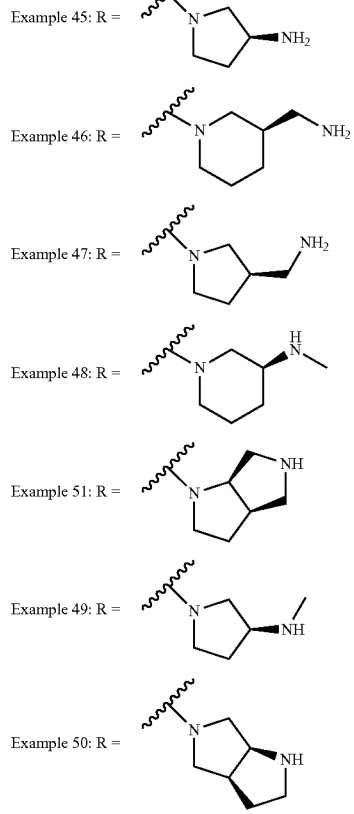

Example 45: R =
Example 46: R =
Example 47: R =
Example 48: R =
Example 51: R =
Example 49: R =
Example 50: R =

To a solution of 61 (20 g, 76.92 mmol) in dry DCM (400 mL), DIBAL-H (1M in Toluene, 154 mL, 153.8 mmol) was slowly added at −78° C. and the temperature was increased to −20° C. The resulting was stirred for another 3 hr at the same temperature. After consumption of starting material, the reaction was quenched with MeOH (160 mL) followed by water (160 mL) and stirred for 30 min. This white suspension was filtered through a pad of Celite and thoroughly washed with DCM (3×200 mL). The mother liquor was concentrated in vacuo to give 112 (17.4 g, 98%) as a yellow solid. $^1$H-NMR (400 MHz; DMSO-d$_6$): δ 8.24 (s, 1H), 8.17 (s, 1H), 7.96 (s, 1H), 5.64 (t, J=5.7 Hz, 1H), 4.62 (d, J=5.6 Hz, 2H).

To a solution of 112 (14 g, 60.34 mmol) in DMSO (200 mL), 1 (17 g, 211.18 mmol), L-proline (3.47 g, 30.17 mmol), CuI (9.2 g, 48.27 mmol) and K$_2$CO$_3$ (20.8 g, 150.8 mmol) were sequentially added at room temperature under N$_2$. The reaction mixture was heated at 130° C. for 3 h. After cooling at room temperature, water (200 mL) was added and reaction mixture was filtered through a pad of Celite, washed with EtOAc (3×50 mL). The filtrate was extracted with ethyl acetate (2×100 mL). The organic layer washed with brine solution (200 mL) and dried (Na$_2$SO$_4$), concentrated in vacuo to give the crude residue. This material was triturated with diethyl ether to give 113 (8 g, 57%) as a light brown solid. MS (ESI+ve): 234.21. $^1$H-NMR (400 MHz; DMSO-d$_6$): δ 8.34-8.30 (m, 2H), 8.12 (s, 1H), 8.01 (s, 1H), 7.64 (bs, 1H), 5.64 (t, J=5.7 Hz, 1H), 4.67 (d, J=5.6 Hz, 2H), 2.17 (s, 3H).

To a solution of 113 (10.0 g, 42.91 mmol) in MeOH (200 mL), 10 mol % Pd on carbon (50% wet, 2.0 g) was added and the reaction mixture was stirred at room temperature under H$_2$ (125 psi) for 16 h. After completion, the reaction mixture was filtered through a pad of Celite, washed with MeOH and concentrated in vacuo to give 114 (8 g, 92%) as a yellow waxy mass. MS (ESI+ve): 204.01. $^1$H-NMR (400 MHz; DMSO-d$_6$): δ 7.89 (s, 1H), 7.21 (s, 1H), 6.58 (s, 1H), 6.53-6.51 (m, 2H), 5.32 (bs, 2H), 5.12 (bs, 1H), 4.38 (bs, 2H), 2.14 (s, 3H) To a suspension of 4-methyl-3-phenoxybenzoic acid (45, 2.25 g, 9.84 mmol) in dry DMF (50 mL), HATU (4.9 g, 12.79 mmol) and DIPEA (3.18 g, 24.6 mmol) were added at room temperature. After 15 min stirring, 114 (2.0 g, 9.84 mmol) was added and reaction was continued at room temperature for 2 h. After completion, the reaction mixture was diluted with water (200 mL) and the yellow suspension obtained was collected by filtration, washed with water, and dried in vacuo to give 115 (2 g, 50%) as a white solid. MS (ESI+ve): 414.04. $^1$H-NMR (400 MHz; DMSO-d$_6$): δ 10.33 (bs, 1H), 7.99 (s, 1H), 7.87 (s, 1H), 7.79 (d, J=7.4 Hz, 1H), 7.67 (s, 1H), 7.55 (s, 1H), 7.50 (d, J=7.8 Hz, 1H), 7.42-7.37 (m, 2H), 7.31 (s, 1H), 7.23 (s, 1H), 7.15-7.11 (m, 1H), 6.97-6.95 (m, 2H), 5.35 (t, J=5.4 Hz, 1H), 4.53 (d, J=5.0 Hz, 2H), 2.26 (s, 3H), 2.16 (s, 3H).

To a solution of 115 (500 mg, 1.21 mmol) in THF (50 mL), Et$_3$N (0.85 mL, 6.05 mmol) was added dropwise. After 15 min stirring, methanesulfonyl chloride (0.19 mL, 2.42 mmol) was slowly added at 0° C. and the reaction was continued at the room temperature for another 1 h.

After consumption of starting material, the reaction mixture was diluted with water (70 mL), and extracted with EtOAc (3×50 mL). The organic layers were combined and washed with brine (50 mL), dried (Na$_2$SO$_4$) and concentrated in vacuo to give 116 (550 mg, 90%) as a brown gummy liquid. This material was used in the next steps without further purification. To a solution of the corresponding Boc-protected amines, 0.8 eq) in dry DMF (5 mL/mmol), K$_2$CO$_3$ (2.5 eq) was added, stirred for 10 min, whereupon 116 (1 eq) was added at room temperature. The reaction was stirred at room temperature for 16 h. After completion of the reaction, the mixture was poured into water (5 mL/mmol) and the solid suspension was filtered and dried in vacuo to give the Boc-protected coupled intermediates, which were used in the next step without further purification.

To a solution of the coupled intermediates (1 eq.) in DCM (20 mL), 4 N HCl in dioxane (4.8 mL) was added at 0° C. and stirred at room temperature for 3 h. The reaction mixtures were concentrated in vacuo to give Examples 45-51, which were purified through prep HPLC or by flash column chromatography. Analytical data for Examples 45-51 are summarized in Table 1.

Example 52. (S)—N-(3-(3-aminopiperidin-1-yl)-5-(4-methyl-1H-imidazol-1-yl)phenyl)-4-methyl-3-phenoxybenzamide

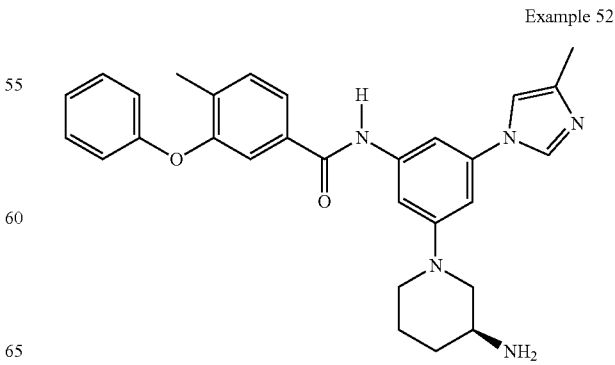

Example 52

This compound was prepared according to the following schematic:

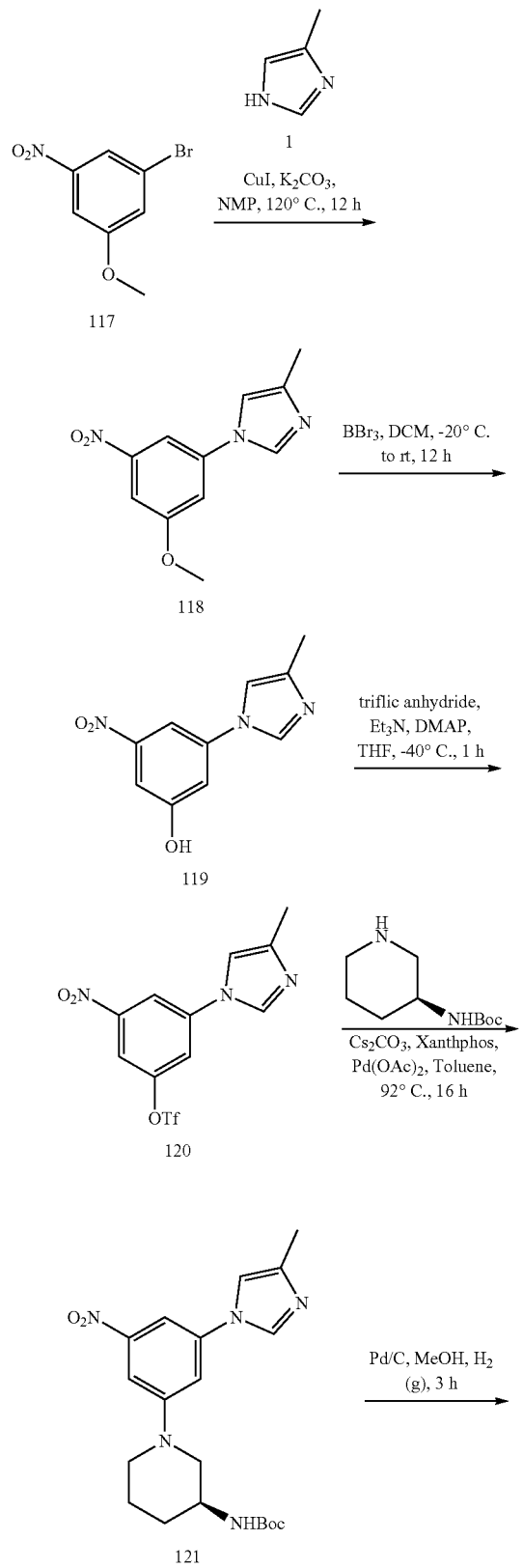

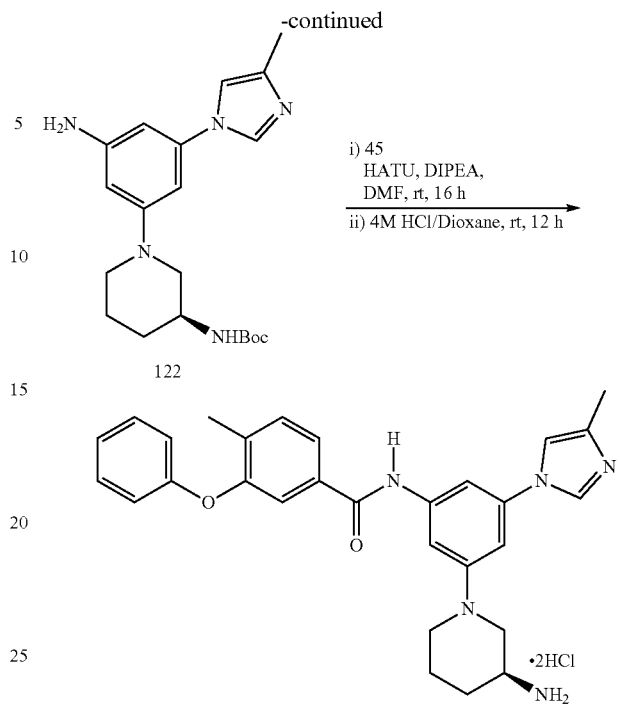

Example 52

To a mixture of 117 (5.0 g, 21.6 mmol) and 4-methyl-1H-imidazole (1, 2.13 g, 25.9 mmol) under N₂, K₂CO₃ (8.9 g, 64.9 mmol) and CuI (2.05 g, 10.8 mmol) were added. The reaction mixture was stirred at 120° C. for 12 h. Progress of the reaction was monitored by TLC. The reaction mixture was allowed to cool to room temperature. The residue was partitioned between EtOAc (3×200 mL) and water (150 mL) and the aqueous layer was extracted with EtOAc (100 mL). The combined organic layers were washed with brine (200 mL), dried over Na₂SO₄, filtered, and concentrated to dryness. The residue was triturated with diethyl ether and pentane to give 118 (2.82 g, 56% yield) as an off-white solid. MS (ESI+ve): 234.08. $^1$H-NMR (400 MHz; DMSO-$d_6$): δ 8.46 (bs, 1H), 8.04 (s, 1H), 7.59-7.54 (m, 3H), 3.94 (s, 3H), 2.61 (s, 3H).

To a stirred solution of 118 (2.5 g, 10.7 mmol) in DCM (60 mL), BBr₃ (3.0 mL, 32.1 mmol) was added under N₂ at −20° C. The reaction mixture was stirred at 20° C. for 16 h. After completion, the reaction mixture was poured into sat. NH₄Cl (200 mL) and extracted with EtOAc (2×300 mL). The organic layer was dried over Na₂SO₄, filtered and concentrated to dryness. The residue was purified by column chromatography [normal phase, silica gel (100-200 mesh), gradient 3% MeOH in DCM] to give 119 (1.21 g, 67% yield) as white solid. MS (ESI+ve): 220.06. $^1$H-NMR (400 MHz; DMSO-$d_6$): δ 10.86 (s, 1H), 7.87 (s, 1H), 7.57 (s, 1H), 7.50 (s, 1H), 7.43 (s, 3H), 2.15 (s, 1H).

To a stirred solution of 119 (1.2 g, 5.47 mmol) in THF (50 mL), Et₃N (2.2 g, 21.8 mmol), DMAP (0.3 g, 2.73 mmol), and triflic anhydride (1.54 g, 5.47 mmol) were added under N₂ at −40° C. The reaction mixture was stirred at −40° C. for 1 h. Progress of the reaction was monitored by TLC. The reaction mixture was poured into water (200 mL) and extracted with EtOAc (2×300 mL). The organic layer was dried over Na₂SO₄, filtered, and concentrated to dryness. The residue was purified by column chromatography [normal phase, silica gel (100-200 mesh), gradient 3% MeOH in DCM] to give 120 (1.23 g, 38% yield) as a white solid. MS (ESI−ve): 350.01. $^1$H-NMR (400 MHz; CDCl₃): δ 8.29 (s, 1H), 8.08 (s, 1H), 7.88 (s, 1H), 7.10 (s, 1H), 7.62 (s, 1H), 2.29 (s, 3H).

To a solution of 120 (1.0 g, 2.9 mmol) in toluene (50 mL), (S)-tert-butylpiperidin-3-yl carbamate, (0.58 g, 2.9 mmol), Xantphos (0.1 g, 0.3 mmol), and Pd(OAc)₂ (0.3 g, 0.01 mmol), were added and the reaction mixture was heated to 90° C. for 16 h. After completion, the reaction mixture was concentrated, diluted with water (80 mL) and extracted with EtOAc (2×120 mL). The organic layer was dried over Na₂SO₄, filtered, and concentrated to dryness. The residue was purified by column chromatography [normal phase, silica gel (100-200 mesh), gradient 2% MeOH in DCM] to give 121 (0.19 g, 16% yield) as a yellow solid. MS (ESI+ve): 402.21. 0.15 g (0.37 mmol) of this material was dissolved in MeOH (25 mL), Pd/C (0.3 g) was added, and the reaction mixture was stirred under H₂ at room temperature for 3 h. Progress of the reaction was monitored by TLC. The reaction mixture was filtered through Celite and the filtrate was concentrated to give 122 as a light brown solid. This material was used for the next step without further purification. MS (ESI+ve): 372.5.

To a stirred solution of 45 (0.60 g, 0.2 mmol) in DMF (5 mL), 122 (0.8 g, 0.2 mmol), HATU (0.25 g, 0.65 mmol), and DIPEA (0.18 mL, 1.0 mmol) were added and the reaction mixture was stirred at room temperature for 16 h. Progress of the reaction was monitored by TLC. The reaction mixture was concentrated to dryness, diluted with water (10 mL) and extracted with EtOAc (2×20 mL). The organic layer was dried over Na₂SO₄, filtered, and concentrated to dryness. The residue was purified by column chromatography [normal phase, silica gel (100-200 mesh), gradient 4% MeOH in DCM] to give the Boc-protected amine (0.46 g, 42% yield) as an off white solid. MS (ESI+ve): 582.3. ¹H-NMR (400 MHz; DMSO-d₆): δ 10.16 (s, 1H), 8.29 (d, J=5.3 Hz, 1H), 7.76 (d, J=5.3 Hz, 1H), 7.53-7.48 (m, 3H), 7.45 (s, 1H), 7.41-7.37 (m, 2H), 7.24 (s, 1H), 7.13 (t, J=7.5 Hz, 1H), 6.95 (d, J=8.3 Hz, 3H), 6.87 (s, 1H), 3.69-3.61 (m, 1H), 3.49-3.41 (m, 1H), 2.71-2.76 (m, 2H), 2.26 (s, 3H), 2.18 (s, 3H), 1.86-1.82 (m, 1H), 1.77-1.75 (m, 1H), 1.56-1.51 (m, 1H), 1.38 (s, 9H), 1.37-1.32 (m, 2H). To a stirred solution of this material) 0.2 g, 0.32 mmol) in 1,4-dioxane (1 mL), 4M HCl in dioxane (4 mL), was added at 0° C. and the reaction mixture was stirred at room temperature for 3 h. Progress of the reaction was monitored by TLC. The reaction mixture was concentrated to dryness. The residue was purified by trituration with ethyl acetate and diethyl ether to give Example 52 (39 mg) as an off white solid. Analytical data for Example 52 are summarized in Table 1.

Example 53. (S)—N-(3-((3-aminopiperidin-1-yl)methyl)-5-(4-methyl-1H-imidazol-1-yl)-phenyl)-3-(4-(hydroxymethyl)phenoxy)benzamide This compound was prepared according to the following schematic:

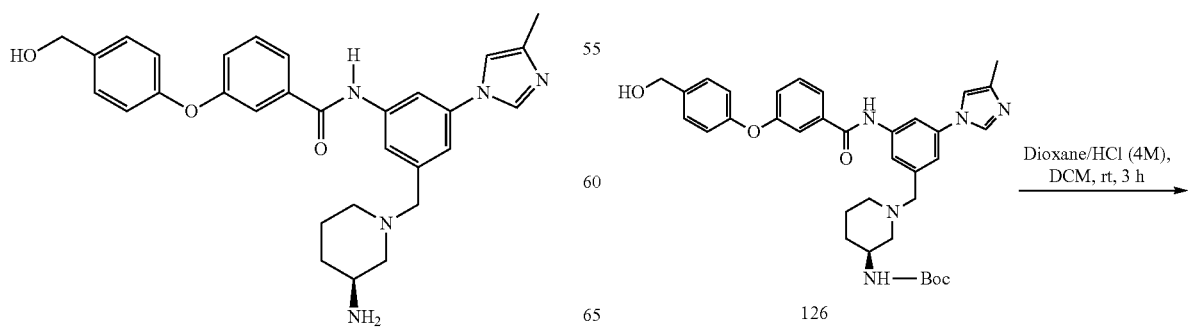

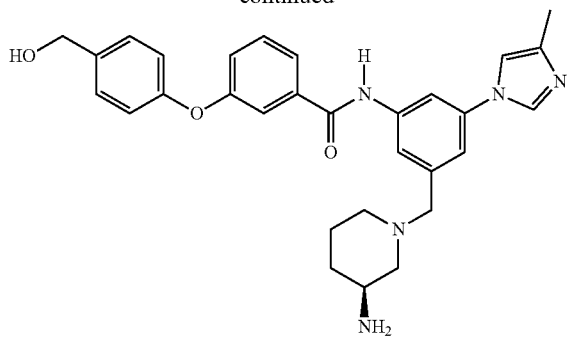

Example 53

To a solution of methyl 3-bromobenzoate (8 g, 52.58 mmol) in DCM (100 mL), (4-cyanophenyl)boronic acid (9.27 g, 63.10 mmol), Et$_3$N (22.2 mL, 157.2 mmol) and Cu(OAc)$_2$ (19.1 g, 105.1 mmol) were added. The reaction mixture was stirred at room temperature under O$_2$ for 2 days. After consumption of starting material, the reaction mixture was filtered through a pad of Celite, washed with DCM (2×50 mL). The filtrate was diluted with water (50 mL) and extracted with DCM (2×50 mL). The combined organic layer was dried with anhydrous Na$_2$SO$_4$, concentrated in vacuo to give 123 (3.0 g, 23%) as a white solid. 2.0 g, 7.90 mmol of 123 in THF: H$_2$O (8:2, 20 mL) was treated with LiOH.H$_2$O (1.66 mg, 39.49 mmol) at room temperature. The reaction mixture was stirred for another 16 h. After consumption of starting material, the reaction mixture was concentrated in vacuo to dryness. The residue was dissolved in water (20 mL) and neutralized by 1M HCl, a white solid was precipitated out, filtered, washed with water, and dried in vacuo to give 124 (1.5 g, 79%) as a white solid. MS (ESI-ve): 238.08. $^1$H-NMR (400 MHz; DMSO-d$_6$): δ 13.27 (bs, 1H), 7.86 (d, J=8.7 Hz, 2H), 7.82 (d, J=7.6 Hz, 1H), 7.61-7.56 (m, 2H), 7.41 (d, J=7.9 Hz, 1H), 7.16 (d, J=6.7 Hz, 2H).

To a suspended solution of 124 (2.25 g, 9.84 mmol) in dry DMF (20 mL), HATU (1.28 g, 3.37 mmol) and DIPEA (1.1 mL, 6.49 mmol) were sequentially added at room temperature. After 15 min stirring, 53 (1.0 g, 2.59 mmol) was added and stirring was continued at the same temperature for 2 h. After completion, the reaction mixture was diluted with water (100 mL), white solid precipitates were obtained, which were collected through filtration, washed with water, and dried in vacuo to give 125 (1.0 g, 64%) as a white solid. MS (ESI+ve): 607.20. $^1$H-NMR (400 MHz; DMSO-d$_6$): δ 10.44 (bs, 1H), 8.03 (s, 1H), 7.94 (s, 1H), 7.92-7.85 (m, 3H), 7.76 (s, 1H), 7.70-7.60 (m, 2H), 7.45-7.40 (m, 1H), 7.34 (s, 1H), 7.24 (s, 1H), 7.17 (d, J=4.9 Hz, 2H), 3.52-3.36 (m, 3H), 2.82-2.72 (m, 1H), 2.70-2.60 (m, 1H), 2.16 (s, 3H), 2.00-1.90 (m, 1H), 1.82-1.76 (m, 1H), 1.72-1.60 (m, 3H), 1.45-1.40 (m, 1H), 1.34 (s, 9H).

To a solution of 125 (300 mg, 0.49 mmol) in AcOH (50 mL), Raney Ni (50 mg) was added and the reaction mixture was stirred at 70° C. under H$_2$ (125 psi) for 3 h. After completion, the reaction mixture was filtered through a pad of Celite and washed with EtOAc (2×20 mL). The filtrate was diluted with water (50 mL) and extracted with EtOAc (2×50 mL). The combined organic layer was dried with anhydrous Na$_2$SO$_4$, and concentrated in vacuo to give 126 (300 mg) as a yellow solid. MS (ESI+ve): 612.23.

This material was dissolved in DCM:MeOH (8:2, 10 mL) and treated with 4M HCl in dioxane (2 mL) at 0° C. and the reaction mixture was stirred at that temperature for 3 h. After completion, the reaction mixture was concentrated in vacuo to dryness. The residue was purified by prep-HPLC (reverse phase, Sunfire C18 (19×250 mm) 10μ, gradient 10-25% ACN in 13 min containing 0.1% TFA in water, RT: 11.77 min, wavelength 214 nm) to give Example 53 (55 mg, 22%) as a white solid. Analytical data for Example 53 are summarized in Table 1.

Example 54. (S)-4-(3-((3-((3-aminopiperidin-1-yl)methyl)-5-(4-methyl-1H-imidazol-1-yl)phenyl)carbamoyl)phenoxy)benzoic acid

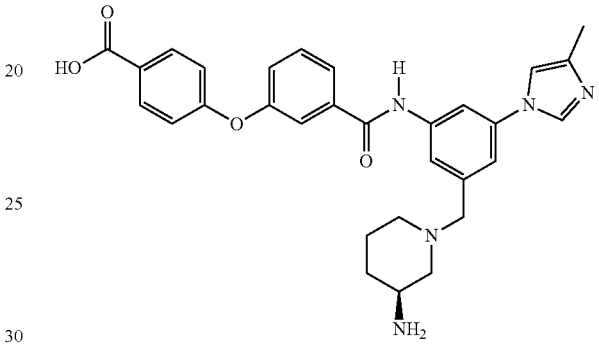

Example 54

This compound was prepared according to the following schematic:

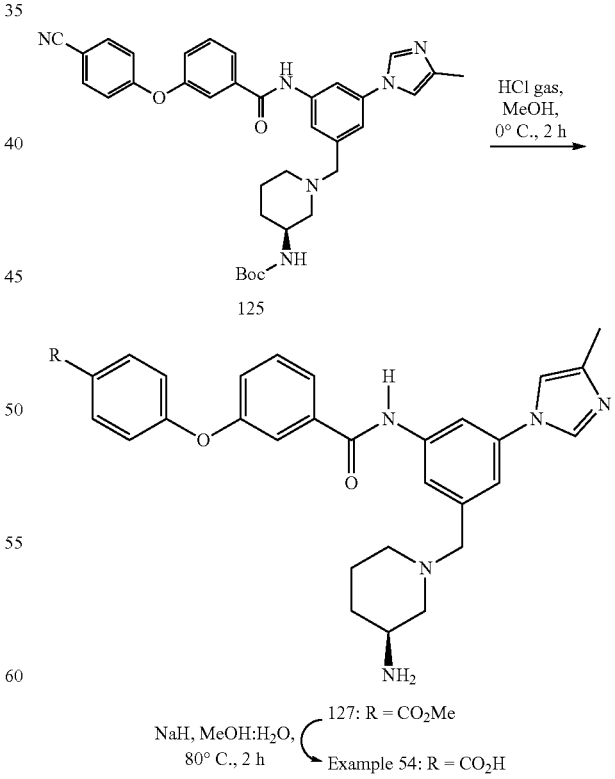

To a solution of 125 (300 mg, 0.49 mmol) in MeOH (20 mL), HCl gas was purged at 0° C. and the reaction mixture was stirred at same temperature for 2 h. After consumption of starting material, the reaction mixture was concentrated in vacuo to give 127 (300 mg, crude) as a white solid. LCMS: m/z 540.48 (M+1). To a solution of this material in MeOH:H$_2$O (8:2, 10 mL), NaOH (47 mg, 1.17 mmol) was added at room temperature. The reaction was stirred at 80° C. for 2 h. After consumption of starting material, the reaction mixture was concentrated in vacuo to dryness. The residue was purified by prep-HPLC (reverse phase, X-Select Hexyl Phenyl (19-250 mm) 15μ, gradient 10-52% ACN in 11 mins containing 0.1% TFA in water, RT: 10.5 min, wavelength 214 nm) to give Example 54 (50 mg, 17%, bis-TFA salt) as a white solid. Analytical data for Example 54 are summarized in Table 1.

Example 55. (S)—N-(3-((3-aminopiperidin-1-yl)methyl)-5-(4-methyl-1H-imidazol-1-yl)-phenyl)-3-(4-carbamoylphenoxy)benzamide Example 55

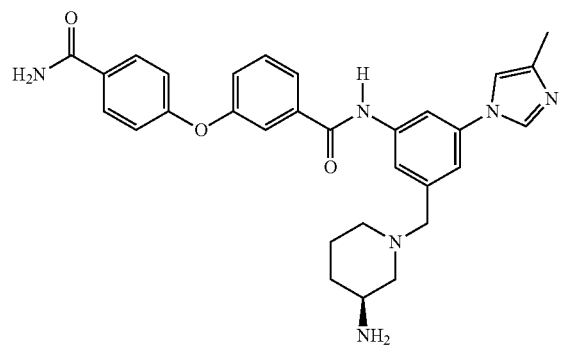

This compound was prepared according to the following schematic:

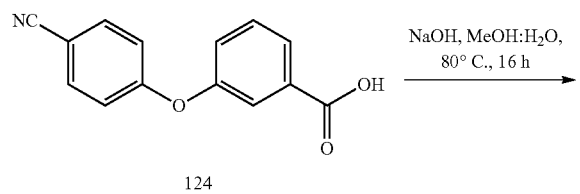

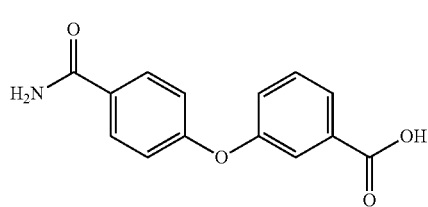

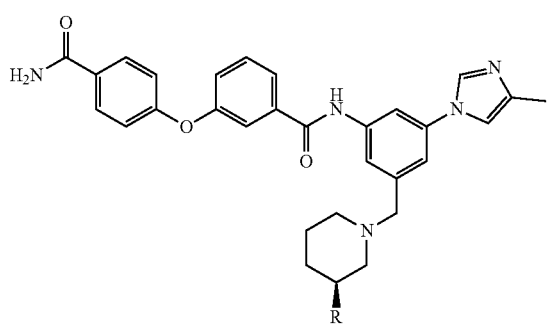

To a solution of 124 (300 mg, 1.25 mmol) in MeOH:H$_2$O (8:2, 20 mL), NaOH (251 g, 6.27 mmol) was added at room temperature. The reaction was stirred at 80° C. for 16 h. After consumption of starting material, the reaction mixture was concentrated in vacuo to dryness. The residue was dissolved in water (20 mL) and neutralized by 1N aqueous HCl, and a white solid precipitated out. The precipitate was filtered, washed with water, and dried in vacuo to give 128 (300 mg) as a white solid. MS (ESI+ve): 258.21.

To a suspended solution of 128 (267 mg, 1.04 mmol) in dry DMF (20 mL), HATU (513 mg, 1.35 mmol) and DIPEA (400 mg, 3.11 mmol) were added at room temperature. After 15 min stirring, 53 (400 mg 1.04 mmol) was added and the reaction was continued at the same temperature for 2 h. After consumption of starting material, the reaction mixture was diluted with water (100 mL), and a yellow solid precipitated out which was filtered, washed with water and dried in vacuo to give crude 129 (600 mg). MS (ESI+ve): 625.19.

To a solution of 129 (400 mg, 0.64 mmol) in DCM (20 mL), 4M HCl in dioxane (5 mL) was added at 0° C. and the reaction mixture was stirred at room temperature for 3 h. After consumption of starting material, the reaction mixture was concentrated in vacuo to dryness. The residue was purified by prep-HPLC (reverse phase, Sunfire C18 (19×250 mm) 10μ, gradient 10-25% ACN in 15 mins containing 0.1% TFA in Water, RT: 10.7 min, wavelength 214 nm) to give Example 55 (85 mg, 25% as bis-TFA salt) as a white solid. Analytical data for Example 55 are summarized in Table 1.

Example 56. (S)—N-(3-((3-aminopiperidin-1-yl)methyl)-5-(4-methyl-1H-imidazol-1-yl)-phenyl)-3-((2-(4-methoxybenzyl)-1-oxo-1,2-dihydroisoquinolin-6-yl)oxy)benzamide
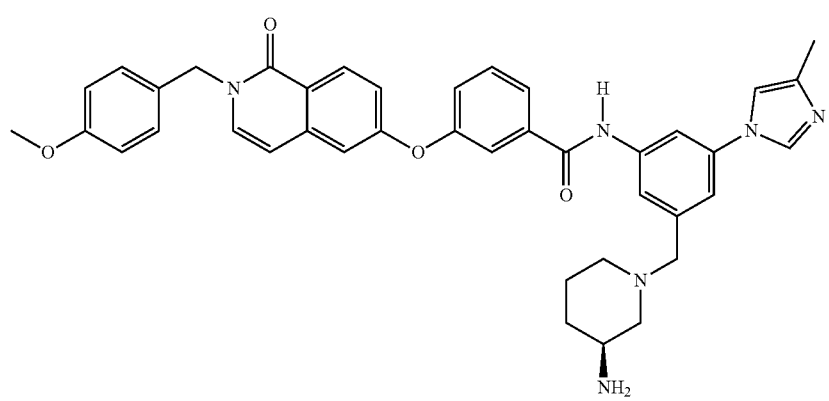
Example 56
Example 57. (S)—N-(3-((3-aminopiperidin-1-yl)methyl)-5-(4-methyl-1H-imidazol-1-yl)-phenyl)-3-((1-oxo-1,2-dihydroisoquinolin-6-yl)oxy)benzamide
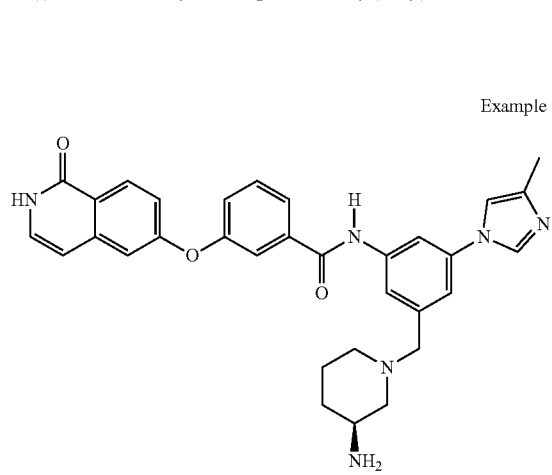
Example 57
These compounds were prepared according to the following schematic:
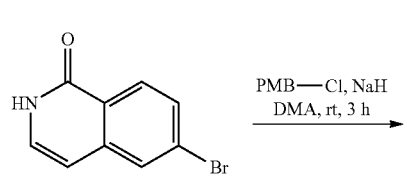
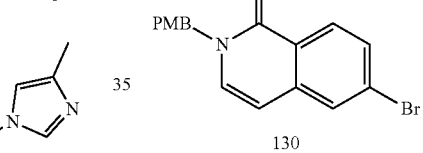
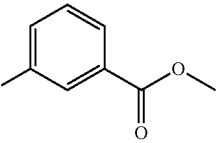
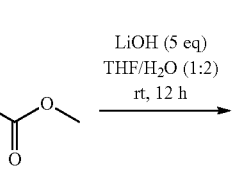
130
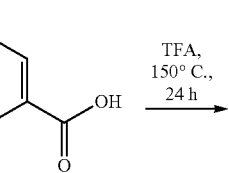
131
132
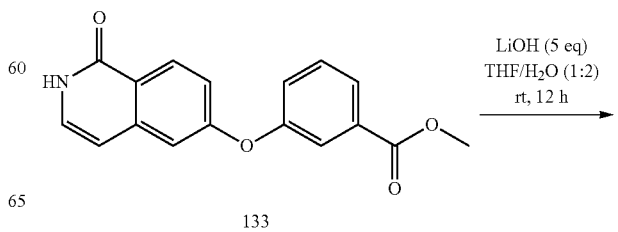
133

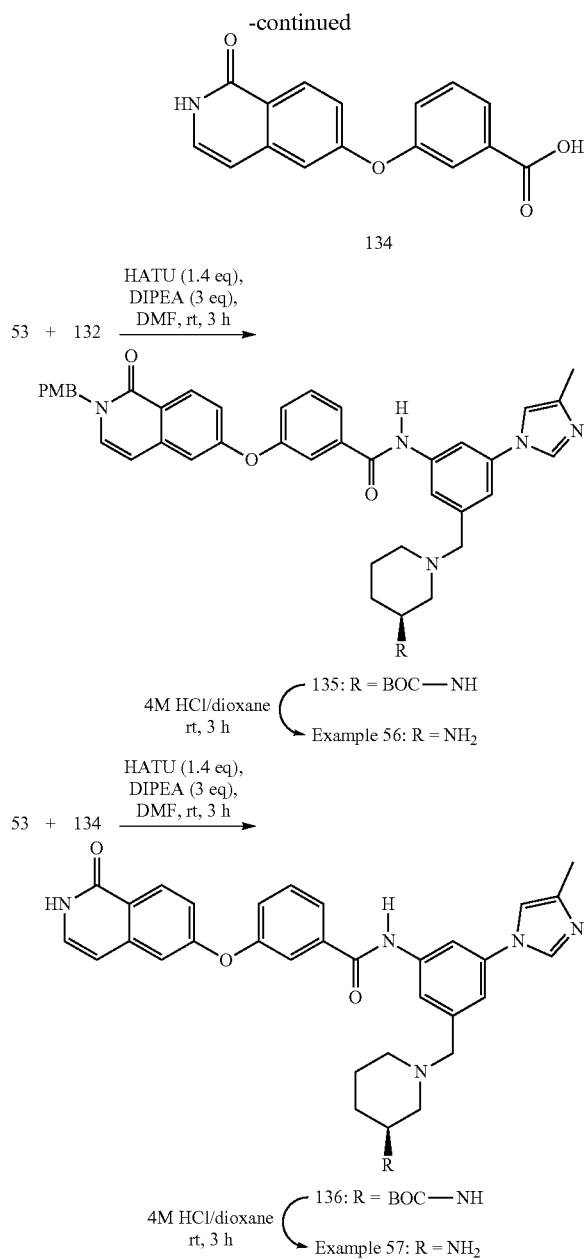

To a solution of 6-bromoisoquinolin-1(2H)-one (0.5 g, 2.23 mmol) in DMA (10 mL), was added NaH (60%, 0.13 g, 3.34 mmol) at room temperature and the mixture was stirred for 30 min. 4-methoxybenzyl chloride (0.52 g, 3.34 mmol) was added to the reaction mixture at room temperature. The reaction mixture was stirred at rt for 3 h. Progress of the reaction was monitored by TLC. The reaction mixture was diluted with water (100 mL) and extracted with EtOAc (2×50 mL). The organic layers were separated, dried ($Na_2SO_4$), filtered and concentrated to afford 130 (1.02 g, crude) as a brown semisolid. This material was used for the next step without further purification. MS (ESI+ye): 344.04. $^1$H-NMR (400 MHz; DMSO-$d_6$): δ 8.12 (d, J=8.56 Hz, 1H), 7.94 (s, 1H), 7.65-7.62 (m, 2H), 7.30-7.26 (m, 2H), 6.91-6.87 (m, 2H), 6.61 (d, J=7.32 Hz, 1H), 5.08 (s, 2H), 3.72 (s, 3H).

To a stirred solution of 130 (1 g, 2.91 mmol) in toluene (20 mL), were added methyl 3-hydroxybenzoate (0.53 g, 3.49 mmol), Cu (0.09 g, 1.45 mmol), CuI (0.27 g, 1.45 mmol) and $K_2CO_3$ (1.2 g, 8.76 mmol) at room temperature. The reaction mixture was stirred at 100° C. for 48 h. Progress of the reaction was monitored by TLC. The reaction mixture was filtered through a Celite bed and washed with EtOAc. The filtrate was evaporated to dryness. The residue was purified by column chromatography [normal phase, silica gel (100-200 mesh), gradient 30% EtOAC in hexane] to afford 131 (0.58 g, 47% yield) as an off white solid. This material was used in the next step without further purification. MS (ESI+ve): 416.13.

To a solution of 131 (0.25 g, 0.60 mmol) in THF/$H_2O$ (2:1), was added LiOH (0.12 g, 3.01 mmol) at room temperature. The reaction mixture was stirred at rt for 12 h. Progress of the reaction was monitored by TLC. The reaction mixture was diluted with water (80 mL) and washed with EtOAc (2×50 mL) to remove non-polar impurities. The aqueous layer was acidified with 1N HCl and extracted with EtOAc (3×60 mL). The combined organic layer was dried ($Na_2SO_4$), filtered and concentrated to afford 132 (0.22 g, crude) as a white solid. This material was used for the next step without further purification. MS (ESI+ve): 402.09.

To a stirred solution of 132 (0.18 g, 0.46 mmol) in DMF (5 mL), 53 (0.15 g, 0.38 mmol), HATU (0.21 g, 0.54 mmol), and DIPEA (0.2 mL, 1.16 mmol) were added. The reaction mixture was stirred at room temperature for 3 h. Progress of the reaction was monitored by TLC. The reaction mixture was concentrated, diluted with water (50 mL) and extracted with EtOAc (2×80 mL). The organic layer was dried over $Na_2SO_4$, filtered, and concentrated to dryness. The residue was purified by column chromatography [normal phase, silica gel (100-200 mesh), gradient 2% MeOH in DCM] to afford 135 (0.13 g, 44%) as an off white solid. MS (ESI+ve): 769.32. $^1$H-NMR (400 MHz; DMSO-$d_6$): δ 10.4 (s, 1H), 8.26 (d, J=8.72 Hz, 1H), 8.01 (s, 1H), 7.93 (s, 1H), 7.87 (d, J=7.64 Hz, 1H), 7.75 (s, 1H), 7.62 (d, J=8.32 Hz, 2H), 7.54 (d, J=7.28 Hz, 1H), 7.39 (d, J=9.4 Hz, 1H), 7.33 (s, 1H), 7.28 (d, J=8.6 Hz, 2H), 7.24-7.21 (m, 2H), 7.15 (s, 1H), 6.88 (d, J=8.32 Hz, 2H), 6.69-6.66 (m, 1H), 6.58 (d, J=7.68 Hz, 1H), 5.08 (s, 2H), 3.71 (s, 3H), 3.53-3.49 (m, 3H), 2.79-2.76 (m, 1H), 2.75-2.71 (m, 2H), 2.16 (s, 3H), 1.93-1.89 (m, 2H), 1.84-1.80 (m, 1H), 1.69-1.62 (m, 2H), 1.33 (s, 9H).

To a solution of 135 (0.05 g, 0.06 mmol) in 1, 4-dioxane (1 mL), 4M HCl in dioxane (0.5 mL) was added at 0° C. and the reaction mixture was stirred at room temperature for 5 h. Progress of the reaction was monitored by TLC. The reaction mixture was concentrated to dryness. The residue was triturated with EtOAc and pentane to afford Example 56 (0.04 g) as a brown solid.

A solution of 131 (0.58 g, 1.39 mmol) in TFA (5 mL) was stirred at 150° C. for 24 h. Progress of the reaction was monitored by TLC. The reaction mixture was quenched with ice cold saturated aq. $NaHCO_3$ solution (80 mL) and extracted with EtOAc (3×60 mL). The combined organic layer was dried ($Na_2SO_4$), concentrated to dryness. The residue was purified by column chromatography [normal phase, silica gel (100-200 mesh), gradient 30% EtOAC in hexane] to afford 133 (0.21 g, 50%) as an off white solid. This material was used for the next step without further purification. MS (ESI+ve): 295.96. This material was dissolved in THF/$H_2O$ (2:1) to which was added LiOH (0.15 g, 3.55 mmol) at room temperature. The reaction mixture was stirred at rt for 12 h. Progress of the reaction was monitored by TLC. The reaction mixture was diluted with water (80 mL) and washed with EtOAc (2×50 mL) to remove non-polar impurities. The aqueous layer was acidified with 1N HCl and extracted with EtOAc (3×60 mL). The combined organic layer was dried (Na$_2$SO$_4$), filtered and concentrated to afford 134 (0.19 g, crude) as an off white solid. MS (ESI+ve): 281.92.

To a stirred solution of 134 (0.19 g, 0.67 mmol) in DMF (5 mL), 53 (0.2 g, 0.51 mmol), HATU (0.28 g, 0.75 mmol), and DIPEA (0.26 mL, 1.55 mmol) were added and the reaction mixture was stirred at room temperature for 3 h. Progress of the reaction was monitored by TLC. After completion, the reaction mixture was concentrated to dryness, diluted with ice cold water (50 mL) and extracted with EtOAc (2×500 mL). The organic layer was dried over Na$_2$SO$_4$, filtered, and concentrated to dryness. The residue was purified by column chromatography [normal phase, silica gel (100-200 mesh), gradient 2% MeOH in DCM] to afford 136 (0.08 g, 23%) as a brown solid. MS (ESI+ve): 649.29. $^1$H-NMR (400 MHz; DMSO-d$_6$): δ 10.4 (s, 1H), 8.21 (d, J=8.16 Hz, 1H), 8.04 (s, 1H), 7.94 (s, 1H), 7.87 (d, J=8.0 Hz, 1H), 7.75 (s, 1H), 7.66-7.61 (m, 2H), 7.40 (d, J=8.44 Hz, 1H), 7.35 (s, 1H), 7.24 (s, 1H), 7.20-7.16 (m, 3H), 6.73 (bs, 1H), 6.49 (d, J=7.28 Hz, 1H), 3.48 (s, 3H), 2.16 (s, 3H), 2.0-1.98 (m, 1H), 1.88-1.85 (m, 2H) 1.66-1.61 (m, 3H), 1.45-1.43 (m, 2H), 1.33 (s, 9H).

To a stirred solution of 136 (0.08 g, 0.12 mmol) in 1,4-dioxane (2 mL), 4M HCl in dioxane (1 mL) was added at 0° C. and the reaction mixture was stirred at room temperature for 5 h. Progress of the reaction was monitored by TLC. The reaction mixture was concentrated to dryness. The residue was triturated with EtOAc and pentane to afford Example 57 0.04 g, 23% yield) as a white solid. Analytical data for Examples 56 and 57 are summarized in Table 1.

Example 58. (S)—N-(3-((3-aminopiperidin-1-yl) methyl)-5-(4-methyl-1H-imidazol-1-yl)-phenyl)-3-((1-oxoisoindolin-5-yl)oxy)benzamide

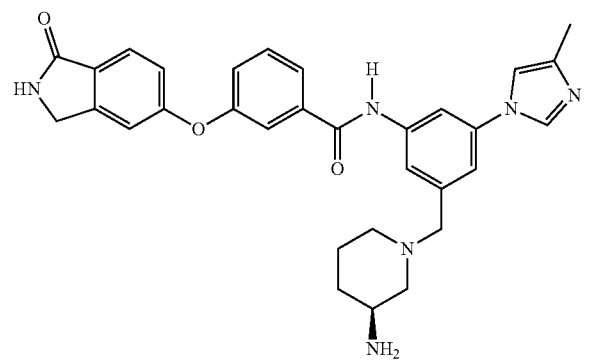

Example 58

This compound was prepared according to the following schematic:

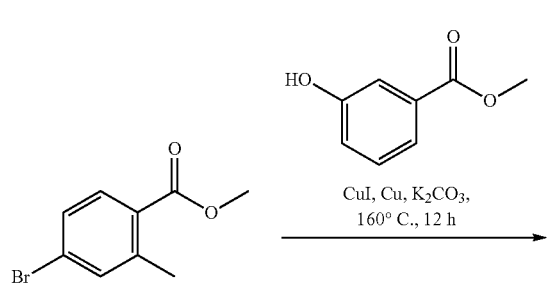

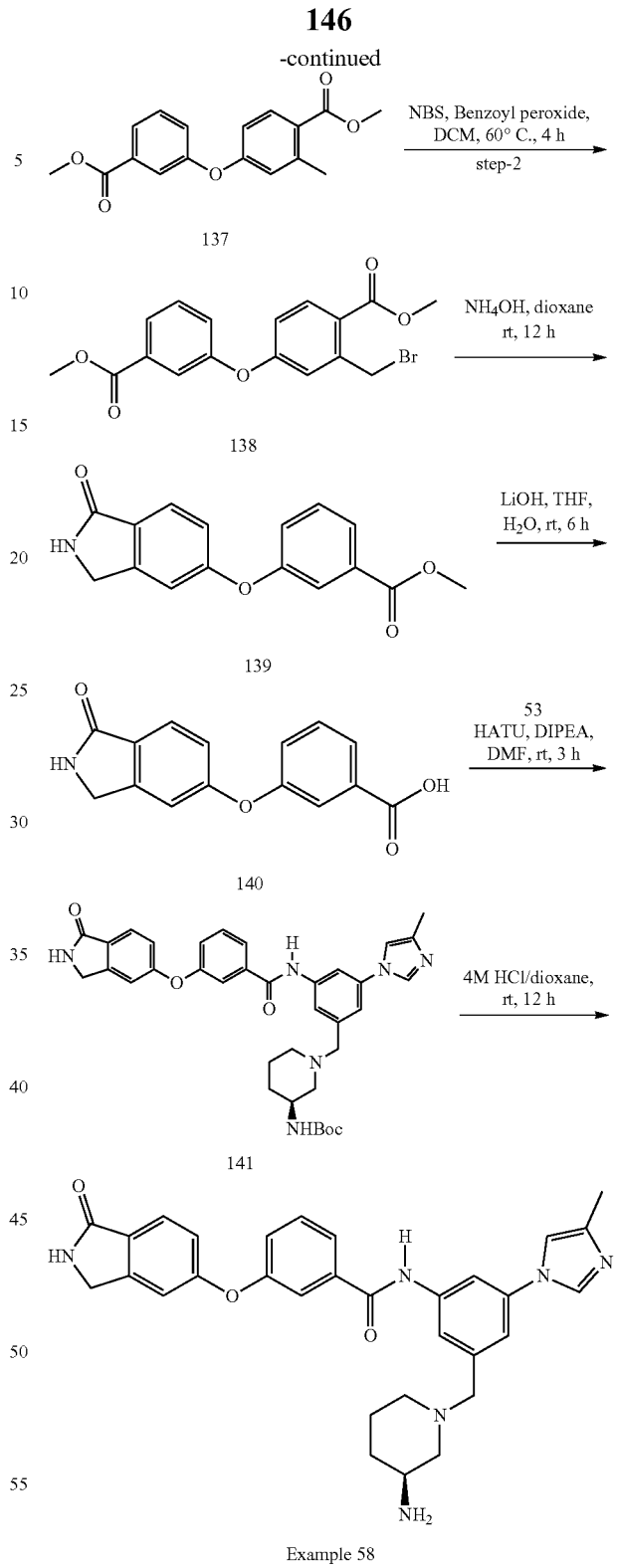

To a mixture of methyl 4-bromo-2-methylbenzoate (5.0 g, 22.1 mmol) and methyl 3-hydroxybenzoate (3.36 g, 22.1 mmol) under N$_2$, K$_2$CO$_3$ (15.2 g, 110 mmol), CuI (0.84 g, 4.42 mmol) and Cu powder (0.28 g, 4.42 mmol) were added. The reaction mixture was stirred at 160° C. for 12 h. Progress of the reaction was monitored by TLC. The reaction mixture was allowed to cool to room temperature. The residue was partitioned between EtOAc (2×300 mL) and water (120 mL) and the aqueous layer was separated and extracted with EtOAc (100 mL). The combined organic layers were washed with brine (200 mL), dried over Na$_2$SO$_4$, filtered, and concentrated to dryness. The residue was purified by column chromatography [normal phase, silica gel (100-200 mesh), gradient 4% ethyl acetate in hexane] to 137 (2.7 g, 41%) as an off white solid. MS (ESI+ve): 300.92. $^1$H-NMR (400 MHz; DMSO-d$_6$): δ 7.89 (d, J=8.6 Hz, 1H), 7.80 (d, J=7.6 Hz, 1H), 7.59 (t, J=7.9 Hz, 1H), 7.53 (s, 1H), 7.41 (d, J=8.0 Hz, 1H), 6.99 (s, 1H), 6.92 (d, J=7.6 Hz, 1H), 3.84 (s, 3H), 3.80 (s, 3H) 2.50 (s, 3H).

To a solution of 137 (2.5 g, 8.3 mmol) in dry DCM (30 mL), NBS (1.48 g, 8.3 mmol) and benzoyl peroxide (2.5 g, 8.3 mmol) were added and the mixture was heated at 60° C. for 4 h. Progress of the reaction was monitored by TLC. The reaction mixture was cooled to room temperature, diluted with water (50 mL) and extracted with DCM (2×100 mL). The combined organic layer was washed with brine solution (50 mL), dried over Na$_2$SO$_4$, filtered, and concentrated to dryness. The residue was purified by column chromatography [normal phase, silica gel (100-200 mesh), gradient 5% ethyl acetate in hexane] to give 138 (1.5 g, 48%) as a yellowish semi-solid. MS (ESI+ve): 378.8. $^1$H-NMR (400 MHz; DMSO-d$_6$): δ 7.92 (d, J=8.8 Hz, 1H), 7.83 (d, J=7.3 Hz, 1H), 7.62 (t, J=8.0 Hz, 1H), 7.58 (s, 1H), 7.45 (d, J=8.0 (Hz, 1H), 7.28 (s, 1H), 7.04 (d, J=8.5 Hz, 1H), 5.01 (s, 2H), 3.85 (s, 6H).

To a solution of 138 (0.8 g, 2.11 mmol) in 1,4-dioxane (10 mL), aq. NH$_4$OH (5 mL) was added at room temperature and the reaction mixture was stirred at room temperature for 12 h. Progress of the reaction was monitored by TLC. The reaction mixture was concentrated, diluted with water (50 mL) and extracted with DCM (2×100 mL). The organic layers were washed with brine solution (50 mL) and dried over Na$_2$SO$_4$, filtered, and concentrated to dryness. The residue was purified by column chromatography [normal phase, silica gel (100-200 mesh), gradient 60% ethyl acetate in hexane] to give 139 (0.51 g, 85%) as an off-white solid. MS (ESI+ve): 283.97. $^1$H-NMR (400 MHz; DMSO-d$_6$): δ 8.48 (bs, 1H), 7.79 (d, J=7.7 Hz, 1H), 7.68 (d, J=8.2 Hz, 1H), 7.60 (t, J=8.0 Hz, 1H), 7.53 (s, 1H), 7.42 (d, J=8.0 Hz, 1H), 7.19 (s, 1H), 7.13 (d, J=8.2 Hz, 1H), 4.33 (s, 2H), 3.83 (s, 3H).

To a solution of 139 (0.5 g, 1.76 mmol) in THF (10 mL), aq. LiOH (0.13 g, 5.3 mmol) was added and the reaction mixture was stirred at room temperature for 6 h. Progress of the reaction was monitored by TLC. The reaction mixture was concentrated, diluted with water (50 mL) and extracted with EtOAc (30 mL). The aqueous layer was acidified with 1N HCl and extracted by DCM (2×100 mL), dried over Na$_2$SO$_4$, filtered, and concentrated to dryness to give 140 (0.36 g, 77%) as an off-white solid. MS (ESI+ve): 270.10. $^1$H-NMR (400 MHz; DMSO-d$_6$): δ 13.1 (bs, 1H), 8.47 (bs, 1H), 7.76 (d, J=7.2 Hz, 1H), 7.68 (d, J=8.4 Hz, 1H), 7.56 (t, J=8.0 Hz, 1H), 7.51 (s, 1H), 7.38 (d, J=7.4 Hz, 1H), 7.18 (s, 1H), 7.13 (d, J=8.0 Hz, 1H), 4.33 (s, 2H).

To a stirred solution of 140 (0.2 g, 0.77 mmol) in DMF (20 mL), 53 (0.3 g, 0.77 mmol), HATU (0.88 g, 2.31 mmol), and DIPEA (1 mL, 3.85 mmol), were added and the reaction mixture was stirred at room temperature for 3 h. Progress of the reaction was monitored by TLC. The reaction mixture was concentrated, diluted with water (50 mL) and extracted with EtOAc (2×50 mL). The organic layer was dried over Na$_2$SO$_4$, filtered, and concentrated to dryness. The residue was purified by column chromatography [normal phase, silica gel (100-200 mesh), gradient 5% MeOH in DCM] to give 141 (0.16 g, 32%) as a yellow solid. MS (ESI+ve): 637.30. $^1$H-NMR (400 MHz; DMSO-d$_6$): δ 10.4 (s, 1H), 8.47 (s, 1H), 8.3 (s, 1H), 7.93 (s, 1H), 7.84 (d, J=7.0 Hz, 1H), 7.70-7.60 (m, 4H), 7.36-7.34 (m, 2H), 7.24 (d, J=9.3 Hz, 1H), 7.19 (s, 1H), 7.15 (d, J=8.0 Hz, 1H), 6.72 (bs, 1H), 4.33 (s, 2H), 3.41 (s, 2H), 2.69-2.65 (m, 1H), 2.16 (m, 3H), 1.94-1.90 (m, 2H), 1.68-1.61 (m, 4H), 1.47-1.44 (m, 2H), 1.34 (s, 9H).

To a stirred solution of 141 (0.15 g, 0.23 mmol) in 1,4-dioxane (5 mL), 4M HCl in dioxane (3 mL), was added at 0° C. and the reaction mixture was stirred at room temperature for 12 h. Progress of the reaction was monitored by TLC. The reaction mixture was concentrated to dryness. The residue was purified by Prep-HPLC using 0.1% TFA as buffer to afford Example 58, 0.12 g as bis-TFA salt) as an off-white solid. Analytical data for Example 58 are summarized in Table 1.

Example 59. (S)—N-(3-((3-aminopiperidin-1-yl)methyl)-5-(4-methyl-1H-imidazol-1-yl)-phenyl)-3-(3-fluorophenoxy)-4-methylbenzamide

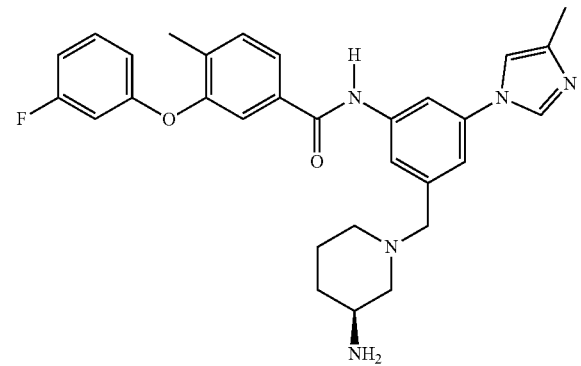

Example 59

This compound was prepared according to the following schematic:

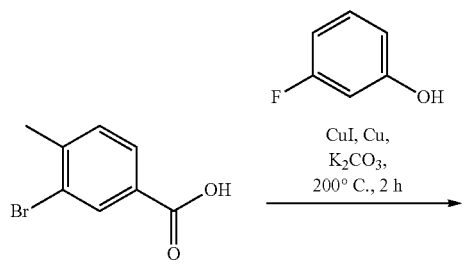

-continued

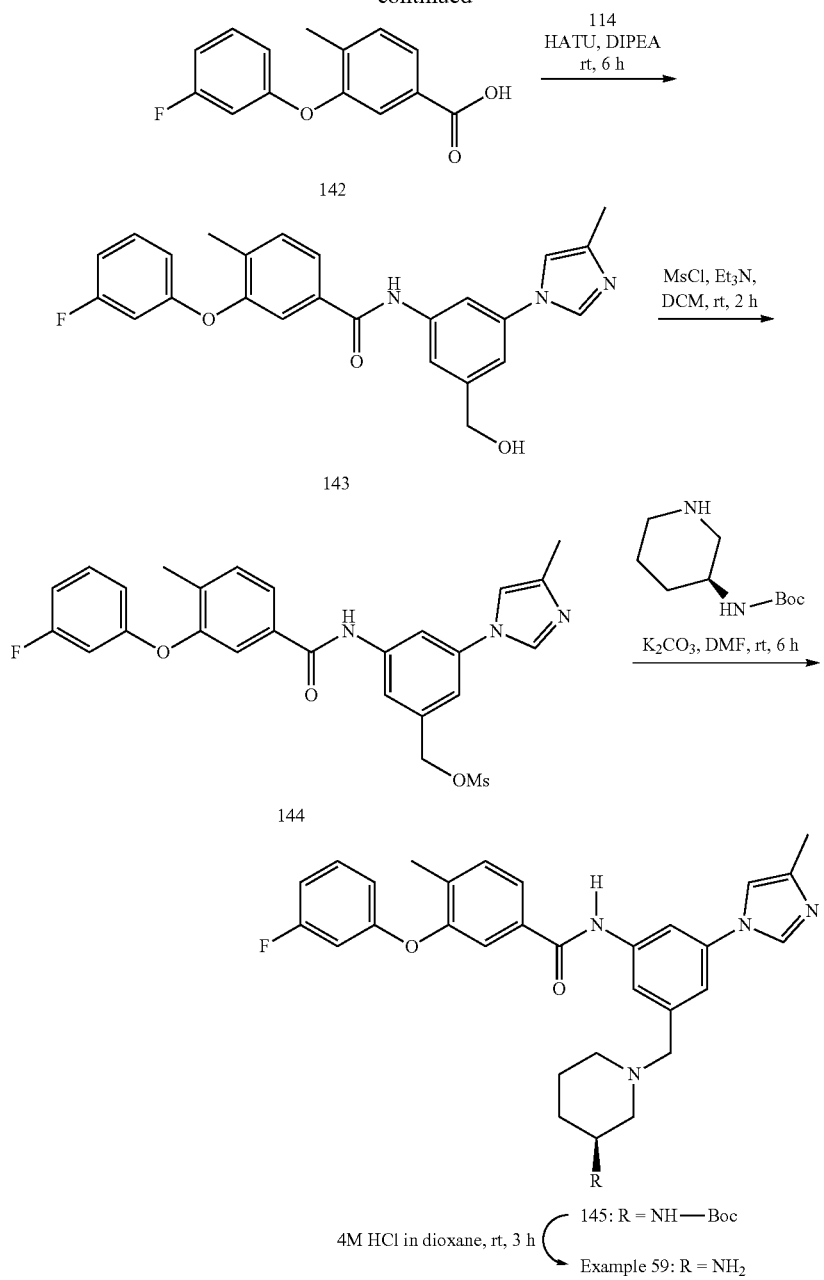

To a mixture of 3-fluorophenol (1, 27.0 g, 242 mmol) and 3-bromo-4-methylbenzoic acid (2, 4 g, 18.6 mmol) under $N_2$, $K_2CO_3$ (12.8 g, 93.4 mmol), CuI (1.77 g, 9.34 mmol) and Cu powder (0.58 g, 9.34 mmol) were added. The reaction mixture was stirred at 200° C. for 12 h. Progress of the reaction was monitored by TLC. The reaction mixture was allowed to cool to room temperature. The residue was partitioned between EtOAc (2×200 mL) and water (120 mL) and the aqueous layer was separated. The aqueous layer was acidified with 1N HCl and extracted by DCM (2×200 mL), the DCM layer dried over $Na_2SO_4$, filtered, and concentrated. The residue was purified by column chromatography [normal phase, silica gel (100-200 mesh), gradient 2% MeOH in DCM] to give 142 (3.5 g, 77%) as a white solid. MS (ESI−ve): 245.0. $^1$H-NMR (400 MHz; DMSO-$d_6$): δ 13.0 (s, 1H), 7.70 (d, J=6.6 Hz, 1H), 7.47 (d, J=7.6 Hz, 1H), 7.41 (d, J=7.2 Hz, 1H), 7.38 (s, 1H), 6.98 (t, J=6.4 Hz, 1H), 6.85 (d, J=7.6 Hz, 1H), 6.77 (d, J=7.7 Hz, 1H), 2.25 (s, 3H).

To a solution of 142 (1.8 g, 7.3 mmol) in DMF (30 mL), 114 (1.0 g, 4.9 mmol), HATU (5.6 g, 14.7 mmol), and DIPEA (4.5 mL, 24.6 mmol) were added and the reaction mixture was stirred at room temperature for 3 h. Progress of the reaction was monitored by TLC. The reaction mixture was concentrated, diluted with water (80 mL) and extracted with EtOAc (2×200 mL). The organic layer was dried over $Na_2SO_4$, filtered, and concentrated to dryness. The residue was purified by column chromatography [normal phase, silica gel (100-200 mesh), gradient 6% MeOH in DCM] to give 143 (0.55 g, 26%) as a yellow solid. MS (ESI+ve): 432.01. $^1$H-NMR (400 MHz; DMSO-$d_6$): δ 10.3 (s, 1H), 8.04 (s, 1H), 7.88-7.82 (m, 2H), 7.67-7.63 (m, 2H), 7.53 (d, J=7.8 Hz, 1H), 7.42 (t, J=8.4 Hz, 1H), 7.33 (s, 1H), 7.18 (s, 1H), 6.98-6.94 (m, 1H), 6.84-6.75 (m, 2H), 5.33 (bs, 1H), 4.54 (d, J=7.2 Hz, 2H), 2.24 (s, 3H), 2.16 (s, 3H).

To a stirred solution of 143 (0.45 g, 1.04 mmol) in DCM (25 mL), Et₃N (0.21 mL, 1.56 mmol) and MSCl (0.12 mL, 1.56 mmol) were added at 0° C. and the reaction mixture was stirred at room temperature for 1 h. Progress of the reaction was monitored by TLC. The reaction mixture was quenched with ice cold water (20 mL) and extracted with DCM (3×30 mL). The organic layer was washed with brine solution (20 mL), dried with anhyd. Na₂SO₄, concentrated in vacuo to give 144 (0.41 g, crude) as a yellow gummy liquid. This material was used in the next step without further purification. MS (ESI+ve): 510.02. Similarly to the procedure described for the coupling of 116 to Boc-protected amines (Examples 45-51), (S)-tert-butylpiperidin-3-yl carbamate was combined with 144 in the presence of HATU and DIPEA in DMF to yield 145.

To a stirred solution of 145 (0.2 g, 0.32 mmol) in 1,4-dioxane (5 mL), 4M HCl in dioxane (3 mL), was added at 0° C. and the reaction mixture was stirred at room temperature for 12 h. Progress of the reaction was monitored by TLC. The reaction mixture was concentrated to dryness. The residue was purified by Prep-HPLC using 0.1% TFA as a buffer to yield Example 59 (0.12 g, bis-TFA salt) as an off white solid. Analytical data for Example 59 are summarized in Table 1.

Example 60. (S)—N-(3-((3-aminopiperidin-1-yl)methyl)-5-(4-methyl-1H-imidazol-1-yl)-phenyl)-3-(3-(difluoromethyl)phenoxy)-4-methylbenzamide

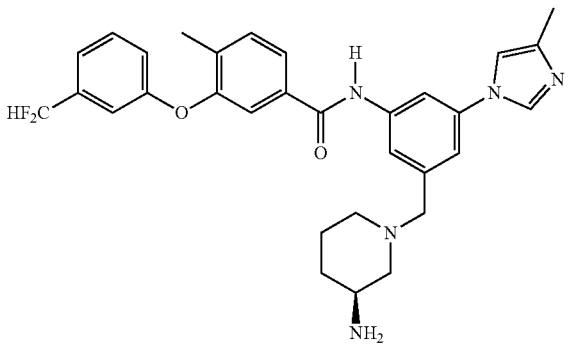

Example 60

This compound was prepared according to the following schematic:

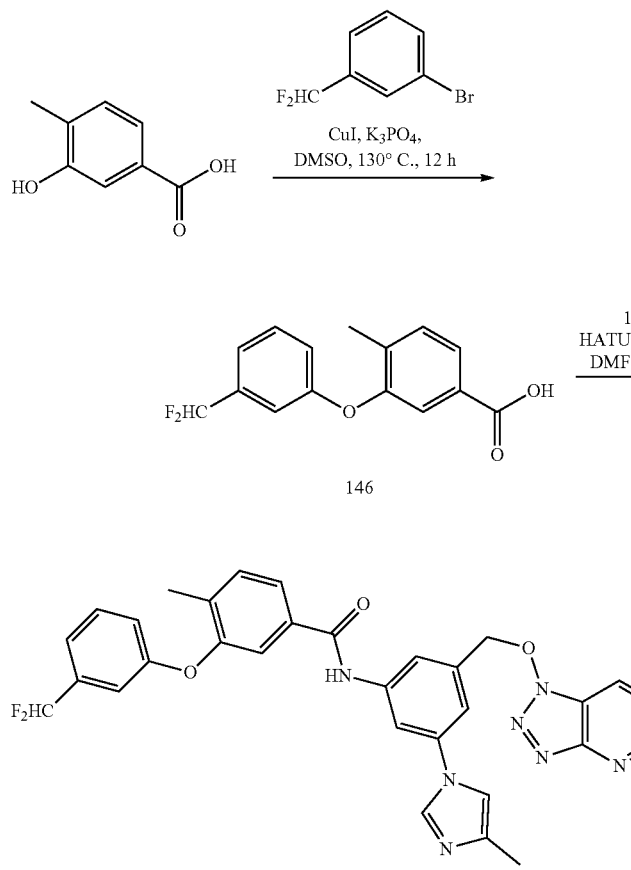

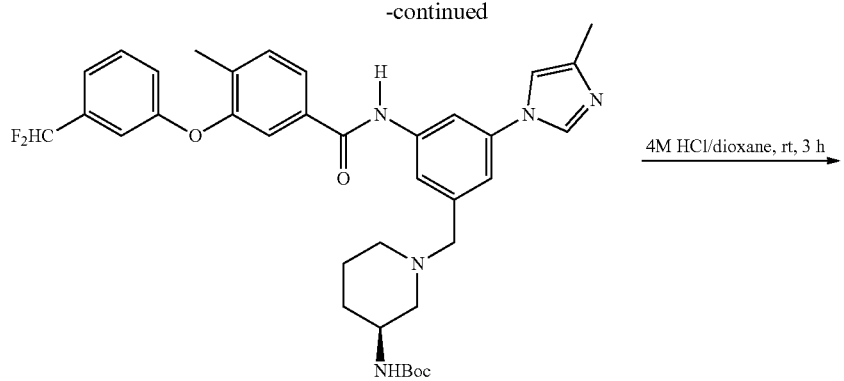

148

4M HCl/dioxane, rt, 3 h

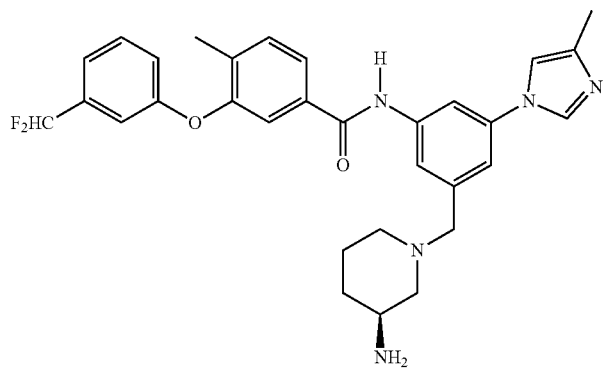

Example 60

To a stirred solution of 1-bromo-3-(difluoromethyl)benzene (1, 1 g, 4.83 mmol) in DMSO (10 mL), 3-hydroxy-4-methylbenzoic acid (2, 0.95 g, 6.2 mmol), $K_3PO_4$ (3.07 g, 14.4 mmol) and CuI (0.5 g, 2.4 mmol) were added at room temperature. The reaction mixture was stirred at 130° C. for 12 h. Progress of the reaction was monitored by TLC. The reaction mixture was cooled to rt, diluted with water (100 mL) and washed with EtOAc (2×50 mL) to remove non-polar impurities. The aqueous layer was acidified with 1N HCl and extracted with EtOAc (3×120 mL). The combined organic layer was dried ($Na_2SO_4$), filtered and concentrated to dryness. The residue was purified by column chromatography [normal phase, silica gel (100-200 mesh), gradient only DCM] to afford 146 (1.12 g, 83%) as a white solid. MS (ESI−ve): 277.02. $^1$H-NMR (400 MHz; DMSO-$d_6$): δ 13.0 (s, 1H), 7.70 (d, J=7.0 Hz, 1H), 7.52-7.49 (m, 2H), 7.30-3.37 (m, 2H), 7.12 (s, 2H), 7.01 (s, 1H), 2.26 (s, 3H).

To a stirred solution of 146 (0.86 g, 3.11 mmol) in DMF (15 mL), 114 (1.0 g, 2.59 mmol), HATU (1.38 g, 3.6 mmol), and DIPEA (1.3 mL, 7.79 mmol) were added and the reaction mixture was stirred at room temperature for 3 h. Progress of the reaction was monitored by TLC. The reaction mixture was concentrated to dryness, diluted with water (80 mL) and extracted with EtOAc (2×200 mL). The organic layers were dried over $Na_2SO_4$, filtered, and concentrated to dryness. The residue was purified by column chromatography [normal phase, silica gel (100-200 mesh), gradient 2% MeOH in DCM] to afford 147 (0.75 g, 50% yield) as a brown solid. MS (ESI+ve): 582.06. $^1$H-NMR (400 MHz; DMSO-$d_6$): δ 10.5 (s, 1H), 8.80 (d, J=4.16 Hz, 1H), 8.69 (s, 1H), 8.61 (d, J=8.36 Hz, 1H), 8.17 (s, 1H), 7.90 (s, 1H), 7.84 (d, J=7.76 Hz, 1H), 7.62-7.57 (m, 6H), 7.33 (d, J=7.4 Hz, 1H), 7.16-7.12 (m, 2H), 7.02 (s, 1H), 5.70 (s, 2H), 2.26 (s, 6H).

To a solution of 147 (0.29 g, 1.45 mmol) in DMSO, DIPEA (0.43 g, 3.35 mmol) was added and the reaction mixture was stirred at 130° C. for 3 h. Progress of the reaction was monitored by TLC. The reaction mixture was concentrated to dryness, diluted with water (50 mL) and extracted with EtOAc (2×80 mL). The organic layers were separated, dried over $Na_2SO_4$, filtered and concentrated to dryness. The residue was purified by column chromatography [normal phase, silica gel (100-200 mesh), gradient 2% MeOH in DCM] to afford 148 (0.45 g, 62%) as an off-white solid. MS (ESI+ve): 646.37. $^1$H-NMR (400 MHz; DMSO-$d_6$): δ 10.3 (s, 1H), 8.01 (s, 1H), 7.92 (s, 1H), 7.84 (d, J=6.92 Hz, 1H), 7.61 (s, 2H), 7.55-7.52 (m, 2H), 7.32 (d, J=6.32 Hz, 2H), 7.22 (s, 1H), 7.16-7.11 (m, 2H), 6.69 (d, J=8.36 Hz, 1H), 3.49-3.43 (m, 3H), 2.88 (s, 1H), 2.75 (s, 1H), 2.73 (s, 1H), 2.25 (s, 3H), 2.16 (s, 3H), 1.90 (s, 1H), 1.79 (s, 1H), 1.67-1.63 (m, 2H), 1.46-1.43 (m, 2H), 1.33 (s, 9H).

To a stirred solution of 148 (0.35 g, 0.54 mmol) in 1,4-dioxane (5 mL), 4M HCl in dioxane (3.5 mL) was added at 0° C. and the reaction mixture was stirred at room temperature for 4 h. Progress of the reaction was monitored by TLC. The reaction mixture was concentrated to dryness. The residue purified by prep HPLC by Prep-HPLC using 0.1% TFA as buffer to afford Example 60 (0.22 g, 74%, bis-TFA salt) as an off-white solid. Analytical data for Example 60 are summarized in Table 1.

TABLE 1

Analytical Data for Examples 1-60

| Example | LCMS | NMR |
|---|---|---|
| 1 | m/z (M + 1) = 530.2 | ¹H NMR (400 MHz, DMSO-d6): δ 10.62 (s, 1H); 9.16 (s, 1H); 8.73 (dd, J = 3.6, 1.6 Hz, 1H); 8.59 (d, J = 5.2 Hz, 1H); 8.35 (s, 1H); 8.30 (s, 1H); 8.28 (d*, 1H); 8.20 (d, J = 1.2 Hz, 1H); 8.15 (s, 1H); 7.91 (dd, J = 9.2, 7.6 Hz, 1H); 7.77 (dd, J = 7.6, 1.6 Hz, 1H); 7.71 (m, 2H); 7.51 (dd, J = 7.6, 4.4 Hz, 1H); 7.48 (s, 1H); 7.46 (d, J = 8.4 Hz, 1H); 2.37 (s, 3H); 2.18 (s, 3H). |
| 2 | m/z (M + 1) = 530.2 | ¹H NMR (400 MHz, DMSO-d6): δ 10.62 (s, 1H); 9.25 (s, 1H); 8.71 (d, J = 1.6 Hz, 1H); 8.70 (d, J = 1.6 Hz, 1H); 8.61 (d, J = 5.2 Hz, 1H); 8.32 (dd, J = 6.4, 1.6 Hz, 1H); 8.21 (d, J = 1.2 Hz, 1H); 8.16 (s, 1H); 8.04 (d, J = 1.6 Hz, 1H); 7.77 (dd, J = 8, 1.6 Hz, 1H); 7.73 (s, 1H); 7.51 (d, J = 5.2 Hz, 1H); 7.49-7.45 (m, 2H); 2.36 (s, 3H); 2.18 (s, 3H). |
| 3 | m/z (M + 1) = 529.2 | ¹H NMR (400 MHz, DMSO-d6): δ 10.71 (s, 1H); 9.07 (s, 1H); 8.92 (br s, H); 8.49 (d, J = 5.6 Hz, 1H); 8.46 (s, 1H); 8.37 (s, 1H); 8.19 (s, 1H); 8.12 (d, J = 6.4 Hz, 2H); 7.82 (s, 1H); 7.76 (s*, 1H); 7.75 (m*, 1H); 7.41-7.50 (m*, 4H); 7.40 (d, J = 1.2 Hz, 1H); 2.33 (s, 3H); 2.27 (s, 3H). |
| 4 | m/z (M + 1) = 453.1 | ¹H NMR (400 MHz, DMSO-d6): δ 10.59 (s, 1H); 9.00 (s, 1H); 8.40 (d, J = 4.4 Hz, 2H); 8.30 (s, 1H); 8.20 (d, J = 0.8 Hz, 1H); 8.15 (m, 1H); 7.74 (d*, 1H); 7.72 (s*, 1H); 7.49 (s, 1H); 7.41 (d, J = 8 Hz, 1H); 6.79 (t, J = 4.8 Hz, 1H); 2.31 (s, 3H); 2.18 (s, 3H). |
| 5 | m/z (M + 1) = 545.4 | ¹H NMR (400 MHz, DMSO-d6): δ 10.14 (s, 1H); 9.03 (s, 1H); 8.49 (d, J = 5.2 Hz, 1H); 8.31 (d, J = 1.2 Hz, 1H); 8.11 (dd, J = 7.6, 1.6 Hz, 2H); 8.01 (d, J = 1.2 Hz, 1H); 7.70 (dd, J = 7.6, 1.6 Hz, 1H); 7.39-7.49 (m*, 6H); 7.33 (s, 1H); 6.82 (s, 1H); 3.32 (m, 4H); 2.83 (m, 4H); 2.35 (s, 3H); 2.16 (s, 3H). |
| 6 | m/z (M + 1) = 559.4 | ¹H NMR (400 MHz, DMSO-d6): δ 10.15 (s, 1H); 9.03 (s, 1H); 8.49 (d, J = 5.2 Hz, 1H); 8.32 (d, J = 1.2 Hz, 1H); 8.12 (dd, J = 7.6, 1.6 Hz, 2H); 8.02 (d, J = 1.2 Hz, 1H); 7.71 (dd, J = 7.6, 1.6 Hz, 1H); 7.45-7.50 (m, 4H); 7.39-7.42 (m, 2H); 7.33 (d, J = 1.2 Hz, 1H); 6.85 (s, 1H); 3.21 (m, 4H); 2.47 (m, 4H); 2.35 (s, 3H); 2.23 (s, 3H); 2.16 (s, 3H). |
| 7 | m/z (M + 1) = 573.4 | ¹H NMR (400 MHz, DMSO-d6): δ 10.34 (s, 1H); 9.03 (s, 1H); 8.50 (d, J = 5.2 Hz, 1H); 8.35 (d, J = 1.2 Hz, 1H); 8.13 (dd, J = 7.6, 1.6 Hz, 2H); 8.01 (d, J = 1.2 Hz, 1H); 7.95 (t, J = 1.6 Hz, 1H); 7.72 (m*, 1H); 7.71 (m*, 1H); 7.39-7.48 (m, 5H); 7.33 (s, 1H); 7.21 (s, 1H); 3.49 (s, 2H); 2.49 (m*, 2H); 2.33-2.49 (m + s, 9H); 2.17 (s, 6H). |
| 8 | m/z (M + 1) = 531.2 | ¹H NMR (400 MHz, DMSO-d6): δ 10.53 (s, 1H); 9.07 (s, 1H); 8.99 (br s, 1H); 8.49 (d, J = 5.2 Hz, 1H); 8.34 (d, J = 1.2 Hz, 1H); 8.24 (s, 1H); 8.13 (d, J = 1.6 Hz, 1H); 8.11 (d, J = 2 Hz, 2H); 7.97 (s, 1H); 7.84 (s, 1H); 7.73-7.79 (m, 2H); 7.58 (d, J = 16 Hz, 1H); 7.40-7.49 (m, 5H); 6.64 (d, J = 16 Hz, 1H); 2.36 (s, 3H); 2.29 (s, 3H). |
| 9 | m/z (M + 1) = 533.3 | ¹H NMR (400 MHz, DMSO-d6): δ 10.48 (s, 1H); 9.46 (s, 1H); 9.05 (s, 1H); 8.49 (d, J = 5.2 Hz, 1H); 8.32 (d, J = 1.2 Hz, 1H); 8.18 (s, 1H); 8.12 (dd, J = 7.6, 1.6 Hz, 1H); 7.93 (s, 1H); 7.71 (d, J = 1.2 Hz, 1H); 7.67 (s, 1H); 7.38-7.49 (m, 6H); 2.91 (t, J = 7.4 Hz, 2H); 2.64 (t, J = 7.4 Hz, 2H); 2.36 (s, 3H); 2.35 (s, 3H). |
| 10 | m/z (M + 1) = 568.3 | ¹H NMR (400 MHz, DMSO-d6): δ 10.33 (s, 1H); 9.05 (s, 1H); 8.49 (d, J = 5.2 Hz, 1H); 8.32 (s, 1H); 8.12 (d, J = 2.4 Hz, 2H); 8.06 (s, 1H); 7.88 (s, 1H); 7.72 (d, J = 7.6 Hz, 1H); 7.66 (s, 1H); 7.39-7.49 (m, 5H); 7.36 (s, 1H); 7.30 (s, 1H); 6.94 (s, 2H); 3.33 (m*, 2H); 3.06 (m, 2H); 2.35 (s, 3H), 2.17 (s, 3H). |
| 11 | m/z (M + 1) = 517.3 | ¹H NMR (400 MHz, DMSO-d6): δ 10.27 (s, 1H); 9.03 (s, 1H); 8.50 (d, J = 5.2 Hz, 1H); 8.33 (s, 1H); 8.12 (dd, J = 7.6, 1.2 Hz, 2H); 8.03 (s, 1H); 7.85 (s, 1H); 7.72 (dd, J = 7.6, 1.2 Hz, 1H); 7.58 (s, 1H); 7.39-7.50 (m, 5H); 7.34 (s, 1H); 7.17 (s, 1H); 2.62 (t, J = 6 Hz, 2H); 2.35 (s, 3H); 2.16 (s, 3H); 1.61 (m, 2H); 1.33 (m, 2H); 0.91 (t, J = 7.6 Hz, 3H). |
| 12 | m/z (M + 1) = 360.2 | ¹H NMR (400 MHz, DMSO-d6): δ 10.61 (s, 1H); 8.30 (s, 1H); 8.21 (d, J = 1.2 Hz, 1H); 8.16 (s, 1H); 7.93 (d, J = 8 Hz, 2H); 7.73 (s, 1H); 7.49 (s, 1H); 7.38 (d, J = 8 Hz, 2H); 2.41 (s, 3H); 2.18 (s, 3H). |
| 13 | m/z (M + 1) = 452.2 | ¹H NMR (400 MHz, DMSO-d6): δ 10.60 (s, 1H); 8.26 (s, 1H); 8.19 (s, 1H); 8.10 (s, 1H); 7.80 (d, J = 7.2 Hz, 1H); 7.72 (s, 1H); 7.54 (s + d*, J = 8 Hz, 2H); 7.43 (s, 1H); 7.39 (t, J = 4 Hz, 2H); 7.14 (t, J = 7.6 Hz, 1H); 6.96 (d, J = 8 Hz, 1H); 2.28 (s, 3H); 2.17 (s, 3H). |
| 14 | m/z (M + 1) = 466.2 | ¹H NMR (400 MHz, DMSO-d6): δ 10.59 (s, 1H); 8.30 (s, 1H); 8.21 (d, J = 1.2 Hz, 1H); 8.14 (s, 1H); 7.73 (s, 1H); 7.63 (s, 1H); 7.57 (dd, J = 5.6, 1.2 Hz, 1H); 7.35-7.52 (m, 8H); 5.24 (s, 2H); 2.29 (s, 3H); 2.18 (s, 3H). |
| 15 | m/z (M + 1) = 565.2 | ¹H NMR (400 MHz, DMSO-d6): δ 10.97 (br s, 1H); 8.96 (s, 1H); 8.47 (d, J = 4.8 Hz, 1H); 8.43 (s, 1H); 8.16 (dd, J = 7.2, 1.2 Hz, 2H); 8.05 (s, 1H); 7.38-7.52 (m*, 8H); 7.27 (s, 2H); 2.31 (s, 3H); 2.08 (s, 3H). |
| 16 | m/z (M + 1) = 510.12 | ¹H NMR (400 MHz, DMSO-d6): δ 10.56 (s, 1H); 10.36 (s, 1H); 9.16 (s, 1H); 8.76 (s, 1H); 8.28 (d, J = 12 Hz, 2H); 8.19 (d, J = 10.8 Hz, 2H); 8.09 (s, 1H); 7.73 (s, 2H); 7.49 (s, 1H); 7.42 (br s, 2H); 2.29 (s, 3H); 2.18 (s, 3H); 2.07 (s, 3H). |

TABLE 1-continued

Analytical Data for Examples 1-60

| Example | LCMS | NMR |
|---|---|---|
| 17 | m/z (M + 1) = 450.09 | $^1$H NMR (400 MHz, DMSO-d6): δ 10.46 (s, 1H); 9.27 (s, 1H); 9.13 (s, 1H); 8.68 (d, J = 4 Hz, 1H); 8.54 (d, J = 5.2 Hz, 1H); 8.44 (d, J = 8 Hz, 1H); 8.29 (s, 1H); 8.24 (s, 1H); 8.07 (d, J = 8 Hz, 1H); 7.74 (d, J = 8 Hz, 1H); 7.59 (t, J = 8 Hz, 1H); 7.50 (m, 4H); 7.57 (m*, 1H); 2.35 (s, 3H). |
| 18 | m/z (M + 1) = 556.1 | $^1$H NMR (400 MHz, DMSO-d6): δ 9.34 (d, J = 3 Hz, 1H); 8.73 (d, J = 4 Hz, 1H); 8.69 (d, J = 5.2 Hz, 1H); 8.57 (s, 1H); 8.49 (d, J = 8 Hz, 1H); 8.31 (s, 1H); 8.12 (s, 2H); 7.93 (s, 1H); 7.85 (s, 1H); 7.65 (d, J = 5.2 Hz, 1H); 7.60 (s*, 1H); 7.57 (m*, 1H); 2.55 (s, 3H); 2.18 (s, 3H). |
| 19 | m/z (M + 1) = 591.3 | $^1$H NMR (400 MHz, DMSO-d6): δ 10.34 (s, 1H); 9.06 (s, 1H); 8.49 (d, J = 5.6 Hz, 1H); 8.31 (d, J = 1.2 Hz, 1H); 8.19 (dd, J = 5.6, 2 Hz, 2H); 8.02 (d, J = 1.2 Hz, 1H); 7.95 (s, 1H); 7.73 (dd, J = 7.6, 1.2 Hz, 1H); 7.68 (s, 1H); 7.40 (m, 2H); 7.31 (m, 3H); 7.22 (s, 1H); 3.48 (AB pattern, J = 13.6, 13.2 Hz, 2H); 2.67 (m, 2H); 2.33 (s, 3H); 2.17 (s, 3H); 1.99 (m, 1H); 1.73 (m, 2H); 1.61 (m, 1H); 1.45 (m, 1H); 1.02 (m, 1H). |
| 20 | m/z (M + 1) = 620.3 | $^1$H NMR (400 MHz, DMSO-d6): δ 10.37 (s, 1H); 9.04 (s, 1H); 8.49 (d, J = 5.2 Hz, 1H); 8.32 (s, 1H); 8.18 (dd, J = 3.6, 3.2 Hz, 2H); 8.00 (d, J = 1.2 Hz, 1H); 7.95 (s, 1H); 7.73 (dd*, J = 7.2, 1.6 Hz, 1H); 7.71 (s*, 1H); 7.40 (m, 2H); 7.32 (m, 3H); 7.23 (s, 1H); 3.89 (d, J = 13 Hz, 1H); 3.48 (d, J = 13 Hz, 1H); 3.12 (m, 1H); 2.91 (m, 1H); 2.67 (t, J = 2 Hz, 1H); 2.42 (s*, 3H); 2.41 (m*, 1H); 2.33 (s, 3H); 1.76 (m, 2H); 1.36-1.46 (m*, 4H). |
| 21 | m/z (M + 1) = 619.3 | $^1$H NMR (400 MHz, DMSO-d6): δ 10.33 (s, 1H); 9.05 (s, 1H); 8.49 (d, J = 4.8 Hz, 1H); 8.32 (s, 1H); 8.19 (dd, J = 5.6, 1.6 Hz, 2H); 8.05 (d, J = 1.2 Hz, 1H); 7.96 (s, 1H); 7.73 (dd, J = 7.6, 1.6 Hz, 1H); 7.64 (s, 1H); 7.28-7.42 (m, 7H); 7.07 (s, 1H); 3.83 (d, J = 13.6 Hz, 1H); 3.15 (d, J = 13.6 Hz, 1H); 2.83 (d, J = 11.6 Hz, 1H); 2.70 (m, 1H); 2.34 (s, 3H); 2.18 (s, 3H); 1.94 (t, J = 9.6 Hz, 1H); 1.78 (m, 1H); 1.76 (m, 1H); 1.65 (m, 1H); 1.54 (m, 1H); 1.39 (m, 1H). |
| 22 | m/z (M + 1) = 613.3 | $^1$H NMR (400 MHz, DMSO-d6): δ 10.32 (br s, 1H); 9.00 (s, 1H); 8.49 (d, J = 4.8 Hz, 1H); 8.46 (d, J = 1.2 Hz, 1H); 8.24 (dd, J = 5.6, 2 Hz, 2H); 7.88 (d, J = 1.2 Hz, 1H); 7.40-7.48 (m, 3H); 7.32 (t, J = 8.4 Hz, 2H); 7.14 (s, 1H); 6.68 (s, 1H); 6.59 (s, 1H); 6.56 (s, 1H); 3.03 (m, 4H); 2.32 (s*, 3H); 2.30 (m*, 4H); 2.14 (s, 3H); 2.07 (s, 3H). |
| 23 | m/z (M + 1) = 564.2 | $^1$H NMR (400 MHz, DMSO-d6): δ 10.19 (s, 1H); 9.03 (s, 1H); 8.49 (d, J = 5.2 Hz, 1H); 8.29 (d, J = 2 Hz, 1H); 8.20 (dd, J = 5.6, 2.4 Hz, 2H); 8.04 (d, J = 1.2 Hz, 1H); 7.71 (dd, J = 8, 1.6 Hz, 1H); 7.52 (s, 1H); 7.39-7.43 (m, 2H); 7.29-7.34 (m, 4H); 6.88 (s, 1H); 3.76 (m, 4H); 3.18 (m, 4H); 2.34 (s, 3H); 2.16 (s, 3H). |
| 24 | m/z (M + 1) = 390.2 | $^1$H NMR (400 MHz, DMSO-d6): δ 10.14 (s, 1H); 8.02 (d, J = 1.2 Hz, 1H); 7.87 (m, 2H); 7.48 (s, 1H); 7.35 (dd, J = 8.4, 4.4 Hz, 4H); 6.85 (s, 1H); 3.23 (m, 4H); 2.47 (m*, 4H); 2.39 (s, 3H); 2.24 (s, 3H); 2.16 (s, 3H). |
| 25 | m/z (M + 1) = 482.2 | $^1$H NMR (400 MHz, DMSO-d6): δ 10.16 (s, 1H); 8.02 (d, J = 1.2 Hz, 1H); 7.77 (dd, J = 7.6, 1.2 Hz, 1H); 7.52 (s*, 1H); 7.51 (d*, J = 7.6 Hz, 1H); 7.38-7.43 (m, 3H); 7.33 (s, 1H); 7.29 (s, 1H); 7.14 (t, J = 5.6 Hz, 1H); 6.96 (d, J = 7.6 Hz, 1H); 6.85 (s, 1H); 3.21 (m, 4H); 2.47 (m*, 4H); 2.27 (s, 3H); 2.23 (s, 3H); 2.15 (s, 3H). |
| 26 | m/z (M + 1) = 526.2 | $^1$H NMR (400 MHz, DMSO-d6): δ 10.16 (s, 1H); 8.02 (d, J = 1.2 Hz, 1H); 7.77 (dd, J = 8, 1.6 Hz, 1H); 7.52 (s*, 1H); 7.51 (d*, 1H); 7.38-7.43 (m, 3H); 7.33 (s, 1H); 7.28 (s, 1H); 7.14 (t, J = 5.6 Hz, 1H); 6.96 (d, J = 8 Hz, 1H); 6.84 (s, 1H); 3.47 (t, J = 6 Hz, 2H); 3.25 (s, 3H); 3.20 (m, 4H); 2.56 (m, 4H); 2.52 (m*, 2H); 2.27 (s, 3H); 2.23 (s, 3H); 2.15 (s, 3H). |
| 27 | m/z (M + 1) = 533.3 | $^1$H NMR (400 MHz, DMSO-d6): δ 10.16 (s, 1H); 9.67 (s, 1H); 8.62 (d, J = 6 Hz, 1H); 8.00 (d, J = 1.6 Hz, 1H); 7.91 (m, 1H); 7.88 (m, 1H); 7.71 (m, 3H); 7.60 (d, J = 8 Hz, 1H); 7.42 (s, 1H); 7.32 (s, 1H); 7.28 (s, 1H); 6.84 (d, J = 1.6 Hz, 1H); 6.82 (m, 1H); 3.19 (m, 4H); 2.46 (m, 4H); 2.32 (s, 3H); 2.22 (s, 3H); 2.14 (s, 3H). |
| 28 | m/z (M + 1) = 519.2 | $^1$H NMR (400 MHz, DMSO-d6): δ 10.23 (s, 1H); 8.10-8.20 (m, 3H); 8.02 (m, 2H); 7.94 (d, J = 1.6 Hz, 1H); 7.79 (t, J = 7.8 Hz, 1H); 7.59 (d, J = 7.8 Hz, 1H); 7.42 (s, 1H); 7.33 (s, 1H); 7.28 (s, 1H); 6.85 (t, J = 1.6 Hz, 1H); 3.21 (m, 4H); 2.46 (m, 4H); 2.35 (s, 3H); 2.23 (s, 3H); 2.15 (s, 3H). |
| 29 | m/z (M + 1) = 578.3 | $^1$H NMR (400 MHz, DMSO-d6): δ 10.17 (s, 1H); 9.04 (s, 1H); 8.49 (d, J = 5.2 Hz, 1H); 8.31 (s, 1H); 8.19 (dd, J = 5.6, 3.2 Hz, 2H); 7.78 (s, 1H); 7.72 (dd, J = 8, 1.6 Hz, 1H); 7.52 (s, 1H); 7.38-7.42 (m, 2H); 7.30 (t, J = 8.8 Hz, 2H); 7.12 (s, 1H); 6.84 (s, 1H); 3.21 (m, 4H); 2.48 (m*, 4H); 2.34 (s, 3H); 2.28 (s, 3H) 2.23 (s, 3H). |
| 30 | m/z (M + 1) = 496.3 | $^1$H NMR (400 MHz, DMSO-d6): δ 10.34 (s, 1H); 8.01 (d, J = 1.2 Hz, 1H); 7.92 (s, 1H); 7.79 (m, 1H); 7.62 (s, 1H); 7.55 (d, J = 1.6 Hz, 1H); 7.52 (d, J = 8.4 Hz, 1H); 7.40 (m, 2H); 7.33 (s, 1H); 7.21 (s, 1H); 7.13 (t, J = 7.6 Hz, 1H); 6.95 (dd, J = 8.4, 1.2 Hz, 2H); 3.47 (AB pattern, J = 13.6 Hz, 2H); 2.63-2.72 (m, 3H); 2.27 (s, 3H); 2.16 (s, 3H); 1.96 (m, 1H); 1.71 (m, 2H); 1.62 (m, 1H); 1.49 (m, 1H); 1.00 (m, 1H). |

TABLE 1-continued

Analytical Data for Examples 1-60

| Example | LCMS | NMR |
|---|---|---|
| 31 | m/z (M + 1) = 497.3 | $^1$H NMR (400 MHz, DMSO-d6): δ 10.00 (s, 1H); 9.03 (s, 1H); 8.49 (d, J = 5.2 Hz, 1H); 8.28 (d, J = 1.2 Hz, 1H); 8.19 (dd, J = 5.6, 3.2 Hz, 2H); 7.67 (dd, J = 7.6, 1.6 Hz, 1H); 7.39 (m, 3H); 7.29 (m, 3H); 7.16 (t, J = 8 Hz, 1H); 6.68 (dd, J = 8, 2 Hz, 1H); 3.12 (m, 4H); 2.49 (m*, 4H); 2.33 (s, 3H); 2.22 (s, 3H). |
| 32 | m/z (M + 1) = 524.46 | $^1$H NMR (partial: isomer mix, 400 MHz, DMSO-d6): δ 10.31 (s, 1H); 8.03 (m, 1H); 7.95 (m, 1H); 7.65 (m, 1H); 7.62 (m, 2H); 7.56 (m, 1H); 7.50 (m, 2H); 7.42 (t, J = 7.3 Hz, 2H); 7.35 (m, 3H); 7.21 (m, 1H); 5.21 (s, 2H); 3.43 (m, 2H); 2.72 (m, 2H); 2.33 (s, 3H); 2.16 (s, 3H); 1.33-1.94 (m*, 7 H); 1.21 (m, 3H), 0.84 (m, 3H). |
| 33 | m/z (M + 1) = 539.22 | $^1$H NMR (isomer mix, 400 MHz, DMSO-d6): δ 10.31 (s, 1H); 8.58 (s, 1H); 8.02 (s, 1H); 7.95 (m, 1H); 7.79 (m, 1H); 7.65 (s, 2H); 7.56 (d, J = 7 Hz, 1H); 7.35 (s, 1H); 7.32 (m, 2H); 7.21 (s, 1H); 5.22 (s, 2H); 3.44 (m, 3H); 2.81 (m, 1H); 2.73 (m, 1H); 2.72 (m, 2H); 2.25 (s, 3H); 2.17 (s, 3H); 2.06 (m, 1H); 1.50-1.7 (m*, 4H); 1.26 (m*), 0.84 (m*, 3H). |
| 34 | m/z (M + 1) = 510.41 | $^1$H NMR (isomer mix, 400 MHz, DMSO-d6): δ 9.93 (br s, 1H); 8.00 (s, 1H); 7.92 (s, 1H); 7.79 (dd, J = 7.8, 1.4 Hz, 1H); 7.63 (s, 1H); 7.54 (d, J = 2.3 Hz, 1H); 7.50 (d, J = 8 Hz, 1H); 7.40 (t, J = 8 Hz, 2H); 7.32 (s, 1H); 7.13 (t, J = 7.4 Hz, 1H); 6.96 (d, J = 7.9 Hz, 2H); 4.55 (d, 1H); 3.48 (br s, 2H); 2.92 (m, 1H); 2.81 (d, J = 10.4 Hz, 1H); 2.73 (d, J = 8.5 Hz, 1H); 2.60 (m*, 1H); 2.27 (s, 3H); 2.16 (s, 3H); 2.00 (m, 1H); 1.69 (m, 2H); 1.44 (m, 2H); 0.84 (d, J = 6.5 Hz, 3H). |
| 35 | m/z (M + 1) = 525.42 | $^1$H NMR (isomer mix, 400 MHz, DMSO-d6): δ 10.32 (s, 1H); 8.22 (s, 1H); 7.99 (s, 1H); 7.86 (s, 1H); 7.77 (d, J = 7.8 Hz, 1H); 7.62 (s, 1H); 7.49 (d, J = 8 Hz, 1H); 7.47 (s, 1H); 7.29 (d, J = 7.5 Hz, 1H); 7.28 (s*, 2H); 7.18 (s, 1H); 3.45 (m*); 2.81 (d, J = 8.1 Hz, 1H); 2.74 (d, J = 8.9 Hz, 1H); 2.45 (s, 3H); 2.28 (s, 3H); 2.14 (s, 3H); 2.81 (d, J = 10.4 Hz, 1H); 2.73 (d, J = 8.5 Hz, 1H); 2.60 (m*, 1H); 2.27 (s, 3H); 2.16 (s, 3H); 1.96 (dd, J = 12, 10.6 Hz, 1H); 1.78 (d, J = 10.4 Hz, 1H); 1.67 (t, J = 11 Hz, 1H); 1.56 (m, 1H); 1.42 (m, 2H) 0.85 (d, J = 6.4 Hz, 3H). |
| 36 | m/z (M + 1) = 539.23 | $^1$H NMR (partial, isomer mix, 400 MHz, DMSO-d6 with D$_2$O): δ 10.55 (s, 1H); 9.18 (br m, 1H); 8.63 (s, 1H); 8.07 (m, 2H); 7.96 (m, 1H); 7.82 (m, 3H); 7.55 (d, J = 7.5 Hz, 2H); 7.18 (d, J = 8.8 Hz, 1H); 5.27 (s, 2H); 2.33 (s, 3H); 2.25 (s, 3H); 0.98 (m, 3H). |
| 37 | m/z (M + 1) = 524.43 | $^1$H NMR (partial, isomer mix, 400 MHz, DMSO-d6 with D$_2$O): δ 10.21 (s, 1H); 8.02. 8.01 (~3:1, 2xs, 1H); 7.74-7.84 (m, 3H); 7.66, 7.64 (~1:3, 2xs, 1H); 7.47 (m, 2H); 7.40 (t, J = 7.4 Hz, 1H); 7.32 (m, 2H); 7.19 (s, 1H); 7.12 (d, J = 9.3 Hz, 1H); 5.20 (s, 2H); 3.46 (m, 2H); 2.7-2.8 (m*, 2H) 2.33 (s, 3H); 2.25 (s, 3H); 1.4-1.96 (m*, 6H); 0.89, 0.93 (~1:3, 2xd, J = 6.5 Hz, 3H). |
| 38 | m/z (M + 1) = 497.35 | $^1$H NMR (400 MHz, DMSO-d6): δ 10.33 (s, 1H); 8.01 (d, J = 0.9 Hz, 1H); 7.92 (br t, 1H); 7.79 (dd, J = 7.8, 1.5 Hz, 1H); 7.61 (s, 1H); 7.54 (d, J = 1.3 Hz, 1H); 7.50 (d, J = 8 Hz, 1H); 7.40 (m, 2H); 7.33 (s, 1H); 7.21 (s, 1H); 7.13 (t, J = 7.4 Hz, 1H); 4.57 (m, 1H); 3.47 (m, 4H); 2.80 (m, 1H); 2.66 (m, 1H); 2.27 (s, 3H); 2.17 (s, 3H); 1.90 (m, 1H); 1.70-1.76 (m, 2H); 1.62 (m, 1H); 1.42 (m, 1H); 1.09 (m, 1H). |
| 39 | m/z (M + 1) = 511.39 | $^1$H NMR (400 MHz, DMSO-d6): δ 10.40 (s, 1H); 8.24 (d, J = 1.8 Hz, 1H); 8.04 (s, 1H); 7.91 (br s, 1H); 7.82 (m, 1H); 7.66 (s, 1H); 7.51 (d, J = 8.2 Hz, 1H); 7.49 (s, 1H); 7.34 (s, 1H); 7.30 (m, 3H); 6.95 (dd, J = 8.4, 1.2 Hz, 2H); 3.57 (d, J = 13.6 Hz, 1H); 3.52 (d, J = 10.8 Hz, 1H); 3.16 (br s, 1H); 2.72 (br d, J = 8 Hz, 1H); 2.43 (s, 3H); 2.30 (s, 3H); 2.16 (s, 3H); 1.80 (m, 1H); 1.72 (m, 1H); 1.44-1.55 (m, 3H); 1.29 (m*, 2H). |
| 40 | m/z (M + 1) = 511.37 | $^1$H NMR (isomer mix, 400 MHz, DMSO-d6): δ 10.33 (s, 1H); 8.00 (s, 1H); 7.92 (s, 1H); 7.79 (dd, J = 7.8, 1.4 Hz, 1H); 7.63 (s, 1H); 7.54 (d, J = 2.3 Hz, 1H); 7.50 (d, J = 8 Hz, 1H); 7.40 (t, J = 8 Hz, 2H); 7.32 (s, 1H); 7.13 (t, J = 7.4 Hz, 1H); 6.96 (d, J = 7.9 Hz, 2H); 4.55 (d, 1H); 3.48 (br s, 2H); 2.92 (m, 1H); 2.81 (d, J = 10.4 Hz, 1H); 2.73 (d, J = 8.5 Hz, 1H); 2.60 (m*, 1H); 2.27 (s, 3H); 2.16 (s, 3H); 2.00 (m, 1H); 1.69 (m, 2H); 1.44 (m, 2H); 0.84 (d, J = 6.5 Hz, 3H). |
| 41 | m/z (M + 1) = 444.12 | $^1$H NMR (isomer mix, 400 MHz, DMSO-d6): δ 11.49 (s, 1H); 10.32 (s, 1H); 8.10 (s, 1H); 8.02 (s, 1H); 7.99 (s, 1H); 7.76 (s, 1H); 7.66 (m, 2H); 7.57 (t, J = 2.5 Hz, 1H); 7.35 (s, 1H); 7.18 (s, 1H); 6.53 (s, 1H); 4.55 (d, J = 5 Hz, 1H); 3.47 (s, 2H); 2.95 (m, 1H); 2.80 (d, J = 9.9 Hz, 1H); 2.74 (d, J = 10.3 Hz, 1H); 2.17 (s, 3H); 1.99 (t, J = 10.7 Hz, 1H); 1.75 (d, J = 9.4 Hz, 1H); 1.67 (t, J = 10.7 Hz, 1H); 1.47 (m, 2H); 0.86 (d, J = 6.6 Hz, 3H). |
| 42 | m/z (M + 1) = 459.15 | $^1$H NMR (isomer mix, 400 MHz, DMSO-d6): δ 10.34 (s, 1H); 8.17 (s, 1H); 8.02 (s, 1H); 7.99 (s, 1H); 7.81 (d, J = 8.4 Hz, 1H); 7.71 (s, 1H); 7.55 (s, J = 8.4 Hz, 1H); 7.35 (s, 1H); 7.19 (s, 1H); 6.53 (s, 1H); 4.55 (br s, 1H); 3.47 (s, 2H); 2.93 (m, 1H); 2.79 (d, J = 10.8 Hz, 1H); 2.74 (d, J = 11 Hz, 1H); 2.18 (s, 3H); 1.99 (t, J = 12.2 Hz, 1H); 1.89 (s, 3H); 1.75 (d, J = 9.2 Hz, 1H); 1.67 (t, J = 11.1 Hz, 1H); 1.45 (m, 2H); 0.86 (d, J = 6.4 Hz, 3H). |

TABLE 1-continued

Analytical Data for Examples 1-60

| Example | LCMS | NMR |
|---|---|---|
| 43 | m/z (M + 1) = 489.2 | $^1$H NMR (isomer mix, 400 MHz, DMSO-d6): δ 12.47 (m, 1H); 10.34 (s, 1H); 8.02 (s, 1H); 7.99 (s, 1H); 7.83 (m*, 1H); 7.81 (s*, 1H); 7.71 (s, 1H); 7.55-7.61 (br m, 1H); 7.34 (s, 1H); 7.19 (s, 1H); 4.89 (br s, 1H); 4.55 (d, J = 5.2 Hz, 1H); 3.86 (br t, 2H); 3.23 (s, 2H); 3.00 (t, J = 6.6 Hz, 2H); 2.93 (m, 1H); 2.79 (d, J = 10.4 Hz, 1H); 2.74 (d, J = 9.8 Hz, 1H); 2.18 (s, 3H); 1.96 (t, J = 10.3 Hz, 1H); 1.90 (s, 3H); 1.75 (br d, J = 10 Hz, 1H); 1.64 (t, J = 11 Hz, 1H); 1.45 (m, 2H); 0.86 (d, J = 6.4 Hz, 3H). |
| 44 | m/z (M + 1) = 459.09 | $^1$H NMR (isomer mix, 400 MHz, DMSO-d6): δ 13.03 (br s, 1H); 10.51 (br s, 1H); 8.12 (s, 1H); 8.03 (s, 1H); 7.98 (s, 1H); 7.83 (d, J = 8.3 Hz, 1H); 7.70 (s*, 1H); 7.67 (d, J = 8.4 Hz, 1H); 7.35 (s, 1H); 7.21 (s, 1H); 4.56 (br s, 1H); 3.47-3.50 (d* + s*, 3H); 2.93 (m, 2H); 2.79 (d, J = 11 Hz, 1H); 2.74 (d, J = 14 Hz, 1H); 2.33 (s, 1H); 2.18 (s, 3H); 2.00 (br t, 1H); 1.75 (br d, J = 9.4 Hz, 1H); 1.67 (t, J = 11 Hz, 1H); 1.47 (m, 2H); 0.84 (d, J = 6.4 Hz, 3H* (signal obscured)) |
| 45 | m/z (M + 1) = 482.2 | $^1$H NMR (400 MHz, DMSO-d6): δ 10.32 (s, 1H); 8.01 (s, 1H); 7.88 (s, 1H); 7.79 (d, J = 7.7 Hz, 1H); 7.65 (s, 1H); 7.54 (s, 1H); 7.50 (d, J = 7.9 Hz, 1H); 7.40 (t, J = 7.7 Hz, 2H); 7.33 (s, 1H); 7.24 (s, 1H); 7.13 (t, J = 7.3 Hz, 1H); 6.97 (d, J = 8 Hz, 2H); 4.16 (br s, 2H); 3.56 (AB pattern, J = 14 Hz, 2H); 3.44 (m, 1H). (400 MHz, MeOH-d4): δ 2.87 (m, 1H); 2.74 (m, 1H); 2.53 (m, 2H); 2.32 (s, 3H); 2.25 (s* + m*, 4H); 1.64 (m, 1H). |
| 46 | m/z (M + 1) = 510.26 | $^1$H NMR (partial, 400 MHz, DMSO-d6 + TFA-D): δ 9.57 (s, 1H); 8.22 (s, 1H); 8.08 (s, 1H); 7.86 (s, 1H); 7.77 (d, J = 8 Hz, 1H); 7.56 (s, 1H); 7.54 (s, 1H); 7.46 (d, J = 7.9 Hz, 1H); 7.34 (t, J = 7.7 Hz, 2H); 7.07 (t, J = 7.6 Hz, 1H); 6.92 (d, J = 8.1 Hz, 2H); 4.34 (AB pattern, 2H); 3.46 (m, 2H). (partial, 400 MHz, MeOH-d4): δ 2.94-2.98 (m, 2H); 2.82-2.90 (m, 3H); 2.43 (s, 3H); 2.33 (s, 3H); 2.27 (m*, 2H); 2.01 (m, 2H);); 1.86 (m, 1H); 1.32 (m, 1H). |
| 47 | m/z (M + 1) = 496.19 | $^1$H NMR (400 MHz, MeOH-d4): δ 9.00 (s, 1H); 8.06 (s, 1H); 8.01 (s, 1H); 7.71 (d, J = 8 Hz, 1H); 7.65 (s, 1H); 7.57 (s, 1H); 7.47-7.50 (m, 2H); 7.36 (t, J = 8 Hz, 2H); 7.07 (t, J = 7.6 Hz, 1H); 6.95 (d, J = 8 Hz, 2H); 4.50 (m, 2H); 3.57 (m, 1H); 3.13 (m*, 2H); 2.78 (m, 1H); 2.41 (s + m*, 4H); 2.33 (s + m*, 4H); 2.27 (m*, 2H); 1.90 (m, 1H). |
| 48 | m/z (M + 1) = 510.23 | $^1$H NMR (400 MHz, DMSO-d6 + TFA-d): δ 9.53 (s, 1H); 8.19 (s, 1H); 8.13 (s, 1H); 7.77 (s, 1H); 7.74 (d, J = 8.1 Hz, 1H); 7.56 (s, 1H); 7.53 (s, 1H); 7.40 (d, J = 7.9 Hz, 1H); 7.29 (t, J = 7.9 Hz, 1H); 7.03 (t, J = 7.3 Hz, 1H); 6.88 (d, J = 8 Hz, 2H); 4.45 (AB pattern, J = 13 Hz, 2H); 3.69 (m, 1H); 3.41 (m, 2H); 2.97 (m, 2H); 2.56 (s, 3H); 2.30 (s, 3H); 2.22 (s, 3H); 2.10 (m, 1H); 1.92 (m, 1H); 1.73 (m, 1H); 1.48 (m, 1H). |
| 49 | m/z (M + 1) = 496.22 | $^1$H NMR (partial, 400 MHz, DMSO-d6 + TFA-d): δ 9.58 (s, 1H); 8.17 (s, 1H); 8.12 (s, 1H); 7.88 (s, 1H); 7.78 (d, J = 9 Hz, 1H); 7.61 (s, 1H); 7.54 (s, 1H); 7.49 (d, J = 8.5 Hz, 1H); 7.36 (t, J = 7.8 Hz, 2H); 7.10 (t, J = 7.3 Hz, 1H); 6.94 (d, J = 8.3 Hz, 2H); 4.50 (s, 2H). 1H NMR (partial, 400 MHz, MeOH-d4): δ 4.13 (br s, 2H); 3.90 (m, 1H); 3.23 (m*, 2H); 2.90 (m, 2H); 2.72 (s, 3H); 2.48 (m, 1H); 2.45 (s, 3H); 2.33 (s, 3H); 2.07 (m, 1H). |
| 50 | m/z (M + 1) = 508.25 | $^1$H NMR (400 MHz, MeOH-d4): δ 9.32 (s, 1H); 8.00 (s, 1H); 7.92 (s, 1H); 7.77 (s, 1H); 7.71 (d, J = 8 Hz, 1H); 7.46-7.49 (m, 3H); 7.36 (t, J = 7.9 Hz, 2H); 7.11 (t, J = 7.4 Hz, 1H); 6.94 (d, J = 8 Hz, 2H); 4.23 (m, 1H); 3.87 (AB pattern, J = 13 Hz, 2H); 3.50 (m, 1H); 3.25 (m*, 2H); 3.11 (m, 1H); 2.95 (d, J = 10 Hz, 1H); 2.78 (dd, J = 11.5, 5.8 Hz, 1H); 2.64 (t, J = 8.5 Hz, 1H); 2.45 (s, 3H); 2.33 (s, 3H); 2.22 (m, 2H); 1.99 (m, 1H). |
| 51 | m/z (M + 1) = 508.24 | $^1$H NMR (400 MHz, MeOH-d4): δ 9.33 (s, 1H); 8.02 (s, 1H); 7.91 (s, 1H); 7.77 (s, 1H); 7.72 (d, J = 7.8 Hz, 1H); 7.55 (s, 1H); 7.49 (s*, 1H); 7.47 (d*, J = 8.1 Hz, 1H); 7.36 (t, J = 7.8 Hz, 2H); 7.11 (t, J = 7.2 Hz, 1H); 6.94 (d, J = 8.1 Hz, 2H); 4.22 (m, 1H); 3.82 (m, 1H); 3.72 (m, 1H); 3.50 (m, 1H); 3.31 (m*, 2H); 3.19-3.23 (m, 3H); 2.57 (m, 1H); 2.56 (s, 3H); 2.33 (s, 3H); 2.31 (m*, 1H); 1.70 (m, 1H). |
| 52 | m/z (M + 1) = 482.23 | $^1$H NMR (400 MHz, DMSO-d6 + TFA-d): δ 9.48 (s, 1H); 7.79 (s, 1H); 7.73 (d, J = 7.9 Hz, 1H); 7.61 (s, 1H); 7.51 (s, 2H); 7.38 (d, J = 7.9 Hz, 1H); 7.30 (t, J = 7.7 Hz, 2H); 7.04 (t, J = 7.2 Hz, 1H); 6.99 (s, 1H); 6.88 (d, J = 7.7 Hz, 2H); 3.69 (m*, 1H); 3.47 (m, 1H); 3.27 (m, 1H); 3.03 (m, 2H); 2.29 (s, 3H); 2.21 (s, 3H); 1.96 (m, 1H); 1.80 (m, 1H); 1.59 (m, 2H). |
| 53 | m/z (M + 1) = 512.22 | $^1$H NMR (400 MHz, MeOH-d4): δ 9.32 (s, 1H); 8.07 (s, 1H); 7.92 (s, 1H); 7.78 (s, 1H); 7.70 (d, J = 7.9 Hz, 1H); 7.53-7.57 (m, 3H); 7.40 (t, J = 8.3 Hz, 2H); 7.23 (d, J = 7.5 Hz, 1H); 7.03 (d, J = 8.3 Hz, 2H); 4.61 (d, 2H); 3.91 (s, 2H); 3.46 (m, 1H); 3.02 (m, 1H); 2.85 (m, 1H); 2.65 (m, 2H); 2.45 (s, 3H); 1.91-2.01 (m, 2H); 1.76 (m, 1H); 1.63 (m, 1H). |

TABLE 1-continued

Analytical Data for Examples 1-60

| Example | LCMS | NMR |
|---|---|---|
| 54 | m/z (M + 1) = 526.23 | $^1$H NMR (400 MHz, DMSO-d6): δ 10.68 (s, 1H); 8.04 (s, 1H); 7.99 (s, 1H); 7.85 (d, J = 8.4 Hz, 2H); 7.80 (d, J = 7.8 Hz, 1H); 7.68 (s, 2H); 7.56 (t, J = 7.9 Hz, 1H); 7.34 (s, 1H); 7.28 (d, J = 8.1 Hz, 1H); 7.24 (s, 1H); 6.93 (d, J = 8.5 Hz, 2H); 3.52 (AB pattern, J = 13.7 Hz, 2H); 3.05 (m, 1H); 2.73 (d, J = 8.3 Hz, 1H); 2.58 (m, 1H); 2.08-2.15 (m* + s, 4H); 1.80 (m, 1H); 1.73 (m, 1H); 1.49 (m, 1H); 1.33 (m, 1H). |
| 55 | m/z (M + 1) = 525.25 | $^1$H NMR (400 MHz, MeOH-d4): δ 9.32 (s, 1H); 8.08 (s, 1H); 7.94 (s, 1H); 7.91 (s, 1H); 7.81 (d, J = 8.1 Hz, 1H); 7.78 (s, 1H); 7.66 (s, 1H); 7.60 (t, J = 7.9 Hz, 1H); 7.53 (s, 1H); 7.34 (d, J = 8.8 Hz, 1H); 7.09 (d, J = 8.6 Hz, 2H); 3.95 (s, 2H); 3.31 (m, 1H); 3.08 (m, 1H); 2.88 (m, 1H); 2.68 (m, 2H); 2.45 (s, 3H); 1.92-2.01 (m, 2H); 1.78 (m, 1H); 1.63 (m, 1H). |
| 56 | m/z (M + 1) = 669.30 | $^1$H NMR (400 MHz, DMSO-d6 + TFA-d): δ 9.59 (s, 1H); 8.27 (d, J = 8.7 Hz, 1H); 8.21 (s, 1H); 8.12 (s, 1H); 7.89 (s, 1H); 7.87 (d*, J = 8.7 Hz, 1H); 7.73 (s, 1H); 7.65 (m, 2H); 7.54 (d, J = 7.4 Hz, 1H); 7.41 (d, J = 8.2 Hz, 1H); 7.28 (d, J = 8.5 Hz, 2H); 7.16-7.20 (m*, 1H); 6.87 (d, J = 8.6 Hz, 2H); 6.55 (d, J = 7.4 Hz, 1H); 5.08 (s, 2H); 4.52 (br s, 2H); 3.70 (s, 3H); 3.44-3.56 (m, 3H); 2.97 (m, 2H); 2.33 (s, 3H); 2.02 (m, 1H); 1.95 (m, 1H); 1.74 (m, 1H); 1.49 (m, 1H). |
| 57 | m/z (M + 1) = 549.26 | $^1$H NMR (400 MHz, MeOH-d4): δ 9.41 (d, J = 1.1 Hz, 1H); 8.32 (d, J = 8.8 Hz, 1H); 8.26 (s, 1H); 8.07 (s, 1H); 7.88 (d* + s, 2H); 7.83 (s, 1H); 7.73 (s, 1H); 7.64 (t, J = 7.9 Hz, 1H); 7.40 (dd, J = 8.1, 1.7 Hz, 1H); 7.22 (dd, J = 8.9, 2.2 Hz, 1H); 7.19 (d* + s, 2H); 6.58 (d, J = 7.1 Hz, 1H); 4.49 (s, 2H); 3.72 (m, 1H); 3.65 (m, 1H); 3.48 (m, 1H); 3.12 (m, 2H); 2.46 (s, 3H); 2.10-2.18 (m, 2H); 2.01 (m, 1H); 1.71 (m, 1H). |
| 58 | m/z (M + 1) = 537.25 | $^1$H NMR (400 MHz, MeOH-d4): δ 9.31 (s, 1H); 8.08 (s, 1H); 7.91 (s, 1H); 7.78-7.83 (m, 3H); 7.67 (br t, 1H); 7.61 (t, J = 8 Hz, 1H); 7.51 (s, 1H); 7.36 (dd, J = 8.1, 2.1 Hz, 1H); 7.22 (s, 1H); 7.17 (dd, J = 8.4, 1.8 Hz, 1H); 4.44 (s, 2H); 3.87 (s, 2H); 3.45 (m, 1H); 3.02 (m, 1H); 2.81 (m, 1H); 2.62 (m, 2H); 2.46 (s, 3H); 1.99 (m, 1H); 1.90 (m, 1H); 1.75 (m, 1H); 1.63 (m, 1H). |
| 59 | m/z (M + 1) = 514.23 | $^1$H NMR (400 MHz, MeOH-d4): δ 9.28 (s, 1H); 8.03 (s, 1H); 7.89 (s, 1H); 7.77 (d* + s, 2H); 7.57 (s, 1H); 7.50 (d* + s, 2H); 7.35 (q, J = 8.1 Hz, 1H); 6.85 (m, 1H); 6.75 (d, J = 8.2 Hz, 1H); 6.67 (d, J = 10.4 Hz, 1H); 3.85 (s, 2H); 3.46 (m, 1H); 2.97 (m, 1H); 2.78 (m, 1H); 2.61 (d, J = 7.7 Hz, 2H); 2.46 (s, 3H); 2.31 (s, 3H); 1.97 (m, 1H); 1.89 (m, 1H); 1.75 (m, 1H); 1.62 (m, 1H). |
| 60 | m/z (M + 1) = 546.26 | $^1$H NMR (400 MHz, MeOH-d4): δ 9.30 (s, 1H); 8.04 (s, 1H); 7.90 (s, 1H); 7.77 (d* + s, 2H); 7.47-7.55 (m*, 4H); 7.28 (d, J = 7.5 Hz, 1H); 7.09 (m, 2H); 6.74 (t, J = 56 Hz (CHF$_2$), 1H); 3.88 (s, 2H); 3.44 (m*, 1H); 3.01 (m, 1H); 2.80 (m, 1H); 2.63 (d, J = 7.1 Hz, 2H); 2.45 (s, 3H); 2.32 (s, 3H); 1.90-1.97 (m, 2H); 1.75 (m, 1H); 1.62 (m, 1H). |

Example 61. Inhibition of PCSK9-LDLR Binding by Selected Compounds of the Invention Compounds were assayed for their ability to inhibit the binding between PCSK9 and the LDL receptor using a CircuLex PCSK9-LDLR in vitro binding assay kit (Catalog # CY-8150. The procedure employed the reagents and buffers included in the kit as follows.

88 μL of 1× reaction buffer were placed into each well. 5 μL of test compounds in 20% DMSO were added into each well. 10 mM solutions of test compounds in DMSO were diluted by 3-fold series to give 8 point concentration curves. The compounds were then diluted 20-fold with the reaction buffer. To each well was then added 7 μL of His-tagged PCSK9 wild type solution (1000 ng/mL) into each well. The plate was then covered with a plate sealer and incubated at room temperature for 3 hours, shaking at 300 rpm on an orbital microplate shaker. The test solutions were washed 4 times with 350 μL wash buffer. 100 μL of biotinylated anti-His-tag monoclonal antibody was added to each well. The plate was covered with a plate sealer, and incubated at room temperature for 1 hour, shaking at 300 rpm. The test solutions were washed 4 times with 350 μL wash buffer. 100 μL of HRP-conjugated streptavidin was added to each well. The plate was covered with a plate sealer and incubated at room temperature for 20 min, shaking at 300 rpm. The test solutions were washed 4 times with 350 μL wash buffer. 100 μL of substrate reagent were added into each well. The plate was covered with a plate sealer, and incubated at room temperature for 15 min, shaking at 300 rpm. Finally, 100 μL of the stop solution was added to each well in the same order as the previously added substrate reagent. Absorbance was measured at 450 nm and 540 nm and IC$_{50}$ curves were plotted.

TABLE 2

Inhibition of PCSK9-LDLR binding: Values in table for inhibition ranges are as follows: >100 μM: −; 10-100 μM: +; 1-10 μM: ++; 0.1-1 μM: +++; <0.1 μM: ++++. Starred values refer to levels of inhibition of binding by less than 35% at the highest concentration tested, due either to solubility limitations or dynamic range limitations of the assay.

| Example | Inhibition | Example | Inhibition | Example | Inhibition |
|---|---|---|---|---|---|
| 1 | + | 2 | ++ | 3 | ++ |
| 4 | + | 5 | +++ | 6 | +++ |
| 7 | +++ | 8 | + | 9 | ++ |
| 10 | + | 11 | ++ | 12 | + |
| 13 | + | 14 | + | 15 | + |
| 16 | + | 17 | − | 18 | ++ |
| 19 | +++ | 20 | + | 21 | ++ |
| 22 | * | 23 | + | 24 | + |

TABLE 2-continued

Inhibition of PCSK9-LDLR binding: Values in table for inhibition ranges are as follows: >100 μM: −; 10-100 μM: +; 1-10 μM: ++; 0.1-1 μM: +++; <0.1 μM: ++++. Starred values refer to levels of inhibition of binding by less than 35% at the highest concentration tested, due either to solubility limitations or dynamic range limitations of the assay.

| Example | Inhibition | Example | Inhibition | Example | Inhibition |
|---|---|---|---|---|---|
| 25 | * | 26 | * | 27 | ++++ |
| 28 | ++ | 29 | + | 30 | +++ |
| 31 | ++ | | | | |

Example 62. Inhibition of LDL Uptake in a Cell-Based Assay

Human liver cells (hepG2) express the LDL receptor, which can take up fluorescent-labeled LDL into the cell. PCSK9 binds to LDL receptor, wherein the complex is internalized and degraded in the lysosome, resulting in lowered LDL uptake in hepG2 cells. Inhibition of PCSK9 inhibition lowers plasma (circulating) LDL-C by increasing LDL incorporation into the cell. See FIG. 1.

The cell-based assay was conducted as follows, according to the procedure outlined in Xu and Liu, J Bioequiv Availab 2013, 5, 7. In this assay the dynamic range of measuring LDL uptake is enhanced by adding a gain-of-function mutant of PCSK9, which significantly reduces LDL uptake via increased LDLR binding, and whose inhibition indicates functional activity against the target, enabling a high-throughput format to be used. Human liver HepG2 cells were seeded in a 96 well plate at 2×105 cells/ml and incubated overnight. PCSK9-D374Y (2 μg/ml) was added, along with test compounds. The wells were incubated for 16 hours, whereupon the medium was replaced with fresh medium containing 10 μg/ml Bodipy FL LDL, and the wells were incubated for a further 4 hours. The wells were washed using warm PBS and then the LDL uptake was quantified on a fluorescent plate reader at excitation/emission wavelengths of 485 and 530 nm respectively.

Figure 2:
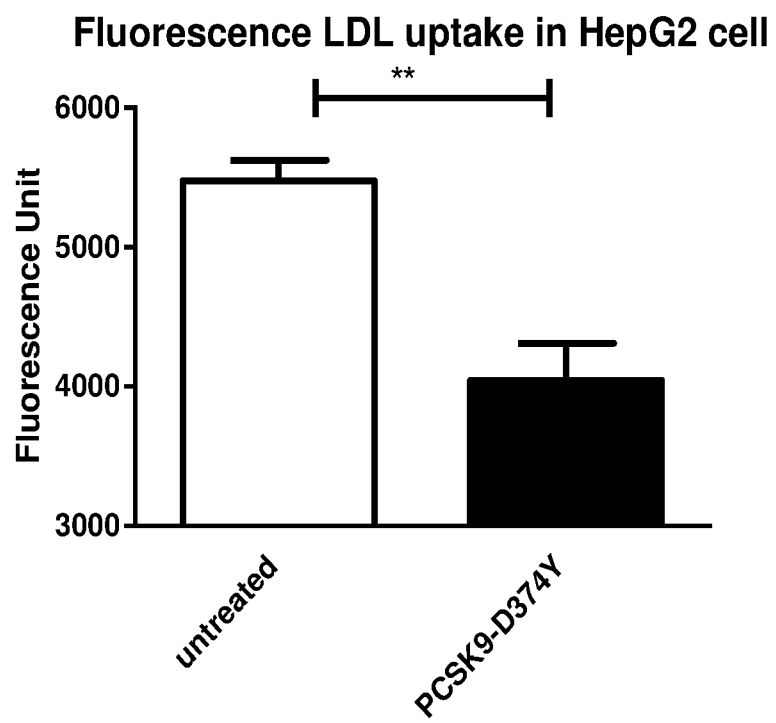
FIG. 2: Fluorescence LDL uptake in HepG2 cells.
Figure 3:
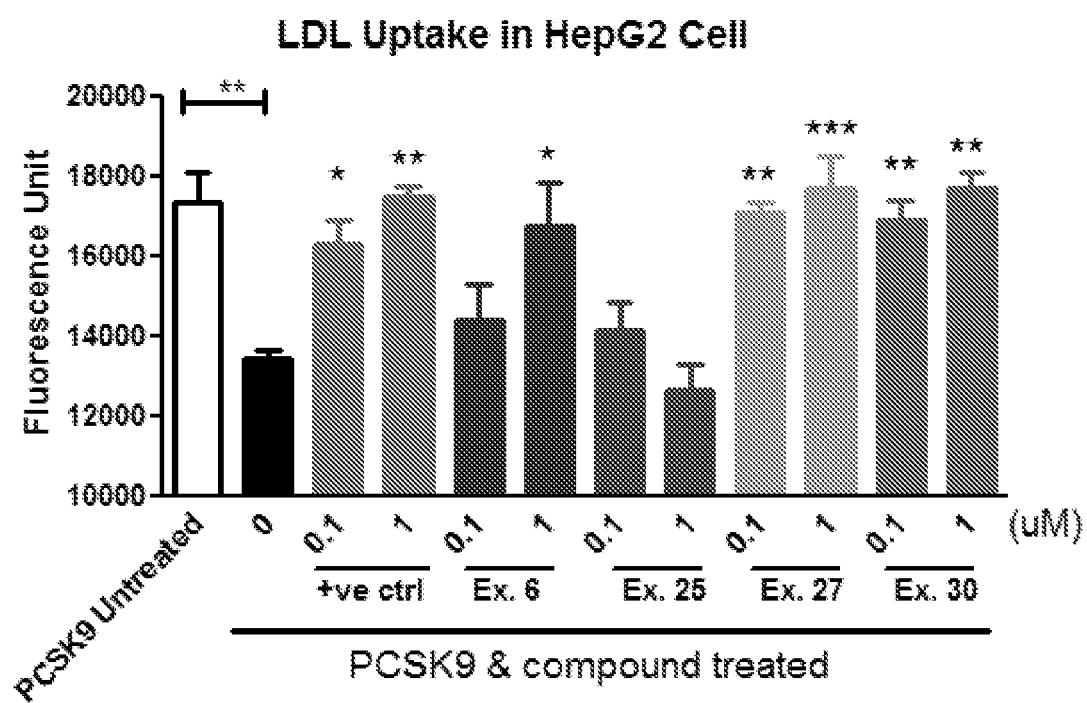
FIG. 3: Promotion of LDL uptake in HepG2 cells by PCSK9 inhibitors.

FIG. 2 indicates the decrease in LDL update in HepG2 cells comparing untreated and PCSK9-D374Y gain-of-function treated cells. Test compounds were measured at their ability to increase LDL uptake at concentrations of 0.1 and 1 μM and the results shown in FIG. 3. The positive control (from WO2014150326, catalogue number AMB-657286 (Ambinter, France) was included. Significant increases in LDL uptake equivalent to untreated cells, to which no PCSK9-D374Y had been added, were observed at both 0.1 and 1 μM concentrations for Examples 27 and 30.

SEQ ID No 1 (homo sapien):
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQSIPWNLERITPPRYRADEYQPPDGGSLVEVYLLDTSIQSDHREIEGRV

MVTDFENVPEED$^{212}$GTRFHRQAS$^{221}$KC$^{223}$DSHGTHLAGVVSGRDAGVAKG

ASMRSLRVLNCQGK$^{258}$GTVSG$^{263}$TLIGLEFIRKSQLVQPVGPLVVLLPLA

GGYSRVLNAACQRLARAGVVLVTAAGNFRDDACLYSPASAPEVITVGATN

AQDQPVTLGTLGTNFGRCVDLFAPGEDIIGASSDCSTCFSQSGTSQAAAH

VAGIAAMMLSAEPELTLAELRQRLIHFSAKDVINEAWFPEDQRVLTPNLV

AALPPSTHGAGWQLFCRTVWSAHSGPTRMATAVARCAPDEELLSCSSFSR

SGKRRGERMEAQGGKLVCRAHNAFGGEGVYAIARCCLLPQANCSVHTAPP

AEASMGTRVHCHQQGHVLTGCSSHWEVEDLGTHKPPVLRPRGQPNQCVGH

REASIHASCCHAPGLECKVKEHGIPAPQEQVTVACEEGWTLTGCSALPGT

SHVLGAYAVDNTCVVRSRDVSTTGSTSEGAVTAVAICCRSRHLAQASQEL

Q

The invention claimed is:

1. A compound according to Formula (I):

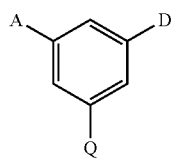

(I)

or a pharmaceutically acceptable salt thereof,
wherein:

A is an optionally substituted 5-membered heteroaryl ring, wherein the substituent is a methyl group;

Q is selected from the group consisting of optionally substituted: $C_2$-$C_6$ alkenyl, $C_2$-$C_6$ haloalkenyl, $C_1$-$C_6$ alkyloxy, $C_2$-$C_6$ alkenyloxy, $C_1$-$C_6$ alkylamino, $C_2$-$C_6$ alkenylamino, $C_2$-$C_6$ alkenylcarboxy, $C_1$-$C_6$ haloalkoxy, $C_2$-$C_6$ haloalkenyloxy, $C_1$-$C_6$ hydroxyalkyl, $C_2$-$C_6$ hydroxyalkenyl, $C_1$-$C_6$ alkylcarboxyamide, $C_2$-$C_6$ alkenylcarboxyamide, $C_1$-$C_6$ alkylsulfanyl, $C_2$-$C_6$ alkenylsulfanyl, $C_1$-$C_6$ alkylsulfenyl, $C_2$-$C_6$ alkenylsulfenyl, $C_1$-$C_6$ alkylsulfonyl, $C_2$-$C_6$ alkenylsulfonyl, $C_1$-$C_6$ alkylsulfonylamino, $C_2$-$C_6$ alkenylsulfonylamino, $C_4$-$C_7$ heterocyclyl, ($C_1$-$C_3$ alkyl)$C_3$-$C_7$ heterocyclyl, ($C_1$-$C_3$ alkyl)$C_3$-$C_7$ cycloalkyl and $C_3$-$C_7$ cycloalkyl;

wherein D is

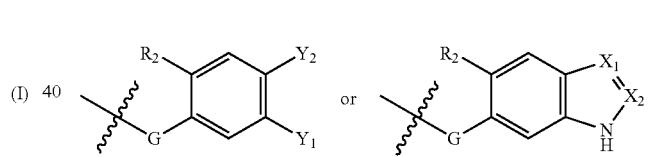

wherein G is selected from the group consisting of —$NR_1C(O)$—, —$C(O)NR_1$—, —$S(O)_2NR_1$—, and —$NR_1S(O)_2$—;

wherein $R_1$ is H or methyl and $R_2$ is H, or wherein G is —$NR_1C(O)$— and $R_1$ and $R_2$, together with the atoms between them, form an optionally substituted $C_3$-$C_6$ heterocyclic ring, thereby creating a bicyclic or tricyclic ring; and wherein $X_1$ is $CR_3$ and $X_2$ is N, or $X_1$ is N and $X_2$ is $CR_3$, or both $X_1$ and $X_2$ are $CR_3$;

wherein $R_3$ is H, $C_1$-$C_2$ alkyl, $C_1$-$C_2$ hydroxyalkyl, $C_1$-$C_2$ alkoxy or $C_1$-$C_2$ alkylamino; and wherein $Y_1$ is H or methyl and $Y_2$ is

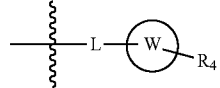

or $Y_2$ is H or methyl and $Y_1$ is

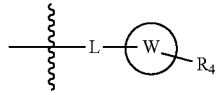

or both $Y_1$ and $Y_2$ are independently selected from H or methyl;
wherein L is selected from the group consisting of —O—, —NH—, —C(O)—, —NH(CH$_2$)$_m$—, $C_1$-$C_3$ alkoxy, $C_1$-$C_3$ alkylamino;
where m is 1 or 2; and
wherein

is optionally substituted aryl or optionally substituted heteroaryl with the proviso that

, named relative to the position of attachment to L, is not pyrazolopyridinyl, ortho-substituted pyridine, 4-pyrimidinyl or imidazole; and
wherein $R_4$ is H, NHC(O)CH$_3$, substituted or unsubstituted aryl, substituted or unsubstituted heteroaryl.

2. The compound of claim 1, or a pharmaceutically acceptable salt thereof, wherein A is selected from

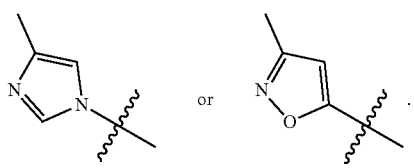

3. The compound of claim 2, or a pharmaceutically acceptable salt-thereof, wherein A is

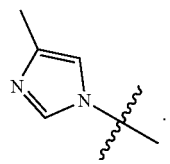 [SMILES: *n1cnc(C)c1]

4. The compound of claim 1, or a pharmaceutically acceptable salt-thereof, wherein G is —NR$_1$C(O)—.

5. The compound of claim 4, or a pharmaceutically acceptable salt thereof, wherein $R_1$ is H.

6. The compound of claim 1, or a pharmaceutically acceptable salt thereof, wherein $Y_2$ is H or methyl and $Y_1$ is

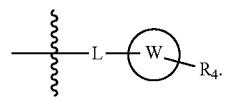

7. The compound of claim 1, or a pharmaceutically acceptable salt thereof, wherein

is optionally substituted aryl.

8. The compound of claim 1, or a pharmaceutically acceptable salt thereof, wherein

is optionally substituted heteroaryl selected from optionally substituted 2-pyrimidinyl, wherein 2-pyrimidinyl refers to the position of attachment to L.

9. The compound of claim 1, or a pharmaceutically acceptable salt thereof, wherein

is optionally substituted heteroaryl selected from an optionally substituted bicyclic heteroaryl group.

10. The compound of claim 1, or a pharmaceutically acceptable salt thereof, wherein Q is optionally substituted $C_4$-$C_7$ heterocyclyl or optionally substituted ($C_1$-$C_3$ alkyl) $C_3$-$C_7$ heterocyclyl.

11. The compound of claim 10, or a pharmaceutically acceptable salt thereof, wherein the optionally substituted $C_4$-$C_7$ heterocyclyl or optionally substituted ($C_1$-$C_3$ alkyl) $C_3$-$C_7$ heterocylyl is selected from the group consisting of an optionally substituted morpholino, optionally substituted piperidinyl, optionally substituted piperazinyl, optionally substituted 4-methyl piperazinyl, optionally substituted 4-($C_3$ alkoxy)piperazinyl, optionally substituted ($C_1$-$C_3$ alkyl)(amino-substituted piperidinyl), optionally substituted ($C_1$-$C_3$ alkyl)(hydroxy-substituted piperidinyl), optionally substituted ($C_1$-$C_3$ alkyl)piperidinyl, and

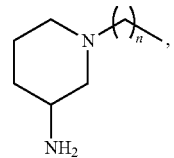

wherein n is 1 or 2.

12. The compound of claim 1, or a pharmaceutically acceptable salt thereof, wherein L is —O— or —NH—.

13. A compound selected from the group consisting of:
Example 5
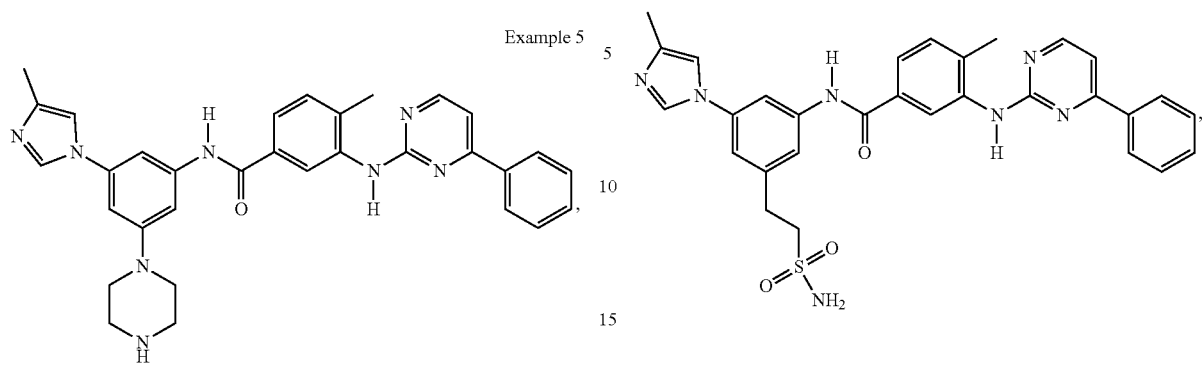
Example 6
Example 10
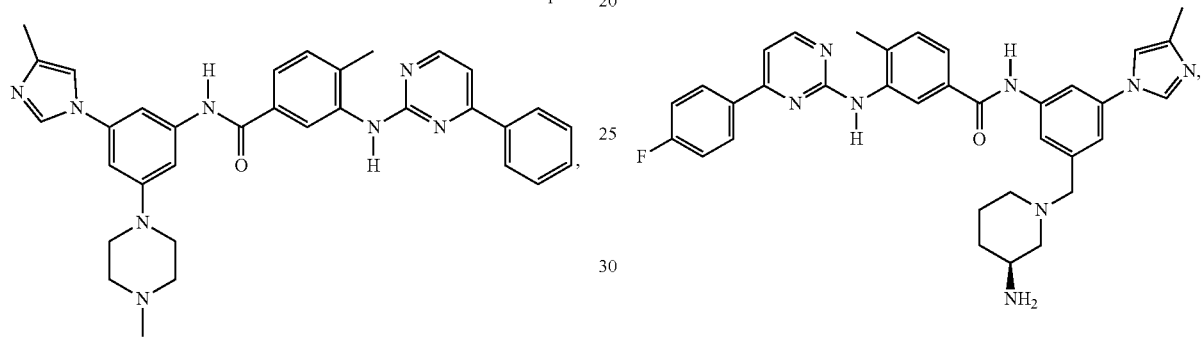
Example 19
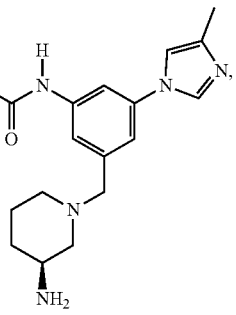
Example 7
Example 20
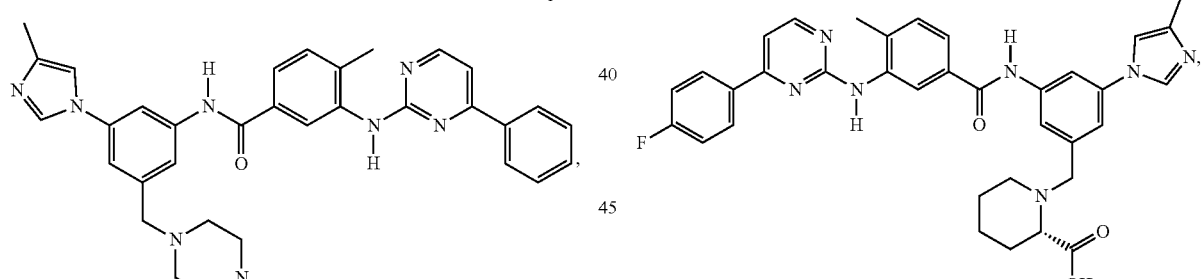
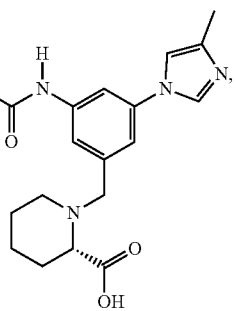
Example 8
Example 21
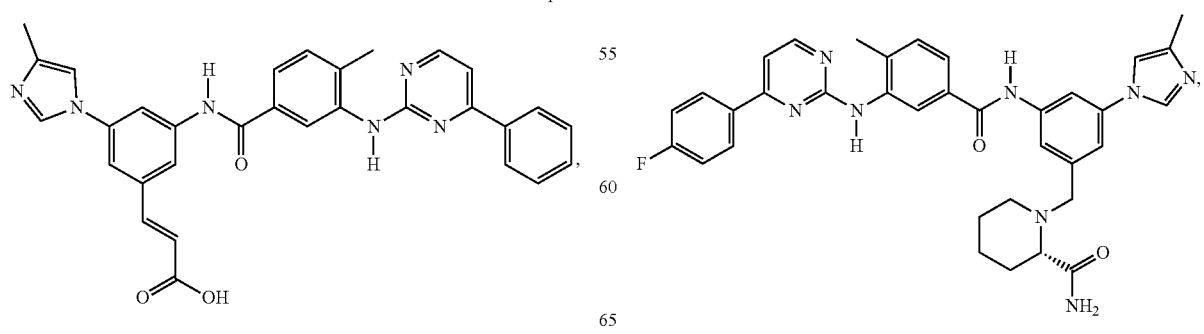
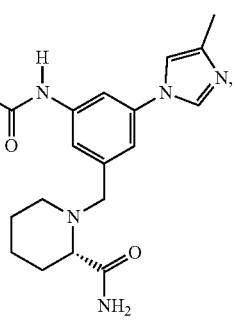

-continued
Example 22
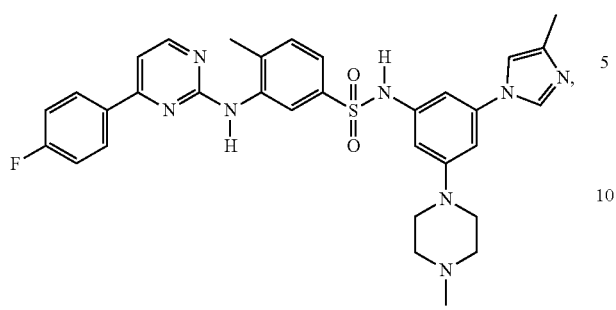
Example 23
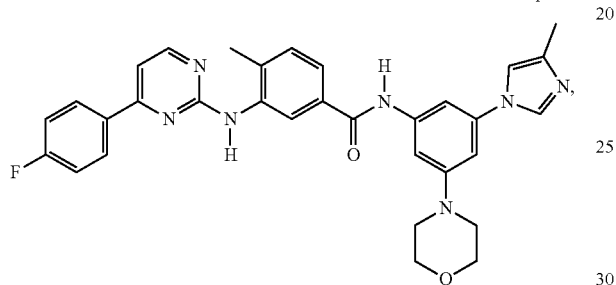
Example 24
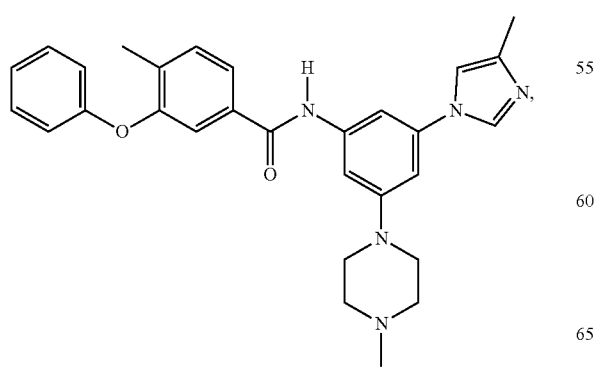
Example 25
-continued
Example 26
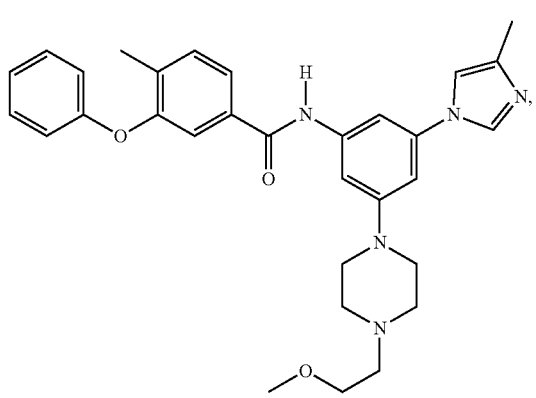
Example 27
Example 28
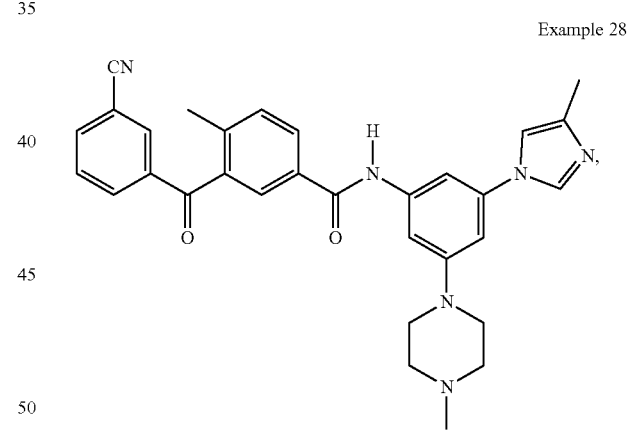
Example 29
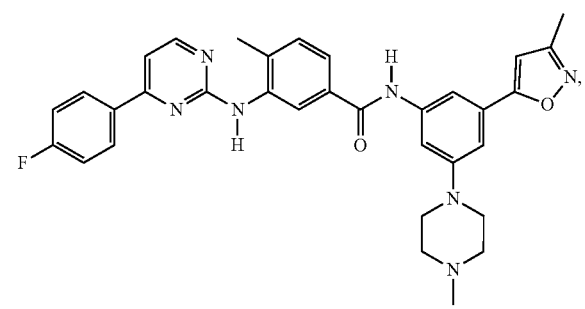

Example 30
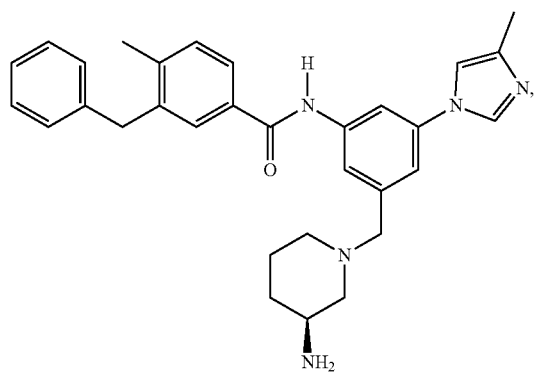
Example 35
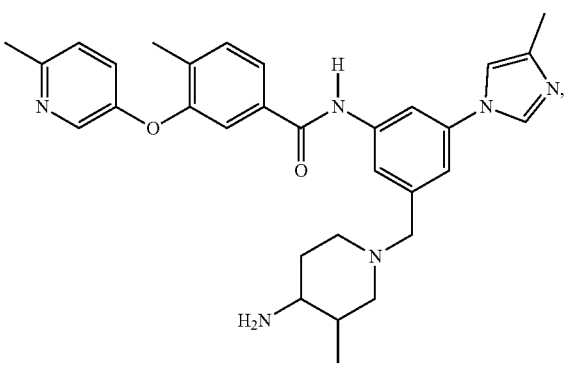
Example 32
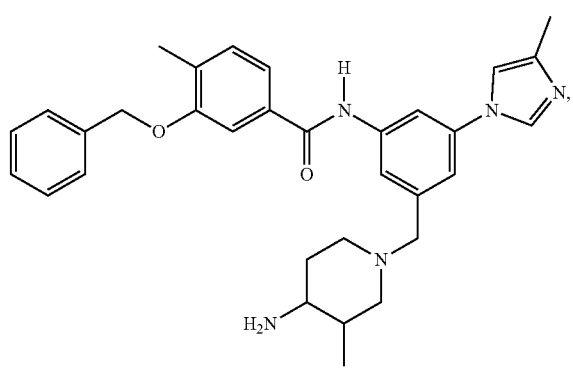
Example 36
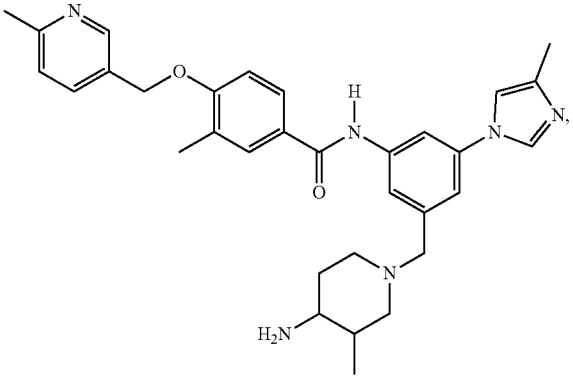
Example 33
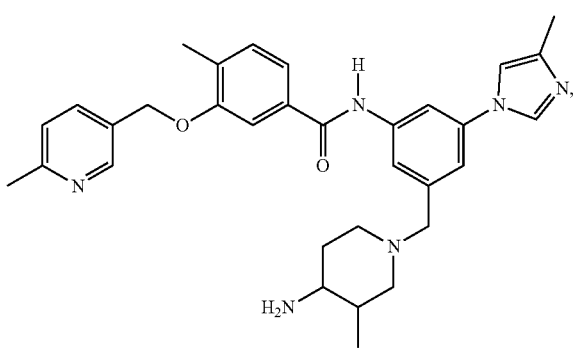
Example 37
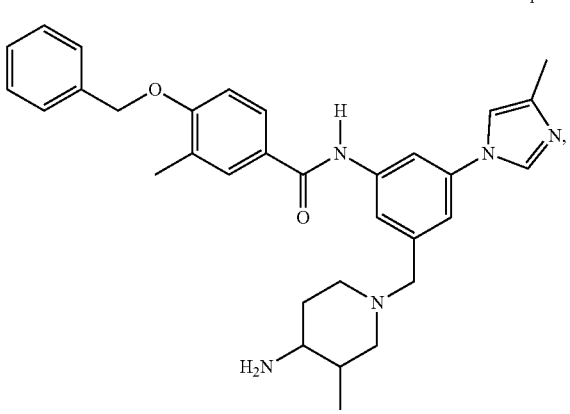
Example 34
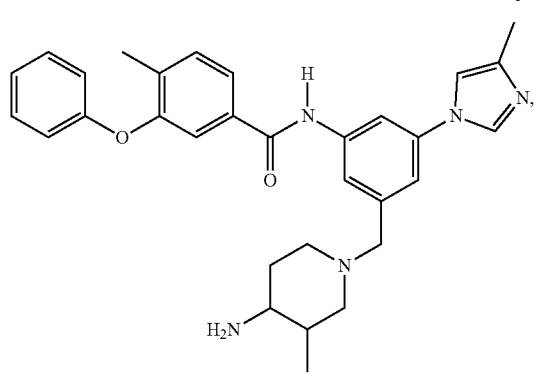
Example 38
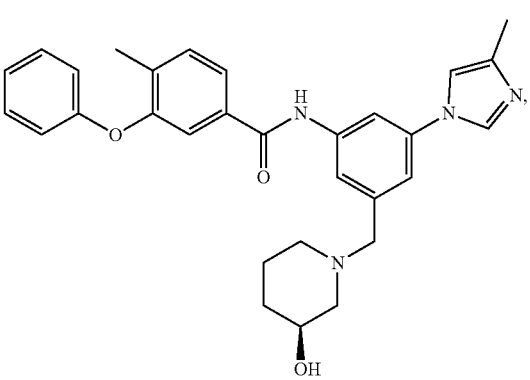

-continued
Example 39
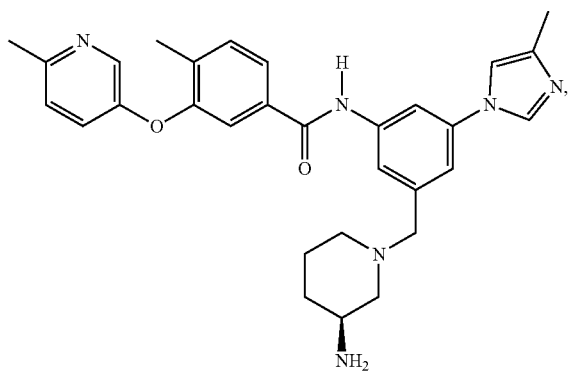
Example 40
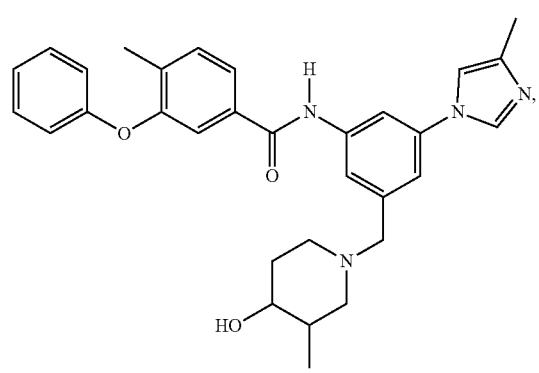
Example 41
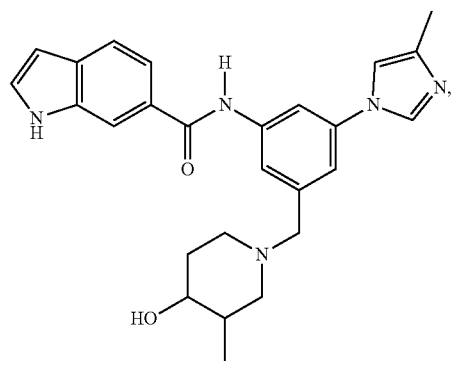
Example 42
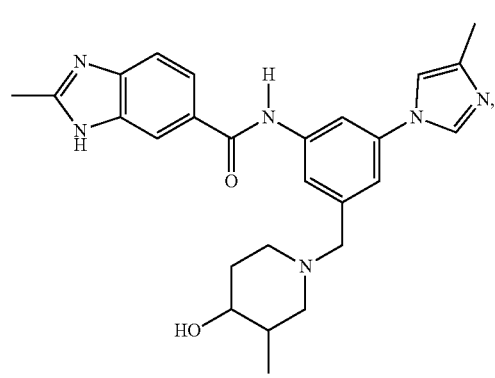
Example 43
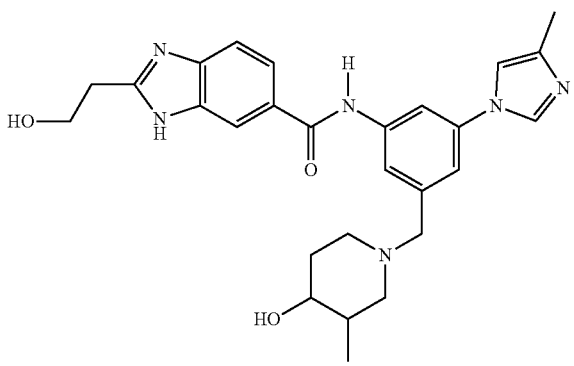
Example 44
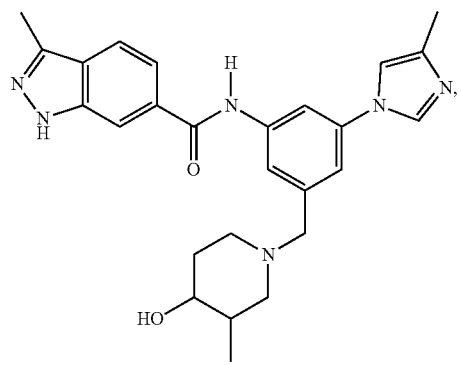
Example 45
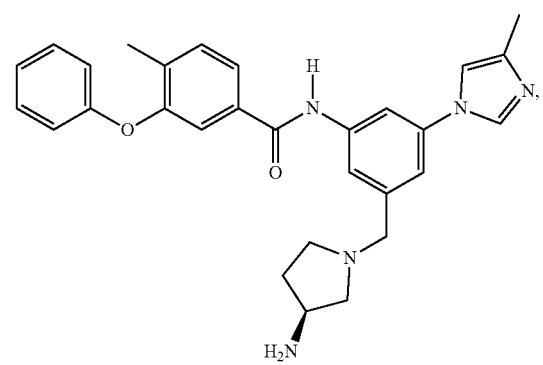
Example 46
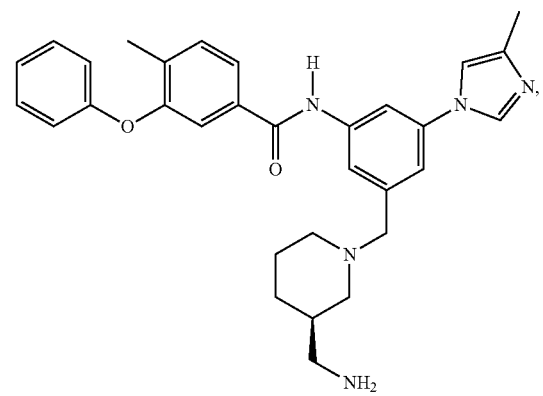

Example 47
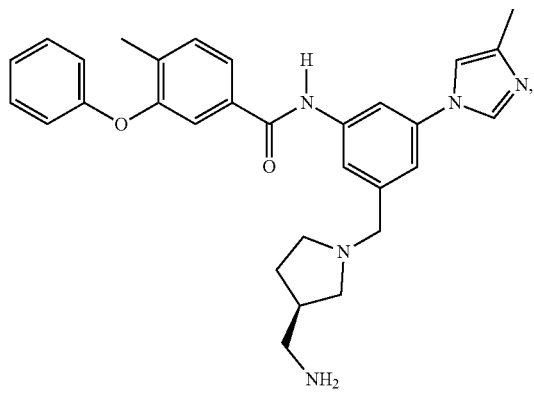
Example 51
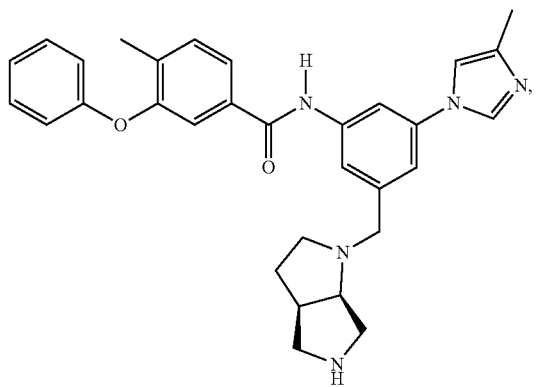
Example 48
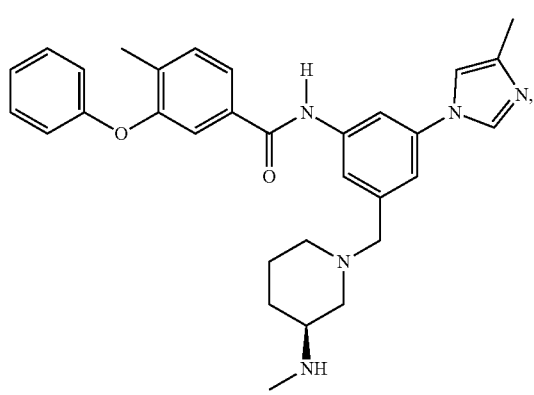
Example 52
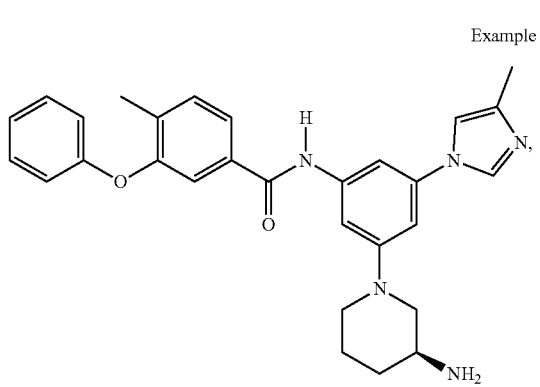
Example 49
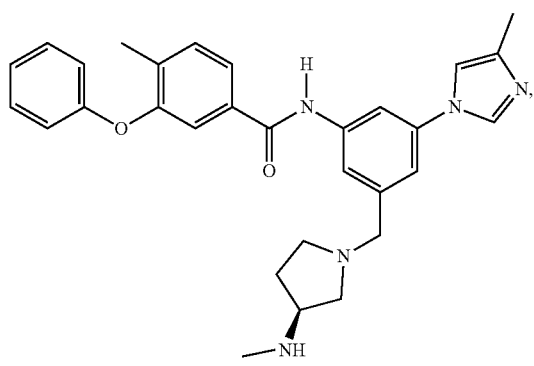
Example 53
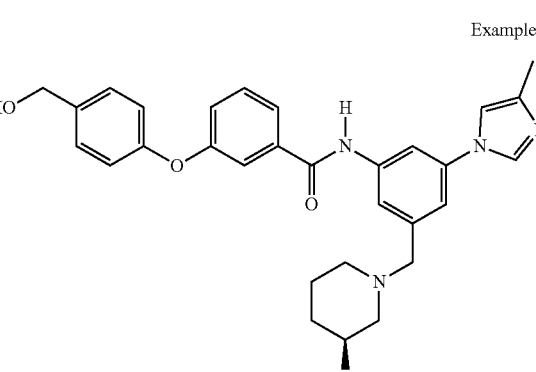
Example 50
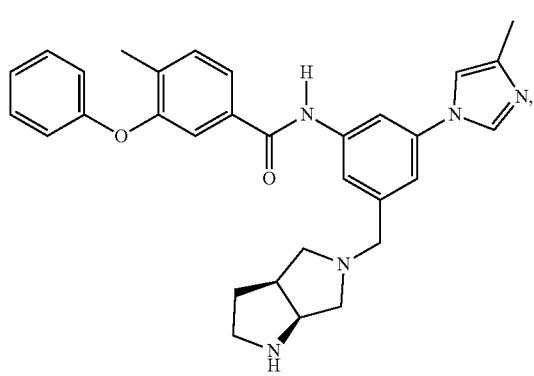
Example 54
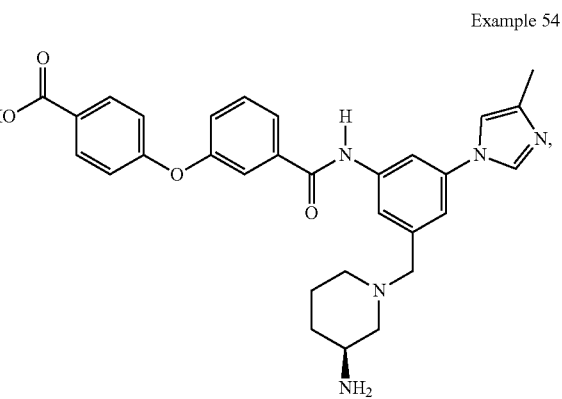

Example 55
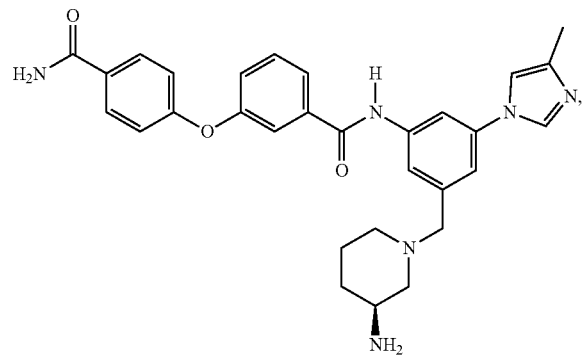
Example 59
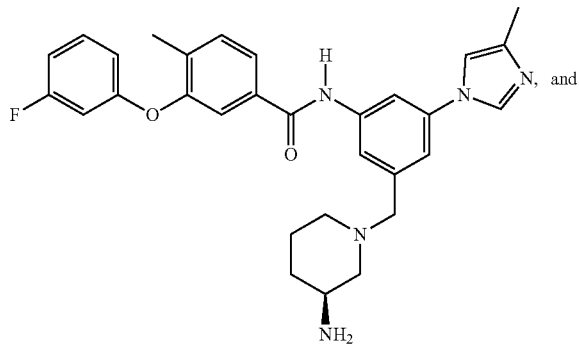
Example 56
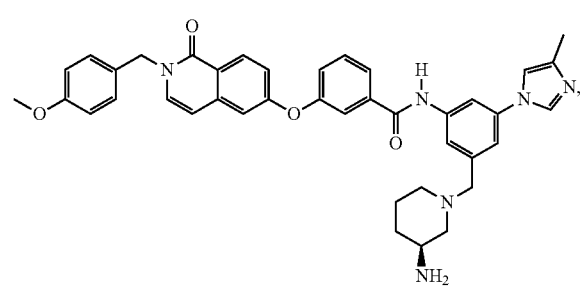
Example 60
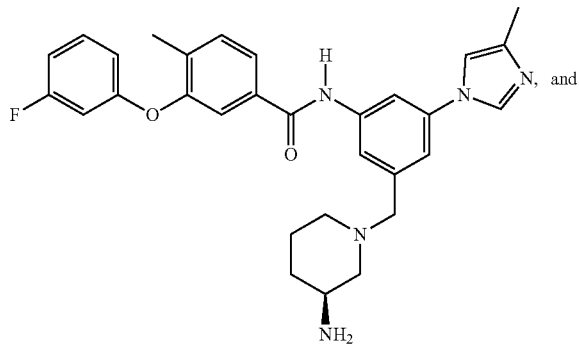
Example 57
or a pharmaceutically acceptable salt thereof.
14. The compound of claim 13 selected from the group consisting of:
Example 5
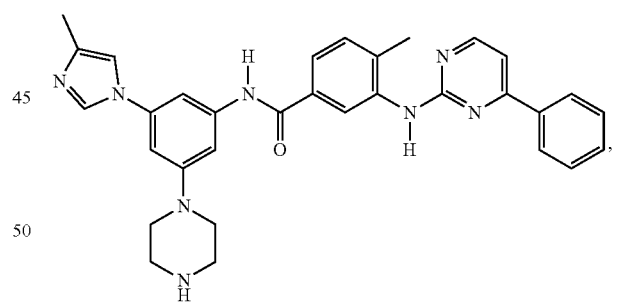
Example 6
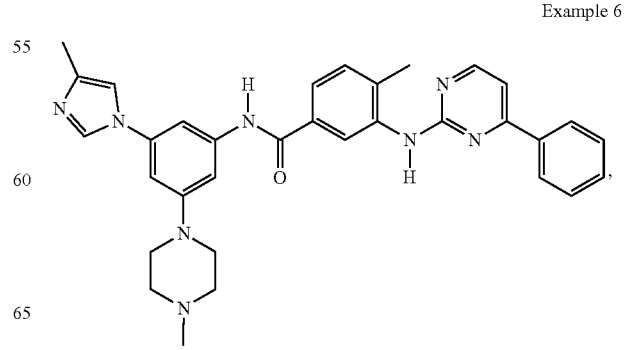

-continued

Example 7

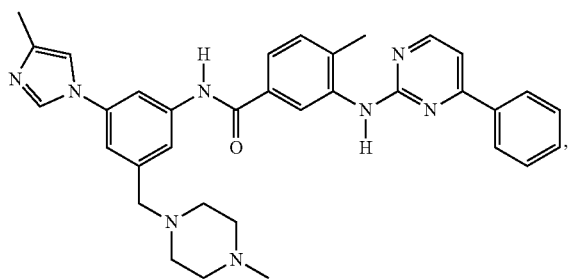

Example 19

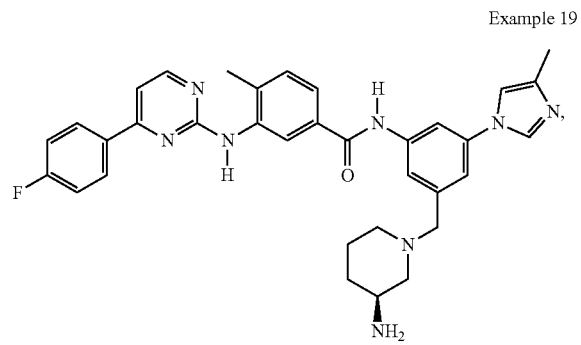

Example 27

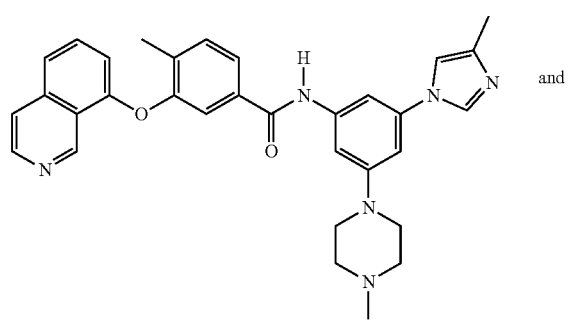

Example 30

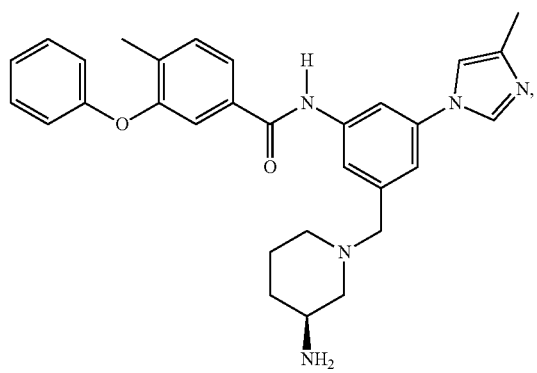

or a pharmaceutically acceptable salt thereof.

15. The compound of claim 13, wherein the compound is:

Example 30

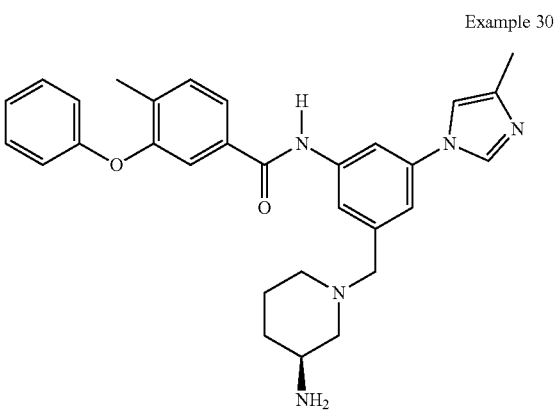 [SMILES: Cc1cn(-c2cc(CN3CCC[C@H](N)C3)cc(NC(=O)c3ccc(C)c(Oc4ccccc4)c3)c2)cn1]

or a pharmaceutically acceptable salt thereof.

16. The compound of claim 1, or a pharmaceutically acceptable salt thereof, wherein:
A is

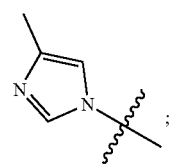 [SMILES: *n1cnc(C)c1]

D is

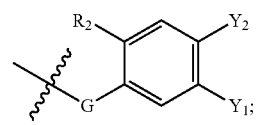

G is —NR$_1$C(O)—;
R$_1$ is H;
R$_2$ is H;
Y$_2$ is H or methyl;
Y$_1$ is

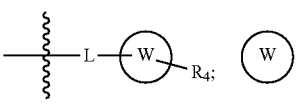

is selected from group consisting of optionally substituted aryl, optionally substituted 2-pyrimidinyl, or optionally substituted isoquinolinyl; wherein 2-pyrimidinyl refers to the position of attachment to L.

17. A composition comprising the compound of claim 1, or a pharmaceutically acceptable salt thereof, and a pharmaceutically acceptable excipient.

18. A composition comprising:
the compound of claim 1, or a pharmaceutically acceptable salt thereof; and
a statin.

* * * * *